(12) United States Patent
Spencer et al.

(10) Patent No.: US 9,315,559 B2
(45) Date of Patent: Apr. 19, 2016

(54) METHODS AND COMPOSITIONS FOR GENERATING AN IMMUNE RESPONSE BY INDUCING CD40 AND PATTERN RECOGNITION RECEPTOR ADAPTERS

(71) Applicant: BAYLOR COLLEGE OF MEDICINE, Houston, TX (US)

(72) Inventors: David Spencer, Houston, TX (US); Priyadharshini Narayanan, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 328 days.

(21) Appl. No.: 13/763,591

(22) Filed: Feb. 8, 2013

(65) Prior Publication Data

US 2014/0087468 A1 Mar. 27, 2014

Related U.S. Application Data

(63) Continuation of application No. 12/563,991, filed on Sep. 21, 2009, now abandoned.

(60) Provisional application No. 61/099,163, filed on Sep. 22, 2008, provisional application No. 61/153,562, filed on Feb. 18, 2009, provisional application No. 61/181,572, filed on May 27, 2009.

(51) Int. Cl.
| | |
|---|---|
| *C07K 19/00* | (2006.01) |
| *C07K 14/705* | (2006.01) |
| *C12N 5/0784* | (2010.01) |
| *C12N 15/86* | (2006.01) |
| *C07K 14/47* | (2006.01) |
| *C12N 9/90* | (2006.01) |
| *A61K 39/00* | (2006.01) |

(52) U.S. Cl.
CPC ....... *C07K 14/70578* (2013.01); *C07K 14/4705* (2013.01); *C12N 5/0639* (2013.01); *C12N 9/90* (2013.01); *C12N 15/86* (2013.01); *A61K 2039/5154* (2013.01); *A61K 2039/5156* (2013.01); *C07K 2319/033* (2013.01); *C12N 2501/52* (2013.01); *C12N 2501/998* (2013.01); *C12N 2510/00* (2013.01); *C12Y 502/01008* (2013.01)

(58) Field of Classification Search
CPC .............. C07K 14/4705; C07K 19/00; C07K 2319/00; C07K 2319/01; C07K 2319/033
USPC ............. 424/93.21; 435/69.1, 69.7, 377, 455; 536/23.4
See application file for complete search history.

(56) References Cited

U.S. PATENT DOCUMENTS

| | | | |
|---|---|---|---|
| 4,514,506 A | 4/1985 | Braatz et al. |
| 5,384,253 A | 1/1995 | Krzyzek et al. |
| 5,538,880 A | 7/1996 | Lundquist et al. |
| 5,550,214 A | 8/1996 | Eberlein et al. |
| 5,550,318 A | 8/1996 | Adams et al. |
| 5,589,343 A | 12/1996 | Marchand et al. |
| 5,610,042 A | 3/1997 | Chang et al. |
| 5,645,992 A | 7/1997 | Lott et al. |
| 5,648,226 A | 7/1997 | Van den Eynde et al. |
| 5,709,995 A | 1/1998 | Chisari et al. |
| 5,719,054 A | 2/1998 | Boursnell et al. |
| 5,741,899 A | 4/1998 | Capon et al. |
| 5,750,395 A | 5/1998 | Fikes et al. |
| 5,780,036 A | 7/1998 | Chisari |
| 5,830,462 A | 11/1998 | Crabtree et al. |
| 5,834,266 A | 11/1998 | Crabtree et al. |
| 5,840,839 A | 11/1998 | Wang et al. |
| 5,869,337 A | 2/1999 | Crabtree et al. |
| 5,869,608 A | 2/1999 | Caldwell et al. |
| 5,871,753 A | 2/1999 | Crabtree et al. |
| 5,925,565 A | 7/1999 | Berlioz et al. |
| 5,935,819 A | 8/1999 | Eichner et al. |
| 5,955,596 A | 9/1999 | Zagursky et al. |
| 5,965,242 A | 10/1999 | Patton et al. |
| 5,994,313 A | 11/1999 | Crabtree et al. |
| 6,011,018 A | 1/2000 | Crabtree et al. |
| 6,043,082 A | 3/2000 | Crabtree et al. |
| 6,046,047 A | 4/2000 | Crabtree et al. |
| 6,046,158 A | 4/2000 | Ariizumi et al. |
| 6,054,436 A | 4/2000 | Crabtree et al. |
| 6,497,876 B1 | 12/2002 | Maraskovsky et al. |
| 6,558,951 B1 | 5/2003 | Tomai et al. |
| 6,670,186 B1 | 12/2003 | Nair et al. |
| 6,943,245 B2 | 9/2005 | Killary et al. |

(Continued)

FOREIGN PATENT DOCUMENTS

| | | |
|---|---|---|
| EP | 0273085 | 7/1984 |
| EP | 0510691 | 10/1992 |

(Continued)

OTHER PUBLICATIONS

Bonnert et al, GenBank U84408, 1997.*

(Continued)

*Primary Examiner* — Kevin Hill
(74) *Attorney, Agent, or Firm* — Grant IP, Inc.

(57) ABSTRACT

Provided are methods for activating an antigen-presenting cell and eliciting an immune response by inducing an inducible pattern recognition receptor adapter, or adapter fragment, and CD40 activity. Also provided are nucleic acid compositions comprising sequences coding for chimeric proteins that include an inducible CD40 peptide and an inducible pattern recognition receptor adapter or adapter fragment.

18 Claims, 63 Drawing Sheets

(56) References Cited

U.S. PATENT DOCUMENTS

| | | | |
|---|---|---|---|
| 7,404,950 | B2 | 7/2008 | Spencer |
| 8,691,210 | B2 | 4/2014 | Lapteva et al. |
| 8,771,671 | B2 | 7/2014 | Spencer |
| 8,999,949 | B2 | 4/2015 | Spencer et al. |
| 2003/0082163 | A1 | 5/2003 | Shu |
| 2003/0091593 | A1 | 5/2003 | Bachmann et al. |
| 2003/0092132 | A1 | 5/2003 | Rodgers |
| 2003/0108527 | A1 | 6/2003 | Seya et al. |
| 2003/0153518 | A1 | 8/2003 | Foxwell et al. |
| 2003/0206917 | A1 | 11/2003 | Tykocinski et al. |
| 2003/0232055 | A1 | 12/2003 | Medzhitov |
| 2004/0019195 | A1 | 1/2004 | Scholm et al. |
| 2004/0209836 | A1 | 10/2004 | Spencer |
| 2005/0215472 | A1 | 9/2005 | Schulke et al. |
| 2007/0081963 | A1 | 4/2007 | Oh et al. |
| 2008/0269160 | A1 | 10/2008 | Spencer et al. |
| 2008/0274140 | A1 | 11/2008 | Weiner et al. |
| 2009/0175880 | A1 | 7/2009 | Keler et al. |
| 2009/0311183 | A1 | 12/2009 | Devy et al. |
| 2010/0196336 | A1 | 8/2010 | Park et al. |
| 2010/0203067 | A1 | 8/2010 | Spencer et al. |
| 2011/0033383 | A1 | 2/2011 | Spencer et al. |
| 2011/0034752 | A1 | 2/2011 | Kessler |
| 2011/0171221 | A1 | 7/2011 | Vieweg |
| 2011/0287038 | A1 | 11/2011 | Slawin et al. |
| 2013/0183333 | A1 | 7/2013 | Spencer et al. |
| 2014/0023647 | A1 | 1/2014 | Slawin et al. |
| 2014/0287490 | A1 | 9/2014 | Spencer et al. |
| 2015/0111294 | A1 | 4/2015 | Spencer et al. |
| 2015/0306140 | A1 | 10/2015 | Spencer et al. |

FOREIGN PATENT DOCUMENTS

| | | |
|---|---|---|
| WO | WO 94/09699 | 5/1994 |
| WO | WO 94/18317 | 8/1994 |
| WO | WO 96/12796 | 5/1996 |
| WO | WO 01/83551 | 11/2001 |
| WO | WO 02/36769 | 5/2002 |
| WO | WO 2008/049113 | 4/2004 |
| WO | WO 2004/073641 | 9/2004 |
| WO | WO 2010/033949 | 3/2006 |
| WO | WO 2011/130566 | 12/2007 |
| WO | WO 2009/061996 | 5/2009 |
| WO | WO 2014/151960 | 9/2014 |

OTHER PUBLICATIONS

Office Action dated Nov. 5, 2013 in U.S. Appl. No. 12/165,360, filed Jun. 30, 2008 and Published as 2008/0269160 on Oct. 30, 2008.
Office Action dated Feb. 24, 2014 in U.S. Appl. No. 12/165,360, filed Jun. 30, 2008 and Published as 2008/0269160 on Oct. 30, 2008.
Office Action dated Nov. 18, 2013 in U.S. Appl. No. 12/445,939, filed Oct. 26, 2010 and Published as 2011/0033383 on Feb. 10, 2011.
Office Action dated Nov. 22, 2013 in U.S. Appl. No. 13/087,329, filed Apr. 14, 2011 and Published as 2011/0287038 on Nov. 24, 2011.
Office Action dated Feb. 6, 2014 in U.S. Appl. No. 13/786,339, filed Mar. 5, 2013 and issued as U.S. Pat. No. 8,999,949 on Apr. 7, 2015.
Office Action dated Aug. 7, 2014 in U.S. Appl. No. 13/786,652, filed Mar. 6, 2013 and Published as 2014/0023647 on Jan. 23, 2014.
Amara et al., "Cell surface tagging and a suicide mechanism in a single chimeric human protein" Hum. Gene Ther. (1999) 10(16):2651-5.
Gay et al., "Assembly and localization of Toll-like receptor signaling complexes", Nature Reviews Immunology (2014) 14:546-558.
Glode, "The case for adjuvant therapy for prostate cancer" Journal of Urology (2006) 176:S30-S33.
Inman et al., "Costimulation, coinhibition and cancer", Current Cancer Drug Targets (2007) 7:15-30.
Kalinski et al., "T-cell priming by type-1 and type-2 polarized dendritic cells: the concept of a third signal" Immunol. Today (1999) 20:561-7.
Kemnade et al., "Off-the-shelf Adenoviralmediated Immunotherapy via Bicistronic Expression of Tumor Antigen and iMyD88/CD40 Adjuvant" Mol. Ther. (2012) 20(7):1462-71.
Leyton et al., "Humanized radioiodinated minibody for imaging of prostate stem cell antigen-expressing tumors", Clinical Cancer Research: an Official Journal of the American Association for Cancer Research (2008) 14:7488-7496.
Martin, "CD40 signaling in CD8+CD40+ T cells turns on contra-T regulatory cell functions", J. Immunol. (2010) 184:5510-8.
Rickert et al., "Signaling by the tumor necrosis factor receptor superfamily in B-cell biology and disease", Immunological Reviews (2011) 244:115-133.
Riviere et al., "Effects of retroviral vector design on expression of human adenosine deaminase in murine bone marrow transplant recipients engrafted with genetically modified cells" PNAS USA (1995) 92:6733-6737.
Schenten et al., "Signaling through the adaptor molecule MyD88 in CD4+ T cells is required to overcome suppression by regulatory T cells", Immunity (2014) 40:78-90.
Timmerman et al., "Dendritic cell vaccines for cancer immunotherapy", Annu. Rev. Med. (1999) 50:507-29.
Wolchok et al., "Guidelines for the evaluation of immune therapy activity in solid tumors: immune-related response criteria", Clin. Cancer Res. (2009) 15(23):7412-7420.
Extended European Search Report dated Aug. 26, 2014 in European Application No. EP 11769619 filed on: Apr. 14, 2011 based on International Application No. PCT/US 2011/032572.
Office Action Dated: Dec. 9, 2014 in U.S. Appl. No. 13/786,339, filed Mar. 5, 2013 and Published as: 2013/0183333 on: Jul. 18, 2013.
Office Action Dated: Aug. 15, 2014 in U.S. Appl. No. 13/786,339, filed Mar. 5, 2013 and Published as: 2013/0183333 on: Jul. 18, 2013.
Office Action Dated: Dec. 1, 2014 in U.S. Appl. No. 13/786,652, filed Mar. 6, 2013 and Published as: 2014/0023647 on: Jan. 23, 2014.
Luke et al., "The family of five: TIR-domain-containing adaptors in Toll-like receptors signaling," Nature Reviews. Immunology, vol. 7, May 2007, pp. 353-364.
Narayanan et al., Abstract 4761: "The iCD40.MyD88 combo-vector: A new platform for enhances DC tumor immunotherapy" Proceedings of the American Association for Cancer Research Annual Meeting, vol. 51, Apr. 15, 2010, p. 1158.
Sonpavde et al., "Vaccine therapy for prostate cancer" Urologic Oncology, Elsevier, New York, NY, USA, vol. 25, No. 6., Nov. 1, 2007, pp. 451-459.
Office Action Dated: Jun. 3, 2013 in U.S. Appl. No. 12/445,939, filed Oct. 26, 2010 and Published as: 2011/0033383 on: Feb. 10, 2011.
"Sipuleucel-T:APC 8015, APC-8015, prostate cancer vaccine—Dendreon." Drugs R D. 2006;7(3):197-201.
Adam et al., "Cross-linking of the p55 Tumor Necrosis Factor Receptor Cytoplasmic Domain by a Dimeric Ligand Induces nuclear Factor-kB and Mediates Cell Death," The Journal of Biological Chemistry vol. 270, No. 29, Jul. 21, 1995, pp. 17482-17487.
Adema et al., "A dendritic-cell-deprived C-C chemokine that preferentially attracts naïve T cells." Nature. Jun. 12, 1997;387(6634):713-717.
Adema et al., "Migration of dendritic cell based cancer vaccines: in vivo veritas?" Curr Opin Immunol. Apr. 2005;17(2):170-174.
Albert et al., "Dendritic cell maturation is required for the crosstolerization of CD8+ T cells." Nat Immunol. Nov. 2001;2(11):1010-1017.
Aliprantis et al., "The apoptotic signaling pathway activated by Toll-like receptor-2," EMBO J. 19(13):3325-3336, (2000).
Amara et al, "A versatile synthetic dimerizer for the regulation of protein-protein interactions." PNAS 1997;94:10618-10623.
Anderson et al., "A homologue of the TNF receptor and its ligand enhance T-cell growth and dendritic-cell function." Nature. Nov. 17, 1997;390(6656)175-179.
Arcone et al., "Identification of sequences responsible for acutephase induction of human C-reactive protein." Nucleic Acids Res. Apr. 25, 1988;16(8):3195-3207.
Ardeshna et al., "The PI3 kinase, p38 SAP kinase, and NF-kappaB signal transduction pathways are involved in the survival and maturation of lipopolysaccharide-stimulated human monocyte-derived dendritic cells." Blood. Aug. 1, 2000;96(3)1039-1046.
Banchereau et al., "Dendritic cells and the control of immunity." Nature. Mar. 19, 1998;392(6673):245-252.

(56) References Cited

OTHER PUBLICATIONS

Banchereau et al., "Dendritic cells as therapeutic vaccines against cancer." Nat Rev Immunol. Apr. 2005;5(4):296-306.
Banchereau et al., "Dendritic cells: controllers of the immune system and a new promise for immunotherapy." Ann NY Acad Sci. Apr. 2003;987180-187.
Banchereau et al., "Immunobiology of dendritic cells." Annu Rev Immunol. 2000; 18:767-811.
Bander et al., "Phase I trial of 177lutetium-labeled J591, a monoclonal antibody to prostate-specific membrane antigen, in patients with androgen-independent prostate cancer." J Clin Oncol. Jul. 20, 2005;23(21):4591-601.
Belshaw et al. (Sep. 1996). "Controlling programmed cell death with a cyclophilin-cyclosporin-based chemical inducer of dimerization." Chemistry & Biology 3(9): pp. 731-738.
Bennett et al., "Apoptosis of rat vascular smooth muscle cells is regulated by p53-dependent and -independent pathways." Circ Res. Aug. 1995;77(2):266-273.
Bennett et al., "Help for cytotoxic-T-cell response is mediated by CD40 signalling." Nature. Jun. 4, 1998;393(6684):478-480.
Bernard et al., "HIV-specific cytotoxic T-lymphocyte activity in immunologically normal HIV-infected persons." AIDS. Nov. 12, 1998;12(16):2125-2139.
Beutler B., "Inferences, questions and possibilities in Toll-like receptor signalling." Nature. Jul. 8, 2004;430(6996):257-263.
Bianco FJ, et al., "Natural History of Biochemically-Recurrent Castrate-Resistant Disease in Men treated with maximal androgen blockage for a Rising PSA after Radical Prostatectomy," Cancer Symposium: Abstract 278, 2005.
Bisping et al., "Targeting receptor kinases by a novel indolinone derivative in multiple myeloma: abrogation of stroma-derived interleukin-6 secretion and induction of apoptosis in cytogenetically defined subgroups." Blood. Mar. 1, 2006;107(5):2079-2089.
Blau et al., "A proliferation switch for genetically modified cells." Proc Natl Acad Sci USA. Apr. 1, 1997;94(7):3076-3081.
Bojak et al., "Muscle specific versus ubiquitous expression of Gag based HIV-1 DNA vaccines: a comparative analysis." Vaccine. May 6, 2002;20(15)1975-1979.
Boldin et al., "Involvement of MACH, a Novel MORT1/FADD-Interacting Protease, in Fas/APO-1- and TNF Receptor-Induced Cell Death," Cell vol. 85, 803-815, Jun. 14, 1996.
Bonnert et al., GeneBank: AAC50954.1; GI: 1814020; Feb. 2, 1997.
Bowie et al, "Deciphering the message in protein sequences: tolerance to amino acid substitutions." Science Mar. 1990; 247:1306-1310.
Burns et al., Inhibition of Interleukin 1 Receptor/Toll-like Receptor Signaling through the Alternatively Spliced, Short Form of MyD88 Is Due to Its Failure to Recruit IRAK-4, J. Exp. Med 197(2):263-268, Jan. 20, 2003.
Carter et al., "Prostate-specific membrane antigen is a hydrolase with substrate and pharmacologic characteristics of a neuropeptidase." Proc Natl Acad Sci U S A. Jan. 23, 1996;93(2):749-53.
Caux et al., "CD34+ hematopoietic progenitors from human cord blood differentiate along two independent dendritic cell pathways in response to GM-CSF+TNF alpha." Adv Exp Med Biol. 1997;417:21-25.
Caux et al., "In vitro regulation of development and function of dendritic cells." Hematol Cell Ther. Oct. 1996;38(5):463.
Cazeaux et al., "Comparative study of immune responses induced after immunization with plasmids encoding the HIV-1 Nef protein under the control of the CMV-IE or the muscle-specific desmin promoter." Vaccine. Sep. 10, 2002;20(27-28):3322-31.
Chan et al., "A Domain in TNF Receptors that mediates ligand-independent receptor assembly and signaling," Science 288, 2351-2354, (2001).
Chan, Francis Ka-Ming, "Three is Better Than One: Pre-Ligand Receptor Assembly in the Regulation of TNF Receptor Signaling," Cytokine, Feb. 2007; 37(2) 101-107.
Chang et al., "Metastatic renal cell carcinoma neovasculature expresses prostate-specific membrane antigen." Urology. Apr. 2001;57(4):801-5.
Chang et al., "Prostate-specific membrane antigen is produced in tumor-associated neovasculature." Clin Cancer Res. Oct. 1999;5(10):2674-81.
Chatterjee et al., "Strategies for efficient gene transfer into hematopoietic cells. The use of adeno-associated virus vectors in gene therapy." Ann NY Acad Sci. Dec. 29, 1995;770:79-90.
Chen C, Okayama H., "High-efficiency transformation of mammalian cells by plasmid DNA." Mol Cell Biol. Aug. 1987;7(8):2745-2752.
Chen et al., "A testicular antigen aberrantly expressed in human cancers detected by autologous antibody screening." Proc Natl Acad Sci USA. Mar. 4, 1997;94(5)1 914-1918.
Cheung et al., "Plasmid encoding papillomavirus Type 16 (HPV16) DNA construced with codon optimization improved the immunogenicity against HPV infection." Vaccine. Dec. 16, 2004;23(5):629-638.
Chiodoni et ai, "Dendritic Cells Infiltrating Tumors Cotransduced with Granulocyte/Macrophage Colony-Stimulating factor (GM-CSF) and CD40 Ligand Genes Take Up and Present Endo-genous Tumor-Associated Antigens, and Prime Naive Mice for a Cytotoxic T Lymphocyte Response," J. Exp. Med. vol. 190, No. 1, Jul. 5, 1999. pp. 125-133.
Choe et al., "Crystal structure of human toll-like receptor 3 (TLR3) ectodomain." Science. Jul. 22, 2005;309(5734):581-585.
Christiansen et al., "N-glycosylation and microtubule integrity are involved in apical targeting of prostate-specific membrane antigen: implications for immunotherapy." Mol Cancer Ther. May 2005;4(5):704-14.
Cisco et al., "Induction of human dendritic cell maturation using transfection with RNA encoding a dominant positive toll-like receptor 4." J Immunol. Jun. 1, 2004;172(11):7162-7168.
Clackson et al., "Redesigning an FKBP-ligand interface to generate chemical dimerizers with novel specificity." Proc Natl Acad Sci USA. Sep. 1, 1998;95(18):10437-10442.
Clackson T., "Dissecting the functions of proteins and pathways using chemically induced dimerization." Chem Biol Drug Des. Jun. 2006;67(6):440-442.
Clarke et al., "Randomized phase II trial of chemoradiotherapy followed by either dose-dense or metronomic temozolomide for newly diagnosed glioblastoma." J Clin Oncol. Aug. 10, 2009;27(23):3861-7.
Clarke SR., "The critical role of CD40/CD40L in the CD4-dependent generation of CD8+ T cell immunity." J Leukoc Biol. May 2000;67(5):607-614.
Clarke, S.J., et al., "A phase I, pharmacokinetic (PK), and preliminary efficacy assessment of ALD518, a humanized anti-IL-6 antibody, in patients with advanced cancer ," 2009, J. Clin. Oncol. 27:15s (suppl.; abstr. 3025).
Coffin "Molecular Mechanisms of Nucleic Acid Integration," Journal of Mecical Virology, 31:43-19 (1990).
Cohen et al., "Nucleotide sequence of the cDNA encoding human tyrosinase-related protein." Nucleic Acids Res. May 11, 1990;18(9):2807-2808.
Contin et al., "Membrane-anchored CD40 is processed by the tumor necrosis factor-alpha-converting enzyme. Implications for CD40 signaling." J Biol Chem. Aug. 29, 2003;278(35):32801-32809.
Coupar et al., "A general methods for the construction of recombinant vaccinia viruses expressing multiple foreign genes." Gene. Aug. 15, 1988;68(1):1-10.
Cranmer et al., "Clinical applications of dendritic cell vaccination in the treatment of cancer." Cancer Immunol Immunother. Apr. 2004;54(4):275-306.
Crawford et al., "A controlled trial of leuprolide with and without flutamide in prostatic carcinoma." N Engl J Med. Aug. 17, 1989;321(7):419-424, w/, erratum N Engl J Med Nov. 16, 1989;321(20):1420.
Cremer et al., "Long-lived immature dendritic cells mediated by Trance-Rank interaction." Blood. Nov. 15, 2002;100(10):3646-3655.

(56) References Cited

OTHER PUBLICATIONS

Cristofanilli et al., "Circulating tumor cells, disease progression, and survival in metastatic breast cancer." N Engl J Med. Aug. 19, 2004;351(8):781-91.

Cyster JG., "Chemokines and cell migration in secondary lymphoid organs." Science. Dec. 10, 1999;286(5447):2098-2102.

Dallal RM, Lotze MT., "The dendritic cell and human cancer vaccines." Curr Opin Immunol. Oct. 2000;12(5):583-588.

Davis et al., "Crystal structure of prostate-specific membrane antigen, a tumor marker and peptidase." Proc Natl Acad Sci USA. Apr. 26, 2005;102(17):5981-5986.

De Becker et al., "The adjuvant monophosphoryl lipid A increases the function of antigen-presenting cells." Int Immunol. Jun. 2000;12(6):807-815.

de Gruijl et al, "Prolonged Maturation and Enhanced Transduction of Dendritic Cells Migrated from Human Skin Explants After In Situ Delivery of CD40-Targeted Adenoviral Vectors," The Journal of Immunology vol. 169,2002 PQS 5322-5331.

de la Thille et al., "Detection of prostate-specific membrane antigen expressing cells in blood obtained from renal cancer patients: a potential biomarker of vascular invasion." Cancer Detect Prev. 2000;24(6):579-88.

De Vries et al., "Effective migration of antigen-pulsed dendritic cells to lymph nodes in melanoma patients is determined by their maturation state." Cancer Res. Jan. 1, 2003;63(1):12-17.

Deml et al. "Multiple effects of codon usage optimization on expression and immunogenicity of DNA candidate vaccines encoding the human immunodeficiency virus type 1 Gag protein," 2001. J. Virol. 75:10991-11001.

Deonarain, "Ligand-targeted receptor-mediated vectors for gene delivery," 1998, Expert Opin. Ther. Pat., vol. 8, pp. 53-69.

Diehl et al., "CD40 activation in vivo overcomes peptide-induced peripheral cytotoxic T-lymphocyte tolerance and augments anti-tumor vaccine efficacy." Nat Med. Jul. 1999;5(7):774-779.

Donnelly et al., "DNA vaccines." Annu Rev Immunol. 1997;15:617-48.

Dudley et al., "Adoptive cell transfer therapy following non-myeloablative but lymphodepleting chemotherapy for the treatment of patients with refractory metastic melanoma." J Clin Oncol. Apr. 1, 2005;23(10):2346-2357.

Elgueta et al., "Molecular mechanism and function of CD40/CD40L engagement in the immune system," Immunological Reviews, 229, (2009) 152-172.

Evel-Kabler et al., "SOCS1 restricts dendritic cells' ability to break self tolerance and induce antitumor immunity by regulating IL-12 production and signaling." J Clin Invest. Jan. 2006;116(1):90-100.

Fan et al., "Improved artificial death switches based on caspases and FADD." Hum Gene Ther. Sep. 20, 1999;10(14):2273-2285.

Farrar et al., "Activation of the Raf-1 kinase cascade by coumermycin-induced dimerization," Nature Sep. 12, 1996;383(6596)178-181.

Fearon et al., "The instructive role of innate immunity in the acquired immune response," Science, Apr. 5, 1996;272(5258):50-53.

Fechheimer et al., "Transfection of mammalian cells with plasmid DNA by scrape loading and sonication loading." Proc Natl Acad Sci USA. Dec. 1987;84(23):8463-8467.

Fernandez et al., "Dendritic cells directly trigger NK cell functions: cross-talk relevant in innate anti-tumor immune responses in vivo." Nat Med. Apr. 1999;5(4):405-411.

Ferrari et al., "Second-strand synthesis is a rate-limiting step for efficient transduction by recombinant adeno-associated virus vectors." J Virol. May 1996;70(5):3227-3234.

Fisher et al., "Transduction with recombinant adeno-associated virus for gene therapy is limited by leading-strand synthesis." J Virol. Jan. 1996;70(1):520-532.

Flotte et al., "Stable in vivo expression of the cystic fibrosis transmembrane conductance regulator with an adeno-associated virus vector." Proc Natl Acad Sci USA. Nov. 15, 1993;90(22):10613-10617.

Flotte TR, Carter BJ. "Adeno-associated virus vectors for gene therapy." Gene Ther. Aug. 1995;2(6):357-362.

Flotte, "Prospects for Virus-Based Gene Therapy for Cystic Fibrosis," Journal of Bioenergetics and Bioinformatics, vol. 25, No. 1, 1993.

Freeman et al., "The role of (111)In Capromab Pendetide (ProstaScintR) immunoscintigraphy in the management of prostate cancer." Q J Nucl Med. Jun. 2002;46(2):131-7.

Fujio Y, Walsh K., "Akt mediates cytoprotection of endothelial cells by vascular endothelial growth factor in an anchorage-dependent manner." J Biol Chem. Jun. 4, 1999;274(23):16349-16354.

Galbiati et al., "N-terminal fatty acylation of the alpha-subunit of the G-protein Gi1 : only the myristoylated protein is a substrate for palmitoylation." Biochem J. Nov. 1994 1;303(Pt 3):697-700.

Gauthier-Campbell et al., "Regulation of dendritic branching and pilopodia formation in hippocampal neurons by specific acylated protein motifs." Mol Biol Cell. May 2004;15(5):2205-2217.

Gefter et al., "A simple method for polyethylene glycol-promoted hybridization of mouse myeloma cells." Somatic Cell Genet. Mar. 1977;3(2):231-236.

GenBank Accession No. M29540, Human carcinoembryonic antigen mRNA (CEA), complete cds, Nov. 1, 1994.

Gestwicki JE, Marinec PS., Chemical control over protein-protein interactions: beyond inhibitors. Comb Chem High Throughput Screen. Sep. 2007;10(8):667-675.

Gilboa E, Vieweg J., "Cancer immunotherapy with mRNA-transfected dendritic cells." Immunol Rev. Jun. 2004;199:251-263.

Gilboa E., "The promise of cancer vaccines." Nat Rev Cancer. May 2004;4(5):401-411.

Gittes RF., "Carcinoma of the prostate." N Engl J Med. Jan. 24, 1991;324(4):236-245.

Goodman et al., "Recombinant adeno-associated virus-mediated gene transfer into hematopoietic progenitor cells." Blood. Sep. 1, 1994;84(5):1492-1500.

Goodwin et al., "Suppression of human T-cell mitogenesis by prostaglandin. Existence of a prostaglandin-producing suppressor cell." J Exp Med. Dec. 1, 1977;146(6):1719-1734.

Goodwin JS., "Immunomodulation by eicosanoids and anti-anflammatory drugs." Curr Opin Immunol. Dec. 1989;2(2):264-268.

Gopal TV., "Gene transfer method for transient gene expression, stable transformation, and cotransformation of suspension cell cultures." Mol Cell Biol. May 1985;5(5):1188-1190.

Gossen et al., "Transcriptional activation by tetracyclines in mammalian cells." Science. Jun. 23, 1995;268(5218)1766-1769.

Gossen M, Bujard H., "Tight control of gene expression in mammalian cells by tetracycline-responsive promoters." Proc Natil Acad Sci USA. Jun. 15, 1992;89(12):5547-5551.

Graham FL, van der Eb AJ., "A new technique for the assay of infectivity of human adenovirus 5 DNA." Virology. Apr. 1973;52(2):456-467.

Granucci et al., "Eerly events in dendritic cell maturation induced by LPS." Microbes Infect. Nov. 1999;1(13):1079-1084.

Granucci et al., "Inducible IL-2 production by dendritic cells revealed by global gene expression analysis." Nat Immunol. Sep. 2001;2(9):882-888.

Granucci et al., "Modulation of cytokine expression in mouse dendritic cell clones." Eur J Immunol. Oct. 1994;24(10):2522-2526.

Grewal IS, Flavell RA., "CD40 and CD154 in cell-mediated immunity." Annu Rev Immunol. 1998;16:111-135.

Hammad et al., "Monocyte-derived dendritic cells induce a house dust mite-specific Th2 allergic inflammation in the lung of humanized SCID mice:involvement of CCR7." J Immunol. Aug. 1, 2002;169(3):1524-1534.

Hanks B.A., et al.. "Re-engineered CD40 receptor enables potent pharmacological activation of dendritic-cell cancer vaccines in vivo" Nature Medicine, vol. 11, No. 2. 2005 pp. 130-137.

Harbury et al., "Crystal structure of an isoleucine-zipper trimer," Nature, vol. 371, Sep. 1, 1994, 80-83.

Hauer et al., "TNF receptor (TNFR)-associated factor (TRAF) 3 serves as an Inhibitor of TRAF2 5-medlated activation of the noncanonical NF-B pathway by TRAF-binding TNFRs." PNAS, vol. 102, No. 8, Feb. 22, 2005; pp. 2874-2879.

(56) References Cited

OTHER PUBLICATIONS

Hay et al., "Replication of Adenovirus Mini-Chromasomes," J. Mol. Biol. (1984) 175, 493-510.

He et al., "A simplified system for generating recombinant adenoviruses." Proc Natl Acad Sci USA. Mar. 3, 1998;95(5):2509-2514.

Hearing et al., "Identification of a repeated sequence element required for efficient encapsidation of the adenovirus type 5 chromosome." J Virol. Aug. 1987;61(8):2555-2558.

Hearing P, Shenk T., "Functional analysis of the nucleotide sequence surrounding the cap site for adenovirus type 5 region E1A messenger RNAs." J Mol Biol. Jul. 15, 1983;167(4):809-822.

Hermans et al., "CD8+ T cell-dependent elimination of dendritic cells in vivo limits the induction of antitumor immunity." J Immunol. Mar. 15, 2000;164(6):3095-3101.

Ho et al., "Dimeric ligands define a role for transcriptional activation domains in reinitiation." Nature. Aug. 29, 1996;382(6594):822-826.

Hodge et al., "Vector-based delivery of tumor-associated antigens and T-cell co-stimulatory molecules in the induction of immune responses and anti-tumor immunity," Cancer Detect Prevent 2002; 26;275-291.

Holler et al., "Development of improved soluble inhibitors of FasL and CD40L based on oligomerized receptors," Journal of Immunolgial Methods 237(2000) 159-173.

Hollstein et al., "Database of p53 gene somatic mutations in human tumors and cell lines." Nucleic Acids Ress. Sep. 1994;22(17):3551-3555.

Holsinger et al., "Signal transduction in T lymphocytes using a conditional allele of Sos." Proc Natl Acad Sci USA. Oct. 10, 1995;92(21):9810-9814.

Horng et al., "Drosophila MyD88 is an adapter in the Toll signaling pathway," PNAS 98(22):12654-12658, Oct. 23, 2001.

Hoshino et al., "Cutting edge:Toll-like receptor 4(TLR4)-deficient mice are hyporesponsive to lipopolysaccharide: evidence for TLR4 as the Lps gene product." J Immunol. Apr. 1, 1999;162(7):3749-3752.

Hostager et al., "Different: CD40-mediated Signaling Events Require Distinct CD40 Structural features," J. Immunol. 157:1047-1053, Aug. 1, 1996.

Hou WS, Van Parijs L., "A Bcl-2-dependent molecular timer regulates the lifespan and immunogenicity of dendritic cells." Nat Immunol. Jun. 2004;5(6):583-589.

Ismaili et al., "Monophosphoryl lipid A activates both human dendritic cells and T cells." J Immunol. Jan. 15, 2002;168(2):926-932.

Israeli et al., "Expression of the prostate-specific membrane antigen." Cancer Res. Apr. 1, 1994;54(7)1807-11.

Israeli et al., "Sensitive nested reverse transcription polymerase chain reaction detection of circulating prostatic tumor cells: comparison of prostate-specific membrane antigen and prostate-specific antigen-based assays." Cancer Res. Dec. 15, 1994;54(24):6306-10.

Israeli et al., Molecular cloning of a complementary DNA encoding a prostate-specific membrane antigen. Cancer Res. Jan. 15, 1993;53(2):227-230.

Iuliucci et al., "Intravenous safety and pharmacokinetics of a novel dimerizer drug, AP1903, in healthy volunteers." J Clin Pharmacol. Aug. 2001;41(8):870-9.

Jackson et al., "A second tyrosinase-related protein, TRP-2, maps to and is mutated at the mouse slaty locus." EMBO J. Feb. 1992;11(2):527-535.

Jacquot et al, "CD154/CD40 and CD70/CD27 interactions have different and sequential functions in T cell-dependent B cell responses: enhancement of plasma cell differentiation by CD27 signaling," J Immunol 1997; 159: 2652-2657.

Janeway et al., "Approaching the asymptote? Evolution and revolution in immunology." Cold Spring Harb Symp Quant Biol. 1989;54 Pt 1:1-13.

Jemal et al., "Cancer statastics, 2008." CA Cancer J Clin. Mar.-Apr. 2008;58(2):71-96.

Jonuleit et al., "Pro-inflammatory cytokines and prostaglandins induce maturation of potent immunostimulatory dendritic cells under fetal calf serum-free conditions," Eur. J. Immunol 27:3135-3142, Dec. 1997.

Josien et al., "Trance, a tumor necrosis factor family member, enhances the longevity and adjuvant properties of dendritic cells in vivo." J Exp Med. Feb. 7, 2000;191(3):495-502.

Kadowaki N. et al., "Subsets of human dendritic cell precursors express different toll-like receptors and respond to different microbial antigens," J Exp Med. 2001, vol. 194, pp. 863-869.

Kagan JC, Medzhitov R., "Phosphoinositide-mediated adaptor recruitment controls Toll-like receptor signaling." Cell. Jun. 2, 2006;125(5):943-955.

Kageyama et al., "Differing utilization of homologous transcription initiation sites of rat K and T kininogen genes under inflammation condition." J Biol Chem. Feb. 15, 1987;262(5):2345-2351.

Kalams et al., "The critical need for CD4 help in maintaining effective cytotoxic T lymphocyte responses." J Exp Med. Dec. 21, 1998;188(12):2199-2204.

Kalinski et al., "Dendritic cells, obtained from peripheral blood precursors in the presence of PGE2, promote Th2 responses." Adv Exp Med Biol. 1997;417:363-367.

Kalinski et al., "Prostaglandin E(2) is a selective inducer of interleukin-12 p40 (IL-12p40) production and an inhibitor of bioactive IL-12p70 heterodimer." Blood. Jun. 2001 1;97(11):3466-3469.

Kandel ES, Hay N., "The regulation and activities of the multifunctional serine/threonine kinase Akt/PKB." Exp Cell Res. Nov. 25, 1999;253(1):210-229.

Kanto et al., "Ceramide mediates tumor-induced dendritic cell apoptosis." J Immunol. Oct. 1, 2001;167(7):3773-3784.

Kantoff et al., "Overall survival analysis of a phase II randomized controlled trial of a Poxviral-based PSA-targeted immunotherapy in metastatic castration-resistant prostate cancer." J Clin Oncol. Mar. 1, 2010;28(7)1099-105.

Kantoff et al., "Sipuleucel-T immunotherapy for castration-resistant prostate cancer." N Engl J Med. Jul. 29, 2010;363(5):411-22.

Kaplitt et al., "Long-term gene expression and phenotypic correction using adeno-associated virus vectors in the mammalian brain." Nat Genet. Oct. 1994;8(2):148-154.

Kaplitt et al., "Long-term gene transfer in porcine myocardium after coronary infusion of an adeno-associated virus vector." Ann Thorac Surg. Dec. 1996;62(6):1669-76.

Kawakami et al., "Identification of a human melanoma antigen recognized by tumor-infiltrating lymphocytes associated with in vivo tumor rejection." Proc Natl Acad Sci USA. Jul. 5, 1994;91(14):6458-6462.

Kawakami et al., "Identification of the immunodominant peptides of the MART-1 human melanoma antigen recognized by the majority of HLA-A2-restricted tumor infiltrating lymphocytes." J Exp Med. Jul. 1, 1994;180(1):347-352.

Kehry, Marilyn R., "CD40-Mediated Signaling in B Cells, Balancing Cell Survival, Growth and Death," The American Association of Immunologists, 1996, 2345-2348.

Kelleher et al., "Lipopolysaccharide Modulation of Dendritic Cells is Insufficient to Mature Dendritic Cells to Generate CTLs from Native Polyclonal CD8+ T Cells In Vitro, Whereas CD40 Ligation is Essential," The Journal of Immunology, The American Society of Immunologists, vol. 167, No. 11, Jan. 1, 2001, pp. 6247-6255.

Kelly WK, Slovin SF., "Chemotherapy for androgen-independent prostate cancer: myth or reality." Curr Oncol Rep. Sep. 2000;2(5):394-401.

Kempf et al, "Improved stimulation of human dendritic cells by receptor engagement with surface-modified microparticles," J Drug Target vol. 11 No. 1, Jan. 2003 pp. 11-18.

Kessler et al., "Gene delivery to skeletal muscle results in sustained expression and systemic delivery of a therapeutic protein." Proc Natl Acad Sci USA. Nov. 26, 1996;93(24):14082-14087.

Kikuchi et al., "Dendritic cells genetically modified to express CD40 ligand and pulsed with antigen can initiate antigen-specific humoral immunity independent of CD4+ T cells." Nat Med. Oct. 2000;6(10):1154-1159.

Klein et al., "High-velocity microprojectiles for delivering nucleic acids into living cells," (1987) Nature, 327,70-73.

(56) References Cited

OTHER PUBLICATIONS

Kobayashi et al., "IRAK-M is a negative regulator of Toll-like receptor signaling." Cell. Jul. 26, 2002;110(2):191-202.

Koeberl et al., "Persistent expression of human clotting factor IX from mouse liver after intravenous injection of adeno-associated virus vectors." Proc Natl Acad Sci USA. Feb. 18, 1997;94(4):1426-1431.

Kohler G, Milstein C., "Continuous cultures of fused cells secreting antibody of predefined specificity." Nature. Aug. 7, 1975;256(5517):495-497.

Kohler G, Milstein C., "Derivation of specific antibody-producing tissue culture and tumor lines by cell fusion." Eur J Immunol. Jul. 1976;6(7):511-519.

Kopytek et al., "Chemically induced dimerization of dihydrofolate reductase by a homobifunctional dimer of methotrexate." Chem Biol. May 2000;7(5):313-321.

Korst et al., "Effect of adenovirus gene transfer vectors on the immunologic functions of mouse dendritic cells." Mol Ther. Mar. 2002;5(3):307-315.

Kraaij et al., "Prostate specific membrane antigen (PSMA) is a tissue-specific target for adenoviral transduction of prostate cancer in vitro." Prostate. Feb. 15, 2005;62(3):253-9.

Kumar et al., "Immunogenicity testing of a novel engineered HIV-1 envelope gp140 DNA vaccine construct." DNA Cell Biol. Jul. 2006;25(7):383-392.

Kutzler et al., "Coimmunization with an optimized IL-15 plasmid results in enhanced function and longevity of CD8 T cells that are partially independent of CD4 T cell help." J Immunol. Jul. 1, 2005;175(1):112-123.

Kutzler MA, Weiner DB., "DNA vaccines: ready for prime time?" Nat Rev Genet. Oct. 2008;9(10):776-788.

Kwon et al., "Isolation and sequence of a cDNA clone for human tyrosinase that maps at the mouse c-albino locus." Proc Natl Acad Sci USA. Nov. 1987;84(21):7473-7477.

Labeur et al., "Generation of tumor immunity by bone marrow-derived dendritic cells correlates with dendritic cell maturation stage." J Immunol. Jan. 1, 1999;162(1):168-175.

Laddy et al., "Heterosubtypic protection against pathogenic human and avian influenza viruses via in vivo electroporation of synthetic consensus DNA antigens." PLoS One. Jun. 25, 2008;3(6):e2517.

Langenkamp et al., "Kinetics of dendritic cell activation: impact on priming of TH1, TH1 and nonpolarized T cells." Nat Immunol. Oct. 2000;1(4):311-316.

Lanzavecchia A, Sallusto F., "Dynamics of T lymphocyte responses: intermediates, effectors, and memory cells." Science. Oct. 6, 2000;290(5489):92-97.

Lanzavecchia A, Sallusto F., "Regulation of T cell immunity by dendritic cells." Cell. Aug. 10, 2001;106(3):263-266.

Lapointe et al., "Human dendritic cells require multiple activation signals for the efficient generation of tumor antigen-specific T lymphocytes." Eur J Immunol. Nov. 2000;30(11):3291-3298.

Lapteva et al., "Development of Novel CD4-Independent iCD40-Dendritic Cell Vaccine for HIV-1 Immunotherapy," vol. 17, No. Suppl 1, May 2009, 12th Annual Meeting of the American Society of Gene Therapy: San Diego, CA, May 27-30, 2009.

Lapteva et al., "Enhance Activation of Human Dendritic Cells by inducible CD40 and Toll-like Receptor-4 Ligation," Cancer Research 2007, 67; (21) Nov. 1, 2007, pp. 10528-10537.

Lee et al., "A clinical grade cocktail of cytokines and PGE2 results in uniform maturation of human monocyte-derived dendritic cells: implications for immunotherapy." Vaccine. Dec. 19, 2002;20 Suppl 4:A8-A22.

Lee et al., "Cytoplasmic domain-mediated dimerizations of toll-like receptor 4 observed by beta-lactamase enzyme fragment complementation." J Biol Chem. Mar. 12, 2004;279(11):10564-10574.

Leo et al., "Partition coefficients and their uses." Chem Rev. Dec. 1971;71(6):525-616.

Levrero et al., "Defective and nondefective adenovirus vectors for expressing foreign genes in vitro and in vivo." Gene. May 30, 1991;101(2):195-202.

Li et al., "A novel conditional Akt 'survival+A185 switch' reversibly protects cells from apoptosis." Gene Ther. Feb. 2002;9(4):233-244.

Li et al., "The HIV-1 Env protein signal sequence retards its cleavage and down-regulates the glycoprotein folding." Virology. Jul. 5, 2000;272(2):417-428.

Liu et al., "Constitutive and antibody-induced internalization of prostate-specific membrane antigen." Cancer Res. Sep. 15, 1998;58(18):4055-60.

Liu et al., "Differential regulation of interleukin (IL)-12 p35 and p40 gene expression and interferon (IFN)-gamma-primed IL-12 production by IFN regulatory factor 1." J Exp Med. Oct. 2003;198(8):1265-1276.

Liu et al., "Monoclonal antibodies to the extracellular domain of prostate-specific membrane antigen also react with tumor vascular endothelium." Cancer Res. Sep. 1, 1997;57(17):3629-34.

Livak et al., "Analysis of relative gene expression data using real-time quantitative PCR and the 2(-Delta Delta C(T)) Method." Methods. Dec. 2001;25(4):402-408.

Lodge et al., Dendridic Cell-based Immunotherapy of Prostate Cancer: Immune Monitoring of a Phase II Clincal Trial, Cancer Res. 60:829-833, 2000.

Loiarro et al., "Peptide-mediated interference of TIR domain dimerization in MyD88 inhibits interleukin-1-dependent activation of NF-{kappa}B." J Biol. Chem. Apr. 22, 2005;280(16)15809-15814.

Luft et al., "Functionally distinct dendritic cell (DC) populations induced by physiologic stimuli: prostaglandin E(2) regulates the migratory capacity of specific DC subsets." Blood. Aug. 15, 2002;100(4):1362-1372.

Luo et al., "Oligomerization activates c-RAF-1 through a Ras-dependent mechanism." Nature. Sep. 12, 1996;383(6596)181-185.

MacCorkle et al., "Synthetic activation of caspases: artificial death switches." Proc Natl Acad Sci USA. Mar 31, 1998;95(7):3655-3660.

Macejak DG, Sarnow P., "Internal initiation of translation mediated by the 5' leader of a cellular mRNA." Nature. Sep. 5, 1991;353(6339):90-94.

Machiels et al., "Prospective randomized study comparing docetaxel, estramustine, and prednisone with docetaxel and prednisone in metastatic hormone-refractory prostate cancer." J Clin Oncol. Nov. 10, 2008;26(32):5261-8.

Malin et al., "Vaccinia expression of *Mycobacterium tuberculosis*-secreted proteins: tissue plasminogen activator signal sequence enhances expression and immunogenicity of *M. tuberculosis* Ag85." Microbes Infect. Nov. 2000;2(14):1677-1685.

Malissen B, Ewbank JJ., "'TaiLoRing' the response of dendritic cells to pathogens." Nat Immunol. Aug. 2005;6(8):750-769.

Mann et al., "Construction of a retrovirus packaging mutant and its use to produce helper-free defective retrovirus." Cell. May 1983;33(1):153-159.

Marsland et al., "CCL19 and CCL21 induce a potent proinflammatory differentiation program in licensed dendritic cells." Immunity. Apr. 2005;22(4):493-505.

Martln-Fontecha et al., "Regulation of dendritic cell migration to the draining lymph node: impact on T lymphocyte traffic and priming." J Exp Med. Aug. 18, 2003;198(4):615-621.

Mazouz et al., "CD40 triggering increases the efficiency of dendritic cells for antitumoral immunization." Cancer Immun. Mar. 27, 2002;2:2.

McCown et al., "Differential and persistent expression patterns of CNS gene transfer by an adeno-associated virus (AAV) vector." Brain Res. Mar. 25, 1996;713(1-2):99-107.

McIlroy et al., "Histamine and prostaglandin E up-regulate the production of Th2-attracting chemokines (CCL17 and CCL22) and down-regulate IFN-gamma-induced CXCL10 production by immature human dendritic cells." Immunology. Apr. 2006;117(4):507-516.

McWhirter et al., "Crystallographic analysis of CD40 recognition and signaling by human TRAF2." Proc Natl Acad Sci USA. Jul. 20, 1999;96(15):8408-8413.

(56) References Cited

OTHER PUBLICATIONS

Medema et al., "Expression of the serpin serine protease inhibitor 6 protects dendritic cells from cytotoxic T lymphocyte-induced apoptosis: differential modulation by T helper type 1 and type 2 cells." J Exp Med. Sep. 3, 2001;194(5):657-667.
Medzhitov et al., "A human homologue of the Drosophila Toll protein signals activation of adaptive immunity." Nature. Jul. 24, 1997;388(6640):394-397.
Megiovanni et al., "Double-stranded RNA stimulation of CD40 ligation of monocyte-derived dendritic cells as models to study their activation and maturation process." Eur Cytokine Netw. Apr.-Jun. 2004;15(2):126-134.
Melief et al., "Effective therapeutic anticancer vaccines based on preCision guiding of cytolytic T lymphocytes" Immunol Rev. vol. 188, Oct. 2002, pp. 177-182.
Meyer et al., "Cutting edge: cyclooxygenase-2 activation suppresses Th1 polarization in response to helicobacter pylori." J Immunol. Oct. 15, 2003;171(8):3913-3917.
Meylan et al., "Intracellular pattern recognition receptors in the host response." Nature. Jul. 6, 2006;442(7098):39-44.
Miga et al., "Dendritic cell longevity and T cell persistence is controlled by CD154-CD40 interactions." Eur J Immunol. Mar. 2001;31(3):959-965.
Mizukami et al., "Adeno-associated virus type 2 binds to a 150-kilodalton cell membrane glycoprotein." Virology. Mar. 1, 1996;217(1):124-130.
Mochizuki et al., "Akt protein kinase inhibits non-apoptotic programmed cell death induced by ceramide." J Biol Chem. Jan. 25, 2002;277(4):2790-2797.
Montgomery et al., "Heterologous and homologous protection against influenza A by DNA vaccination: optimization of DNA vectors." DNA Cell Biol. Nov. 1993;12(9):777-783.
Morgan et al., "Cancer regression in patients after transfer of genetically engineered lymphocytes." Science. Oct. 6, 2006;314(5796):126-129.
Morse et al., "Migration of human dendritic cells after injection in patients with metastic malignancies." Cancer Res. Jan. 1, 1999;5((1):56-58.
Mukherjee et al., "Lipid-dependent recruitment of neuronal Src to lipid rafts in the brain." J Biol Chem. Oct. 17, 2003;278(42):40806-40814.
Nabel et al., "Recombinant gene expression in vivo within endothelial cells of the arterial wall." Science. Jun. 16, 1989;244(4910)1342-1344.
Nakagami et al., "Safety and efficacy of docetaxel, estramustine phosphate and hydrocortisone in hormone-refractory prostate cancer patients." Int J Urol. Jul. 2010;17(7):629-34.
Napolitani et al., "Selected Toll-like receptor agonist combinations synergistically trigger a T helper type 1-polarizing program in dendrinic cells," Nat Immunol. Aug. 2005; vol. 6. No. 8, pp. 769-776.
Narayanan et al. A composite MyD88/CD40 switch synergistically activates mouse and human dendritic cells for enhanced antitumor efficacy. J Clin Invest. 2011, vol. 121(4), p. 1524-1529.
Narum et al., "Codon optimization of gene fragments encoding Plasmodium falciparum merzoite proteins enhances DNA vaccine protein expression and immunogenicity in mice." Infect Immun. Dec. 2001;69(12):7250-7253.
Nestle et al., "Dendritic cells: On the move from bench to bedside." Nat Med. Jul. 2001;7(7):761-765.
Ni et al., "Molecular basis for CD40 signaling mediated by TRAF3." Proc Natl Acad Sci USA. Sep. 12, 2000;97(19):10395-10399.
Nicolau et al., "Liposomes as carriers for in vivo gene transfer and expression." Methods Enzymol. 1987;149:157-176.
Nishiya et al., "Ligand-regulated chimeric receptor approach reveals distinctive subcellular localization and signaling properties of the Toll-like receptors," J. Biol, Chem. 279(18):19008-19017, 2004.
Nociari et al., "A novel one-step, highly sensitive fluorometric assay to evaluate cell-mediated cytotoxicity." J Immunol Methods. Apr. 15, 1998;213(2)157-167.

Nopora A, Brocker T., "Bcl-2 controls dendritic cell longevity in vivo." J Immunol. Sep. 15, 2002;169(6):3006-3014.
Oehm et al., "Purification and Molecular Cloning of the APO-1 Cell Surface Antigen, a Member of the Tumor Necrosis Factorperve Growth Factor Receptor Superfamily, Sequence Identity With the Fas Antigen," The Journal of Biological Chemistry, vol. 267, No. 15, May 25, 1992 10709-10715.
Ohshima et al., "Expression and function of OX40 ligand on human dendritic cells." J Immunol. Oct. 15, 1997;159(8):3838-3848.
Oliviero et al., "The human haptoglobin gene: transcriptional regulation during development and acute phase induction." EMBO J. Jul. 1987;6(7)1905-1912.
O'Neill et al., "Manipulating dendritic cell biology for the active immunotherapy of cancer." Blood. Oct. 15, 2004;104(8):2235-2246.
O'Sullivan B, Thomas R., "CD40 and dendritic cell function." Crit Rev Immunol. 2003;23(1-2):83-107.
Ozinsky et al., "The repertoire for pattern recognition of pathogens by the innate immune system is defined by cooperation between toll-like receptors." Proc Natl Acad Sci USA. Dec. 5, 2000;97(25):13766-13771.
Page et al., "A nonisotopic method for the measurement of cell membrane integrity." Anticancer Res. Jul.-Aug. 1998;18(4A):2313-2316.
Palecek et al., "Integrin-ligand binding properties govern cell migration speed through cell-substratum adhesiveness." Nature. Feb. 6, 1997;385(6616):537-540.
Park et al, "An essential role for Akt1 in dendritic cell function and tumor immunotherapy," Nature Biology, vol. 24, No. 12, Dec. 2006, pp. 1581-1590.
Park et al., "Cutting Edge: CpG DNA inhibits dendritic cell apoptosis by up-regulating cellular inhibitor of apoptosis proteins through the phosphatidylinositide-3'-OH kinase pathway." J Immunol. Jan. 1, 2002;168(1):5-8.
Pasare C, Medzhitov R., "Toll pathway-dependent blockade of CD4+CD25+ T cell-mediated suppression by dendritic cells." Science. Feb. 14, 2003;299(5609)1033-1036.
Paskind et al., "Dependence of Moloney murine leukemia virus production on cell growth." Virology. Sep. 1975;67(1):242-248.
Pelletier J, Sonenberg N., "Internal initiation of translation of eukaryotic mRNA directed by a sequence derived from poliovirus RNA." Nature. Jul. 28, 1988;334(6180):320-325.
Perales et al., "Gene transfer in vivo: sustained expression and regulation of genes introduced into the liver by receptor-targeted uptake." Proc Natl Acad Sci USA. Apr. 26, 1994;91(9):4086-4090.
Ping et al., "Altered beta-adrenergic receptor signaling in heart failure, in vivo gene transfer via adeno and adeno-associated virus." Microcirculation. Jun. 1996;3(2):225-228.
Pinto et al., "Prostate-specific membrane antigen: a novel folate hydrolase in human prostatic carcinoma cells." Clin Cancer Res. Sep. 1996;2(9):1445-51.
Poli V, Cortese R., "Interleukin 6 induces a liver-specific nuclear protein that binds to the promoter of acute-phase genes." Proc Natl Acad Sci USA. Nov. 1989;86(21):8202-8206.
Potter et al., "Enhancer-dependent expression of human kappa immunoglobulin genes introduced into mouse pre-B lymphocytes by electroporation." Proc Natl Acad Sci USA. Nov. 1984;81(22):7161-7165.
Prins et al., "The TLR-7 agonist, imiquimod, enhances dendritic cell survival and promotes tumor antigen-specific T cell priming: relation to central nervous system antitumor immunity." J Immunol. Jan. 1, 2006;176(1):157-164.
Prowse KR, Baumann H., "Hepatocyte-stimulating factor, beta 2 interferon, and interleukin-1 enhance expresson of the rat alpha 1-acid glycoprotein gene via a distal upstream regulatory region." Mol Cell Biol. Jan. 1988;8(1):42-51.
Pruschy et al., "Mechanistic Sutdies of a Signaling Pathway Activated by the Organic Dimerizer FK1012," Chemistry and biology 1994 vol. 1, No. 3, 164-172.
Puccetti et al., "Effects of IL-12 and IL-23 on antigen-presenting cells at the interface between innate and adaptive immunity." Crit Rev Immunol. 2002;22(5-6):373-390.

(56) References Cited

OTHER PUBLICATIONS

Pullen et al., "CD40 signaling through tumor necrosis factor receptor-associated factors (TRAFs). Binding site specificity and activation of downstream pathways by distinct TRAFs." J Biol Chem. May 14, 1999;274(20)14246-14254.
Ramos et al., "An Inducible Caspase 9 Suicide Gene to Improve the Safety of Mesenchymal Stromal Cell Therapies," Stem Cells, Translational and Clinical Research, Apr. 15, 2010, pp. 1-16.
Re F, Strominger JL., "Toll-Ike receptor 2(TLR2) and TLR4 differentially activate human dendritic cells." J Biol Chem. Oct. 5, 2001;276(40):37692-37699.
Reis e Sousa C., "Dendritic cells as sensors of infection." Immunity. May 2001;14(5):495-498.
Renan MJ., "Cancer genes: current status, future prospects, and applications in radiotherapy/oncology." Radiother Oncol. Nov. 1990;19(3):197-218.
Rescigno et al., "Dendritic cell survival and maturation are regulated by different signaling pathways." J Exp Med. Dec. 7, 1998;188(11):2175-2180.
Richard et al, "Expansion of Genetically modified Primary Human HemopOietic cells Using Chemical Inducers of Dimerization," Blood vol. 95, 2000 pp. 430-436.
Ridge et al., "A conditioned dendritic cell can be a temporal bridge between a CD4+ T-helper and a T-Killer cell." Nature. Jun. 4, 1998;393(6684):474-478.
Ridgway D., "The first 1000 dendritic cell vaccinees." Cancer Invest. 2003;21(6):873-886.
Riol-Blanco et al., "The chemokine receptor CCR7 activates in dendritic cells two signaling modules that independently regulate chemotaxis and migratory speed." J Immunol. Apr. 1, 2005;174(7):4070-4080.
Rippe et al., "DNA-mediated gene transfer into adult rat hepatocytes in primary culture." Mol Cell Biol. Feb. 1990;10(2):689-695.
Rivera et al., "A humanized system for pharmacologic control of gene expression." Nat Med. Sep. 1996;2(9):1028-1032.
Rivera, V.M., "Controlling Gene Expression USing SynthetiC Ligands," Methods: A companion to Methods in Enzymology vol. 14,1998 pp. 421-429.
Ron et al., "Angiotensinogen gene-nducible enhancer-binding protein 1, a member of a new family of large nuclear proteins that recognize nuclear factor kappa B-binding sites through a zinc finger motif." Mol Cell Biol. May 1991;11(5):2887-2895.
Ronni et al., "Common interaction surfaces of the toll-like receptor 4 cytoplasmic domain stimulate multiple nuclear targets," Molecular and Cellular Biology, Apr. 2003, vol. 23, No. 7, pp. 2543-2555.
Rosenberg SA., "A new era for cancer immunotherapy based on the genes that encode cancer antigens." Immunity. Mar. 1999;10(3):281-287.
Roux et al., "A versatile and potentially general approach to the targeting of specific cell types by retrovirus: application to the infection of human cells by means of major histocompatibility complex class I and class II antigens by mouse ecotropic murine leukemia virus-derived viruses." Proc Natl Acad Sci USA. Dec. 1989;86(23):9079-9083.
Rudinger, "Characteristics in the amino acids as components of a peptide hormone sequence" Chapter 1 in Peptide Hormones, Biological Council, The Co-ordinating Committee for Symposia on Drug Action, Edited by J.A. Parsons, University Park Press, Baltimore, London, Tokyo, Jun. 1976; pp. 1-7.
Salkowski et al., "Lipopolysaccharide and monophosphoryl lipid A differentially regulate interleukin-12, gamma interferon, and interleukin-10 mRNA production in murine macrophages." Infect Immun. Aug. 1997;65(8):3239-3247.
Sallusto et al., "Rapid and coordinated switch in chemokine receptor expression during dendritic cell maturation." Eur J Immunol. Sep. 1998;28(9):2760-2769.
Samulski et al., "A recombinant plasmid from which an infectious adeno-associated virus genome can be excised in vitro and its use to study viral replication." J Virol. Oct. 1987;61(10):3096-3101.
Sanchez-Sanchez et al., "The multiple personalities of the chemokine receptor CCR7 in dendritic cells." J Immunol. May 1, 2006;176(9):5153-5159.
Sato et al., "Combination of monocyte-derived dendrinic cells and activated T cells which express CD40 ligand an new approach to cancer Immunotherapy," Cancer Imminol Immunther, vol. 53, No. 1, Jan. 2004, pp. 53-61.
Scandella et al., "CCL19/CCL21-triggered signal transduction and migration of dendritic cells requires prostaglandin E2." Blood. Mar. 1, 2004;103(5):1595-1601.
Scandella et al., "Prostaglandin E2 is a key factor for CCR7 surface expression and migration of monocyte-derved dendritic cells." Blood. Aug. 15, 2002;100(4):1354-1361.
Schellhammer et al., "Prostate specific antigen decreases after withdrawal of antiandrogen therapy with bicalutamide or flutamide in patients receiving combined androgen blockade." J Urol. May 1997;157(5):1731-1735.
Scher et al., "Clinical trials in relapsed prostate cancer: defining the target." J Natl Cancer Inst. Nov. 20, 1996;88(22):1623-1634.
Scher et al., "Design and end points of clinical trials for patients with progressive prostate cancer and castrate levels of testosterone: recommendations of the Prostate Cancer Clinical Trials Working Group." J Clin Oncol. Mar. 1, 2008;26(7)1148-59.
Scher Hi, Kelly WK., "Flutamide withdrawal syndrome: its impact on clinical trials in hormone-refractory prostate cancer." J Clin Oncol. Aug. 1993;11(8):1566-1572.
Schneider et al., "Inactivation of the human immunodeficiency virus type 1 inhibitory elements allows Rev-independent expression of Gag and Gag/protease and particle formation." J Virol. Jul. 1997;71(7):4892-4903.
Schoenberger et al., "T-cell help for cytotoxic T lymphocytes is mediated by CD40-CD40L interactions." Nature. Jun. 4, 1998;393(6684):480-483.
Schuler et al., "The use of dendritic cells in cancer immunotherapy." Curr Opin Immunol. Apr. 2003; 15(2):138-147.
Schultz et al., "CD40 triggering of heterodimeric IL-12 p70 production by dendritic cells in vivo requires a microbial priming signal," Immunity, vol. 13, No. 4, Oct. 2000. pp. 453-462.
Schuster, et al., "ALD518, a humanized anti-IL-6 antibody, treats anemia in patients with advanced non-small cell lung cancer (NSCLC): Results of a phase II, randomized, double-blind, placebo-controlled trial," 2010, J. Clin. Oncol. 28-7s (suppl.; abstr. 7631).
Schweitzer BA, Kool ET., "Aromatic Nonpolar Nucleosides as Hydrophobic Isosteres of Pyrimidine and Purine Nucleosides." J Org Chem. Dec. 1, 1994;59(24):7238-7242.
Shaffer et al., "Circulating tumor cell analysis in patients with progressive castration-resistant prostate cancer." Clin Cancer Res. Apr. 1, 2007;13(7):2023-9.
Shen et al., "Silencing of SOCS1 enhances antigen presentation by dendritic cells and antigen-specific anti-tumor immunity." Nat Biotechnol. Dec. 2004;22(12)1546-1553.
Silver et al., "Prostate-specific membrane antigen expression in normal and malignant human tissues." Clin Cancer Res. Jan. 1997;3(1):81-5.
Simpson et al., "Consequences of Fas-ligand and perforin expression by colon T cells in a mouse model of inflammatory bowel disease." Gastroenterology Oct. 1998; 115(4):849-855.
Small EJ, Srinivas S., "The antiandrogen withdrawal syndrome. Experience in a large cohort of unselected patients with advanced prostate cancer." Cancer. Oct. 15, 1995;76(8):1428-1434.
Small EJ, Vogelzang NJ., "Second-line hormonal therapy for advanced prostate cancer: a shifting paradigm." J Clin Oncol. Jan. 1997;15(1):382-388.
Smith et al., "Cognate CD4(+) T cell licensing of dendritic cells in CD8(+) T cell immunity." Nat Immunol. Nov. 2004;5(11):1142-1148.
Smith et al., "DNA/MVA vaccine for HIV type 1:effects of codon-optimization and the expression of aggregates or virus-like particles on the immunogenicity of the DNA prime." AIDS Res Hum Retroviruses. Dec. 2004;20(12)1335-1347.
Snyder et al., "Prostaglandins modulate macrophage la expression." Nature. Sep. 9, 1982;299(5879)163-165.

(56) References Cited

OTHER PUBLICATIONS

Sorensen et al., "Endostatin reduces cascularization, blood flow, and growth in a rat gliosarcoma." Neuro Oncol. Jan. 2002;4(1):1-8.
Spencer et al., "A general strategy for producing conditional alleles of Src-like tyrosine kinases." Proc Natl Acad Sci USA Oct. 10, 1995;92(21):9805-9809.
Spencer et al., "Controlling signal transduction with synthetic ligands." Science. Nov. 12, 1993;262(5136)1019-1024.
Spencer et al., "Functional analysis of Fas signaling in vivo using synthetic inducers of dimerization." Curr Biol. Jul. 1, 1996;6(7):839-847.
Sporri R, Reis e Sousa C., "Inflammatory mediators are insufficient for full dendritic cell activation and promote expansion of CD4+ T cell populations lacking helper function." Nat Immunol. Feb. 2005;6(2):163-170.
Steinman et al., "Tolerogenic dendritic cells." Annu Rev Immunol. 2003;21:685-711.
Steinman RM, Pope M., "Exploiting dendritic cells to improve vaccine efficacy." J Clin Invest. Jun. 2002;109(12):1519-1526.
Strasser et al., "Integrin Activation by Regulated Dimerization and Oligomerization of Platelet Endothelial Cell Adhesion Molecule (PECAM)-1 from Within the Cell," Immunity Review 30, Feb. 20, 2009, 180-192.
Strober et al., "Signalling pathways and molecular interactions of NOD1 and NOD2." Nat Rev Immunol. Jan. 2006;6(1):9-20.
Su et al., "Alternatively spliced variants of prostate-specific membrane antigen RNA: ratio of expression as a potential measurement of progression." Cancer Res. Apr. 1, 1995;55(7):1441-1443.
Su et al., "Telomerase mRNA-transfected dendritic cells stimulate antigen-specific CD8+ and CD4+ T cell responses in patients with metastatic prostate cancer." J Immunol. Mar. 15, 2005;174(6):3798-3807.
Suarez-Alvarez et al, Epigenetic Mechanisms Regulate MHC and Antigen Processing Moleculers in Human Embryonic and Induced Pluripotent Stem Cells. PLoS One (April) 5(4):e10192, 2010, pp. 1-12.
Suda et al., "Molecular Cloning and Expression of the Fas Ligand, a Novel Member of the Tumor Necrosis Factor Family," Cell vol. 75, 1169-1176 Dec. 17, 1993.
Tai et al., "Mechanisms by which SGN-40, a Humanized Anti-CD40 Antibody, Induces Cytotoxicity in Human Multiple Myeloma Celis: ClinicalImplications," Cancer Research, Apr. 15, 2004, vol. 64, pp. 2846-2852.
ten Klooster JP, Hordijk PL., "Targeting and localized signalling by small GTPases." Biol Cell. Jan. 2007;99(1):1-12.
Tepler et al., "The gene for the rat mast cell high affinity IgE receptor alpha chain. Structure and alternative mRNA splicing patterns." J Biol Chem. Apr. 5, 1989;264(10):5912-5915.
Termeer et al., "Oligosaccharides of hyaluronan are potent activators of dendritic cells." J Immunol. Aug. 15, 2000;165(4):1863-1870.
Thompson et al., "The low-toxicity versions of LPS, MPL adjuvant and RC529, are efficient adjuvants for CD4+ T Cells." J Leukoc Biol. Dec. 2005;78(6):1273-1280.
Tibbetts C., "Viral DNA sequence from incomplete particles of human adenovirus type 7." Cell. Sep. 1977;12(1):243-249.
Tone M . et al., "Regulation of CD40 function by its isoforms generated through alternative splicing," PNAS. Feb. 13, 2001, vol. 98, No. 4, pp. 1751-1756.
Tong et al, "Prospects for CD40-directed Experimental Therapy of Human Cancer," Cancer Gene Therapy vol. 10, 2003,pp. 1-13.
Troyer et al., "Detection and characterization of the prostate-specific membrane antigen (PSMA) in tissue extracts and body fluids." Int J Cancer. Sep. 4, 1995;62(5):552-8.
Tur-Kaspa et al., "Use of electroporation to introduce biologically active foreign genes into primary rat hepatocytes." Mol Cell Biol. Feb. 1986;6(2):716-718.
van der Pouw Krann T.C., et al., "Prostaglandin E2 is a potent inhibitor of human interleukin12 production," J Exp Med., 1995, vol. 181, pp. 775-779.

Vassiliou et al., "Prostaglandin E2 promotes the survival of bone marrow-derived dendritic cells." J Immunol. Dec. 1, 2004;173(11):6955-6964.
Vidalain et al., "CD40 signaling in human dendritic cells is initiated within membrane rafts." EMBO J. 2000; 19:3304-3313.
Vieweg J, Jackson A., "Modulation of antitumor responses by dendritic cells." Springer Semin Immunopathol. Jan. 2005;26(3):329-341.
Vincent et al., "Targeting of proteins to membranes through hedgehog auto-processing." Nat Biotechnol. Aug. 2003;21(8):936-940.
Vonderheide et al., "CD40 activation of carcinoma cells increases expression of adhesion and major histocompatibility molecules but fails to induce either CD80/CD86 expression or T cell alloreactivity." Int J Oncol. Oct. 2001;19(4):791-798.
Wagner et al., "Transferrin-polycation conjugates as carriers for DNA uptake into cells." Proc Natl Acad Sci USA. May 1990;87(9):3410-3414.
Wang et al., "Relative contributions of codon usage, promoter efficiency and leader sequence to the antigen expression and immunogenicity of HIV-1 Env DNA vaccine." Vaccine. May 22, 2006;24(21):4531-4540.
Werneburg et al., "Molecular Characterization of CD40 Signaling Intermediates," The Journal of Biological Chemistry, vol. 276, Nov. 16, 2001, 43334-43342.
Werts et al., "TIR, CARD and PYRIN: three domains for an antimicrobial triad." Cell Death Differ. May 2006;14(5):798-815.
Wesemann et al., "Suppressor of cytokine signaling 1 inhibits cytokine induction of CD40 expression in macrophages." J Immunol. Sep. 1, 2002;169(5):2354-2360.
Wilson et al., "A 58-base-par region of the human C3 gene confers synergistic inducibility by interleukin-1 and interleukin-6." Mol Cell Biol. Dec. 1990;10(12):6181-6191.
Wilson et al., "Implantation of vascular grafts lined with genetically modified endothelial cells." Science. Jun. 16, 1989;244(4910):1344-1346.
Woltman et al., "Rapamycin specifically interferes with GM-CSF signaling in human dendritic cells, leading to apoptosis via increased p27KIP1 expression." Blood. Feb. 15, 2003;101(4):1439-1445.
Wong et al., "Fas Antigen and p55 TNF Receptor Signal Apoptosis Through Distinct Pathways," Journal of Immunology, 1994, 152: pp. 1751-1755.
Wong P, Famer EG., "Feedback regulation of pathogen-specific T cell priming." Immunity. Apr. 2003;18(4):499-511.
Wright et al., "Upregulation of prostate-specific membrane antigen after androgen-deprivation therapy." Urology. Aug. 1996;48(2):326-34.
Wu and Wu, "Liver-directed gene delivery," Adv Drug Delivery Rev, 1993;12:159-167.
Wu et al., "Codon optimization reveals critical factors for high level expression of two rare codon genes in *Escherichia coli*: RNA stability and secondary structure but not tRNA abundance." Biochem Biophys Res Commun. Jan. 2, 2004;313(1):89-96.
Wu GY, Wu CH., "Receptor-mediated in vitro gene transformation by a soluble DNA carrier system." J Biol Chem. Apr. 5, 1987;262(10):4429-32.
Xiao et al., "Efficient long-term gene transfer into muscle tissue of immunocompetent mice by adeno-associated virus vector." J Virol. Nov. 1996;70(11):8098-8108.
Xiao et al., "Establishment of a Cell Model Based on FKBP12 Dimerization for Screening of FK506-like Neurotrophic small Molecular Compounds." J Biomol Screen. Apr. 2006;11(3):225-235.
Xie et al., "Adenovirus-mediated tissue-targeted expression of a caspase-9-based artificial death switch for the treatment of prostate cancer." Cancer Res. Sep. 15, 2001;61(18):6795-6804.
Xu et al., "Optimization of transcriptional regulatory elements for constructing plasmid vectors." Gene. Jul. 11, 2001;272(1-2):149-156.
Yadava A, Ockenhouse CF., "Effect of codon optimization on expression levels of a functionally folded malaria vaccine candidate in prokaryotic and eukaryotic expression systems." Infect Immun. Sep. 2003;71(9):4961-4969.

(56) References Cited

OTHER PUBLICATIONS

Yan et al., "Enhanced cellular immune responses elicited by an engineered HIV-1 subtype B consensus-based envelope DNA vaccine." Mol Ther. Feb. 2007;15(2):411-421.
Yanagawa Y, Onoe K., "CCL19 induces rapid dendritic extension of murine dendritic cells." Blood. Sep. 15, 2002;100(6):1948-1956.
Yang et al., "In vivo and in vitro gene transfer to mammalian somatic cells by particle bombardment." Proc Natl Acad Sci USA. Dec. 1990;87(24):9568-9572.
Yang et al., "Induction of inflammation by West Nile virus capsid through the caspase-9 apoptotic pathway." Emerg Infect Dis. Dec. 2002;8(12):1379-1384.
Zechner et al., "Recombinant human cachectin/tumor necrosis factor by not interleukin-1 alpha downregulates lipoprotein lipase gene expression at the transcriptional level in mouse 3T3-L1 adipocytes." Mol Cell Biol. Jun. 1988;8(6):2394-2401.
Zhang et al., "Integrin-nucleated Toll-like receptor (TLR) dimerization reveals subcellular targeting of TLRs and distinct mechanisms of TLR4 activation and signaling." FEBS Lett. Dec. 4, 2002;532(1-2):171-176.
Zhang et al., "mRNA secondary structure at start AUG codon is a key limiting factor for human protein expression in *Escherichia coli*." Biochem Biophys Res Commun. Oct. 13, 2006;349(1):69-78.
Zhao et al., "Integrin Activation by Regulated Dimerization and Oligomerization of Platelet Endothelial Cell Adhesion Molecule (PECAM)-1 from Within the Cell," Jan. 8, 2001, The Journal of Cell Biology, vol. 152, 65-73.
Zhou et al., "Multiple RNA splicing and the presence of cryptic RNA splice donor and acceptor sites may contribute to low expression levels and poor immunogenicity of potential DNA vaccines containing the env gene of equine infectious anemia virus (EIAV)." Vet Microbiol. Aug. 25, 2002;88(2)127-151.
Zitvogel et al., "Therapy of murine tumors with tumor peptide-pulsed dendritic cells: dependence on T cells, B7 costimulation, and T helper cell 1-associated cytokines." J Exp Med. Jan. 1, 1996;183(1):87-97.
Zlatkine et al., "Retargeting of cytosolic proteins to the plasma membrane by the Lck protein tyrosine kinase dual acylation motif." J Cell Sci. Mar. 1997;110(Pt5):673-679.
zur Medege et al., "Expression and immunogenicity of sequence-modified human immunodeficiency virus type 1 subtype B pol and gagpol DNA vaccines." J Virol. Jun. 2003;77(11):6197-6207.
Extended European Search Report dated: Sep. 5, 2012 in European Patent Application No. EP 11193762, filed: Oct. 19, 2007.
Extended European Search Report dated: Sep. 12, 2012 in European Patent Application No. EP 11193768 filed: Oct. 19, 2007.
Supplementary European Search Report dated Oct. 4, 2006 in European Application EP04712328, filed on Feb. 18, 2004.
International Preliminary Report on Patentability mailed on: Sep. 29, 2005 in International Patent Application: PCT/US2004/04757 filed on: Feb. 18, 2004 and published as WO 2004/073641 on: Sep. 2, 2004.
International Search Report mailed on: Jan. 13, 2005 in International Patent Application: PCT/US2004/04757 filed on: Feb. 18, 2004 and published as WO 2004/073641 on: Sep. 2, 2004.
Extended European Search Report dated Aug. 9, 2012 in European Application No. EP 09815355 filed on: Sep. 21, 2009 based on International Application No. PCT/US 2009/057738.
International Search Report and Written Opinion dated: Nov. 17, 2008 in International Application No. PCT/US07/81963 filed Oct. 19, 2007 and published as: WO/2008/049113 on Apr. 24, 2008.
International Preliminary Report on Patentability dated: Apr. 22, 2009 in International Application No. PCT/US07/81963 filed Oct. 19, 2007 and published as: WO/2008/049113 on Apr. 24, 2008.
International Preliminary Report on Patentability mailed: Mar. 31, 2011, for International Application No. PCT/US2009/057738, filed Sep. 21, 2009 and published as WO2010033949 on Mar. 25, 2010.
International Search Report and Written Opinion mailed: Feb. 2, 2010, for International Application No. PCT/US2009/057738, filed Sep. 21, 2009 and published as WO2010033949 on Mar. 25, 2010.
International Search Report and Written Opinion dated: Oct. 21, 2011 in International Application No. PCT/US11/032572 filed Apr. 14, 2011 and published as: WO/2011/130566 on Oct. 20, 2011.
Office Action Dated: Mar. 21, 2008 in U.S. Appl. No. 10/781,384, filed Feb. 18, 2004 and issued as: U.S. Pat. No. 7,404,950 on: Jul. 29, 2008.
Office Action Dated: Jun. 27, 2007 in U.S. Appl. No. 10/781,384, filed Feb. 18, 2004 and issued as: U.S. Pat. No. 7,404,950 on: Jul. 29, 2008.
Office Action Dated: Dec. 27, 2006 in U.S. Appl. No. 10/781,384, filed Feb. 18, 2004 and issued as: U.S. Pat. No. 7,404,950 on: Jul. 29, 2008.
Office Action Dated: May 5, 2006 in U.S. Appl. No. 10/781,384, filed Feb. 18, 2004 and issued as: U.S. Pat. No. 7,404,950 on: Jul. 29, 2008.
Office Action Dated: May 20, 2011 in U.S. Appl. No. 12/165,360, filed Jun. 30, 2008 and Published as: 2008/0269160 on: Oct. 30, 2008.
Office Action Dated: Oct. 22, 2010 in U.S. Appl. No. 12/165,360, filed Jun. 30, 2008 and Published as: 2008/0269160 on: Oct. 30, 2008.
Office Action Dated: Dec. 26, 2012 in U.S. Appl. No. 12/445,939, filed Oct. 26, 2010 and Published as: 2011/0033383 on: Feb. 10, 2011.
Office Action Dated: Aug. 17, 2012 in U.S. Appl. No. 12/563,991, filed Sep. 21, 2009 and Published as: 2010/0203067 on: Aug. 12, 2010.
Office Action Dated: Feb. 7, 2012 in U.S. Appl. No. 12/563,991, filed Sep. 21, 2009 and Published as: 2010/0203067 on: Aug. 12, 2010.
Office Action Dated: Mar. 13, 2013 in U.S. Appl. No. 13/087,329, filed Apr. 14, 2011 and Published as: 2011/0287038 on: Nov. 24, 2011.
Bollard et al., "Adapting a transforming growth factor beta-related tumor protection strategy to enhance antitumor immunity" Blood (2002) 99:3179-3187.
Caux et al., "Activation of human dendritic cells through CD40 cross-linking" J. Exp. Med. (1994) 180:1263-72.
Ferraro et al., "Co-delivery of PSA and PSMA DNA vaccines with electroporation induces potent immune responses" Human Vaccines (2011) 7:120-127.
Inaba et al., "Generation of large Nos. of dendritic cells from mouse bone marrow cultures supplemented with granulocyte/macrophage colony-stimulating factor" J. Exp. Med. (1992) 176:1693-702.
Krug et al., "Toll-like receptor expression reveals CpG DNA as a unique microbial stimulus for plasmacytoid dendritic cells which synergizes with CD40 ligand to induce high amounts of IL-12" Eur. J. Immunol. (2001) 31(10):3026-3037.
Medzhitov et al., "MyD88 is an adaptor protein in the hToll/IL-1 receptor family signaling pathways" Mol. Cell. (1998) 2(2):253-258.
Sardesai et al., "Electroporation delivery of DNA vaccines: prospects for success" Current Opinion in Immunol. (2011) 23:421-9.
Schuler et al., "Dendritic cells as adjuvants for immune-mediated resistance to tumors" J. Exp. Med. (1997) 186:1183-7.
Wagner et al., "IL-12p70-Dependent Th1 Induction by Human B Cells Requires Combined Activation with CD40 Ligand and CpG DNA" Journal of Immunology (2004) 172:954-963.
Vieweg, "Immunotherapy for Advanced Prostate Cancer," vol. 9 Suppl. 1 (2007) Reviews in Urology S29-S38.
Narayanan et al., "A composite MyD88/CD40 switch synergistically activates mouse and human dendritic cells for enhanced antitumor efficacy" J. Clin. Invest. (2011) vol. 121(4), p. 1524-1534, and Supplementary Materials pp. 1-16.
Extended European Search Report dated Jul. 10, 2015 in European Application No. EP 15157213.8, filed on Feb. 18, 2004 and published as EP 2 933 334 on Oct. 21, 2015.
Office Action dated Oct. 20, 2015 in U.S. Appl. No. 13/087,329, filed Apr. 14, 2011 and Published as US 2011/0287038 on Nov. 24, 2011.
Office Action dated Oct. 20, 2015 in U.S. Appl. No. 13/786,652, filed Mar. 6, 2013 and Published as 2014/0023647 on Jan. 23, 2014.

\* cited by examiner

*FIG. 10C Continued*

RESULTS OF IFNβ-SEAP REPORTER ASSAY WITH iRIG-I & iTRIF

- ♦ Fv' FvlsTRIF(1µg)
- ■ Fv' FvlsTRIF(0.3µg)
- ▲ Fv' FvlsTRIF(0.1µg)
- ✕ Fv' FvlsTRIF(0.03µg)
- ✱ Fv' FvlsTRIF(0.01µg)
- ● MFv' Fvls
- + Fv' FvlsRIG-I

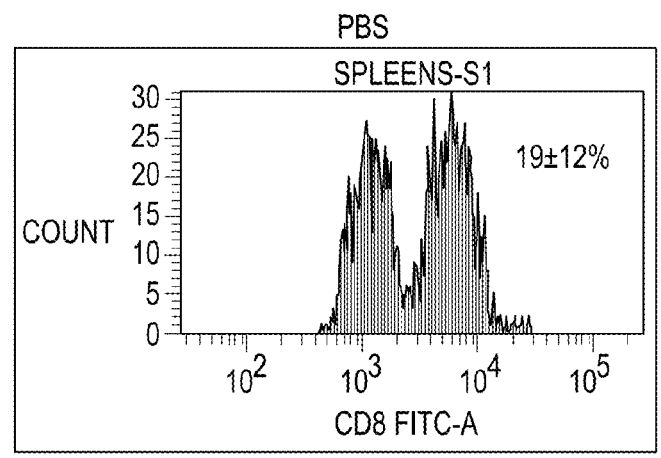
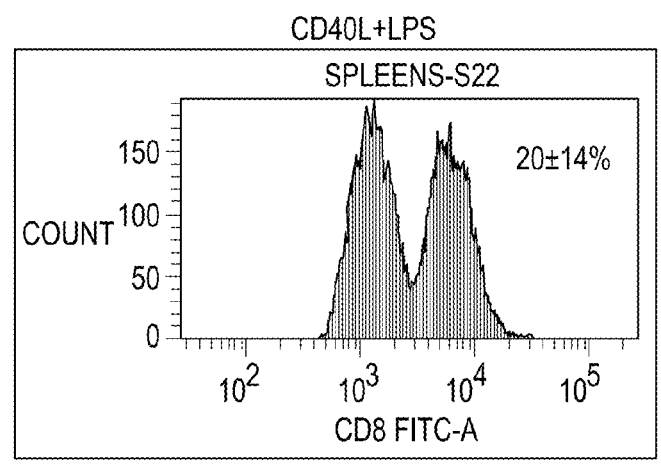
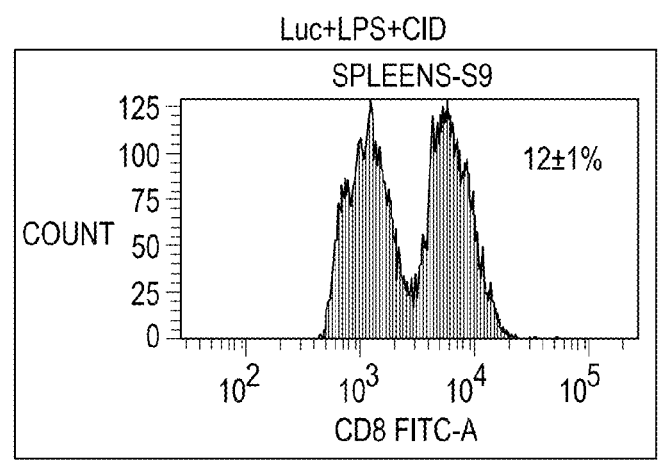
FIG. 41

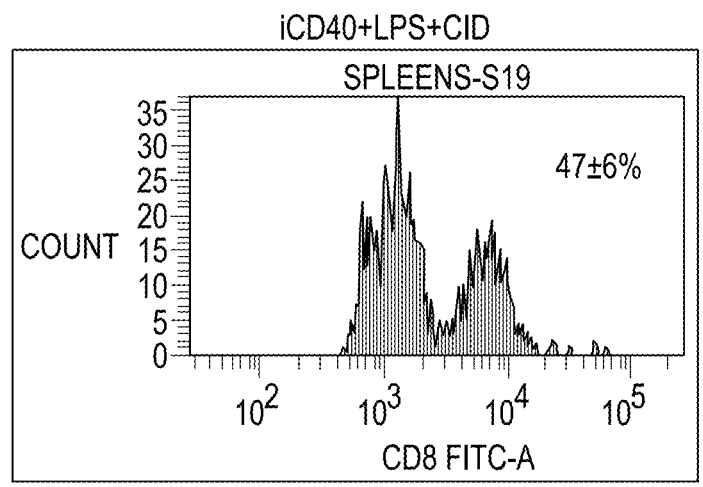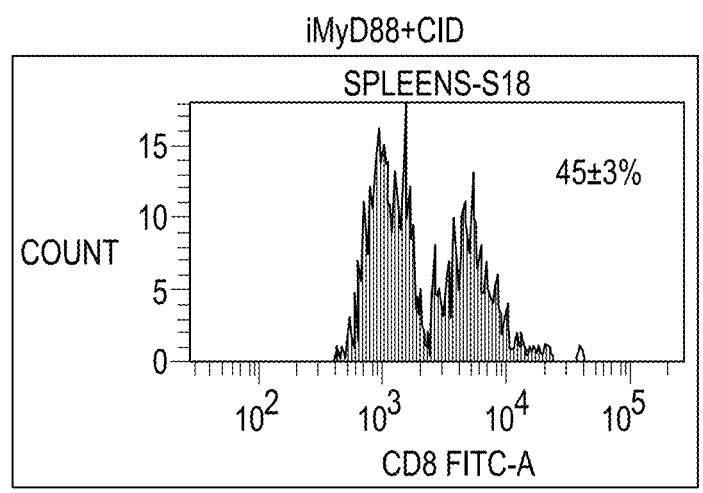
FIG. 41 Continued

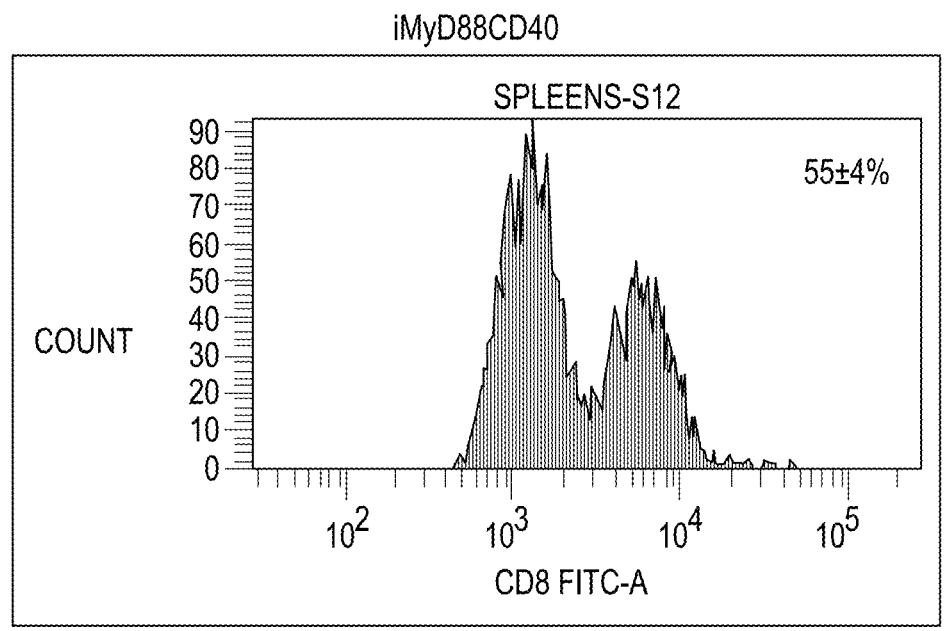
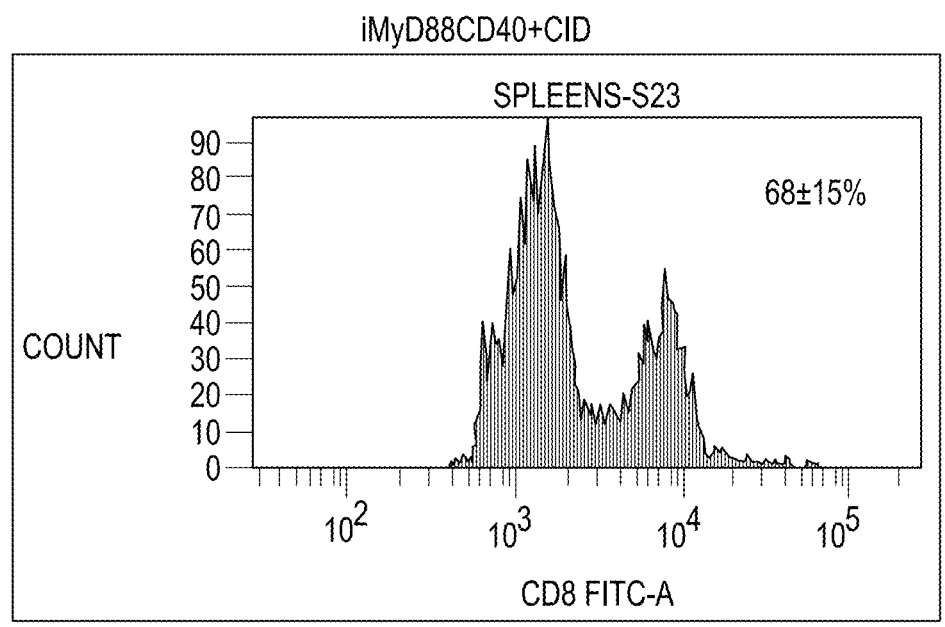
*FIG. 41 Continued*

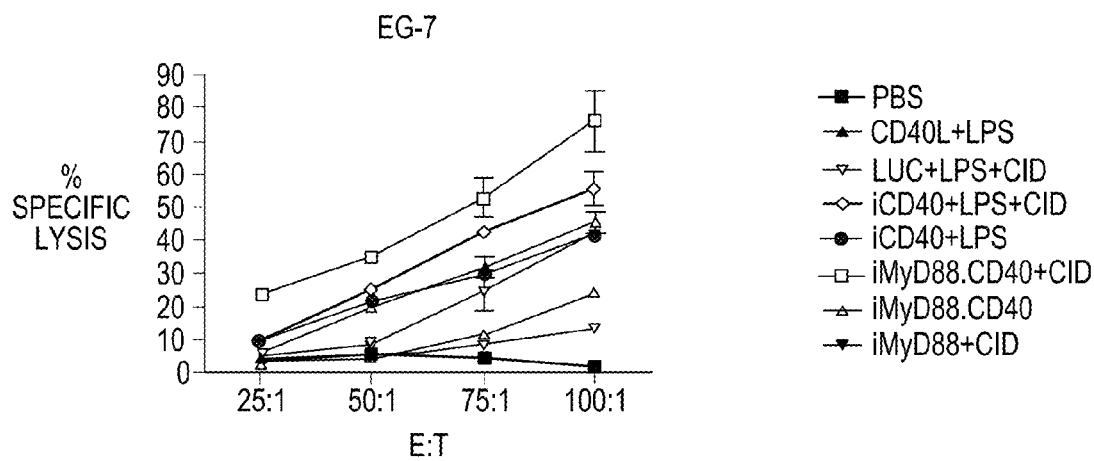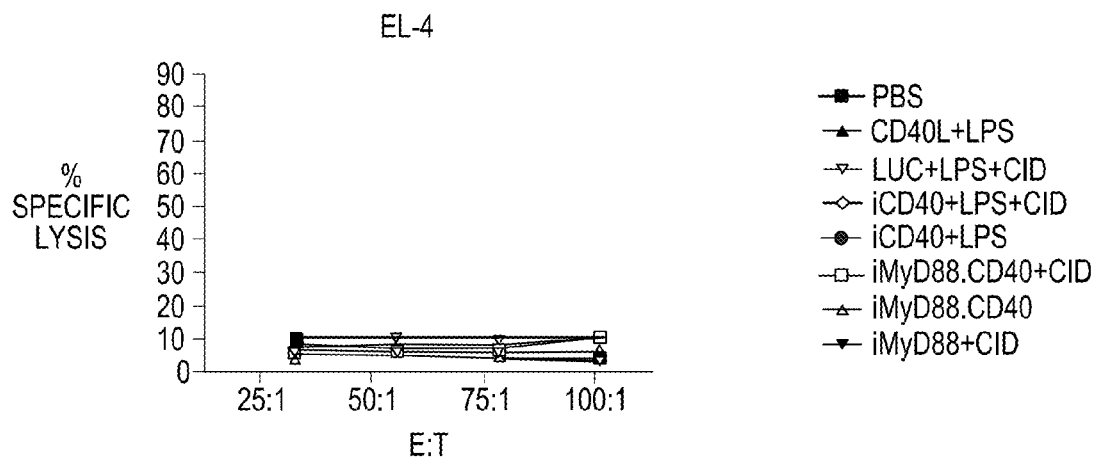
FIG. 46

SEQUENCE LISTING

```
<160> NUMBER OF SEQ ID NOS: 54

<210> SEQ ID NO 1
<211> LENGTH: 1616
<212> TYPE: DNA
<213> ORGANISM: Homo sapiens

<400> SEQUENCE: 1
gccaaggctg gggcagggga gtcagcagag gcctcgctcg ggcgcccagt ggtcctgccg      60
cctggtctca cctcgctatg gttcgtctgc ctctgcagtg cgtcctctgg ggctgcttgc     120
tgaccgctgt ccatccagaa ccacccactg catgcagaga aaaacagtac ctaataaaca     180
gtcagtgctg ttctttgtgc cagccaggac agaaactggt gagtgactgc acagagttca     240
ctgaaacgga atgccttcct tgcggtgaaa gcgaattcct agacacctgg aacagagaga     300
cacactgcca ccagcacaaa tactgcgacc ccaacctagg gcttcgggtc agcagaagg      360 gcacctcaga aacagacacc atctgcacct gtgaagaagg ctggcactgt acgagtgagg     420
cctgtgagag ctgtgtcctg caccgctcat gctcgcccgg ctttggggtc aagcagattg     480
ctacaggggt ttctgatacc atctgcgagc cctgcccagt cggcttcttc tccaatgtgt     540
catctgcttt cgaaaaatgt cacccttgga caagctgtga gaccaaagac ctggttgtgc     600
aacaggcagg cacaaacaag actgatgttg tctgtggtcc ccaggatcgg ctgagagccc     660
tggtggtgat ccccatcatc ttcgggatcc tgtttgccat cctcttggtg ctggtcttta     720
tcaaaaaggt ggccaagaag ccaaccaata aggccccccca ccccaagcag gaaccccagg    780
agatcaattt tcccgacgat cttcctggct ccaacactgc tgctccagtg caggagactt     840
tacatggatg ccaaccggtc acccaggagg atggcaaaga gagtcgcatc tcagtgcagg     900
agagacagtg aggctgcacc cacccaggag tgtggccacg tgggcaaaca ggcagttggc     960
cagagagcct ggtgctgctg ctgctgtggc gtgagggtga ggggctggca ctgactgggc    1020
atagctcccc gcttctgcct gcaccctgc agtttgagac aggagacctg gcactggatg    1080
cagaaacagt tcaccttgaa gaacctctca cttcaccctg gagcccatcc agtctcccaa    1140
cttgtattaa agacagaggc agaagtttgg tggtggtggt gttggggtat ggtttagtaa    1200
tatccaccag accttccgat ccagcagttt ggtgcccaga gaggcatcat ggtggcttcc    1260
ctgcgcccag gaagccatat acacagatgc ccattgcagc attgtttgtg atagtgaaca    1320
actggaagct gcttaactgt ccatcagcag gagactggct aaataaaatt agaatatatt    1380
tatacaacag aatctcaaaa acactgttga gtaaggaaaa aaaggcatgc tgctgaatga    1440
tgggtatgga acttttttaaa aaagtacatg cttttatgta tgtatattgc ctatggatat    1500
atgtataaat acaatatgca tcatatattg atataacaag ggttctggaa gggtacacag    1560
aaaacccaca gctcgaagag tggtgacgtc tgggggtgggg aagaagggtc tgggg         1616

<210> SEQ ID NO 2
<211> LENGTH: 277
<212> TYPE: PRT
<213> ORGANISM: Homo sapiens
```

<400> SEQUENCE: 2

Met Val Arg Leu Pro Leu Gln Cys Val Leu Trp Gly Cys Leu Leu Thr
1               5                   10                  15

Ala Val His Pro Glu Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Cys Leu Pro Cys Gly Glu
        50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
        130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
        210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
            245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 3
<211> LENGTH: 2096
<212> TYPE: DNA
<213> ORGANISM: Homo sapiens

<400> SEQUENCE: 3
gcggatccgc atcatcatca tcatcacagc tccggaatcg agggacgtgg taaatcctcc      60
aatgaagcta ctaacattac tccaaagcat aatatgaaag catttttgga tgaattgaaa     120
gctgagaaca tcaagaagtt cttatataat tttacacaga taccacattt agcaggaaca     180
gaacaaaact ttcagcttgc aaagcaaatt caatcccagt ggaaagaatt tggcctggat     240
tctgttgagc tagcacatta tgatgtcctg ttgtcctacc caaataagac tcatcccaac     300
tacatctcaa taattaatga agatggaaat gagattttca acacatcatt atttgaacca     360
cctcctccag gatatgaaaa tgtttcggat attgtaccac ctttcagtgc tttctctcct     420

-continued

| | |
|---|---|
| caaggaatgc cagagggcga tctagtgtat gttaactatg cacgaactga agacttcttt | 480 |
| aaattggaac gggacatgaa aatcaattgc tctgggaaaa ttgtaattgc cagatatggg | 540 |
| aaagttttca gaggaaataa ggttaaaaat gcccagctgg caggggccaa aggagtcatt | 600 |
| ctctactccg accctgctga ctactttgct cctggggtga agtcctatcc agatggttgg | 660 |
| aatcttcctg gaggtggtgt ccagcgtgga aatatcctaa atctgaatgg tgcaggagac | 720 |
| cctctcacac caggttaccc agcaaatgaa tatgcttata ggcgtggaat tgcagaggct | 780 |
| gttggtcttc caagtattcc tgttcatcca attggatact atgatgcaca gaagctccta | 840 |
| gaaaaaatgg gtggctcagc accaccagat agcagctgga gaggaagtct caaagtgccc | 900 |
| tacaatgttg gacctggctt tactggaaac ttttctacac aaaaagtcaa gatgcacatc | 960 |
| cactctacca atgaagtgac aagaatttac aatgtgatag gtactctcag aggagcagtg | 1020 |
| gaaccagaca gatatgtcat tctgggaggt caccgggact catgggtgtt tggtggtatt | 1080 |
| gaccctcaga gtggagcagc tgttgttcat gaaattgtga ggagctttgg aacactgaaa | 1140 |
| aaggaagggt ggagacctag aagaacaatt ttgtttgcaa gctgggatgc agaagaattt | 1200 |
| ggtcttcttg gttctactga gtgggcagag gagaattcaa gactccttca gagcgtggc | 1260 |
| gtggcttata ttaatgctga ctcatctata gaaggaaact acactctgag agttgattgt | 1320 |
| acaccgctga tgtacagctt ggtacacaac ctaacaaaag agctgaaaag ccctgatgaa | 1380 |
| ggctttgaag gcaaatctct ttatgaaagt tggactaaaa aaagtccttc cccagagttc | 1440 |
| agtggcatgc ccaggataag caaattggga tctggaaatg attttgaggt gttcttccaa | 1500 |
| cgacttggaa ttgcttcagg cagagcacgg tatactaaaa attgggaaac aaacaaattc | 1560 |
| agcggctatc cactgtatca cagtgtctat gaaacatatg agttggtgga aaagttttat | 1620 |
| gatccaatgt ttaaatatca cctcactgtg gcccaggttc gaggagggat ggtgtttgag | 1680 |
| ctagccaatt ccatagtgct ccctttgat tgtcgagatt atgctgtagt tttaagaaag | 1740 |
| tatgctgaca aaatctacag tatttctatg aaacatccac aggaaatgaa gacatacagt | 1800 |
| gtatcatttg attcactttt ttctgcagta aagaattta cagaaattgc ttccaagttc | 1860 |
| agtgagagac tccaggactt tgacaaaagc aagcatgtca tctatgctcc aagcagccac | 1920 |
| aacaagtatg caggggagtc attcccagga atttatgatg ctctgtttga tattgaaagc | 1980 |
| aaagtggacc cttccaaggc ctggggagaa gtgaagagac agatttatgt tgcagccttc | 2040 |
| acagtgcagg cagctgcaga gactttgagt gaagtagcct aagcggccgc atagca | 2096 |

<210> SEQ ID NO 4
<211> LENGTH: 719
<212> TYPE: PRT
<213> ORGANISM: Homo sapiens

<400> SEQUENCE: 4

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
65                  70                  75                  80

-continued

```
Pro His Leu Ala Gly Thr Glu Gln Asn Phe Gln Leu Ala Lys Gln Ile
                85                  90                  95
Gln Ser Gln Trp Lys Glu Phe Gly Leu Asp Ser Val Glu Leu Ala His
            100                 105                 110
Tyr Asp Val Leu Leu Ser Tyr Pro Asn Lys Thr His Pro Asn Tyr Ile
        115                 120                 125
Ser Ile Ile Asn Glu Asp Gly Asn Glu Ile Phe Asn Thr Ser Leu Phe
    130                 135                 140
Glu Pro Pro Pro Pro Gly Tyr Glu Asn Val Ser Asp Ile Val Pro Pro
145                 150                 155                 160
Phe Ser Ala Phe Ser Pro Gln Gly Met Pro Glu Gly Asp Leu Val Tyr
                165                 170                 175
Val Asn Tyr Ala Arg Thr Glu Asp Phe Phe Lys Leu Glu Arg Asp Met
            180                 185                 190
Lys Ile Asn Cys Ser Gly Lys Ile Val Ile Ala Arg Tyr Gly Lys Val
        195                 200                 205
Phe Arg Gly Asn Lys Val Lys Asn Ala Gln Leu Ala Gly Ala Lys Gly
    210                 215                 220
Val Ile Leu Tyr Ser Asp Pro Ala Asp Tyr Phe Ala Pro Gly Val Lys
225                 230                 235                 240
Ser Tyr Pro Asp Gly Trp Asn Leu Pro Gly Gly Val Gln Arg Gly
                245                 250                 255
Asn Ile Leu Asn Leu Asn Gly Ala Gly Asp Pro Leu Thr Pro Gly Tyr
            260                 265                 270
Pro Ala Asn Glu Tyr Ala Tyr Arg Arg Gly Ile Ala Glu Ala Val Gly
        275                 280                 285
Leu Pro Ser Ile Pro Val His Pro Ile Gly Tyr Tyr Asp Ala Gln Lys
    290                 295                 300
Leu Leu Glu Lys Met Gly Gly Ser Ala Pro Pro Asp Ser Ser Trp Arg
305                 310                 315                 320
Gly Ser Leu Lys Val Pro Tyr Asn Val Gly Pro Gly Phe Thr Gly Asn
                325                 330                 335
Phe Ser Thr Gln Lys Val Lys Met His Ile His Ser Thr Asn Glu Val
            340                 345                 350
Thr Arg Ile Tyr Asn Val Ile Gly Thr Leu Arg Gly Ala Val Glu Pro
        355                 360                 365
Asp Arg Tyr Val Ile Leu Gly Gly His Arg Asp Ser Trp Val Phe Gly
    370                 375                 380
Gly Ile Asp Pro Gln Ser Gly Ala Ala Val Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
            420                 425                 430
Glu Trp Ala Glu Glu Asn Ser Arg Leu Leu Gln Glu Arg Gly Val Ala
        435                 440                 445
Tyr Ile Asn Ala Asp Ser Ser Ile Glu Gly Asn Tyr Thr Leu Arg Val
    450                 455                 460
Asp Cys Thr Pro Leu Met Tyr Ser Leu Val His Asn Leu Thr Lys Glu
465                 470                 475                 480
Leu Lys Ser Pro Asp Glu Gly Phe Glu Gly Lys Ser Leu Tyr Glu Ser
                485                 490                 495
Trp Thr Lys Lys Ser Pro Ser Pro Glu Phe Ser Gly Met Pro Arg Ile
```

```
                500             505             510
Ser Lys Leu Gly Ser Gly Asn Asp Phe Glu Val Phe Gln Arg Leu
            515             520             525
Gly Ile Ala Ser Gly Arg Ala Arg Tyr Thr Lys Asn Trp Glu Thr Asn
        530             535             540
Lys Phe Ser Gly Tyr Pro Leu Tyr His Ser Val Tyr Glu Thr Tyr Glu
545             550             555             560
Leu Val Glu Lys Phe Tyr Asp Pro Met Phe Lys Tyr His Leu Thr Val
                565             570             575
Ala Gln Val Arg Gly Gly Met Val Phe Glu Leu Ala Asn Ser Ile Val
            580             585             590
Leu Pro Phe Asp Cys Arg Asp Tyr Ala Val Val Leu Arg Lys Tyr Ala
            595             600             605
Asp Lys Ile Tyr Ser Ile Ser Met Lys His Pro Gln Glu Met Lys Thr
            610             615             620
Tyr Ser Val Ser Phe Asp Ser Leu Phe Ser Ala Val Lys Asn Phe Thr
625             630             635             640
Glu Ile Ala Ser Lys Phe Ser Glu Arg Leu Gln Asp Phe Asp Lys Ser
                645             650             655
Lys His Val Ile Tyr Ala Pro Ser Ser His Asn Lys Tyr Ala Gly Glu
                660             665             670
Ser Phe Pro Gly Ile Tyr Asp Ala Leu Phe Asp Ile Glu Ser Lys Val
            675             680             685
Asp Pro Ser Lys Ala Trp Gly Glu Val Lys Arg Gln Ile Tyr Val Ala
            690             695             700
Ala Phe Thr Val Gln Ala Ala Glu Thr Leu Ser Glu Val Ala
705             710             715

<210> SEQ ID NO 5
<211> LENGTH: 528
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gtcgacatgg ctgcaggagg tcccggcgcg gggtctgcgg ccccggtctc ctccacatcc     60
tcccttcccc tggctgctct caacatgcga gtgcggcgcc gcctgtctct gttcttgaac    120
gtgcggacac aggtggcggc cgactggacc gcgctggcgg aggagatgga ctttgagtac    180
ttggagatcc ggcaactgga gacacaagcg gaccccactg gcaggctgct ggacgcctgg    240
cagggacgcc ctggcgcctc tgtaggccga ctgctcgagc tgcttaccaa gctgggccgc    300
gacgacgtgc tgctggagct gggacccagc attgaggagg attgccaaaa gtatatcttg    360
aagcagcagc aggaggaggc tgagaagcct ttacaggtgg ccgctgtaga cagcagtgtc    420
ccacggacag cagagctggc gggcatcacc acacttgatg accccctggg gcatatgcct    480
gagcgtttcg atgccttcat ctgctattgc cccagcgaca tcgtcgac              528

<210> SEQ ID NO 6
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 6

```
Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Thr Lys Leu
                85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Gln Glu Glu Ala Glu Lys Pro
            115                 120                 125

Leu Gln Val Ala Ala Val Asp Ser Ser Val Pro Arg Thr Ala Glu Leu
        130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170
```

<210> SEQ ID NO 7
<211> LENGTH: 678
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
ctcgagggcg tccaagtcga aaccattagt cccggcgatg gcagaacatt tcctaaaagg      60
ggacaaacat gtgtcgtcca ttatacaggc atgttggagg acggcaaaaa ggtggacagt     120
agtagagatc gcaataaacc tttcaaattc atgttgggaa acaagaagt cattagggga      180
tgggaggagg gcgtggctca aatgtccgtc ggccaacgcg ctaagctcac catcagcccc     240
gactacgcat acggcgctac cggacatccc ggaattattc cccctcacgc taccttggtg     300
tttgacgtcg aactgttgaa gctcgaagtc gagggagtgc aggtggaaac catctcccca     360
ggagacgggc gcaccttccc caagcgcggc cagacctgcg tggtgcacta caccgggatg     420
cttgaagatg gaagaaagt tgattcctcc cgggacagaa acaagccctt taagtttatg     480
ctaggcaagc aggaggtgat ccgaggctgg gaagaagggg ttgcccagat gagtgtgggt     540
cagagagcca aactgactat atctccagat tatgcctatg gtgccactgg gcacccaggc     600
atcatcccac acatgccac tctcgtcttc gatgtggagc ttctaaaact ggaatctggc      660
ggtggatccg gagtcgag                                                    678
```

<210> SEQ ID NO 8
<211> LENGTH: 222
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu Val Glu Gly Val Gln
            100                 105                 110

Val Glu Thr Ile Ser Pro Gly Asp Gly Arg Thr Phe Pro Lys Arg Gly
        115                 120                 125

Gln Thr Cys Val Val His Tyr Thr Gly Met Leu Glu Asp Gly Lys Lys
    130                 135                 140

Val Asp Ser Ser Arg Asp Arg Asn Lys Pro Phe Lys Phe Met Leu Gly
145                 150                 155                 160

Lys Gln Glu Val Ile Arg Gly Trp Glu Glu Gly Val Ala Gln Met Ser
                165                 170                 175

Val Gly Gln Arg Ala Lys Leu Thr Ile Ser Pro Asp Tyr Ala Tyr Gly
            180                 185                 190

Ala Thr Gly His Pro Gly Ile Ile Pro Pro His Ala Thr Leu Val Phe
        195                 200                 205

Asp Val Glu Leu Leu Lys Leu Glu Ser Gly Gly Ser Gly
    210                 215                 220
```

<210> SEQ ID NO 9
<211> LENGTH: 2148
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
ctcgagatgg cctgcacagg cccatcactt cctagcgcct tcgacattct aggtgcagca    60
ggccaggaca agctcttgta tctgaagcac aaactgaaga ccccacgccc aggctgccag   120
gggcaggacc tcctgcatgc catggttctc ctgaagctgg ccaggaaact gaggccagg    180
atctctctag aggcattgaa ggccgatgcg gtgcccggc tggtggcccg ccagtgggct   240
ggcgtggaca gcaccgagga cccagaggag cccccagatg tgtcctgggc tgtggcccgc   300
ttgtaccacc tgctggctga ggagaagctg tgccccgcct cgctgcggga cgtggcctac   360
caggaagccg tccgcaccct cagctccagg gacgaccacc ggctggggga acttcaggat   420
gaggcccgaa accggtgtgg gtgggacatt gctgggatc agggagcat ccggacgctc    480
cagtccaatc tgggctgcct cccaccatcc tcggctttgc cctctgggac caggagcctc   540
ccacgcccca ttgacggtgt ttcggactgg agccaagggt gctccctgcg atccactggc   600
agccctgcct ccctggccag caacttggaa atcagccagt ccctaccat gcccttcctc   660
agcctgcacc gcagcccaca tgggcccagc aagctctgtg acgaccccca ggccagcttg   720
```

-continued

```
gtgcccgagc ctgtccccgg tggctgccag gagcctgagg agatgagctg gccgccatcg    780
ggggagattg ccagcccacc agagctgcca agcagcccac ctcctgggct tcccgaagtg    840
gccccagatg caacctccac tggcctccct gatacccccg cagctccaga accagcacc    900
aactacccag tggagtgcac cgaggggtct gcaggccccc agtctctccc cttgcctatt    960
ctggagccgg tcaaaaaccc ctgctctgtc aaagaccaga cgccactcca actttctgta   1020
gaagatacca cctctccaaa taccaagccg tgcccaccta ctcccaccac cccagaaaca   1080
tcccctcctc ctcctcctcc tcctccttca tctactcctt gttcagctca cctgaccccc   1140
tcctcccctgt tcccttcctc cctggaatca tcatcggaac agaaattcta aactttgtg   1200
atcctccacg ccagggcaga cgaacacatc gccctgcggg ttcgggagaa gctggaggcc   1260
cttggcgtgc ccgacggggc caccttctgc gaggatttcc aggtgccggg gcgcggggag   1320
ctgagctgcc tgcaggacgc catagaccac tcagctttca tcatcctact tctcacctcc   1380
aacttcgact gtcgcctgag cctgcaccag gtgaaccaag ccatgatgag caacctcacg   1440
cgacaggggt cgccagactg tgtcatcccc ttcctgcccc tggagagctc cccggcccag   1500
ctcagctccg acacggccag cctgctctcc gggctggtgc ggctggacga acactcccag   1560
atcttcgcca ggaaggtggc caacaccttc aagccccaca ggcttcaggc ccgaaaggcc   1620
atgtggagga aggaacagga cacccgagcc ctgcgggaac agagccaaca cctggacggt   1680
gagcggatgc aggcggcggc actgaacgca gcctactcag cctacctcca gagctacttg   1740
tcctaccagg cacagatgga gcagctccag gtggcttttg ggagccacat gtcatttggg   1800
actggggcgc cctatggggc tcgaatgccc tttgggggcc aggtgcccct gggagccccg   1860
ccaccctttc ccacttggcc ggggtgcccg cagccgccac ccctgcacgc atggcaggct   1920
ggcaccccc caccgccctc cccacagcca gcagcctttc cacagtcact gcccttcccg   1980
cagtccccag ccttccctac ggcctcaccc gcacccctc agagcccagg ctgcaaccc   2040
ctcattatcc accacgcaca gatggtacag ctggggctga caaccacat gtggaaccag   2100
agagggtccc aggcgcccga ggacaagacg caggaggcag aagtcgac              2148
```

<210> SEQ ID NO 10
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Ala Cys Thr Gly Pro Ser Leu Pro Ser Ala Phe Asp Ile Leu Gly
1               5                   10                  15

Ala Ala Gly Gln Asp Lys Leu Leu Tyr Leu Lys His Lys Leu Lys Thr
            20                  25                  30

Pro Arg Pro Gly Cys Gln Gly Gln Asp Leu Leu His Ala Met Val Leu
        35                  40                  45

Leu Lys Leu Gly Gln Glu Thr Glu Ala Arg Ile Ser Leu Glu Ala Leu
    50                  55                  60

Lys Ala Asp Ala Val Ala Arg Leu Val Ala Arg Gln Trp Ala Gly Val
65                  70                  75                  80

Asp Ser Thr Glu Asp Pro Glu Glu Pro Asp Val Ser Trp Ala Val
            85                  90                  95

Ala Arg Leu Tyr His Leu Leu Ala Glu Glu Lys Leu Cys Pro Ala Ser
            100                 105                 110
```

Leu Arg Asp Val Ala Tyr Gln Glu Ala Val Arg Thr Leu Ser Ser Arg
                115                 120                 125

Asp Asp His Arg Leu Gly Glu Leu Gln Asp Glu Ala Arg Asn Arg Cys
            130                 135                 140

Gly Trp Asp Ile Ala Gly Asp Pro Gly Ser Ile Arg Thr Leu Gln Ser
145                 150                 155                 160

Asn Leu Gly Cys

<210> SEQ ID NO 11
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
ctcgagacca ccgagcagcg acgcagcctg caagccttcc aggattatat ccggaagacc     60
ctggacccta cctacatcct gagctacatg gcccctggt ttagggagga agaggtgcag     120
tatattcagg ctgagaaaaa caacaagggc ccaatggagg ctgccacact ttttctcaag    180
ttcctgttgg agctccagga ggaaggctgg ttccgtggct ttttggatgc cctagaccat    240
gcaggttatt ctggacttta tgaagccatt gaaagttggg atttcaaaaa aattgaaaag    300
ttggaggagt atagattact tttaaaacgt ttacaaccag aatttaaaac cagaattatc    360
ccaaccgata tcatttctga tctgtctgaa tgtttaatta atcaggaatg tgaagaaatt    420
ctacagattt gctctactaa ggggatgatg gcaggtgcag agaaattggt ggaatgcctt    480
ctcagatcag acaaggaaaa ctggcccaaa actttgaaac ttgctttgga gaaagaaagg    540
aacaagttca gtgaactgtg gattgtagag aaaggtataa aagatgttga aacagaagat    600
cttgaggata gatggaaac ttctgacata cagattgtcg ac                        642

<210> SEQ ID NO 12
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr Thr Glu Gln Arg Arg Ser Leu Gln Ala Phe Gln Asp Tyr Ile Arg
1               5                   10                  15

Lys Thr Leu Asp Pro Thr Tyr Ile Leu Ser Tyr Met Ala Pro Trp Phe
            20                  25                  30

Arg Glu Glu Val Gln Tyr Ile Gln Ala Glu Lys Asn Asn Lys Gly
            35                  40                  45

Pro Met Glu Ala Ala Thr Leu Phe Leu Lys Phe Leu Leu Glu Leu Gln
        50                  55                  60

Glu Glu Gly Trp Phe Arg Gly Phe Leu Asp Ala Leu Asp His Ala Gly
65                  70                  75                  80

Tyr Ser Gly Leu Tyr Glu Ala Ile Glu Ser Trp Asp Phe Lys Lys Ile
                85                  90                  95

Glu Lys Leu Glu Glu Tyr Arg Leu Leu Leu Lys Arg Leu Gln Pro Glu
            100                 105                 110

Phe Lys Thr Arg Ile Ile Pro Thr Asp Ile Ile Ser Asp Leu Ser Glu
            115                 120                 125

Cys Leu Ile Asn Gln Glu Cys Glu Glu Ile Leu Gln Ile Cys Ser Thr
            130                 135                 140

Lys Gly Met Met Ala Gly Ala Glu Lys Leu Val Glu Cys Leu Leu Arg
145                 150                 155                 160

Ser Asp Lys Glu Asn Trp Pro Lys Thr Leu Lys Leu Ala Leu Glu Lys
                165                 170                 175

Glu Arg Asn Lys Phe Ser Glu Leu Trp Ile Val Glu Lys Gly Ile Lys
            180                 185                 190

Asp Val Glu Thr Glu Asp Leu Glu Asp Lys Met Glu Thr Ser Asp Ile
        195                 200                 205

Gln Ile
    210

<210> SEQ ID NO 13
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ctcgagatgg gggaagaggg tggttcagcc tctcacgatg aggaggaaag agcaagtgtc      60
ctcctcggac attctccggg ttgtgaaatg tgctcgcagg aggcttttca ggcacagagg     120
agccagctgg tcgagctgct ggtctcaggg tccctggaag gcttcgagag tgtcctggac     180
tggctgctgt cctgggaggt cctctcctgg aggactacg agggcttcca cctcctgggc     240
cagcctctct cccacttggc caggcgcctt ctggacaccg tctggaataa gggtacttgg     300
gcctgtcaga agctcatcgc ggctgcccaa gaagcccagg ccgacagcca gtccccaag      360 ctgcatggct gctgggaccc ccactcgctc cacccagccc gagacctgca gagtcaccgg     420
ccagccattg tcaggaggct ccacagccat gtggagaaca tgctggacct ggcatgggag     480
cggggtttcg tcagccagta tgaatgtgat gaaatcaggt tgccgatctt cacaccgtcc     540
cagagggcaa gaaggctgct tgatcttgcc acggtgaaag cgaatggatt ggctgccttc     600
cttctacaac atgttcagga attaccagtc ccattggccc tgcctttgga agctgccaca     660
tgcaagaagt atatggccaa gctgaggacc acgtgtctg ctcagtctcg cttcctcagt     720
acctatgatg gagcagagac gctctgcctg gaggacatat acacagagaa tgtcctggag     780
gtcgtcgac                                                             789

<210> SEQ ID NO 14
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Gly Glu Glu Gly Gly Ser Ala Ser His Asp Glu Glu Arg Ala
1               5                   10                  15

Ser Val Leu Leu Gly His Ser Pro Gly Cys Glu Met Cys Ser Gln Glu
            20                  25                  30

Ala Phe Gln Ala Gln Arg Ser Gln Leu Val Glu Leu Leu Val Ser Gly
        35                  40                  45

Ser Leu Glu Gly Phe Glu Ser Val Leu Asp Trp Leu Leu Ser Trp Glu

Val Leu Ser Trp Glu Asp Tyr Glu Gly Phe His Leu Gly Gln Pro
 65                  70                  75                  80

Leu Ser His Leu Ala Arg Arg Leu Leu Asp Thr Val Trp Asn Lys Gly
                 85                  90                  95

Thr Trp Ala Cys Gln Lys Leu Ile Ala Ala Gln Glu Ala Gln Ala
            100                 105                 110

Asp Ser Gln Ser Pro Lys Leu His Gly Cys Trp Asp Pro His Ser Leu
            115                 120                 125

His Pro Ala Arg Asp Leu Gln Ser His Arg Pro Ala Ile Val Arg Arg
    130                 135                 140

Leu His Ser His Val Glu Asn Met Leu Asp Leu Ala Trp Glu Arg Gly
145                 150                 155                 160

Phe Val Ser Gln Tyr Glu Cys Asp Glu Ile Arg Leu Pro Ile Phe Thr
                165                 170                 175

Pro Ser Gln Arg Ala Arg Arg Leu Leu Asp Leu Ala Thr Val Lys Ala
            180                 185                 190

Asn Gly Leu Ala Ala Phe Leu Leu Gln His Val Gln Glu Leu Pro Val
        195                 200                 205

Pro Leu Ala Leu Pro Leu Glu Ala Ala Thr Cys Lys Lys Tyr Met Ala
    210                 215                 220

Lys Leu Arg Thr Thr Val Ser Ala Gln Ser Arg Phe Leu Ser Thr Tyr
225                 230                 235                 240

Asp Gly Ala Glu Thr Leu Cys Leu Glu Asp Ile Tyr Thr Glu Asn Val
                245                 250                 255

Leu Glu Val

<210> SEQ ID NO 15
<211> LENGTH: 888
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atggctgcag gaggtcccgg cgcggggtct gcggccccgg tctcctccac atcctccctt      60
cccctggctg ctctcaacat gcgagtgcgg cgccgcctgt ctctgttctt gaacgtgcgg     120
acacaggtgg cggccgactg gaccgcgctg gcggaggaga tggactttga gtacttggag     180
atccggcaac tggagacaca gcggaccccc actggcaggc tgctggacgc ctggcaggga     240
cgccctggcg cctctgtagg ccgactgctc gagctgctta ccaagctggg ccgcgacgac     300
gtgctgctgg agctgggacc cagcattgag gaggattgcc aaaagtatat cttgaagcag     360
cagcaggagg aggctgagaa gcctttacag gtggccgctg tagacagcag tgtcccacgg     420
acagcagagc tggcgggcat caccacactt gatgaccccc tggggcatat gcctgagcgt     480
ttcgatgcct tcatctgcta ttgccccagc gacatccagt ttgtgcagga gatgatccgg     540
caactggaac agacaaacta tcgactgaag ttgtgtgtgt ctgaccgcga tgtcctgcct     600
ggcacctgtg tctggtctat tgctagtgag ctcatcgaaa agaggtgccg ccggatggtg     660
gtggttgtct ctgatgatta cctgcagagc aaggaatgtg acttccagac caaatttgca     720
ctcagcctct ctccaggtgc ccatcagaag cgactgatcc ccatcaagta caaggcaatg     780
aagaaagagt tccccagcat cctgaggttc atcactgtct gcgactacac caaccctgc      840 accaaatctt ggttctggac tcgccttgcc aaggccttgt ccctgccc                   888

<210> SEQ ID NO 16
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
            180                 185                 190

Val Ser Asp Arg Asp Val Leu Pro Gly Thr Cys Val Trp Ser Ile Ala
        195                 200                 205

Ser Glu Leu Ile Glu Lys Arg Cys Arg Arg Met Val Val Val Val Ser
210                 215                 220

Asp Asp Tyr Leu Gln Ser Lys Glu Cys Asp Phe Gln Thr Lys Phe Ala
225                 230                 235                 240

Leu Ser Leu Ser Pro Gly Ala His Gln Lys Arg Leu Ile Pro Ile Lys
                245                 250                 255

Tyr Lys Ala Met Lys Lys Glu Phe Pro Ser Ile Leu Arg Phe Ile Thr
            260                 265                 270

Val Cys Asp Tyr Thr Asn Pro Cys Thr Lys Ser Trp Phe Trp Thr Arg
        275                 280                 285

Leu Ala Lys Ala Leu Ser Leu Pro
290                 295

<210> SEQ ID NO 17
<211> LENGTH: 16
<212> TYPE: PRT
<213> ORGANISM: Homo sapiens

<400> SEQUENCE: 17

Met Gly Ser Asn Lys Ser Lys Pro Lys Asp Ala Ser Gln Arg Arg Arg

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 18

Met Gly Cys Xaa Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Leu Trp Gly Pro Arg Ala Leu Val
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ile Leu Gly Phe Val Phe Thr Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Leu Tyr Asn Thr Val Ala Thr Leu
1               5

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Asn Asn Phe Thr Val Ser Phe Trp Leu Arg Val Pro Lys Val Ser
1               5                   10                  15

Ala Ser His Leu Glu
            20

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atatactcga gaaaaaggtg gccaagaagc caacc                                35

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atatagtcga ctcactgtct ctcctgcact gagatg                               36

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ile Ile Asn Phe Glu Lys Leu
1               5

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgatcactcg agggctggag gatatctttt tattgg                               36

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgatcggtcg acatgtacag agtttttgga tccaagtg                             38

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgatcactcg agtataagtt ctattttcac ctgatgcttc                              40

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgatcggtcg acgatagatg ttgcttcctg ccaattg                                 37

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgatcagtcg acgatgtgtg gtatatttac catttctg                                38

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgatcggtcg acgaccgttt ccttgaacac ctgac                                   35

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgatcactcg aggatgtttg gtttatatat aatgtgtg                                38

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcggtcgacg tattgcttaa tggaatcgac atac                                    34

```
<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgatcactcg aggacctctg gtactgcttc cacc                                34

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgatctgtcg acttcggccg tgggtccctg gc                                  32

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aatctaccgc ggccaccatg atgtctgcct cgcgcctg                            38

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcagttctcg aggatagatg ttgcttcctg ccaattg                             37

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acatagtcga cctgtctctc ctgcactgag atg                                 33

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atagcactcg agatggggga agagggtggt tcag                                34
```

```
<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cttcatgtcg acgacctcca ggacattctc tgtg                                 34

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atagcactcg agaccaccga gcagcgacgc ag                                   32

<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cttcatgtcg acaatctgta tgtcagaagt ttccatc                              37

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acatcaactc gagatggctg caggaggtcc cgg                                  33

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
actcatagtc gaccagggac aaggccttgg caag                                 34

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acatcaactc gagatggcct gcacaggccc atcac                                35

<210> SEQ ID NO 47
```

```
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
actcatagtc gacttctgcc tcctgcgtct tgtcc                               35

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aactagacgc gtactactaa aatgtaaatg acataggaaa ac                      42

<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gacttgaagc ttaacacgaa cagtgtcgcc tactac                             36

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggaggcggag gcagcggagg tggcggttcc ggaggcggag gttct                   45

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Gly Gly Ser Gly Gly Gly Gly Ser Gly Gly Gly Gly Ser
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Ser Gln Ala Val His Ala Ala His Ala Glu Ile Asn Glu Ala Gly
1               5                   10                  15

Arg
```

```
<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Val Tyr Asp Phe Phe Val Trp Leu
1               5

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 54

Cys Ala Ala Xaa
1
```

METHODS AND COMPOSITIONS FOR GENERATING AN IMMUNE RESPONSE BY INDUCING CD40 AND PATTERN RECOGNITION RECEPTOR ADAPTERS

RELATED PATENT APPLICATIONS

This patent application is a continuation application of U.S. patent application Ser. No. 12/563,991, filed Sep. 21, 2009, and entitled "METHODS AND COMPOSITIONS FOR GENERATING AN IMMUNE RESPONSE BY INDUCING CD40 AND PATTERN RECOGNITION RECEPTOR ADAPTERS', naming David Spencer and Priyadharshini NARAYANAN as inventors, which is non-provisional claiming priority to U.S. Provisional Application Ser. No. 61/181,572, filed May 27, 2009, and entitled "Methods and Compositions for Generating an Immune Response by Inducing CD40 and Pattern Recognition Receptor Adapters;" to U.S. Provisional Application Ser. No. 61/153,562, filed Feb. 18, 2009, and entitled "Methods and Compositions for Generating an Immune Response by Inducing CD40 and Pattern Recognition Receptor Adapters;" and to U.S. Provisional Application Ser. No. 61/099,163, filed Sep. 22, 2008, and entitled "Methods and Compositions for Generating an Immune Response by Inducing CD40 and Pattern Recognition Receptor Adapters;" which are all referred to and all incorporated herein by reference in their entirety.

STATEMENT OF FEDERALLY SPONSORED RESEARCH

This invention was made with Government support under NIH Grant Number R01-CA120411. The Government may have certain rights in this invention.

FIELD OF THE INVENTION

The invention relates generally to the field of immunology, and in particular, methods and compositions for activating antigen-presenting cells and for inducing immune responses.

SEQUENCE LISTING

The instant application contains a Sequence Listing which has been submitted via EFS-Web and is hereby incorporated by reference in its entirety. Said ASCII copy, created on Dec. 22, 2009, is named BEL-2004-UT.txt, and is 43,282 bytes in size.

BACKGROUND

Due to their unique method of processing and presenting antigens and the potential for high-level expression of costimulatory and cytokine molecules, dendritic cells (DC) are effective antigen-presenting cells (APCs) for priming and activating naïve T cells (Banchereau J, Paczesny S, Blanco P, et al. Dendritic cells: controllers of the immune system and a new promise for immunotherapy. Ann N Y Acad Sci. 2003; 987:180-187). This property has led to their widespread use as a cellular platform for vaccination in a number of clinical trials with encouraging results (O'Neill D W, Adams S, Bhardwaj N. Manipulating dendritic cell biology for the active immunotherapy of cancer. Blood. 2004; 104:2235-2246; Rosenberg S A. A new era for cancer immunotherapy based on the genes that encode cancer antigens. Immunity. 1999; 10:281-287). However, the clinical efficacy of DC vaccines in cancer patients has been unsatisfactory, probably due to a number of key deficiencies, including suboptimal activation, limited migration to draining lymph nodes, and an insufficient life span for optimal T cell activation in the lymph node environment.

A parameter in the optimization of DC-based cancer vaccines is the interaction of DCs with immune effector cells, such as CD4+, CD8+ T cells and T regulatory (Treg) cells. In these interactions, the maturation state of the DCs is a key factor in determining the resulting effector functions (Steinman R M, Hawiger D, Nussenzweig M C. Tolerogenic dendritic cells. Annu Rev Immunol. 2003; 21:685-711). To maximize CD4+ and CD8+ T cell priming while minimizing Treg expansion, DCs need to be fully mature, expressing high levels of co-stimulatory molecules, (like CD40, CD80, and CD86), and pro-inflammatory cytokines, like IL-12p70 and IL-6. Equally important, the DCs must be able to migrate efficiently from the site of vaccination to draining lymph nodes to initiate T cell interactions (Vieweg J, Jackson A. Modulation of antitumor responses by dendritic cells. Springer Semin Immunopathol. 2005; 26:329-341).

For the ex vivo maturation of monocyte-derived immature DCs, the majority of DC-based trials have used a standard maturation cytokine cocktail (MC), comprised of TNF-alpha, IL-1 beta, IL-6, and $PGE_2$. The principal function of prostaglandin E2 (PGE2) in the standard maturation cocktail is to sensitize the CC chemokine receptor 7 (CCR7) to its ligands, CC chemokine ligand 19 (CCL19) and CCL21 and thereby enhance the migratory capacity of DCs to the draining lymph nodes (Scandella E, Men Y, Gillessen S, Forster R, Groettrup M. Prostaglandin E2 is a key factor for CCR7 surface expression and migration of monocyte-derived dendritic cells. Blood. 2002; 100:1354-1361; Luft T, Jefford M, Luetjens P, et al. Functionally distinct dendritic cell (DC) populations induced by physiologic stimuli: prostaglandin E(2) regulates the migratory capacity of specific DC subsets. Blood. 2002; 100:1362-1372). However, PGE2 has also been reported to have numerous properties that are potentially deleterious to the stimulation of an immune response, including suppression of T-cell proliferation, (Goodwin J S, Bankhurst A D, Messner R P. Suppression of human T-cell mitogenesis by prostaglandin. Existence of a prostaglandin-producing suppressor cell. J Exp Med. 1977; 146:1719-1734; Goodwin J S. Immunomodulation by eicosanoids and anti-inflammatory drugs. Curr Opin Immunol. 1989; 2:264-268) inhibition of pro-inflammatory cytokine production (e.g., IL-12p70 and TNF-alpha (Kalinski P, Vieira P L, Schuitemaker J H, de Jong E C, Kapsenberg M L. Prostaglandin E(2) is a selective inducer of interleukin-12 p40 (IL-12p40) production and an inhibitor of bioactive IL-12p70 heterodimer. Blood. 2001; 97:3466-3469; van der Pouw Kraan T C, Boeije L C, Smeenk R J, Wijdenes J, Aarden L A. Prostaglandin-E2 is a potent inhibitor of human interleukin 12 production. J Exp Med. 1995; 181:775-779)), and down-regulation of major histocompatibility complex (MHC) II surface expression (Snyder D S, Beller D I, Unanue E R. Prostaglandins modulate macrophage Ia expression. Nature. 1982; 299:163-165). Therefore, maturation protocols that can avoid PGE2 while promoting migration are likely to improve the therapeutic efficacy of DC-based vaccines.

A DC activation system based on targeted temporal control of the CD40 signaling pathway has been developed to extend the pro-stimulatory state of DCs within lymphoid tissues. DC functionality was improved by increasing both the amplitude and the duration of CD40 signaling (Hanks B A, Jiang J, Singh R A, et al. Re-engineered CD40 receptor enables potent pharmacological activation of dendritic-cell cancer vaccines in vivo. Nat. Med. 2005; 11:130-137). To accomplish this, the CD40 receptor was re-engineered so that the cytoplasmic domain of CD40 was fused to synthetic ligand-binding domains along with a membrane-targeting sequence. Administration of a lipid-permeable, dimerizing drug, AP20187 (AP), called a chemical inducer of dimerization (CID) (Spencer D M, Wandless T J, Schreiber S L, Crabtree G R. Controlling signal transduction with synthetic ligands. Science. 1993; 262:1019-1024), led to the in vivo induction of CD40-dependent signaling cascades in murine DCs. This induction strategy significantly enhanced the immunogenicity against both defined antigens and tumors in vivo beyond that achieved with other activation modalities (Hanks B A, et al., Nat. Med. 2005; 11:130-137). The robust potency of this chimeric ligand-inducible CD40 (named iCD40) in mice suggested that this method might enhance the potency of human DC vaccines, as well.

Pattern recognition receptor (PRR) signaling, an example of which is Toll-like receptor (TLR) signaling also plays a critical role in the induction of DC maturation and activation; human DCs express, multiple distinct TLRs (Kadowaki N, Ho S, Antonenko S, et al. Subsets of human dendritic cell precursors express different toll-like receptors and respond to different microbial antigens. J Exp Med. 2001; 194:863-869). The eleven mammalian TLRs respond to various pathogen-derived macromolecules, contributing to the activation of innate immune responses along with initiation of adaptive immunity. Lipopolysaccharide (LPS) and a clinically relevant derivative, monophosphoryl lipid A (MPL), bind to cell surface TLR-4 complexes (Kadowaki N, Ho S, Antonenko S, et al. Subsets of human dendritic cell precursors express different toll-like receptors and respond to different microbial antigens. J Exp Med. 2001; 194:863-869), leading to various signaling pathways that culminate in the induction of transcription factors, such as NF-kappaB and IRF3, along with mitogen-activated protein kinases (MAPK) p38 and c-Jun kinase (JNK) (Ardeshna K M, Pizzey A R, Devereux S, Khwaja A. The PI3 kinase, p38 SAP kinase, and NF-kappaB signal transduction pathways are involved in the survival and maturation of lipopolysaccharide-stimulated human monocyte-derived dendritic cells. Blood. 2000; 96:1039-1046; Ismaili J, Rennesson J, Aksoy E, et al. Monophosphoryl lipid A activates both human dendritic cells and T cells. J. Immunol. 2002; 168:926-932). During this process DCs mature, and partially upregulate pro-inflammatory cytokines, like IL-6, IL-12, and Type I interferons (Rescigno M, Martino M, Sutherland C L, Gold M R, Ricciardi-Castagnoli P. Dendritic cell survival and maturation are regulated by different signaling pathways. J Exp Med. 1998; 188:2175-2180). LPS-induced maturation has been shown to enhance the ability of DCs to stimulate antigen-specific T cell responses in vitro and in vivo (Lapointe R, Toso J F, Butts C, Young H A, Hwu P. Human dendritic cells require multiple activation signals for the efficient generation of tumor antigen-specific T lymphocytes. Eur J Immunol. 2000; 30:3291-3298). Methods for activating an antigen-presenting cell, comprising transducing the cell with a nucleic acid coding for a CD40 peptide have been described in U.S. Pat. No. 7,404,950, and methods for activating an antigen-presenting cell, comprising transfecting the cell with a nucleic acid coding for a chimeric protein including an inducible CD40 peptide and a Pattern Recognition Receptor, or other downstream proteins in the pathway have been described in International Patent Application No. PCT/US2007/081963, filed Oct. 19, 2007, published as WO 2008/049113, which are hereby incorporated by reference herein.

SUMMARY

An inducible CD40 (iCD40) system has been applied to human dendritic cells (DCs) and it has been demonstrated that combining iCD40 signaling with Pattern recognition receptor (PRR) adapter ligation causes persistent and robust activation of human DCs. These features form the basis of cancer immunotherapies for treating such cancers as advanced, hormone-refractory prostate cancer, for example. Accordingly, it has been discovered that the combination of inducing CD40 and an inducible PRR adapter synergistically activates antigen-presenting cells and induces an immune response against an antigen. Inducible PRR adapters include, for example, MyD88 and TRIF; inducible Pattern Recognition Receptors, such as, for example, NOD-like receptors, for example, NOD1 or NOD2, and RIG-like helicases, for example, RIG-I or Mda-5, may also be used in combination with inducible CD40. Provided herein are methods for activating antigen-presenting cells, comprising transducing an antigen-presenting cell with a nucleic acid having a nucleotide sequence that encodes a chimeric protein, wherein the chimeric protein comprises (i) a membrane targeting region, (ii) a ligand-binding region (iii) a cytoplasmic CD40 polypeptide region, and (iv) a peptide selected from the group consisting of a truncated MyD88 peptide lacking the TIR domain and a TRIF peptide; and contacting the antigen-presenting cell with a non-protein multimeric ligand that binds to the ligand-binding region; whereby the antigen-presenting cell is activated.

Thus, provided herein are methods for activating an antigen-presenting cell, which comprise transfecting or transducing an antigen-presenting cell with a nucleic acid having a nucleotide sequence that encodes a chimeric protein, wherein the chimeric protein comprises a membrane targeting region, a ligand-binding region, a cytoplasmic CD40 polypeptide region, and a peptide selected from the group consisting of a MyD88 peptide, a truncated MyD88 peptide lacking the TIR domain, a NOD2 peptide, a RIG-1 peptide, and a TRIF peptide; and contacting the antigen-presenting cell with a non-protein multimeric ligand that binds to the ligand-binding region; whereby the antigen-presenting cell is activated. The cytoplasmic CD40 polypeptide region of the methods and compositions may, for example, have a peptide sequence of the cytoplasmic region of SEQ ID NO: 2, and may, for example, be encoded by a polynucleotide sequence coding for a cytoplasmic polypeptide region in SEQ ID NO: 1.

Also provided are methods for method for activating an antigen-presenting cell, which comprise transfecting or transducing an antigen-presenting cell with a nucleic acid having a nucleotide sequence that encodes a chimeric protein, wherein the chimeric protein comprises a membrane targeting region, a ligand-binding region, and a truncated MyD88 peptide lacking the TIR domain; and contacting the antigen-presenting cell with a non-protein multimeric ligand that binds to the ligand-binding region; whereby the antigen-presenting cell is activated. The chimeric protein may further comprise a CD40 polypeptide region.

Further provided are compositions comprising a nucleic acid having a nucleotide sequence that encodes a chimeric protein, wherein the chimeric protein comprises a membrane targeting region, a ligand-binding region, a cytoplasmic CD40 polypeptide region, and a peptide selected from the group consisting of a MyD88 peptide, a truncated MyD88 peptide lacking the TIR domain, a NOD2 peptide, a RIG-1 peptide, and a TRIF peptide.

An antigen-presenting cell is "activated," when one or more activities associated with activated antigen-presenting cells may be observed and/or measured by one of ordinary skill in the art. For example, an antigen-presenting cell is activated when following contact with an expression vector presented herein, an activity associated with activation may be measured in the expression vector-contacted cell as compared to an antigen-presenting cell that has either not been contacted with the expression vector, or has been contacted with a negative control vector. In one example, the increased activity may be at a level of two, three, four, five, six, seven, eight, nine, or ten fold, or more, than that of the non-contacted cell, or the cell contacted with the negative control. For example, one of the following activities may be enhanced in an antigen-presenting cell that has been contacted with the expression vector: co-stimulatory molecule expression on the antigen-presenting cell, nuclear translocation of NF-kappaB in antigen-presenting cells, DC maturation marker expression, such as, for example, toll-like receptor expression or CCR7 expression, specific cytotoxic T lymphocyte responses, such as, for example, specific lytic activity directed against tumor cells, or cytokine (for example, IL-2) or chemokine expression. Methods of assaying the activation of antigen-presenting cells are presented herein, for example, in Examples 11-17.

An amount of a composition that activates antigen-presenting cells that "enhances" an immune response refers to an amount in which an immune response is observed that is greater or intensified or deviated in any way with the addition of the composition when compared to the same immune response measured without the addition of the composition. For example, the lytic activity of cytotoxic T cells can be measured, for example, using a $^{51}$Cr release assay, with and without the composition. The amount of the substance at which the CTL lytic activity is enhanced as compared to the CTL lytic activity without the composition is said to be an amount sufficient to enhance the immune response of the animal to the antigen. For example, the immune response may be enhanced by a factor of at least about 2, or, for example, by a factor of about 3 or more. The amount of cytokines secreted may also be altered.

The enhanced immune response may be an active or a passive immune response. Alternatively, the response may be part of an adaptive immunotherapy approach in which antigen-presenting cells are obtained with from a subject (e.g., a patient), then transduced or transfected with a composition comprising the expression vector or construct presented herein. The antigen-presenting cells may be obtained from, for example, the blood of the subject or bone marrow of the subject. The antigen-presenting cells may then be administered to the same or different animal, or same or different subject (e.g., same or different donors). In certain embodiments the subject (for example, a patient) has or is suspected of having a cancer, such as for example, prostate cancer, or has or is suspected of having an infectious disease. In other embodiments the method of enhancing the immune response is practiced in conjunction with a known cancer therapy or any known therapy to treat the infectious disease.

The steps of the methods provided may be performed using any suitable method known to and selected by the person of ordinary skill, these methods include, without limitation, methods of transducing, transforming, or otherwise providing nucleic acid to the antigen-presenting cell, presented herein. In some embodiments, the truncated MyD88 peptide is encoded by the nucleotide sequence of SEQ ID NO: 5 (with or without DNA linkers). In other embodiments, the peptide is a TRIF peptide. Often, the peptide is encoded by the nucleotide sequence of SEQ ID NO: 9 (with or without DNA linkers). In some embodiments, the CD40 cytoplasmic polypeptide region is encoded by a polynucleotide sequence in SEQ ID NO: 1. In some embodiments of the methods or compositions, the peptide has a peptide sequence selected from the group consisting of SEQ ID NO: 6, SEQ ID NO: 10, SEQ ID NO: 12, SEQ ID NO: 14, and SEQ ID NO: 16 or wherein the peptide is encoded by a nucleotide sequence selected from the group consisting of SEQ ID NO: 9, SEQ ID NO: 11, SEQ ID NO: 13, and SEQ ID NO: 15. IN Certain embodiments, the truncated MyD88 has the peptide sequence of SEQ ID NO: 6, and, may, for example, be encoded by the nucleotide sequence of SEQ ID NO: 5. Often, the nucleic acid comprises a promoter sequence operably linked to the polynucleotide sequence. In general, the term "operably linked" is meant to indicate that the promoter sequence is functionally linked to a second sequence, wherein the promoter sequence initiates and mediates transcription of the DNA corresponding to the second sequence. Those of ordinary skill in the art may select an appropriate promoter sequence, including, without limitation, a promoter sequence discussed herein.

Those of ordinary skill in the art may select any appropriate known membrane targeting region, including, without limitation a myristoylation-targeting region, palmitoylation targeting region, prenylation region, or receptor transmembrane region. Often, the membrane targeting region is a myristoylation targeting region.

In certain embodiments, the ligand-binding region is selected from the group consisting of FKBP ligand-binding region, cyclophilin receptor ligand-binding region, steroid receptor ligand-binding region, cyclophilin receptors ligand-binding region, and tetracycline receptor ligand-binding region. Often, the ligand-binding region comprises a Fv'Fvls sequence. Sometimes, the Fv'Fvls sequence further comprises an additional Fv' sequence.

In some embodiments, the ligand is a small molecule. Those of ordinary skill in the art may select the appropriate ligand for the selected ligand-binding region. Often, the ligand is dimeric, sometimes, the ligand is a dimeric FK506 or a dimeric FK506 analog. In certain embodiments, the ligand is AP1903. In certain embodiments, the ligand is AP20187.

In some embodiments, the nucleic acid is contained within a viral vector. Those of ordinary skill in the art may select the appropriate viral vector. In certain embodiments, the viral vector is an adenoviral vector. It is understood that in some embodiments, the antigen-presenting cell is contacted with the viral vector ex vivo, and in some embodiments, the antigen-presenting cell is contacted with the viral vector in vivo.

In some embodiments, the antigen-presenting cell is a dendritic cell, for example, a mammalian dendritic cell. Often, the antigen-presenting cell is a human dendritic cell.

In certain embodiments, the antigen-presenting cell is also contacted with an antigen. Often, the antigen-presenting cell is contacted with the antigen ex vivo. Sometimes, the antigen-presenting cell is contacted with the antigen in vivo. In some embodiments, the antigen-presenting cell is in a subject and an immune response is generated against the antigen. Sometimes, the immune response is a cytotoxic T-lymphocyte (CTL) immune response. Sometimes, the immune response is generated against a tumor antigen. In certain embodiments, the antigen-presenting cell is activated without the addition of an adjuvant.

In some embodiments, the antigen-presenting cell is transduced with the nucleic acid ex vivo and administered to the subject by intradermal administration. In some embodiments, the antigen-presenting cell is transduced with the nucleic acid ex vivo and administered to the subject by subcutaneous administration. Sometimes, the antigen-presenting cell is transduced with the nucleic acid ex vivo. Sometimes, the antigen-presenting cell is transduced with the nucleic acid in vivo.

Provided also is a method for inducing a cytotoxic T lymphocyte (CTL) immune response against an antigen, which comprises: contacting a human antigen-presenting cell sensitized with an antigen with: (a) a multimeric molecule having two or more regions that bind to and multimerize native CD40, and (b) an inducible PRR adapter, for example, MyD88, truncated MyD88, or TRIF; whereby a CTL immune response is induced against the antigen. By MyD88 is meant the myeloid differentiation primary response gene 88, for example, but not limited to the human version, cited as ncbi Gene ID 4615. By TRIF is meant the TIR-domain-containing adapter-inducing interferon-beta. By "truncated," is meant that the protein is not full length and may lack, for example, a domain. For example, a truncated MyD88 is not full length and may, for example, be missing the TIR domain. One example of a truncated MyD88 is indicated as MyD88L herein, and is also presented as SEQ ID NOS: 5 (nucleic acid sequence) and 6 (peptide sequence). SEQ ID NO: 5 includes the linkers added during subcloning. Those of ordinary skill in the art recognize that by a nucleic acid sequence coding for "truncated MyD88" is meant the nucleic acid sequence coding for the truncated MyD88 peptide, the term may also refer to the nucleic acid sequence including the portion coding for any amino acids added as an artifact of cloning, including any amino acids coded for by the linkers. In such methods, the multimeric molecule can be an antibody that binds to an epitope in the CD40 extracellular domain (e.g., humanized anti-CD40 antibody; Tai et al., Cancer Research 64, 2846-2852 (2004)), can be a CD40 ligand (e.g., U.S. Pat. No. 6,497,876 (Maraskovsky et al.)) or may be another co-stimulatory molecule (e.g., B7/CD28). It is understood by those of ordinary skill in the art that conservative variations in sequence, that do not affect the function, as assayed herein, are within the scope of the present claims.

Also provided herein are compositions comprising a nucleic acid having a polynucleotide sequence that encodes a chimeric protein, wherein the chimeric protein comprises (i) a membrane targeting region, (ii) a ligand-binding region (iii) a cytoplasmic CD40 polypeptide region, and (iv) a peptide selected from the group consisting of a truncated MyD88 peptide lacking the TIR domain and a TRIF peptide. In some embodiments, the truncated MyD88 peptide is encoded by the nucleotide sequence of SEQ ID NO: 5. In other embodiments, the peptide is a TRIF peptide. Often, the peptide is encoded by the nucleotide sequence of SEQ ID NO: 9. IN some embodiments, the CD40 cytoplasmic polypeptide region is encoded by a polynucleotide sequence in SEQ ID NO: 1. Often, the nucleic acid comprises a promoter sequence operably linked to the polynucleotide sequence. Those of ordinary skill in the art may select an appropriate promoter sequence, including, without limitation, a promoter sequence discussed herein.

Those of ordinary skill in the art may select any appropriate known membrane targeting region, including, without limitation a myristoylation-targeting region, palmitoylation targeting region, prenylation region, or receptor transmembrane region. Often, the membrane targeting region is a myristoylation targeting region.

In certain embodiments, the ligand-binding region is selected from the group consisting of FKBP ligand-binding region, cyclophilin receptor ligand-binding region, steroid receptor ligand-binding region, cyclophilin receptors ligand-binding region, and tetracycline receptor ligand-binding region. Often, the ligand-binding region comprises a Fv'Fvls sequence. Sometimes, the Fv'Fvls sequence further comprises an additional Fv' sequence.

In some embodiments, the nucleic acid is contained within a viral vector. Those of ordinary skill in the art may select the appropriate viral vector. In certain embodiments, the viral vector is an adenoviral vector. It is understood that in some embodiments, the antigen-presenting cell is contacted with the viral vector ex vivo, and in some embodiments, the antigen-presenting cell is contacted with the viral vector in vivo.

In some embodiments, methods are provided for activating an antigen-presenting cell, comprising transducing an antigen-presenting cell with a nucleic acid having a nucleotide sequence that encodes a chimeric protein, wherein the chimeric protein comprises (i) a membrane targeting region, (ii) a ligand-binding region, and (iii) a MyD88 peptide or a truncated MyD88 peptide lacking the TIR domain; and contacting the antigen-presenting cell with a non-protein multimeric ligand that binds to the ligand-binding region; whereby the antigen-presenting cell is activated. Often, the MyD88 peptide is truncated, including, without limitation, a truncated MyD88 peptide that is encoded by the nucleotide sequence of SEQ ID NO: 5. The steps of the methods provided may be performed using any suitable method known to and selected by the person of ordinary skill, these methods include, without limitation, methods of transducing, transforming, or otherwise providing nucleic acid to the antigen-presenting cell, presented herein. Often, the nucleic acid comprises a promoter sequence operably linked to the polynucleotide sequence. Those of ordinary skill in the art may select an appropriate promoter sequence, including, without limitation, a promoter sequence discussed herein.

Those of ordinary skill in the art may select any appropriate known membrane targeting region, including, without limitation a myristoylation-targeting region, palmitoylation targeting region, prenylation region, or receptor transmembrane region. Often, the membrane targeting region is a myristoylation targeting region.

In certain embodiments, the ligand-binding region is selected from the group consisting of FKBP ligand-binding region, cyclophilin receptor ligand-binding region, steroid receptor ligand-binding region, cyclophilin receptors ligand-binding region, and tetracycline receptor ligand-binding region. Often, the ligand-binding region comprises a Fv'Fvls sequence. Sometimes, the Fv'Fvls sequence further comprises an additional Fv' sequence.

In some embodiments, the ligand is a small molecule. Those of ordinary skill in the art may select the appropriate ligand for the selected ligand-binding region. Often, the ligand is dimeric, sometimes, the ligand is a dimeric FK506 or a dimeric FK506 analog. In certain embodiments, the ligand is AP1903. In certain embodiments, the ligand is AP20187.

In some embodiments, the nucleic acid is contained within a viral vector. Those of ordinary skill in the art may select the appropriate viral vector. In certain embodiments, the viral vector is an adenoviral vector. It is understood that in some embodiments, the antigen-presenting cell is contacted with the viral vector ex vivo, and in some embodiments, the antigen-presenting cell is contacted with the viral vector in vivo.

In some embodiments, the antigen-presenting cell is a dendritic cell, for example, a mammalian dendritic cell. Often, the antigen-presenting cell is a human dendritic cell.

In certain embodiments, the antigen-presenting cell is also contacted with an antigen. Often, the antigen-presenting cell is contacted with the antigen ex vivo. Sometimes, the antigen-presenting cell is contacted with the antigen in vivo. In some embodiments, the antigen-presenting cell is in a subject and an immune response is generated against the antigen. Sometimes, the immune response is a cytotoxic T-lymphocyte (CTL) immune response. Sometimes, the immune response is generated against a tumor antigen. In certain embodiments, the antigen-presenting cell is activated without the addition of an adjuvant.

In some embodiments, the antigen-presenting cell is transduced with the nucleic acid ex vivo and administered to the subject by intradermal administration. In some embodiments, the antigen-presenting cell is transduced with the nucleic acid ex vivo and administered to the subject by subcutaneous administration. Sometimes, the antigen-presenting cell is transduced with the nucleic acid ex vivo. Sometimes, the antigen-presenting cell is transduced with the nucleic acid in vivo.

Also provided herein are compositions that may be used, for example, in the methods of the present invention. Thus, provided are compositions comprising a nucleic acid having a polynucleotide sequence that encodes a chimeric protein, wherein the chimeric protein comprises (i) a membrane targeting region, (ii) a ligand-binding region (iii) a cytoplasmic CD40 polypeptide region, and (iv) a MyD88 peptide or a truncated MyD88 peptide lacking the TIR domain. In some embodiments, the MyD88 peptide is truncated. Sometimes, the truncated MyD88 peptide is encoded by the nucleotide sequence of SEQ ID NO: 5. Often, the nucleic acid comprises a promoter sequence operably linked to the polynucleotide sequence. Those of ordinary skill in the art may select an appropriate promoter sequence, including, without limitation, a promoter sequence discussed herein.

Those of ordinary skill in the art may select any appropriate known membrane targeting region, including, without limitation a myristoylation-targeting region, palmitoylation targeting region, prenylation region, or receptor transmembrane region. Often, the membrane targeting region is a myristoylation targeting region.

In certain embodiments, the ligand-binding region is selected from the group consisting of FKBP ligand-binding region, cyclophilin receptor ligand-binding region, steroid receptor ligand-binding region, cyclophilin receptors ligand-binding region, and tetracycline receptor ligand-binding region. Often, the ligand-binding region comprises a Fv'Fvls sequence. Sometimes, the Fv'Fvls sequence further comprises an additional Fv' sequence.

In some embodiments, the nucleic acid is contained within a viral vector. Those of ordinary skill in the art may select the appropriate viral vector. In certain embodiments, the viral vector is an adenoviral vector. It is understood that in some embodiments, the antigen-presenting cell is contacted with the viral vector ex vivo, and in some embodiments, the antigen-presenting cell is contacted with the viral vector in vivo.

Also provided are compositions comprising a cell transduced with a nucleic acid composition of any of the embodiments presented herein. In some embodiments, the cell is an antigen-presenting cell. Often, the cell is a dendritic cell, including, without limitation, a mammalian cell, for example, but without limitation, a human dendritic cell.

Also provided is the use of a composition comprising a nucleic acid having a nucleotide sequence that encodes a chimeric protein, wherein the chimeric protein comprises (i) a membrane targeting region, (ii) a ligand-binding region (iii) a cytoplasmic CD40 polypeptide region, and (iv) a peptide selected from the group consisting of a MyD88 peptide, a truncated MyD88 peptide lacking the TIR domain, a NOD2 peptide, a RIG-1 peptide, and a TRIF peptide, in the manufacture of a medicament for therapy of a condition by activating an immune response. In another embodiment is the use of a composition comprising a cell transduced or transfected with a nucleic acid having a nucleotide sequence that encodes a chimeric protein, wherein the chimeric protein comprises (i) a membrane targeting region, (ii) a ligand-binding region (iii) a cytoplasmic CD40 polypeptide region, and (iv) a peptide selected from the group consisting of a MyD88 peptide, a truncated MyD88 peptide lacking the TIR domain, a NOD2 peptide, a RIG-1 peptide, and a TRIF peptide, in the manufacture of a medicament for therapy of a condition by activating an immune response. The composition may be used, for example, to transfect or transduce an antigen-presenting cell. The peptide may, for example, be a truncated MyD88 peptide. The condition may, for example, be a hyperproliferative disease, or, for example, an infectious disease.

In the methods for inducing an immune response presented herein, the antigen-presenting cell can be transduced ex vivo or in vivo with a nucleic acid that encodes the chimeric protein. The antigen-presenting cell may be sensitized to the antigen at the same time the antigen-presenting cell is contacted with the multimeric ligand, or the antigen-presenting cell can be pre-sensitized to the antigen before the antigen-presenting cell is contacted with the multimerization ligand. In some embodiments, the antigen-presenting cell is contacted with the antigen ex vivo. In certain embodiments the antigen-presenting cell is transduced with the nucleic acid ex vivo and administered to the subject by intradermal administration, and sometimes the antigen-presenting cell is transduced with the nucleic acid ex vivo and administered to the subject by subcutaneous administration. The antigen may be a tumor antigen, and the CTL immune response can induced by migration of the antigen-presenting cell to a draining lymph node.

In the methods herein, the inducible CD40 portion of the peptide may be located either upstream or downstream from the inducible PRR adapter protein portion. Also, the inducible CD40 portion and the inducible PRR adapter protein portions may be transfected or transduced into the cells either on the same vector, in cis, or on separate vectors, in trans.

Also provided herein is a method for assessing migration of an antigen-presenting cell to a lymph node, which comprises: (a) injecting into a subject an antigen-presenting cell that produces a detectable protein, and (b) determining the amount of the detectable protein in the lymph node of the animal, whereby migration of the antigen-presenting cell to the lymph node is assessed from the amount of the detectable protein in the lymph node. In such methods the animal can be a rodent, such as a rat or a mouse (e.g., irradiated mouse). In some embodiments, the detectable protein is a luciferase protein, such as a chick beetle (e.g., *Pyrophorus plagiophalamus*) red-shifted luciferase protein. In certain embodiments, the antigen-presenting cell has been transduced with a nucleic acid having a polynucleotide sequence that encodes the detectable protein. In certain embodiments, the lymph node is the popliteal lymph node or inguinal lymph node. The antigen-presenting cell can be a dendritic cell, such as a human dendritic cell. In certain embodiments, the lymph node is removed from the animal before the amount of detectable protein is determined, and sometimes the D-Luciferin is administered to the removed lymph node. The amount of the detectable protein may be qualitative (e.g., relative amounts compared across different samples) and can be quantitative (e.g., a concentration). The amount of the detectable protein may be determined by directly detecting the protein. For example, the protein may be fluorescent (e.g., green fluorescent protein or a red-shifted or blue-shifted version) or can be bound to a fluorescent label (e.g., an antibody linked to a fluorophore). Alternatively, the amount of the detectable protein can determined indirectly by administering a substrate to the animal that is converted into a detectable product by the protein and detecting the detectable product. For example, the amount of a luciferase protein can determined by administering D-Luciferin to the animal and detecting the D-Luciferin product generated by the luciferase produced in the antigen-presenting cell.

In certain embodiments, the membrane targeting region is a myristoylation-targeting region, although the membrane-targeting region can be selected from other types of transmembrane-targeting regions, such as regions described hereafter. In some embodiments the ligand is a small molecule, and sometimes the molecule is dimeric. Examples of dimeric molecules are dimeric FK506 and dimeric FK506 analogs. In certain embodiments the ligand is AP1903 or AP20187. In some embodiments, the chimeric protein includes one or more ligand-binding regions, such as two or three ligand-binding regions, for example. The ligand-binding regions often are tandem.

The nucleic acid in certain embodiments is contained within a viral vector, such as an adenoviral vector for example. The antigen-presenting cell in some embodiments is contacted with an antigen, sometimes ex vivo. In certain embodiments the antigen-presenting cell is in a subject and an immune response is generated against the antigen, such as a cytotoxic T-lymphocyte (CTL) immune response. In certain embodiments, an immune response is generated against a tumor antigen (e.g., PSMA). In some embodiments, the nucleic acid is prepared ex vivo and administered to the subject by intradermal administration or by subcutaneous administration, for example. Sometimes the antigen-presenting cell is transduced or transfected with the nucleic acid ex vivo or in vivo. In some embodiments, the nucleic acid comprises a promoter sequence operably linked to the polynucleotide sequence. Alternatively, the nucleic acid comprises an ex vivo-transcribed RNA, containing the protein-coding region of the chimeric protein.

BRIEF DESCRIPTION OF THE DRAWINGS

FIG. 1. Schematic diagram of iCD40 and expression in human DCs.

FIG. 27 is a graph of results of an IFN-beta-SEAP reporter assay in iRIG-1 and iTRIF transfected cells.

FIG. 41 presents representative results of a CTL assay in mice induced by transduced dendritic cells.

FIG. 43 presents the results of a tumor growth inhibition assay in mice treated with Ad5-iCD40.MyD88 transduced cells.

FIG. 44 discloses 'SIINFEKL' as SEQ ID NO: 26.

FIG. 46 presents the results of a cytotoxic lymphocyte assay using splenocytes from the treated mice as effectors.

DETAILED DESCRIPTION

Figure 1A:
FIG. 1A. The human CD40 cytoplasmic domain can be subcloned downstream of a myristoylation-targeting domain (M) and two tandem domains (Fv) (Clackson T, Yang W, Rozamus L W, et al. Redesigning an FKBP-ligand interface to generate chemical dimerizers with novel specificity. Proc Natl Acad Sci USA. 1998; 95:10437-10442). The expression of M-Fv-Fv-CD40 chimeric protein, referred to here as inducible CD40 (iCD40) can be under cytomegalovirus (CMV) promoter control.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "allogeneic" as used herein, refers to HLA or MHC loci that are antigenically distinct. Thus, cells or tissue transferred from the same species can be antigenically distinct. Syngeneic mice can differ at one or more loci (congenics) and allogeneic mice can have the same background.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates. Exemplary organisms include but are not limited to, *Helicobacters, Campylobacters, Clostridia, Corynebacterium diphtheriae, Bordetella pertussis*, influenza virus, parainfluenza viruses, respiratory syncytial virus, *Borrelia burgdorfei, Plasmodium*, herpes simplex viruses, human immunodeficiency virus, papillomavirus, *Vibrio cholera, E. coli*, measles virus, rotavirus, *shigella, Salmonella typhi, Neisseria gonorrhea*. Therefore, a skilled artisan realizes that any macromolecule, including virtually all proteins or peptides, can serve as antigens. Furthermore, antigens can be derived from recombinant or genomic DNA. A skilled artisan realizes that any DNA that contains nucleotide sequences or partial nucleotide sequences of a pathogenic genome or a gene or a fragment of a gene for a protein that elicits an immune response results in synthesis of an antigen. Furthermore, one skilled in the art realizes that the present invention is not limited to the use of the entire nucleic acid sequence of a gene or genome. It is readily inherent that the present invention includes, but is not limited to, the use of partial nucleic acid sequences of more than one gene or genome and that these nucleic acid sequences are arranged in various combinations to elicit the desired immune response.

The term "antigen-presenting cell" is any of a variety of cells capable of displaying, acquiring, or presenting at least one antigen or antigenic fragment on (or at) its cell surface. In general, the term "antigen-presenting cell" can be any cell that accomplishes the goal of the invention by aiding the enhancement of an immune response (i.e., from the T-cell or -B-cell arms of the immune system) against an antigen or antigenic composition. Such cells can be defined by those of skill in the art, using methods disclosed herein and in the art. As is understood by one of ordinary skill in the art (see for example Kuby, 2000, Immunology, 4.sup.th edition, W.H. Freeman and company, incorporated herein by reference), and used herein in certain embodiments, a cell that displays or presents an antigen normally or preferentially with a class II major histocompatibility molecule or complex to an immune cell is an "antigen-presenting cell." In certain aspects, a cell (e.g., an APC cell) may be fused with another cell, such as a recombinant cell or a tumor cell that expresses the desired antigen. Methods for preparing a fusion of two or more cells is well known in the art, such as for example, the methods disclosed in Goding, J. W., Monoclonal Antibodies: Principles and Practice, pp. 65-66, 71-74 (Academic Press, 1986); Campbell, in: Monoclonal Antibody Technology, Laboratory Techniques in Biochemistry and Molecular Biology, Vol. 13, Burden & Von Knippenberg, Amsterdam, Elseview, pp. 75-83, 1984; Kohler & Milstein, Nature, 256:495-497, 1975; Kohler & Milstein, Eur. J. Immunol., 6:511-519, 1976, Gefter et al., Somatic Cell Genet., 3:231-236, 1977, each incorporated herein by reference. In some cases, the immune cell to which an antigen-presenting cell displays or presents an antigen to is a CD4+ TH cell. Additional molecules expressed on the APC or other immune cells may aid or improve the enhancement of an immune response. Secreted or soluble molecules, such as for example, cytokines and adjuvants, may also aid or enhance the immune response against an antigen. Such molecules are well known to one of skill in the art, and various examples are described herein.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "iCD40 molecule" is defined as an inducible CD40. This iCD40 can bypass mechanisms that extinguish endogenous CD40 signaling. The term "iCD40" embraces "iCD40 nucleic acids," "iCD40 polypeptides" and/or iCD40 expression vectors. Yet further, it is understood the activity of iCD40 as used herein is driven by CID.

As used herein, the term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There are times when the full or partial genomic sequence is preferred, such as where the non-coding regions are required for optimal expression or where non-coding regions such as introns are to be targeted in an antisense strategy.

The term ""dendritic cell" (DC) is an antigen-presenting cell existing in vivo, in vitro, ex vivo, or in a host or subject, or which can be derived from a hematopoietic stem cell or a monocyte. Dendritic cells and their precursors can be isolated from a variety of lymphoid organs, e.g., spleen, lymph nodes, as well as from bone marrow and peripheral blood. The DC has a characteristic morphology with thin sheets (lamellipodia) extending in multiple directions away from the dendritic cell body. Typically, dendritic cells express high levels of MHC and costimulatory (e.g., B7-1 and B7-2) molecules. Dendritic cells can induce antigen specific differentiation of T cells in vitro, and are able to initiate primary T cell responses in vitro and in vivo.

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest. The term "therapeutic construct" may also be used to refer to the expression construct or transgene. One skilled in the art realizes that the expression construct or transgene may be used, for example, as a therapy to treat hyperproliferative diseases or disorders, such as cancer, thus the expression construct or transgene is a therapeutic construct or a prophylactic construct.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are described infra.

As used herein, the term "ex vivo" refers to "outside" the body. One of skill in the art is aware that ex vivo and in vitro can be used interchangeably.

As used herein, the term "functionally equivalent," as used herein, as, for example it refers to a CD40 nucleic acid fragment, variant, or analog, refers to a nucleic acid that codes for a CD40 polypeptide, or a CD40 polypeptide, that stimulates an immune response to destroy tumors or hyperproliferative disease. "Functionally equivalent" refers, for example, to a CD40 polypeptide that is lacking the extracellular domain, but is capable of amplifying the T cell-mediated tumor killing response by upregulating dendritic cell expression of antigen presentation molecules.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

As used herein, the term "gene" is defined as a functional protein, polypeptide, or peptide-encoding unit. As will be understood by those in the art, this functional term includes genomic sequences, cDNA sequences, and smaller engineered gene segments that express, or are adapted to express, proteins, polypeptides, domains, peptides, fusion proteins, and mutants.

The term "immunogenic composition" or "immunogen" refers to a substance that is capable of provoking an immune response. Examples of immunogens include, e.g., antigens, autoantigens that play a role in induction of autoimmune diseases, and tumor-associated antigens expressed on cancer cells.

The term "immunocompromised" as used herein is defined as a subject that has reduced or weakened immune system. The immunocompromised condition may be due to a defect or dysfunction of the immune system or to other factors that heighten susceptibility to infection and/or disease. Although such a categorization allows a conceptual basis for evaluation, immunocompromised individuals often do not fit completely into one group or the other. More than one defect in the body's defense mechanisms may be affected. For example, individuals with a specific T-lymphocyte defect caused by HIV may also have neutropenia caused by drugs used for antiviral therapy or be immunocompromised because of a breach of the integrity of the skin and mucous membranes. An immunocompromised state can result from indwelling central lines or other types of impairment due to intravenous drug abuse; or be caused by secondary malignancy, malnutrition, or having been infected with other infectious agents such as tuberculosis or sexually transmitted diseases, e.g., syphilis or hepatitis.

As used herein, the term "pharmaceutically or pharmacologically acceptable" refers to molecular entities and compositions that do not produce adverse, allergic, or other untoward reactions when administered to an animal or a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells presented herein, its use in therapeutic compositions is contemplated. Supplementary active ingredients also can be incorporated into the compositions.

As used herein, the term "polynucleotide" is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Furthermore, one skilled in the art is cognizant that polynucleotides include mutations of the polynucleotides, include but are not limited to, mutation of the nucleotides, or nucleosides by methods well known in the art.

As used herein, the term "polypeptide" is defined as a chain of amino acid residues, usually having a defined sequence. As used herein the term polypeptide is interchangeable with the terms "peptides" and "proteins".

As used herein, the term "promoter" is defined as a DNA sequence recognized by the synthetic machinery of the cell, or introduced synthetic machinery, required to initiate the specific transcription of a gene.

As used herein, the term "regulate an immune response" or "modulate an immune response" refers to the ability to modify the immune response. For example, the composition is capable of enhancing and/or activating the immune response. Still further, the composition is also capable of inhibiting the immune response. The form of regulation is determined by the ligand that is used with the composition. For example, a dimeric analog of the chemical results in dimerization of the co-stimulatory polypeptide leading to activation of the DCs, however, a monomeric analog of the chemical does not result in dimerization of the co-stimulatory polypeptide, which would not activate the DCs.

The term "transfection" and "transduction" are interchangeable and refer to the process by which an exogenous DNA sequence is introduced into a eukaryotic host cell. Transfection (or transduction) can be achieved by any one of a number of means including electroporation, microinjection, gene gun delivery, retroviral infection, lipofection, superfection and the like.

As used herein, the term "syngeneic" refers to cells, tissues or animals that have genotypes that are identical or closely related enough to allow tissue transplant, or are immunologically compatible. For example, identical twins or animals of the same inbred strain. Syngeneic and isogeneic can be used interchangeable.

The term "subject" as used herein includes, but is not limited to, an organism or animal; a mammal, including, e.g., a human, non-human primate (e.g., monkey), mouse, pig, cow, goat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

As used herein, the term "under transcriptional control" or "operatively linked" is defined as the promoter is in the correct location and orientation in relation to the nucleic acid to control RNA polymerase initiation and expression of the gene.

As used herein, the terms "treatment", "treat", "treated", or "treating" refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse.

As used herein, the term "vaccine" refers to a formulation which contains a composition presented herein which is in a form that is capable of being administered to an animal. Typically, the vaccine comprises a conventional saline or buffered aqueous solution medium in which the composition is suspended or dissolved. In this form, the composition can be used conveniently to prevent, ameliorate, or otherwise treat a condition. Upon introduction into a subject, the vaccine is able to provoke an immune response including, but not limited to, the production of antibodies, cytokines and/or other cellular responses.

Dendritic Cells

The innate immune system uses a set of germline-encoded receptors for the recognition of conserved molecular patterns present in microorganisms. These molecular patterns occur in certain constituents of microorganisms including: lipopolysaccharides, peptidoglycans, lipoteichoic acids, phosphatidyl cholines, bacteria-specific proteins, including lipoproteins, bacterial DNAs, viral single and double-stranded RNAs, unmethylated CpG-DNAs, mannans and a variety of other bacterial and fungal cell wall components. Such molecular patterns can also occur in other molecules such as plant alkaloids. These targets of innate immune recognition are called Pathogen Associated Molecular Patterns (PAMPs) since they are produced by microorganisms and not by the infected host organism (Janeway et al. (1989) Cold Spring Harb. Symp. Quant. Biol., 54: 1-13; Medzhitov et al., Nature, 388:394-397, 1997).

The receptors of the innate immune system that recognize PAMPs are called Pattern Recognition Receptors (PRRs) (Janeway et al., 1989; Medzhitov et al., 1997). These receptors vary in structure and belong to several different protein families. Some of these receptors recognize PAMPs directly (e.g., CD14, DEC205, collectins), while others (e.g., complement receptors) recognize the products generated by PAMP recognition. Members of these receptor families can, generally, be divided into three types: 1) humoral receptors circulating in the plasma; 2) endocytic receptors expressed on immune-cell surfaces, and 3) signaling receptors that can be expressed either on the cell surface or intracellularly (Medzhitov et al., 1997; Fearon et al. (1996) Science 272: 50-3).

Cellular PRRs are expressed on effector cells of the innate immune system, including cells that function as professional antigen-presenting cells (APC) in adaptive immunity. Such effector cells include, but are not limited to, macrophages, dendritic cells, B lymphocytes and surface epithelia. This expression profile allows PRRs to directly induce innate effector mechanisms, and also to alert the host organism to the presence of infectious agents by inducing the expression of a set of endogenous signals, such as inflammatory cytokines and chemokines, as discussed below. This latter function allows efficient mobilization of effector forces to combat the invaders.

The primary function of dendritic cells (DCs) is to acquire antigen in the peripheral tissues, travel to secondary lymphoid tissue, and present antigen to effector T cells of the immune system (Banchereau, J., et al., Annu Rev Immunol, 2000, 18: p. 767-811; Banchereau, J., & Steinman, R. M. Dendritic cells and the control of immunity. Nature 392, 245-252 (1998)). As DCs carry out their crucial role in the immune response, they undergo maturational changes allowing them to perform the appropriate function for each environment (Termeer, C. C., et al., J Immunol, 2000, Aug. 15. 165: p. 1863-70). During DC maturation, antigen uptake potential is lost, the surface density of major histocompatibility complex (MHC) class I and class II molecules increases by 10-100 fold, and CD40, costimulatory and adhesion molecule expression also greatly increases (Lanzavecchia, A. and F. Sallusto, Science, 2000. 290: p. 92-96). In addition, other genetic alterations permit the DCs to home to the T cell-rich paracortex of draining lymph nodes and to express T-cell chemokines that attract naïve and memory T cells and prime antigen-specific naïve TH0 cells (Adema, G. J., et al., Nature, 1997, Jun. 12. 387: p. 713-7). During this stage, mature DCs present antigen via their MHC II molecules to CD4+ T helper cells, inducing the upregulation of T cell CD40 ligand (CD40L) that, in turn, engages the DC CD40 receptor. This DC:T cell interaction induces rapid expression of additional DC molecules that are crucial for the initiation of a potent CD8+ cytotoxic T lymphocyte (CTL) response, including further upregulation of MHC I and II molecules, adhesion molecules, costimulatory molecules (e.g., B7.1, B7.2), cytokines (e.g., IL-12) and anti-apoptotic proteins (e.g., Bcl-2) (Anderson, D. M., et al., Nature, 1997, Nov. 13. 390: p. 175-9; Ohshima, Y., et al., J Immunol, 1997, Oct. 15. 159: p. 3838-48; Sallusto, F., et al., Eur J Immunol, 1998, Sep. 28: p. 2760-9; Caux, C. Adv Exp Med. Biol. 1997, 417:21-5;). CD8+ T cells exit lymph nodes, reenter circulation and home to the original site of inflammation to destroy pathogens or malignant cells.

One key parameter influencing the function of DCs is the CD40 receptor, serving as the "on switch" for DCs (Bennett, S. R., et al., Nature, 1998, Jun. 4. 393: p. 478-80; Clarke, S. R., J Leukoc Biol, 2000, May. 67: p. 607-14; Fernandez, N. C., et al., Nat Med, 1999, April 5: p. 405-11; Ridge, J. P., D. R. F, and P. Nature, 1998, Jun. 4. 393: p. 474-8; Schoenberger, S. P., et al., Nature, 1998, Jun. 4. 393: p. 480-3). CD40 is a 48-kDa transmembrane member of the TNF receptor superfamily (McWhirter, S. M., et al., Proc Natl Aced Sci USA, 1999, Jul. 20. 96: p. 8408-13). CD40-CD40L interaction induces CD40 trimerization, necessary for initiating signaling cascades involving TNF receptor associated factors (TRAFs) (Ni, C., et al., PNAS, 2000, 97(19): 10395-10399; Pullen, S. S., et al., J Biol Chem, 1999, May 14.274: p. 14246-54). CD40 uses these signaling molecules to activate several transcription factors in DCs, including NF-kappa B, AP-1, STAT3, and p38MAPK (McWhirter, S. M., et al., 1999).

A novel DC activation system is provided based on recruiting signaling molecules or co-stimulatory polypeptides to the plasmid membrane of the DCs resulting in prolonged/increased activation and/or survival in the DCs. Co-stimulatory polypeptides include any molecule or polypeptide that activates the NF-kappaB pathway, Akt pathway, and/or p38 pathway. The DC activation system is based upon utilizing a recombinant signaling molecule fused to a ligand-binding domains (i.e., a small molecule binding domain) in which the co-stimulatory polypeptide is activated and/or regulated with a ligand resulting in oligomerization (i.e., a lipid-permeable, organic, dimerizing drug). Other systems that may be used to crosslink or for oligomerization of co-stimulatory polypeptides include antibodies, natural ligands, and/or artificial cross-reacting or synthetic ligands. Yet further, other dimerization systems contemplated include the coumermycin/DNA gyrase B system.

Co-stimulatory polypeptides that can be used include those that activate NF-kappaB and other variable signaling cascades for example the p38 pathway and/or Akt pathway. Such co-stimulatory polypeptides include, but are not limited to Pattern Recognition Receptors, C-reactive protein receptors (i.e., Nod1, Nod2, PtX3-R), TNF receptors (i.e., CD40, RANK/TRANCE-R, OX40, 4-1BB), and HSP receptors (Lox-1 and CD-91). Pattern Recognition Receptors include, but are not limited to endocytic pattern-recognition receptors (i.e., mannose receptors, scavenger receptors (i.e., Mac-1, LRP, peptidoglycan, techoic acids, toxins, CD11c/CR4)); external signal pattern-recognition receptors (Toll-like receptors (TLR1, TLR2, TLR3, TLR4, TLR5, TLR6, TLR7, TLR8, TLR9, TLR10), peptidoglycan recognition protein, (PGRPs bind bacterial peptidoglycan, and CD14); internal signal pattern-recognition receptors (i.e., NOD-receptors 1 & 2), RIG1, and PRRs shown in FIG. 8. Those of ordinary skill in the art are also aware of other Pattern Recognition Receptors suitable for the present methods and composition, including those discussed in, for example, Werts C., et al., Cell Death and Differentiation (2006) 13:798-815; Meylan, E., et al., Nature (2006) 442:39-44; and Strober, W., et al., Nature Reviews (2006) 6:9-20.

Engineering Expression Constructs

Also provided are expression construct encoding a co-stimulatory polypeptide and a ligand-binding domain, all operatively linked. More particularly, more than one ligand-binding domain is used in the expression construct. Yet further, the expression construct contains a membrane-targeting sequence. One with skill in the art realizes that appropriate expression constructs may include a co-stimulatory polypeptide element on either side of the above FKBP ligand-binding elements. The expression construct may be inserted into a vector, for example a viral vector or plasmid.

A. Co-Stimulatory Polypeptides

Co-stimulatory polypeptide molecules are capable of amplifying the T-cell-mediated response by upregulating dendritic cell expression of antigen presentation molecules. Co-stimulatory proteins that are contemplated include, for example, but are not limited to, the members of tumor necrosis factor (TNF) family (i.e., CD40, RANK/TRANCE-R, OX40, 4-1B), Toll-like receptors, C-reactive protein receptors, Pattern Recognition Receptors, and HSP receptors. Typically, the cytoplasmic domains from these co-stimulatory polypeptides are used in the expression vector. The cytoplasmic domain from one of the various co-stimulatory polypeptides, including mutants thereof, where the recognition sequence involved in initiating transcription associated with the cytoplasmic domain is known or a gene responsive to such sequence is known.

In specific embodiments, the co-stimulatory polypeptide molecule is CD40. The CD40 molecule comprises a nucleic acid molecule which: (1) hybridizes under stringent conditions to a nucleic acid having the sequence of a known CD40 gene and (2) codes for an CD40 polypeptide. The CD40 polypeptide may, in certain examples, lack the extracellular domain. Exemplary polynucleotide sequences that encode CD40 polypeptides include, but are not limited to SEQ. ID. NO: 1 and CD40 isoforms from other species. It is contemplated that other normal or mutant variants of CD40 can be used in the present methods and compositions. Thus, a CD40 region can have an amino acid sequence that differs from the native sequence by one or more amino acid substitutions, deletions and/or insertions. For example, one or more TNF receptor associated factor (TRAF) binding regions may be eliminated or effectively eliminated (e.g., a CD40 amino acid sequence is deleted or altered such that a TRAF protein does not bind or binds with lower affinity than it binds to the native CD40 sequence). In particular embodiments, a TRAF 3 binding region is deleted or altered such that it is eliminated or effectively eliminated (e.g., amino acids 250-254 may be altered or deleted; Hauer et al., PNAS 102(8): 2874-2879 (2005)).

In certain embodiments, the present methods involve the manipulation of genetic material to produce expression constructs that encode an inducible form of CD40 (iCD40). Such methods involve the generation of expression constructs containing, for example, a heterologous nucleic acid sequence encoding CD40 cytoplasmic domain and a means for its expression. The vector can be replicated in an appropriate helper cell, viral particles may be produced therefrom, and cells infected with the recombinant virus particles.

Thus, the CD40 molecule presented herein may, for example, lack the extracellular domain. In specific embodiments, the extracellular domain is truncated or removed. It is also contemplated that the extracellular domain can be mutated using standard mutagenesis, insertions, deletions, or substitutions to produce an CD40 molecule that does not have a functional extracellular domain. A CD40 nucleic acid may have the nucleic acid sequence of SEQ. ID. NO: 1. The CD40 nucleic acids also include homologs and alleles of a nucleic acid having the sequence of SEQ. ID. NO: 1, as well as, functionally equivalent fragments, variants, and analogs of the foregoing nucleic acids. Methods of constructing an inducible CD40 vector are described in, for example, U.S. Pat. No. 7,404,950, issued Jul. 29, 2008.

In the context of gene therapy, the gene will be a heterologous polynucleotide sequence derived from a source other than the viral genome, which provides the backbone of the vector. The gene is derived from a prokaryotic or eukaryotic source such as a bacterium, a virus, yeast, a parasite, a plant, or even an animal. The heterologous DNA also is derived from more than one source, i.e., a multigene construct or a fusion protein. The heterologous DNA also may include a regulatory sequence, which is derived from one source and the gene from a different source.

B. Ligand-Binding Regions

The ligand-binding ("dimerization") domain of the expression construct can be any convenient domain that will allow for induction using a natural or unnatural ligand, for example, an unnatural synthetic ligand. The ligand-binding domain can be internal or external to the cellular membrane, depending upon the nature of the construct and the choice of ligand. A wide variety of ligand-binding proteins, including receptors, are known, including ligand-binding proteins associated with the cytoplasmic regions indicated above. As used herein the term "ligand-binding domain can be interchangeable with the term "receptor". Of particular interest are ligand-binding proteins for which ligands (for example, small organic ligands) are known or may be readily produced. These ligand-binding domains or receptors include the FKBPs and cyclophilin receptors, the steroid receptors, the tetracycline receptor, the other receptors indicated above, and the like, as well as "unnatural" receptors, which can be obtained from antibodies, particularly the heavy or light chain subunit, mutated sequences thereof, random amino acid sequences obtained by stochastic procedures, combinatorial syntheses, and the like. Examples include, for example, those described in Kopytek, S. J., et al., Chemistry & Biology 7:313-321 (2000) and in Gestwicki, J. E., et al., Combinatorial Chem. & High Throughput Screening 10:667-675 (2007); Clackson T (2006) Chem Biol Drug Des 67:440-2; Clackson, T. "Controlling Protein-Protein Interactions Using Chemical Inducers and Disrupters of Dimerization," in *Chemical Biology: From Small Molecules to Systems Biology and Drug Design* (Schreiber, s., et al., eds., Wiley, 2007)).

For the most part, the ligand-binding domains or receptor domains will be at least about 50 amino acids, and fewer than about 350 amino acids, usually fewer than 200 amino acids, either as the natural domain or truncated active portion thereof. The binding domain may, for example, be small (<25 kDa, to allow efficient transfection in viral vectors), monomeric (this rules out the avidin-biotin system), nonimmunogenic, and should have synthetically accessible, cell permeable, nontoxic ligands that can be configured for dimerization.

The receptor domain can be intracellular or extracellular depending upon the design of the expression construct and the availability of an appropriate ligand. For hydrophobic ligands, the binding domain can be on either side of the membrane, but for hydrophilic ligands, particularly protein ligands, the binding domain will usually be external to the cell membrane, unless there is a transport system for internalizing the ligand in a form in which it is available for binding. For an intracellular receptor, the construct can encode a signal peptide and transmembrane domain 5' or 3' of the receptor domain sequence or may have a lipid attachment signal sequence 5' of the receptor domain sequence. Where the receptor domain is between the signal peptide and the transmembrane domain, the receptor domain will be extracellular.

The portion of the expression construct encoding the receptor can be subjected to mutagenesis for a variety of reasons. The mutagenized protein can provide for higher binding affinity, allow for discrimination by the ligand of the naturally occurring receptor and the mutagenized receptor, provide opportunities to design a receptor-ligand pair, or the like. The change in the receptor can involve changes in amino acids known to be at the binding site, random mutagenesis using combinatorial techniques, where the codons for the amino acids associated with the binding site or other amino acids associated with conformational changes can be subject to mutagenesis by changing the codon(s) for the particular amino acid, either with known changes or randomly, expressing the resulting proteins in an appropriate prokaryotic host and then screening the resulting proteins for binding.

Antibodies and antibody subunits, e.g., heavy or light chain, particularly fragments, more particularly all or part of the variable region, or fusions of heavy and light chain to create high-affinity binding, can be used as the binding domain. Antibodies that are contemplated include ones that are an ectopically expressed human product, such as an extracellular domain that would not trigger an immune response and generally not expressed in the periphery (i.e., outside the CNS/brain area). Such examples, include, but are not limited to low affinity nerve growth factor receptor (LNGFR), and embryonic surface proteins (i.e., carcinoembryonic antigen).

Yet further, antibodies can be prepared against haptenic molecules, which are physiologically acceptable, and the individual antibody subunits screened for binding affinity. The cDNA encoding the subunits can be isolated and modified by deletion of the constant region, portions of the variable region, mutagenesis of the variable region, or the like, to obtain a binding protein domain that has the appropriate affinity for the ligand. In this way, almost any physiologically acceptable haptenic compound can be employed as the ligand or to provide an epitope for the ligand. Instead of antibody units, natural receptors can be employed, where the binding domain is known and there is a useful ligand for binding.

C. Oligomerization

The transduced signal will normally result from ligand-mediated oligomerization of the chimeric protein molecules, i.e., as a result of oligomerization following ligand-binding, although other binding events, for example allosteric activation, can be employed to initiate a signal. The construct of the chimeric protein will vary as to the order of the various domains and the number of repeats of an individual domain.

For multimerizing the receptor, the ligand for the ligand-binding domains/receptor domains of the chimeric surface membrane proteins will usually be multimeric in the sense that it will have at least two binding sites, with each of the binding sites capable of binding to the ligand receptor domain. Desirably, the subject ligands will be a dimer or higher order oligomer, usually not greater than about tetrameric, of small synthetic organic molecules, the individual molecules typically being at least about 150 Da and less than about 5 kDa, usually less than about 3 kDa. A variety of pairs of synthetic ligands and receptors can be employed. For example, in embodiments involving natural receptors, dimeric FK506 can be used with an FKBP12 receptor, dimerized cyclosporin A can be used with the cyclophilin receptor, dimerized estrogen with an estrogen receptor, dimerized glucocorticoids with a glucocorticoid receptor, dimerized tetracycline with the tetracycline receptor, dimerized vitamin D with the vitamin D receptor, and the like. Alternatively higher orders of the ligands, e.g., trimeric can be used. For embodiments involving unnatural receptors, e.g., antibody subunits, modified antibody subunits or modified receptors, and the like, any of a large variety of compounds can be used. A significant characteristic of these ligand units is that each binding site is able to bind the receptor with high affinity and they are able to be dimerized chemically. Also, those of ordinary skill in the art are aware of methods to balance the hydrophobicity/hydrophilicity of the ligands so that they are able to dissolve in serum at functional levels, yet diffuse across plasma membranes for most applications.

In certain embodiments, the present methods utilize the technique of chemically induced dimerization (CID) to produce a conditionally controlled protein or polypeptide. In addition to this technique being inducible, it also is reversible, due to the degradation of the labile dimerizing agent or administration of a monomeric competitive inhibitor.

The CID system uses synthetic bivalent ligands to rapidly crosslink signaling molecules that are fused to ligand-binding domains. This system has been used to trigger the oligomerization and activation of cell surface (Spencer, D. M., et al., Science, 1993. 262: p. 1019-1024; Spencer D. M. et al., Curr Biol 1996, 6:839-847; Blau, C. A. et al., Proc Natl Acad. Sci. USA 1997, 94:3076-3081), or cytosolic proteins (Luo, Z. et al., Nature 1996, 383:181-185; MacCorkle, R. A. et al., Proc Natl Acad Sci USA 1998, 95:3655-3660), the recruitment of transcription factors to DNA elements to modulate transcription (Ho, S, N. et al., Nature 1996, 382:822-826; Rivera, V. M. et al., Nat. Med. 1996, 2:1028-1032) or the recruitment of signaling molecules to the plasma membrane to stimulate signaling (Spencer D. M. et al., Proc. Natl. Acad. Sci. USA 1995, 92:9805-9809; Holsinger, L. J. et al., Proc. Natl. Acad. Sci. USA 1995, 95:9810-9814).

The CID system is based upon the notion that surface receptor aggregation effectively activates downstream signaling cascades. In the simplest embodiment, the CID system uses a dimeric analog of the lipid permeable immunosuppressant drug, FK506, which loses its normal bioactivity while gaining the ability to crosslink molecules genetically fused to the FK506-binding protein, FKBP12. By fusing one or more FKBPs and a myristoylation sequence to the cytoplasmic signaling domain of a target receptor, one can stimulate signaling in a dimerizer drug-dependent, but ligand and ectodomain-independent manner. This provides the system with temporal control, reversibility using monomeric drug analogs, and enhanced specificity. The high affinity of third-generation AP20187/AP1903 CIDs for their binding domain, FKBP12 permits specific activation of the recombinant receptor in vivo without the induction of non-specific side effects through endogenous FKBP12. In addition, the synthetic ligands are resistant to protease degradation, making them more efficient at activating receptors in vivo than most delivered protein agents.

The ligands used are capable of binding to two or more of the ligand-binding domains. One skilled in the art realizes that the chimeric proteins may be able to bind to more than one ligand when they contain more than one ligand-binding domain. The ligand is typically a non-protein or a chemical. Exemplary ligands include, but are not limited to dimeric FK506 (e.g., FK1012).

Since the mechanism of CD40 activation is fundamentally based on trimerization, this receptor is particularly amenable to the CID system. CID regulation provides the system with 1) temporal control, 2) reversibility by addition of a non-active monomer upon signs of an autoimmune reaction, and 3) limited potential for non-specific side effects. In addition, inducible in vivo DC CD40 activation would circumvent the requirement of a second "danger" signal normally required for complete induction of CD40 signaling and would potentially promote DC survival in situ allowing for enhanced T cell priming. Thus, engineering DC vaccines to express iCD40 amplifies the T cell-mediated killing response by upregulating DC expression of antigen presentation molecules, adhesion molecules, TH1 promoting cytokines, and pro-survival factors.

Other dimerization systems contemplated include the coumermycin/DNA gyrase B system. Coumermycin-induced dimerization activates a modified Raf protein and stimulates the MAP kinase cascade. See Farrar et al., 1996.

D. Membrane-Targeting

A membrane-targeting sequence provides for transport of the chimeric protein to the cell surface membrane, where the same or other sequences can encode binding of the chimeric protein to the cell surface membrane. Molecules in association with cell membranes contain certain regions that facilitate the membrane association, and such regions can be incorporated into a chimeric protein molecule to generate membrane-targeted molecules. For example, some proteins contain sequences at the N-terminus or C-terminus that are acylated, and these acyl moieties facilitate membrane association. Such sequences are recognized by acyltransferases and often conform to a particular sequence motif. Certain acylation motifs are capable of being modified with a single acyl moiety (often followed by several positively charged residues (e.g. human c-Src: M-G-S-N-K-S-K-P-K-D-A-S-Q-R-R-R (SEQ ID NO: 17)) to improve association with anionic lipid head groups) and others are capable of being modified with multiple acyl moieties. For example the N-terminal sequence of the protein tyrosine kinase Src can comprise a single myristoyl moiety. Dual acylation regions are located within the N-terminal regions of certain protein kinases, such as a subset of Src family members (e.g., Yes, Fyn, Lck) and G-protein alpha subunits. Such dual acylation regions often are located within the first eighteen amino acids of such proteins, and conform to the sequence motif Met-Gly-Cys-Xaa-Cys, (SEQ ID NO: 18) where the Met is cleaved, the Gly is N-acylated and one of the Cys residues is S-acylated. The Gly often is myristoylated and a Cys can be palmitoylated. Acylation regions conforming to the sequence motif Cys-Ala-Ala-Xaa (SEQ ID NO: 54), (so called "CAAX boxes"), which can modified with C15 or C10 isoprenyl moieties, from the C-terminus of G-protein gamma subunits and other proteins (e.g., World Wide Web address ebi.ac.uk/interpro/DisplaylproEntry?ac=IPR001230) also can be utilized. These and other acylation motifs are known to the person of ordinary skill in the art (e.g., Gauthier-Campbell et al., Molecular Biology of the Cell 15: 2205-2217 (2004); Glabati et al., Biochem. J. 303: 697-700 (1994) and Zlakine et al., J. Cell Science 110: 673-679 (1997)), and can be incorporated in chimeric molecules to induce membrane localization. In certain embodiments, a native sequence from a protein containing an acylation motif is incorporated into a chimeric protein. For example, in some embodiments, an N-terminal portion of Lck, Fyn or Yes or a G-protein alpha subunit, such as the first twenty-five N-terminal amino acids or fewer from such proteins (e.g., about 5 to about 20 amino acids, about 10 to about 19 amino acids, or about 15 to about 19 amino acids of the native sequence with optional mutations), may be incorporated within the N-terminus of a chimeric protein. In certain embodiments, a C-terminal sequence of about 25 amino acids or less from a G-protein gamma subunit containing a CAAX box motif sequence (e.g., about 5 to about 20 amino acids, about 10 to about 18 amino acids, or about 15 to about 18 amino acids of the native sequence with optional mutations) can be linked to the C-terminus of a chimeric protein.

In some embodiments, an acyl moiety has a log p value of +1 to +6, and sometimes has a log p value of +3 to +4.5. Log p values are a measure of hydrophobicity and often are derived from octanol/water partitioning studies, in which molecules with higher hydrophobicity partition into octanol with higher frequency and are characterized as having a higher log p value. Log p values are published for a number of lipophilic molecules and log p values can be calculated using known partitioning processes (e.g., Chemical Reviews, Vol. 71, Issue 6, page 599, where entry 4493 shows lauric acid having a log p value of 4.2). Any acyl moiety can be linked to a peptide composition described above and tested for antimicrobial activity using known methods and those described hereafter. The acyl moiety sometimes is a C1-C20 alkyl, C2-C20 alkenyl, C2-C20 alkynyl, C3-C6 cycloalkyl, C1-C4 haloalkyl, C4-C12 cyclalkylalkyl, aryl, substituted aryl, or aryl (C1-C4) alkyl, for example. Any acyl-containing moiety sometimes is a fatty acid, and examples of fatty acid moieties are propyl (C3), butyl (C4), pentyl (C5), hexyl (C6), heptyl (C7), octyl (C8), nonyl (C9), decyl (C10), undecyl (C11), lauryl (C12), myristyl (C14), palmityl (C16), stearyl (C18), arachidyl (C20), behenyl (C22) and lignoceryl moieties (C24), and each moiety can contain 0, 1, 2, 3, 4, 5, 6, 7 or 8 unsaturations (i.e., double bonds). An acyl moiety sometimes is a lipid molecule, such as a phosphatidyl lipid (e.g., phosphatidyl serine, phosphatidyl inositol, phosphatidyl ethanolamine, phosphatidyl choline), sphingolipid (e.g., shingomyelin, sphingosine, ceramide, ganglioside, cerebroside), or modified versions thereof. In certain embodiments, one, two, three, four or five or more acyl moieties are linked to a membrane association region.

A chimeric protein herein also may include a single-pass or multiple pass transmembrane sequence (e.g., at the N-terminus or C-terminus of the chimeric protein). Single pass transmembrane regions are found in certain CD molecules, tyrosine kinase receptors, serine/threonine kinase receptors, TGFbeta, BMP, activin and phosphatases. Single pass transmembrane regions often include a signal peptide region and a transmembrane region of about 20 to about 25 amino acids, many of which are hydrophobic amino acids and can form an alpha helix. A short track of positively charged amino acids often follows the transmembrane span to anchor the protein in the membrane. Multiple pass proteins include ion pumps, ion channels, and transporters, and include two or more helices that span the membrane multiple times. All or substantially all of a multiple pass protein sometimes is incorporated in a chimeric protein. Sequences for single pass and multiple pass transmembrane regions are known and can be selected for incorporation into a chimeric protein molecule by the person of ordinary skill in the art.

Any membrane-targeting sequence can be employed that is functional in the host and may, or may not, be associated with one of the other domains of the chimeric protein. In some embodiments, such sequences include, but are not limited to myristoylation-targeting sequence, palmitoylation-targeting sequence, prenylation sequences (i.e., farnesylation, geranylgeranylation, CAAX Box), protein-protein interaction motifs or transmembrane sequences (utilizing signal peptides) from receptors. Examples include those described in, for example, ten Klooster J P et al, Biology of the Cell (2007) 99, 1-12, Vincent, S., et al., Nature Biotechnology 21:936-40, 1098 (2003).

Additional protein domains exist that can increase protein retention at various membranes. For example, an ~120 amino acid pleckstrin homology (PH) domain is found in over 200 human proteins that are typically involved in intracellular signaling. PH domains can bind various phosphatidylinositol (PI) lipids within membranes (e.g. PI (3,4,5)-$P_3$, PI (3,4)-$P_2$, PI (4,5)-$P_2$) and thus play a key role in recruiting proteins to different membrane or cellular compartments. Often the phosphorylation state of PI lipids is regulated, such as by PI-3 kinase or PTEN, and thus, interaction of membranes with PH domains is not as stable as by acyl lipids.

E. Selectable Markers

In certain embodiments, the expression constructs contain nucleic acid constructs whose expression is identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) are employed. Immunologic surface markers containing the extracellular, non-signaling domains or various proteins (e.g. CD34, CD19, LNGFR) also can be employed, permitting a straightforward method for magnetic or fluorescence antibody-mediated sorting. The selectable marker employed is not believed to be important, so long as it is capable of being expressed simultaneously with the nucleic acid encoding a gene product. Further examples of selectable markers are well known to one of skill in the art and include reporters such as EGFP, beta-gal or chloramphenicol acetyltransferase (CAT).

F. Control Regions

1. Promoters

The particular promoter employed to control the expression of a polynucleotide sequence of interest is not believed to be important, so long as it is capable of directing the expression of the polynucleotide in the targeted cell. Thus, where a human cell is targeted, it may be preferable to position the polynucleotide sequence-coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it is desirable to prohibit or reduce expression of one or more of the transgenes. Examples of transgenes that are toxic to the producer cell line are pro-apoptotic and cytokine genes. Several inducible promoter systems are available for production of viral vectors where the transgene products are toxic (add in more inducible promoters).

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter, which drives expression of the gene of interest, is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, Proc. Natl. Acad. Sci. USA, 89:5547-5551, 1992; Gossen et al., Science, 268:1766-1769, 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system may be used so that the producer cells could be grown in the presence of tetracycline or doxycycline and prevent expression of a potentially toxic transgene, but when the vector is introduced to the patient, the gene expression would be constitutively on.

In some circumstances, it is desirable to regulate expression of a transgene in a gene therapy vector. For example, different viral promoters with varying strengths of activity are utilized depending on the level of expression desired. In mammalian cells, the CMV immediate early promoter is often used to provide strong transcriptional activation. The CMV promoter is reviewed in Donnelly, J. J., et al., 1997. Annu. Rev. Immunol. 15:617-48. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that are used depending on the desired effect include SV40, RSV LTR, HIV-1 and HIV-2 LTR, adenovirus promoters such as from the E1A, E2A, or MLP region, AAV LTR, HSV-TK, and avian sarcoma virus.

Similarly tissue specific promoters are used to effect transcription in specific tissues or cells so as to reduce potential toxicity or undesirable effects to non-targeted tissues. These promoters may result in reduced expression compared to a stronger promoter such as the CMV promoter, but may also result in more limited expression, and immunogenicity. (Bojak, A., et al., 2002. Vaccine. 20:1975-79; Cazeaux., N., et al., 2002. Vaccine 20:3322-31). For example, tissue specific promoters such as the PSA associated promoter or prostate-specific glandular kallikrein, or the muscle creatine kinase gene may be used where appropriate.

In certain indications, it is desirable to activate transcription at specific times after administration of the gene therapy vector. This is done with such promoters as those that are hormone or cytokine regulatable. Cytokine and inflammatory protein responsive promoters that can be used include K and T kininogen (Kageyama et al., (1987) J. Biol. Chem., 262, 2345-2351), c-fos, TNF-alpha, C-reactive protein (Arcone, et al., (1988) Nucl. Acids Res., 16(8), 3195-3207), haptoglobin (Oliviero et al., (1987) EMBO J., 6, 1905-1912), serum amyloid A2, C/EBP alpha, IL-1, IL-6 (Poli and Cortese, (1989) Proc. Nat'l Acad. Sci. USA, 86, 8202-8206), Complement C3 (Wilson et al., (1990) Mol. Cell. Biol., 6181-6191), IL-8, alpha-1 acid glycoprotein (Prowse and Baumann, (1988) Mol Cell Biol, 8, 42-51), alpha-1 antitrypsin, lipoprotein lipase (Zechner et al., Mol. Cell. Biol., 2394-2401, 1988), angiotensinogen (Ron, et al., (1991) Mol. Cell. Biol., 2887-2895), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 anti-chymotrypsin. Other promoters include, for example, SV40, MMTV, Human Immunodeficiency Virus (MV), Moloney virus, ALV, Epstein Barr virus, Rous Sarcoma virus, human actin, myosin, hemoglobin, and creatine.

It is envisioned that any of the above promoters alone or in combination with another can be useful depending on the action desired. Promoters, and other regulatory elements, are selected by those of ordinary skill in the art such that they are functional in the desired cells or tissue. In addition, this list of promoters should not be construed to be exhaustive or limiting, those of skill in the art will know of other promoters that are used in conjunction with the promoters and methods disclosed herein.

2. Enhancers

Enhancers are genetic elements that increase transcription from a promoter located at a distant position on the same molecule of DNA. Early examples include the enhancers associated with immunoglobulin and T cell receptors that both flank the coding sequence and occur within several introns. Many viral promoters, such as CMV, SV40, and retroviral LTRs are closely associated with enhancer activity and are often treated like single elements. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance and often independent of orientation; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization. A subset of enhancers are locus-control regions (LCRs) that can not only increase transcriptional activity, but (along with insulator elements) can also help to insulate the transcriptional element from adjacent sequences when integrated into the genome.

Any promoter/enhancer combination (as per the Eukaryotic Promoter Data Base EPDB) can be used to drive expression of the gene, although many will restrict expression to a particular tissue type or subset of tissues. (reviewed in, for example, Kutzler, M. A., and Weiner, D. B., 2008. Nature Reviews Genetics 9:776-88). Examples include, but are not limited to, enhancers from the human actin, myosin, hemoglobin, muscle creatine kinase, sequences, and from viruses CMV, RSV, and EBV. Those of ordinary skill in the art will be able to select appropriate enhancers for particular applications. Eukaryotic cells can support cytoplasmic transcription from certain bacterial promoters if the appropriate bacterial polymerase is provided, either as part of the delivery complex or as an additional genetic expression construct.

3. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the present methods, and any such sequence is employed such as human or bovine growth hormone and SV40 polyadenylation signals and LTR polyadenylation signals. One non-limiting example is the SV40 polyadenylation signal present in the pCEP3 plasmid (Invitrogen, Carlsbad, Calif.). Also contemplated as an element of the expression cassette is a terminator. These elements can serve to enhance message levels and to minimize read through from the cassette into other sequences. Termination or poly(A) signal sequences may be, for example, positioned about 11-30 nucleotides downstream from a conserved sequence (AAUAAA) at the 3' end of the mRNA. (Montgomery, D. L., et al., 1993. DNA Cell Biol. 12:777-83; Kutzler, M. A., and Weiner, D. B., 2008. Nature Rev. Gen. 9:776-88).

4. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be in-frame with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements is used to create multigene, or polycistronic messages. IRES elements are able to bypass the ribosome-scanning model of 5' methylated cap-dependent translation and begin translation at internal sites (Pelletier and Sonenberg, Nature, 334:320-325, 1988). IRES elements from two members of the picornavirus family (polio and encephalomyocarditis) have been described (Pelletier and Sonenberg, 1988), as well an IRES from a mammalian message (Macejak and Sarnow, Nature, 353:90-94, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

G. Sequence Optimization

Protein production may also be increased by optimizing the codons in the transgene. Species specific codon changes, known to those of ordinary skill in the art may be used to increase protein production. Also, codons may be optimized to produce an optimized RNA, which may result in more efficient translation. By optimizing the codons to be incorporated in the RNA, elements such as those that result in a secondary structure that causes instability, secondary mRNA structures that can, for example, inhibit ribosomal binding, or cryptic sequences that can inhibit nuclear export of mRNA can be removed. (Kutzler, M. A., and Weiner, D. B., 2008. Nature Rev. Gen. 9:776-88; Yan., J. et al., 2007. Mol. Ther. 15:411-21; Cheung, Y. K., et al., 2004. Vaccine 23:629-38; Narum., D. L., et al., 2001. 69:7250-55; Yadava, A., and Ockenhouse, C. F., 2003. Infect. Immun. 71:4962-69; Smith., J. M., et al., 2004. AIDS Res. Hum. Retroviruses 20:1335-47; Zhou, W., et al., 2002. Vet. Microbiol. 88:127-51; Wu, X., et al., 2004. Biochem. Biophys. Res. Commun. 313:89-96; Zhang, W., et al., 2006. Biochem. Biophys. Res. Commun. 349:69-78; Deml, L. A., et al., 2001. J. Virol. 75:1099-11001; Schneider, R. M., et al., 1997. J. Virol. 71:4892-4903; Wang, S. D., et al., 2006. Vaccine 24:4531-40; zur Megede, J., et al., 2000. J. Virol. 74:2628-2635).

H. Leader Sequences

Leader sequences may be added, as known to those of ordinary skill in the art, to enhance the stability of mRNA and result in more efficient translation. The leader sequence is usually involved in targeting the mRNA to the endoplasmic reticulum. Examples include, the signal sequence for the HIV-1 envelope glycoprotein (Env), which delays its own cleavage, and the IgE gene leader sequence (Kutzler, M. A., and Weiner, D. B., 2008. Nature Rev. Gen. 9:776-88; Li, V., et al., 2000. Virology 272:417-28; Xu, Z. L., et al. 2001. Gene 272:149-56; Malin, A. S., et al., 2000. Microbes Infect. 2:1677-85; Kutzler, M. A., et al., 2005. J. Immunol. 175:112-125; Yang., J. S., et al., 2002. Emerg. Infect. Dis. 8:1379-84; Kumar., S., et al., 2006. DNA Cell Biol. 25:383-92; Wang, S., et al., 2006. Vaccine 24:4531-40). The IgE leader may be used to enhance insertion into the endoplasmic reticulum (Tepler, I, et al. (1989) J. Biol. Chem. 264:5912).

Expression of the transgenes may be optimized and/or controlled by the selection of appropriate methods for optimizing expression, known to those of ordinary skill in the art. These methods include, for example, optimizing promoters, delivery methods, and gene sequences, (for example, as presented in Laddy, D. J., et al., 2008. PLoS. ONE 3 e2517; Kutzler, M. A., and Weiner, D. B., 2008. Nature Rev. Gen. 9:776-88).

Methods of Gene Transfer

In order to mediate the effect of the transgene expression in a cell, it will be necessary to transfer the expression constructs into a cell. Such transfer may employ viral or non-viral methods of gene transfer. This section provides a discussion of methods and compositions of gene transfer.

A transformed cell comprising an expression vector is generated by introducing into the cell the expression vector. Suitable methods for polynucleotide delivery for transformation of an organelle, a cell, a tissue or an organism for use with the current methods include virtually any method by which a polynucleotide (e.g., DNA) can be introduced into an organelle, a cell, a tissue or an organism, as described herein or as would be known to one of ordinary skill in the art.

A host cell can, and has been, used as a recipient for vectors. Host cells may be derived from prokaryotes or eukaryotes, depending upon whether the desired result is replication of the vector or expression of part or all of the vector-encoded polynucleotide sequences. Numerous cell lines and cultures are available for use as a host cell, and they can be obtained through the American Type Culture Collection (ATCC), which is an organization that serves as an archive for living cultures and genetic materials. In specific embodiments, the host cell is a dendritic cell, which is an antigen-presenting cell.

It is well within the knowledge and skill of a skilled artisan to determine an appropriate host. Generally this is based on the vector backbone and the desired result. A plasmid or cosmid, for example, can be introduced into a prokaryote host cell for replication of many vectors. Bacterial cells used as host cells for vector replication and/or expression include DH5alpha, JM109, and KC8, as well as a number of commercially available bacterial hosts such as SURE® Competent Cells and SOLOPACK Gold Cells (STRATAGENE®, La Jolla, Calif.). Alternatively, bacterial cells such as *E. coli* LE392 could be used as host cells for phage viruses. Eukaryotic cells that can be used as host cells include, but are not limited to yeast, insects and mammals. Examples of mammalian eukaryotic host cells for replication and/or expression of a vector include, but are not limited to, HeLa, NIH3T3, Jurkat, 293, COS, CHO, Saos, and PC12. Examples of yeast strains include, but are not limited to, YPH499, YPH500 and YPH501.

Nucleic acid vaccines are known to those of ordinary skill in the art, and include, for example, non-viral DNA vectors, "naked" DNA and RNA, and viral vectors. Methods of transforming cells with these vaccines, and for optimizing the expression of genes included in these vaccines are known and are also discussed herein.

A. Examples of Methods of Nucleic Acid or Viral Vector Transfer

1. Ex Vivo Transformation

Methods for transfecting vascular cells and tissues removed from an organism in an ex vivo setting are known to those of skill in the art. For example, canine endothelial cells have been genetically altered by retroviral gene transfer in vitro and transplanted into a canine (Wilson et al., Science, 244:1344-1346, 1989). In another example, Yucatan minipig endothelial cells were transfected by retrovirus in vitro and transplanted into an artery using a double-balloon catheter (Nabel et al., Science, 244(4910):1342-1344, 1989). Thus, it is contemplated that cells or tissues may be removed and transfected ex vivo using the polynucleotides presented herein. In particular aspects, the transplanted cells or tissues may be placed into an organism. Thus, it is well within the knowledge of one skilled in the art to isolate dendritic cells from an animal, transfect the cells with the expression vector and then administer the transfected or transformed cells back to the animal.

2. Injection

In certain embodiments, a polynucleotide may be delivered to an organelle, a cell, a tissue or an organism via one or more injections (i.e., a needle injection), such as, for example, subcutaneously, intradermally, intramuscularly, intravenously, intraperitoneally, etc. Methods of injection of vaccines are well known to those of ordinary skill in the art (e.g., injection of a composition comprising a saline solution). Further embodiments include the introduction of a polynucleotide by direct microinjection. The amount of the expression vector used may vary upon the nature of the antigen as well as the organelle, cell, tissue or organism used.

Intradermal, intranodal, or intralymphatic injections are some of the more commonly used methods of DC administration. Intradermal injection is characterized by a low rate of absorption into the bloodstream but rapid uptake into the lymphatic system. The presence of large numbers of Langerhans dendritic cells in the dermis will transport intact as well as processed antigen to draining lymph nodes. Proper site preparation is necessary to perform this correctly (i.e., hair must be clipped in order to observe proper needle placement). Intranodal injection allows for direct delivery of antigen to lymphoid tissues. Intralymphatic injection allows direct administration of DCs.

3. Electroporation

In certain embodiments, a polynucleotide is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference).

Transfection of eukaryotic cells using electroporation has been quite successful. Mouse pre-B lymphocytes have been transfected with human kappa-immunoglobulin genes (Potter et al., (1984) Proc. Nat'l Acad. Sci. USA, 81, 7161-7165), and rat hepatocytes have been transfected with the chloramphenicol acetyltransferase gene (Tur-Kaspa et al., (1986) Mol. Cell. Biol., 6, 716-718) in this manner.

4. Calcium Phosphate

In other embodiments, a polynucleotide is introduced to the cells using calcium phosphate precipitation. Human KB cells have been transfected with adenovirus 5 DNA (Graham and van der Eb, (1973) Virology, 52, 456-467) using this technique. Also in this manner, mouse L(A9), mouse C127, CHO, CV-1, BHK, NIH3T3 and HeLa cells were transfected with a neomycin marker gene (Chen and Okayama, Mol. Cell. Biol., 7(8):2745-2752, 1987), and rat hepatocytes were transfected with a variety of marker genes (Rippe et al., Mol. Cell Biol., 10:689-695, 1990).

5. DEAE-Dextran

In another embodiment, a polynucleotide is delivered into a cell using DEAE-dextran followed by polyethylene glycol. In this manner, reporter plasmids were introduced into mouse myeloma and erythroleukemia cells (Gopal, T. V., Mol Cell Biol. 1985 May; 5(5):1188-90).

6. Sonication Loading

Additional embodiments include the introduction of a polynucleotide by direct sonic loading. LTK-fibroblasts have been transfected with the thymidine kinase gene by sonication loading (Fechheimer et al., (1987) Proc. Nat'l Acad. Sci. USA, 84, 8463-8467).

7. Liposome-Mediated Transfection

In a further embodiment, a polynucleotide may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, (1991) In: Liver Diseases, Targeted Diagnosis and Therapy Using Specific Receptors and Ligands. pp. 87-104). Also contemplated is a polynucleotide complexed with Lipofectamine (Gibco BRL) or Superfect (Qiagen).

8. Receptor Mediated Transfection

Still further, a polynucleotide may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity.

Certain receptor-mediated gene targeting vehicles comprise a cell receptor-specific ligand and a polynucleotide-binding agent. Others comprise a cell receptor-specific ligand to which the polynucleotide to be delivered has been operatively attached. Several ligands have been used for receptor-mediated gene transfer (Wu and Wu, (1987) J. Biol. Chem., 262, 4429-4432; Wagner et al., Proc. Natl. Acad. Sci. USA, 87(9):3410-3414, 1990; Perales et al., Proc. Natl. Acad. Sci. USA, 91:4086-4090, 1994; Myers, EPO 0273085), which establishes the operability of the technique. Specific delivery in the context of another mammalian cell type has been described (Wu and Wu, Adv. Drug Delivery Rev., 12:159-167, 1993; incorporated herein by reference). In certain aspects, a ligand is chosen to correspond to a receptor specifically expressed on the target cell population.

In other embodiments, a polynucleotide delivery vehicle component of a cell-specific polynucleotide-targeting vehicle may comprise a specific binding ligand in combination with a liposome. The polynucleotide(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a polynucleotide to cells that exhibit upregulation of the EGF receptor.

In still further embodiments, the polynucleotide delivery vehicle component of a targeted delivery vehicle may be a liposome itself, which may, for example, comprise one or more lipids or glycoproteins that direct cell-specific binding. For example, lactosyl-ceramide, a galactose-terminal asialoganglioside, have been incorporated into liposomes and observed an increase in the uptake of the insulin gene by hepatocytes (Nicolau et al., (1987) Methods Enzymol., 149, 157-176). It is contemplated that the tissue-specific transforming constructs may be specifically delivered into a target cell in a similar manner.

9. Microprojectile Bombardment

Microprojectile bombardment techniques can be used to introduce a polynucleotide into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., (1987) Nature, 327, 70-73). There are a wide variety of microprojectile bombardment techniques known in the art, many of which are applicable to the present methods.

In this microprojectile bombardment, one or more particles may be coated with at least one polynucleotide and delivered into cells by a propelling force. Several devices for accelerating small particles have been developed. One such device relies on a high voltage discharge to generate an electrical current, which in turn provides the motive force (Yang et al., (1990) Proc. Nat'l Acad. Sci. USA, 87, 9568-9572). The microprojectiles used have consisted of biologically inert substances such as tungsten or gold particles or beads. Exemplary particles include those comprised of tungsten, platinum, and, in certain examples, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

B. Examples of Methods of Viral Vector-Mediated Transfer

In certain embodiments, a transgene is incorporated into a viral particle to mediate gene transfer to a cell. Typically, the virus simply will be exposed to the appropriate host cell under physiologic conditions, permitting uptake of the virus. The present methods are advantageously employed using a variety of viral vectors, as discussed below.

1. Adenovirus

Adenovirus is particularly suitable for use as a gene transfer vector because of its mid-sized DNA genome, ease of manipulation, high titer, wide target-cell range, and high infectivity. The roughly 36 kb viral genome is bounded by 100-200 base pair (bp) inverted terminal repeats (ITR), in which are contained cis-acting elements necessary for viral DNA replication and packaging. The early (E) and late (L)

regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, M. J. (1990) Radiother Oncol., 19, 197-218). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence, which makes them useful for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present methods, it is possible to achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay, R. T., et al., J Mol Biol. 1984 Jun. 5; 175(4):493-510). Therefore, inclusion of these elements in an adenoviral vector should permit replication.

In addition, the packaging signal for viral encapsulation is localized between 194-385 bp (0.5-1.1 map units) at the left end of the viral genome (Hearing et al., J. (1987) Virol., 67, 2555-2558). This signal mimics the protein recognition site in bacteriophage lambda DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., Gene, 101:195-202, 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element derives from the packaging function of adenovirus.

It has been shown that a packaging signal for adenovirus exists in the left end of the conventional adenovirus map (Tibbetts et. al. (1977) Cell, 12, 243-249). Later studies showed that a mutant with a deletion in the E1A (194-358 bp) region of the genome grew poorly even in a cell line that complemented the early (E1A) function (Hearing and Shenk, (1983) J. Mol. Biol. 167, 809-822). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved toward the interior of the Ad5 DNA molecule (Hearing et al., J. (1987) Virol., 67, 2555-2558).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals is packaged selectively when compared to the helpers. If the preference is great enough, stocks approaching homogeneity should be achieved.

To improve the tropism of ADV constructs for particular tissues or species, the receptor-binding fiber sequences can often be substituted between adenoviral isolates. For example the Coxsackie-adenovirus receptor (CAR) ligand found in adenovirus 5 can be substituted for the CD46-binding fiber sequence from adenovirus 35, making a virus with greatly improved binding affinity for human hematopoietic cells. The resulting "pseudotyped" virus, Ad5f35, has been the basis for several clinically developed viral isolates. Moreover, various biochemical methods exist to modify the fiber to allow re-targeting of the virus to target cells, such as dendritic cells. Methods include use of bifunctional antibodies (with one end binding the CAR ligand and one end binding the target sequence), and metabolic biotinylation of the fiber to permit association with customized avidin-based chimeric ligands. Alternatively, one could attach ligands (e.g. anti-CD205 by heterobifunctional linkers (e.g. PEG-containing), to the adenovirus particle.

2. Retrovirus

The retroviruses are a group of single-stranded RNA viruses characterized by an ability to convert their RNA to double-stranded DNA in infected cells by a process of reverse-transcription (Coffin, (1990) In: Virology, ed., New York: Raven Press, pp. 1437-1500). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and psi components is constructed (Mann et al., (1983) Cell, 33, 153-159). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas, J. F., and Rubenstein, J. L. R., (1988) In: Vectors: a Survey of Molecular Cloning Vectors and Their Uses, Rodriquez and Denhardt, Eds.). Nicolas and Rubenstein; Temin et al., (1986) In: Gene Transfer, Kucherlapati (ed.), New York: Plenum Press, pp. 149-188; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., (1975) Virology, 67, 242-248).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., (1989) Proc. Nat'l Acad. Sci. USA, 86, 9079-9083). Using antibodies against major histocompatibility complex class I and class II antigens, the infection of a variety of human cells that bore those surface antigens was demonstrated with an ecotropic virus in vitro (Roux et al., 1989).

3. Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low-level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., J. Virol., 61:3096-3101 (1987)), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, (1995) Ann. N.Y. Acad. Sci., 770; 79-90; Chatteijee, et al., (1995) Ann. N.Y. Acad. Sci., 770, 79-90; Ferrari et al., (1996) J. Virol., 70, 3227-3234; Fisher et al., (1996) J. Virol., 70, 520-532; Flotte et al., Proc. Nat'l Acad. Sci. USA, 90, 10613-10617, (1993); Goodman et al. (1994), Blood, 84, 1492-1500; Kaplitt et al., (1994) Nat'l Genet., 8, 148-153; Kaplitt, M. G., et al., Ann Thorac Surg. 1996 December; 62(6):1669-76; Kessler et al., (1996) Proc. Nat'l Acad. Sci. USA, 93, 14082-14087; Koeberl et al., (1997) Proc. Nat'l Acad. Sci. USA, 94, 1426-1431; Mizukami et al., (1996) Virology, 217, 124-130).

AAV-mediated efficient gene transfer and expression in the lung has led to clinical trials for the treatment of cystic fibrosis (Carter and Flotte, 1995; Flotte et al., Proc. Nat'l Acad. Sci. USA, 90, 10613-10617, (1993)). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., (1996) J. Virol., 70, 520-532; Flotte et al., 1993; Kaplitt et al., 1994; 1996; Koeberl et al., 1997; McCown et al., (1996) Brain Res., 713, 99-107; Ping et al., (1996) Microcirculation, 3, 225-228; Xiao et al., (1996) J. Virol., 70, 8098-8108).

4. Other Viral Vectors

Other viral vectors are employed as expression constructs in the present methods and compositions. Vectors derived from viruses such as vaccinia virus (Ridgeway, (1988) In: Vectors: A survey of molecular cloning vectors and their uses, pp. 467-492; Baichwal and Sugden, (1986) In, Gene Transfer, pp. 117-148; Coupar et al., Gene, 68:1-10, 1988) canary poxvirus, and herpes viruses are employed. These viruses offer several features for use in gene transfer into various mammalian cells.

Once the construct has been delivered into the cell, the nucleic acid encoding the transgene are positioned and expressed at different sites. In certain embodiments, the nucleic acid encoding the transgene is stably integrated into the genome of the cell. This integration is in the cognate location and orientation via homologous recombination (gene replacement) or it is integrated in a random, non-specific location (gene augmentation). In yet further embodiments, the nucleic acid is stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

Enhancement of an Immune Response

In certain embodiments, a novel DC activation strategy is contemplated, that incorporates the manipulation of signaling co-stimulatory polypeptides that activate NF-kappaB pathways, Akt pathways, and/or p38 pathways. This DC activation system can be used in conjunction with or without standard vaccines to enhance the immune response since it replaces the requirement for CD4+ T cell help during APC activation (Bennett, S. R., et al., Nature, 1998, Jun. 4. 393: p. 478-80; Ridge, J. P., D. R. F, and P. Nature, 1998, Jun. 4. 393: p. 474-8; Schoenberger, S. P., et al., Nature, 1998, Jun. 4. 393: p. 480-3). Thus, the DC activation system presented herein enhances immune responses by circumventing the need for the generation of MHC class II-specific peptides.

In specific embodiments, the DC activation is via CD40 activation. Thus, DC activation via endogenous CD40/CD40L interactions may be subject to downregulation due to negative feedback, leading rapidly to the "IL-12 burn-out effect". Within 7 to 10 hours after CD40 activation, an alternatively spliced isoform of CD40 (type II) is produced as a secretable factor (Tone, M., et al., Proc Natl Acad Sci USA, 2001. 98(4): p. 1751-1756). Type II CD40 may act as a dominant negative receptor, downregulating signaling through CD40L and potentially limiting the potency of the immune response generated. Therefore, the present methods co-opt the natural regulation of CD40 by creating an inducible form of CD40 (iCD40), lacking the extracellular domain and activated instead by synthetic dimerizing ligands (Spencer, D. M., et al., Science, 1993. 262: p. 1019-1024) through a technology termed chemically induced dimerization (CID).

The present methods comprise methods of enhancing the immune response in an subject comprising the step of administering either the expression vector, expression construct or transduced antigen-presenting cells to the subject. The expression vector encodes a co-stimulatory polypeptide, such as iCD40.

In certain embodiments the antigen-presenting cells are comprised in an animal, such as human, non-human primate, cow, horse, pig, sheep, goat, dog, cat, or rodent. The subject may be, for example, human, for example, a patient suffering from an infectious disease, and/or a subject that is immunocompromised, or is suffering from a hyperproliferative disease.

In further embodiments, the expression construct and/or expression vector can be utilized as a composition or substance that activates antigen-presenting cells. Such a composition that "activates antigen-presenting cells" or "enhances the activity antigen-presenting cells" refers to the ability to stimulate one or more activities associated with antigen-presenting cells. Such activities are well known by those of skill in the art. For example, a composition, such as the expression construct or vector of the present methods, can stimulate upregulation of co-stimulatory molecules on antigen-presenting cells, induce nuclear translocation of NF-kappaB in antigen-presenting cells, activate toll-like receptors in antigen-presenting cells, or other activities involving cytokines or chemokines.

The expression construct, expression vector and/or transduced antigen-presenting cells can enhance or contribute to the effectiveness of a vaccine by, for example, enhancing the immunogenicity of weaker antigens such as highly purified or recombinant antigens, reducing the amount of antigen required for an immune response, reducing the frequency of immunization required to provide protective immunity, improving the efficacy of vaccines in subjects with reduced or weakened immune responses, such as newborns, the aged, and immunocompromised individuals, and enhancing the immunity at a target tissue, such as mucosal immunity, or promote cell-mediated or humoral immunity by eliciting a particular cytokine profile.

Yet further, an immunocompromised individual or subject is a subject that has a reduced or weakened immune response. Such individuals may also include a subject that has undergone chemotherapy or any other therapy resulting in a weakened immune system, a transplant recipient, a subject currently taking immunosuppressants, an aging individual, or any individual that has a reduced and/or impaired CD4 T helper cells. It is contemplated that the present methods can be utilized to enhance the amount and/or activity of CD4 T helper cells in an immunocompromised subject.

In specific embodiments, prior to administering the transduced antigen-presenting cell, the cells are challenged with antigens (also referred herein as "target antigens"). After challenge, the transduced, loaded antigen-presenting cells are administered to the subject parenterally, intradermally, intranodally, or intralymphatically. Additional parenteral routes include, but are not limited to subcutaneous, intramuscular, intraperitoneal, intravenous, intraarterial, intramyocardial, transendocardial, transepicardial, intrathecal, and infusion techniques.

The target antigen, as used herein, is an antigen or immunological epitope on the antigen, which is crucial in immune recognition and ultimate elimination or control of the disease-causing agent or disease state in a mammal. The immune recognition may be cellular and/or humoral. In the case of intracellular pathogens and cancer, immune recognition may, for example, be a T lymphocyte response.

The target antigen may be derived or isolated from, for example, a pathogenic microorganism such as viruses including HIV, (Korber et al, eds HIV Molecular Immunology Database, Los Alamos National Laboratory, Los Alamos, N. Mex. 1977) influenza, Herpes simplex, human papilloma virus (U.S. Pat. No. 5,719,054), Hepatitis B (U.S. Pat. No. 5,780,036), Hepatitis C (U.S. Pat. No. 5,709,995), EBV, Cytomegalovirus (CMV) and the like. Target antigen may be derived or isolated from pathogenic bacteria such as, for example, from *Chlamydia* (U.S. Pat. No. 5,869,608), *Mycobacteria, Legionella, Meningiococcus*, Group A *Streptococcus, Salmonella, Listeria, Hemophilus influenzae* (U.S. Pat. No. 5,955,596) and the like.

Target antigen may be derived or isolated from, for example, pathogenic yeast including *Aspergillus*, invasive *Candida* (U.S. Pat. No. 5,645,992), *Nocardia, Histoplasmosis, Cryptosporidia* and the like.

Target antigen may be derived or isolated from, for example, a pathogenic protozoan and pathogenic parasites including but not limited to *Pneumocystis carinii, Trypanosoma, Leishmania* (U.S. Pat. No. 5,965,242), *Plasmodium* (U.S. Pat. No. 5,589,343) and *Toxoplasma gondii*.

Target antigen includes an antigen associated with a pre-neoplastic or hyperplastic state. Target antigen may also be associated with, or causative of cancer. Such target antigen may be, for example, tumor specific antigen, tumor associated antigen (TAA) or tissue specific antigen, epitope thereof, and epitope agonist thereof. Such target antigens include but are not limited to carcinoembryonic antigen (CEA) and epitopes thereof such as CAP-1, CAP-1-6D and the like (GenBank Accession No. M29540), MART-1 (Kawakarni et al, J. Exp. Med. 180:347-352, 1994), MAGE-1 (U.S. Pat. No. 5,750,395), MAGE-3, GAGE (U.S. Pat. No. 5,648,226), GP-100 (Kawakami et al Proc. Nat'l Acad. Sci. USA 91:6458-6462, 1992), MUC-1, MUC-2, point mutated ras oncogene, normal and point mutated p53 oncogenes (Hollstein et al Nucleic Acids Res. 22:3551-3555, 1994), PSMA (Israeli et al Cancer Res. 53:227-230, 1993), tyrosinase (Kwon et al PNAS 84:7473-7477, 1987) TRP-1 (gp75) (Cohen et al Nucleic Acid Res. 18:2807-2808, 1990; U.S. Pat.

No. 5,840,839), NY-ESO-1 (Chen et al PNAS 94: 1914-1918, 1997), TRP-2 (Jackson et al EMBO J, 11:527-535, 1992), TAG72, KSA, CA-125, PSA, HER-2/neu/c-erb/B2, (U.S. Pat. No. 5,550,214), BRC-I, BRC-II, bcr-abl, pax3-fkhr, ews-fli-1, modifications of TAAs and tissue specific antigen, splice variants of TAAs, epitope agonists, and the like. Other TAAs may be identified, isolated and cloned by methods known in the art such as those disclosed in U.S. Pat. No. 4,514,506. Target antigen may also include one or more growth factors and splice variants of each.

An antigen may be expressed more frequently in cancer cells than in non-cancer cells. The antigen may result from contacting the modified dendritic cell with prostate specific membrane antigen (PSMA) or fragment thereof. In certain embodiments, the modified dendritic cell is contacted with a PSMA fragment having the amino acid sequence of SEQ ID NO: 4 (e.g., encoded by the nucleotide sequence of SEQ ID NO: 3).

For organisms that contain a DNA genome, a gene encoding a target antigen or immunological epitope thereof of interest is isolated from the genomic DNA. For organisms with RNA genomes, the desired gene may be isolated from cDNA copies of the genome. If restriction maps of the genome are available, the DNA fragment that contains the gene of interest is cleaved by restriction endonuclease digestion by methods routine in the art. In instances where the desired gene has been previously cloned, the genes may be readily obtained from the available clones. Alternatively, if the DNA sequence of the gene is known, the gene can be synthesized by any of the conventional techniques for synthesis of deoxyribonucleic acids.

Genes encoding an antigen of interest can be amplified, for example, by cloning the gene into a bacterial host. For this purpose, various prokaryotic cloning vectors can be used. Examples are plasmids pBR322, pUC and pEMBL.

The genes encoding at least one target antigen or immunological epitope thereof can be prepared for insertion into the plasmid vectors designed for recombination with a virus by standard techniques. In general, the cloned genes can be excised from the prokaryotic cloning vector by restriction enzyme digestion. In most cases, the excised fragment will contain the entire coding region of the gene. The DNA fragment carrying the cloned gene can be modified as needed, for example, to make the ends of the fragment compatible with the insertion sites of the DNA vectors used for recombination with a virus, then purified prior to insertion into the vectors at restriction endonuclease cleavage sites (cloning sites).

Antigen loading of dendritic cells with antigens may be achieved, for example, by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide. Antigens from cells or MHC molecules may be obtained by acid-elution or other methods known in the art (see Zitvogel L, et al., J Exp Med 1996. 183:87-97).

In further embodiments, the transduced antigen-presenting cell is transfected with tumor cell mRNA. The transduced transfected antigen-presenting cell is administered to an animal to effect cytotoxic T lymphocytes and natural killer cell anti-tumor antigen immune response and regulated using dimeric FK506 and dimeric FK506 analogs. The tumor cell mRNA may be, for example, mRNA from a prostate tumor cell.

Yet further, the transduced antigen-presenting cell is pulsed with tumor cell lysates. The pulsed transduced antigen-presenting cells are administered to an animal to effect cytotoxic T lymphocytes and natural killer cell anti-tumor antigen immune response and regulated using dimeric FK506 and dimeric FK506 analogs. The tumor cell lysate may be, for example, a prostate tumor cell lysate.

One skilled in the art is fully aware that activation of the co-stimulatory molecule of the present relies upon oligomerization of ligand-binding domains, for example CID, to induce its activity. In specific embodiments, the ligand is a non-protein. For example, the ligand may be a dimeric FK506 or dimeric FK506 analogs, which result in enhancement or positive regulation of the immune response. The use of monomeric FK506 or monomeric FK506 analogs results in inhibition or reduction in the immune response negatively.

T-lymphocytes may be activated by contact with the antigen-presenting cell that comprises the expression vector discussed herein where the antigen-presenting cell has been challenged, transfected, pulsed, or electrofused with an antigen.

Electrofusing is a method of generating hybrid cells. There are several advantages in producing cell hybrids by electrofusion. For example, fusion parameters can be easily and accurately electronically controlled to conditions depending on the cells to be fused. Further, electrofusion of cells has shown to the ability to increase fusion efficiency over that of fusion by chemical means or via biological fusogens. Electrofusion is performed by applying electric pulses to cells in suspension. By exposing cells to an alternating electric field, cells are brought close to each other in forming pearl chains in a process termed dielectrophoresis alignment. Subsequent higher voltage pulses cause cells to come into closer contact, reversible electropores are formed in reversibly permeabilizing and mechanically breaking down cell membranes, resulting in fusion.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a naïve CD8 T cell that recognizes an antigen-MHC complex proliferates and differentiates into an effector cell called a cytotoxic CD8 T lymphocyte (CTL). CTLs eliminate cells of the body displaying antigen, such as virus-infected cells and tumor cells, by producing substances that result in cell lysis.

CTL activity can be assessed by methods described herein or as would be known to one of skill in the art. For example, CTLs may be assessed in freshly isolated peripheral blood mononuclear cells (PBMC), in a phytohaemaglutinin-stimulated IL-2 expanded cell line established from PBMC (Bernard et al., AIDS, 12(16):2125-2139, 1998) or by T cells isolated from a previously immunized subject and restimulated for 6 days with DC infected with an adenovirus vector containing antigen using standard 4 hour $^{51}$Cr release microtoxicity assays. One type of assay uses cloned T-cells. Cloned T-cells have been tested for their ability to mediate both perforin and Fas ligand-dependent killing in redirected cytotoxicity assays (Simpson et al., Gastroenterology, 115(4): 849-855, 1998). The cloned cytotoxic T lymphocytes displayed both Fas- and perforin-dependent killing. Recently, an in vitro dehydrogenase release assay has been developed that takes advantage of a new fluorescent amplification system (Page, B., et al., Anticancer Res. 1998 July-August; 18(4A): 2313-6). This approach is sensitive, rapid, and reproducible and may be used advantageously for mixed lymphocyte reaction (MLR). It may easily be further automated for large-scale cytotoxicity testing using cell membrane integrity, and is thus considered. In another fluorometric assay developed for detecting cell-mediated cytotoxicity, the fluorophore used is the non-toxic molecule AlamarBlue (Nociari et al., J. Immunol. Methods, 213(2): 157-167, 1998). The AlamarBlue is fluorescently quenched (i.e., low quantum yield) until mitochondrial reduction occurs, which then results in a dramatic increase in the AlamarBlue fluorescence intensity (i.e., increase in the quantum yield). This assay is reported to be extremely sensitive, specific and requires a significantly lower number of effector cells than the standard $^{51}$Cr release assay.

Other immune cells that are induced by the present methods include natural killer cells (NK). NKs are lymphoid cells that lack antigen-specific receptors and are part of the innate immune system. Typically, infected cells are usually destroyed by T cells alerted by foreign particles bound to the cell surface MHC. However, virus-infected cells signal infection by expressing viral proteins that are recognized by antibodies. These cells can be killed by NKs. In tumor cells, if the tumor cells lose expression of MHC I molecules, then it may be susceptible to NKs.

Formulations and Routes for Administration to Patients

Where clinical applications are contemplated, it will be necessary to prepare pharmaceutical compositions—expression constructs, expression vectors, fused proteins, transduced cells, activated DCs, transduced and loaded DCs—in a form appropriate for the intended application. Generally, this will entail preparing compositions that are essentially free of pyrogens, as well as other impurities that could be harmful to humans or animals.

One may generally desire to employ appropriate salts and buffers to render delivery vectors stable and allow for uptake by target cells. Buffers also may be employed when recombinant cells are introduced into a patient. Aqueous compositions comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. A pharmaceutically acceptable carrier includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells, its use in therapeutic compositions is contemplated. Supplementary active ingredients also can be incorporated into the compositions.

The active compositions may include classic pharmaceutical preparations. Administration of these compositions will be via any common route so long as the target tissue is available via that route. This includes, for example, oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, discussed herein.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In certain examples, isotonic agents, for example, sugars or sodium chloride may be included. Prolonged absorption of the injectable compositions can be brought about by the use in the compositions of agents delaying absorption, for example, aluminum monostearate and gelatin.

For oral administration, the compositions may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including, for example: gels, pastes, powders and slurries. The active ingredient may be added in a therapeutically effective amount to a paste dentifrice that may include, for example, water, binders, abrasives, flavoring agents, foaming agents, and humectants.

The compositions may be formulated in a neutral or salt form. Pharmaceutically-acceptable salts include, for example, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed, will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Methods for Treating a Disease

The present methods also encompasses methods of treatment or prevention of a disease caused by pathogenic microorganisms and/or a hyperproliferative disease.

Diseases may be treated or prevented include diseases caused by viruses, bacteria, yeast, parasites, protozoa, cancer cells and the like. The pharmaceutical composition (transduced DCs, expression vector, expression construct, etc.) may be used as a generalized immune enhancer (DC activating composition or system) and as such has utility in treating diseases. Exemplary diseases that can be treated and/or prevented include, but are not limited, to infections of viral etiology such as HIV, influenza, Herpes, viral hepatitis, Epstein Bar, polio, viral encephalitis, measles, chicken pox, Papilloma virus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

Preneoplastic or hyperplastic states which may be treated or prevented using the pharmaceutical composition (transduced DCs, expression vector, expression construct, etc.) include but are not limited to preneoplastic or hyperplastic states such as colon polyps, Crohn's disease, ulcerative colitis, breast lesions and the like.

Cancers which may be treated using the pharmaceutical composition include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like.

Other hyperproliferative diseases that may be treated using DC activation system presented herein include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

In the method of treatment, the administration of the pharmaceutical composition (expression construct, expression vector, fused protein, transduced cells, activated DCs, transduced and loaded DCs) may be for either "prophylactic" or "therapeutic" purpose. When provided prophylactically, the pharmaceutical composition is provided in advance of any symptom. The prophylactic administration of pharmaceutical composition serves to prevent or ameliorate any subsequent infection or disease. When provided therapeutically, the pharmaceutical composition is provided at or after the onset of a symptom of infection or disease. Thus the compositions presented herein may be provided either prior to the anticipated exposure to a disease-causing agent or disease state or after the initiation of the infection or disease.

The term "unit dose" as it pertains to the inoculum refers to physically discrete units suitable as unitary dosages for mammals, each unit containing a predetermined quantity of pharmaceutical composition calculated to produce the desired immunogenic effect in association with the required diluent. The specifications for the novel unit dose of an inoculum are dictated by and are dependent upon the unique characteristics of the pharmaceutical composition and the particular immunologic effect to be achieved.

An effective amount of the pharmaceutical composition would be the amount that achieves this selected result of enhancing the immune response, and such an amount could be determined as a matter of routine by a person skilled in the art. For example, an effective amount of for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition presented herein without necessitating undue experimentation.

A. Genetic Based Therapies

In certain embodiments, a cell is provided with an expression construct capable of providing a co-stimulatory polypeptide, such as CD40 to the cell, such as an antigen-presenting cell and activating CD40. The lengthy discussion of expression vectors and the genetic elements employed therein is incorporated into this section by reference. In certain examples, the expression vectors may be viral vectors, such as adenovirus, adeno-associated virus, herpes virus, vaccinia virus and retrovirus. In another example, the vector may be a lysosomal-encapsulated expression vector.

Those of skill in the art are well aware of how to apply gene delivery to in vivo and ex vivo situations. For viral vectors, one generally will prepare a viral vector stock. Examples of viral vector-mediated gene delivery ex vivo are presented in the present application. For in vivo delivery, depending on the kind of virus and the titer attainable, one will deliver, for example, $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

B. Cell Based Therapy

Another therapy that is contemplated is the administration of transduced antigen-presenting cells. The antigen-presenting cells may be transduced in vitro. Formulation as a pharmaceutically acceptable composition is discussed herein.

In cell based therapies, the transduced antigen-presenting cells may be, for example, transfected with target antigen nucleic acids, such as mRNA or DNA or proteins; pulsed with cell lysates, proteins or nucleic acids; or electrofused with cells. The cells, proteins, cell lysates, or nucleic acid may derive from cells, such as tumor cells or other pathogenic microorganism, for example, viruses, bacteria, protozoa, etc.

C. Combination Therapies

In order to increase the effectiveness of the expression vectors presented herein, it may be desirable to combine these compositions and methods with an agent effective in the treatment of the disease.

In certain embodiments, anti-cancer agents may be used in combination with the present methods. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

In further embodiments antibiotics can be used in combination with the pharmaceutical composition to treat and/or prevent an infectious disease. Such antibiotics include, but are not limited to, amikacin, aminoglycosides (e.g., gentamycin), amoxicillin, amphotericin B, ampicillin, antimonials, atovaquone sodium stibogluconate, azithromycin, capreomycin, cefotaxime, cefoxitin, ceftriaxone, chloramphenicol, clarithromycin, clindamycin, clofazimine, cycloserine, dapsone, doxycycline, ethambutol, ethionamide, fluconazole, fluoroquinolones, isoniazid, itraconazole, kanamycin, ketoconazole, minocycline, ofloxacin), para-aminosalicylic acid, pentamidine, polymixin definsins, prothionamide, pyrazinamide, pyrimethamine sulfadiazine, quinolones (e.g., ciprofloxacin), rifabutin, rifampin, sparfloxacin, streptomycin, sulfonamides, tetracyclines, thiacetazone, trimethaprim-sulfamethoxazole, viomycin or combinations thereof.

More generally, such an agent would be provided in a combined amount with the expression vector effective to kill or inhibit proliferation of a cancer cell and/or microorganism. This process may involve contacting the cell(s) with an agent(s) and the pharmaceutical composition at the same time or within a period of time wherein separate administration of the pharmaceutical composition and an agent to a cell, tissue or organism produces a desired therapeutic benefit. This may be achieved by contacting the cell, tissue or organism with a single composition or pharmacological formulation that includes both the pharmaceutical composition and one or more agents, or by contacting the cell with two or more distinct compositions or formulations, wherein one composition includes the pharmaceutical composition and the other includes one or more agents.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing.

The administration of the pharmaceutical composition may precede, be co-current with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein and one or more agents may be employed.

EXAMPLES

The examples set forth below illustrate but do not limit the invention.

Example 1

Materials and Methods

Described hereafter are materials and methods utilized in studies described in subsequent Examples.

Tumor Cell Lines and Peptides

NA-6-Mel, T2, SK-Mel-37 and LNCaP cell lines were purchased from the American Type Culture Collection (ATCC) (Manassas, Va.). HLA-A2-restricted peptides MAGE-3 p271-279 (FLWGPRALV (SEQ ID NO: 19)), influenza matrix (IM) p58-66 (GILGFVFTL (SEQ ID NO: 20)), and HIV-1 gag p77-85 (SLYNTVATL (SEQ ID NO: 21)) were used to analyze CD8+ T cell responses. In T helper cell polarization experiments, tetanus toxoid peptide TTp30 FNNFTVSFWLRVPKVSASHLE (SEQ ID NO: 22) was used. All peptides were synthesized by Genemed Synthesis Inc (San Francisco, Calif.), with an HPLC-determined purity of >95%.

Recombinant Adenovirus Encoding Human Inducible CD40

The human CD40 cytoplasmic domain was Pfu I polymerase (Stratagene, La Jolla, Calif.) amplified from human monocyte-derived DC cDNA using an Xho I-flanked 5' primer (5hCD40X), 5'-atatactcgagaaaaaggtggccaa-gaagccaacc-3' (SEQ ID NO: 23), and a Sal I-flanked 3' primer (3hCD40S), 5'-atatagtcgactcactgtctctcctgcactgagatg-3' (SEQ ID NO: 24). The PCR fragment was subcloned into Sal I-digested pSH1/M-FvFvls-E15 and sequenced to create pSH1/M-FvFvls-CD40-E. Inducible CD40 was subsequently subcloned into a non-replicating E1, E3-deleted Ad5/f35-based vector expressing the transgene under a cytomegalovirus early/immediate promoter. The iCD40-encoding sequence was confirmed by restriction digest and sequencing. Amplification, purification, and titration of all adenoviruses were carried out in the Viral Vector Core Facility of Baylor College of Medicine.

Western Blot

Total cellular extracts were prepared with RIPA buffer containing a protease inhibitor cocktail (Sigma-Aldrich, St. Louis, Mo.) and quantitated using a detergent-compatible protein concentration assay (Bio-Rad, Hercules, Calif.). 10-15 micrograms of total protein were routinely separated on 12% SDS-PAGE gels, and proteins were transferred to nitrocellulose membranes (Bio-Rad). Blots were hybridized with goat anti-CD40 (T-20, Santa Cruz Biotechnology, Santa Cruz, Calif.) and mouse anti-alpha-tubulin (Santa Cruz Biotechnology) Abs followed by donkey anti-goat and goat anti-mouse IgG-HRP (Santa Cruz Biotechnology), respectively. Blots were developed using the SuperSignal West Dura Stable substrate system (Pierce, Rockford, Ill.).

Generation and Stimulation of Human DCs

Peripheral blood mononuclear cells (PBMCs) from healthy donors were isolated by density centrifugation of heparinized blood on Lymphoprep (Nycomed, Oslo, Norway). PBMCs were washed with PBS, resuspended in CellGenix DC medium (Freiburg, Germany) and allowed to adhere in culture plates for 2 h at 37° C. and 5% $CO_2$. Non-adherent cells were removed by extensive washings, and adherent monocytes were cultured for 5 days in the presence of 500 U/ml hIL-4 and 800 U/ml hGM-CSF (R&D Systems, Minneapolis, Minn.). As assessed by morphology and FACS analysis, the resulting immature DCs (imDCs) were MHC-class I, IIhi, and expressed CD40lo, CD80lo, CD83lo, CD86lo. The imDCs were CD14neg and contained <3% of contaminating CD3+ T, CD19+ B, and CD16+ NK cells.

Approximately $2 \times 10^6$ cells/ml were cultured in a 24-well dish and transduced with adenoviruses at 10,000 viral particle (vp)/cell (~160 MOO for 90 min at 37° C. and 5% $CO_2$. Immediately after transduction DCs were stimulated with MPL, FSL-1, Pam3CSK4 (InvivoGen, San Diego, Calif.), LPS (Sigma-Aldrich, St. Louis, Mo.), AP20187 (kind gift from ARIAD Pharmaceuticals, Cambridge, Mass.) or maturation cocktail (MC), containing 10 ng/ml TNF-alpha, 10 ng/ml IL-1beta, 150 ng/ml IL-6 (R&D Systems, Minneapolis, Minn.) and 1 microgram/ml of PGE2 (Cayman Chemicals, Ann Arbor, Mich.). In T cell assays DCs were pulsed with 50 micrograms/ml of PSMA or MAGE 3 peptide 24 hours before and after adenoviral transduction.

Surface Markers and Cytokine Production

Cell surface staining was done with fluorochrome-conjugated monoclonal antibodies (BD Biosciences, San Diego, Calif.). Cells were analyzed on a FACSCalibur cytometer (BD Biosciences, San Jose, Calif.). Cytokines were measured in culture supernatants using enzyme-linked immunosorbent assay kits for human IL-6 and IL-12p70 (BD Biosciences).

Real Time Q-PCR Assay for Human SOCS1

Total RNA was purified and reverse transcribed with random hexamers using SuperScript II RTase (Invitrogen, Carlsbad, Calif.). mRNA levels were quantified in DCs by subjecting cDNA to TaqMan PCR analysis using the GeneAmp 5700 Sequence Detection System (Applied Biosystems, Foster City, Calif.). Pre-developed sequence detection reagents (Applied Biosystems) specific for human SOCS1 and 18S rRNA, including forward and reverse primers as well as a fluorogenic TaqMan FAM-labeled hybridization probe, were supplied as mixtures and were used at 1 microliter/20 microliter PCR. Samples were run in duplicates. The level of SOCS1 expression in each sample was normalized to the level of 18S rRNA from the same sample using the comparative 2-delta delta CT method (Livak K J, Schmittgen TD. Analysis of relative gene expression data using real-time quantitative PCR and the 2(-Delta Delta C(T)) Method. Methods. 2001; 25:402-408).

DC Migration Assay

Chemotaxis of DCs was measured by migration through a polycarbonate filter with 8 micrometer pore size in 96-Multiwell HTS Fluoroblok plates (BD Biosciences). Assay medium (250 microliters) containing 100 ng/ml CCL19 (R&D Systems) or assay medium alone (as a control for spontaneous migration) were loaded into the lower chamber. DCs (50,000) were labeled with Green-CMFDA cell tracker (Invitrogen), unstimulated or stimulated for 48 h with the indicated reagents, and were added to the upper chamber in a total volume of 50 microliters for 1 hour at 37° C. and 5% $CO_2$. Fluorescence of cells, which had migrated through the microporous membrane, was measured using the FLUOstar OPTIMA reader (BMG Labtech Inc., Durham, N.C.). The mean fluorescence of spontaneously migrated cells was subtracted from the total number of migrated cells for each condition.

IFN-Gamma ELISPOT Assay

DCs from HLA-A2-positive healthy volunteers were pulsed with MAGE-3 A2.1 peptide (residues 271-279; FLWGPRALV (SEQ ID NO: 19)) on day 4 of culture, followed by transduction with Ad-iCD40 and stimulation with various stimuli on day 5. Autologous T cells were purified from PBMCs by negative selection (Miltenyi Biotec, Auburn, Calif.) and mixed with DCs at DC:T cell ratio 1:3. Cells were incubated in complete RPMI with 20 U/ml hIL-2 (R&D Systems) and 25 micrograms/ml of MAGE 3 A2.1 peptide. T cells were restimulated at day 7 and assayed at day 14 of culture.

ELISPOT Quantitation

Flat-bottom, 96-well nitrocellulose plates (MultiScreen-HA; Millipore, Bedford, Mass.) were coated with IFN-gamma mAb (2 μg/ml, 1-D1K; Mabtech, Stockholm, Sweden) and incubated overnight at 4° C. After washings with PBS containing 0.05% TWEEN 20, plates were blocked with complete RPMI for 2 h at 37° C. A total of $1 \times 10^5$ presensitized CD8+ T effector cells were added to each well and incubated for 20 h with 25 micrograms/ml peptides. Plates were then washed thoroughly with PBS containing 0.05% TWEEN 20, and anti-IFN-mAb (0.2 microg/ml, 7-B6-1-biotin; Mabtech) was added to each well. After incubation for 2 h at 37° C., plates were washed and developed with streptavidin-alkaline phosphatase (1 microg/ml; Mabtech) for 1 h at room temperature. After washing, substrate (3-amino-9-ethyl-carbazole; Sigma-Aldrich) was added and incubated for 5 min. Plate membranes displayed dark-pink spots that were scanned and analyzed by ZellNet Consulting Inc. (Fort Lee, N.J.).

Chromium Release Assay

Antigen recognition was assessed using target cells labeled with Chromium-51 (Amersham) for 1 hour at 37° C. and washed three times. Labeled target cells (5000 cells in 50 microliters) were then added to effector cells (100 microliters) at the indicated effector:target cell ratios in V-bottom microwell plates at the indicated concentrations. Supernatants were harvested after 6-h incubation at 37° C., and chromium release was measured using MicroBeta Trilux counter (Perkin-Elmer Inc, Torrance Calif.). Assays involving LNCaP cells were run for 18 hours. The percentage of specific lysis was calculated as: 100*[(experimental−spontaneous release)/(maximum−spontaneous release)].

Tetramer Staining

HLA-A2 tetramers assembled with MAGE-3.A2 peptide (FLWGPRALV (SEQ ID NO: 19)) were obtained from Baylor College of Medicine Tetramer Core Facility (Houston, Tex.). Presensitized CD8+ T cells in 50 μl of PBS containing 0.5% FCS were stained with PE-labeled tetramer for 15 min on ice before addition of FITC-CD8 mAb (BD Biosciences). After washing, results were analyzed by flow cytometry.

Polarization of Naïve T Helper Cells

Naïve CD4+CD45RA+ T-cells from HLA-DR11.5-positive donors (genotyped using FASTYPE HLA-DNA SSP typing kit; BioSynthesis, Lewisville, Tex.) were isolated by negative selection using naïve CD4+ T cell isolation kit (Miltenyi Biotec, Auburn, Calif.). T cells were stimulated with autologous DCs pulsed with tetanus toxoid (5 FU/ml) and stimulated with various stimuli at a stimulator to responder ratio of 1:10. After 7 days, T cells were restimulated with autologous DCs pulsed with the HLA-DR11.5-restricted helper peptide TTp30 and transduced with adenovector Ad-iCD40. Cells were stained with PE-anti-CD4 Ab (BD Biosciences), fixed and permeabilized using BD Cytofix/Cytoperm kit (BD Biosciences), then stained with hIFN-gamma mAb (eBioscience, San Diego, Calif.) and analyzed by flow cytometry. Supernatants were analyzed using human TH1/TH2 BD Cytometric Bead Array Flex Set on BD FACSArray Bioanalyzer (BD Biosciences).

PSMA Protein Purification

The baculovirus transfer vector, pAcGP67A (BD Biosciences) containing the cDNA of extracellular portion of PSMA (residues 44-750) was kindly provided by Dr Pamela J. Bjorkman (Howard Hughes Medical Institute, California Institute of Technology, Pasadena, Calif.). PSMA was fused with a hydrophobic secretion signal, Factor Xa cleavage site, and N-terminal 6x-His affinity tag (SEQ ID NO: 25). High titer baculovirus was produced by the Baculovirus/Monoclonal antibody core facility of Baylor College of Medicine. PSMA protein was produced in High 5 cells infected with recombinant virus, and protein was purified from cell supernatants using Ni-NTA affinity columns (Qiagen, Chatsworth, Calif.) as previously described (Cisco R M, Abdel-Wahab Z, Dannull J, et al. Induction of human dendritic cell maturation using transfection with RNA encoding a dominant positive toll-like receptor 4. J Immunol. 2004; 172:7162-7168). After purification the ~100 kDa solitary band of PSMA protein was detected by silver staining of acrylamide gels.

Migration of Human DCs in Mouse Host

In order to assess the migration of human DCs in vivo, adenovector Ad5-CBR, which expresses red-shifted (emission peak=613 nM) luciferase from *Pyrophorus plagiophalamus* click beetles (Promega, Madison, Wis.) was developed. Human DCs were transduced with ~50 MOI of Ad5-CBR, and 160 MOI of Ad5f35-iCD40. DCs were then matured with MC or 1 microgram/ml LPS (Sigma-Aldrich, St. Louis, Mo.). Mouse bone marrow derived DCs were obtained as described before 13 and were matured with 1 micrograms/ml LPS. Approximately $2 \times 10^6$ DCs were injected into the left and right hind footpads of irradiated (250 Rads) Balb/c mice (both hind legs of three mice per group, n=6). Mice were i.p. injected with D-Luciferin (~1 mg/25 g animal) and imaged over several days using an IVIS™ 100 imaging system (Xenogen Corp., Alameda, Calif.). Luminescent signal was measured in 3 mice per group, and popliteal and inguinal lymph nodes (LN) were removed at day 2 post-DC inoculation. The LNs' signal was measured and the background was subtracted for each group (n=6).

Data Analysis

Results are expressed as the mean±standard error. Sample size was determined with a power of 0.8, with a one-sided alpha-level of 0.05. Differences between experimental groups were determined by the Student t test.

Example 2

Expression of iCD40 and Induction of DC Maturation

Figure 1B:
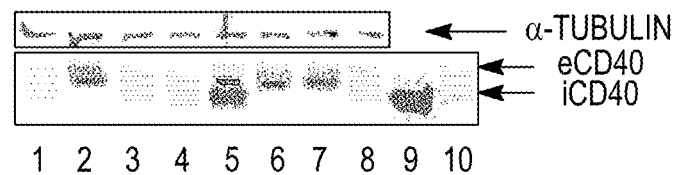
FIG. 1B. The expression of endogenous (eCD40) and recombinant inducible (iCD40) forms of CD40 assessed by Western blot. Lane 1, wild type DCs (endogenous CD40 control); lane 2, DCs stimulated with 1 microgram/ml of LPS; lanes 3 and 4, DCs transduced with 10,000 VP/cell (MOI~160) of Ad5/f35-iCD40 (iCD40-DCs) with and without AP20187 dimerizer drug respectively; lane 5, iCD40-DCs stimulated with LPS and AP20187; lane 6, DCs stimulated with CD40L (CD40 ligand, a protein a TNF family member) and LPS; lane 7, DCs transduced with Ad5/f35-GFP (GFP-DCs) at MOI 160 and stimulated with AP20187 and LPS; lane 8, GFP-DCs stimulated with AP20187; lane 9, 293 T cells transduced with Ad5/f35-iCD40 (positive control for inducible form of CD40). The expression levels of alpha-tubulin served as internal control.

To investigate whether iCD40 signaling can enhance the immunogenic functions of human DCs, adenovirus, Ad5/f35-ihCD40 (simplified to Ad-iCD40) was generated, expressing inducible human CD40 receptor, based on the previously described mouse iCD40 vector 13 (FIG. 1). Those of ordinary skill in the art will recognize that this is an example of an assay that may be used to examine DC maturation after transduction of a chimeric iCD40 protein, such as, for example, iCD40-MyD88, or other chimera examples herein. The human CD40 cytoplasmic signaling domain was cloned downstream of a myristoylation-targeting domain and two tandem domains (from human FKBP12(V36), designated as "Fv'"), which bind dimerizing drug AP20187 (Clackson T, Yang W, Rozamus L W, et al. Redesigning an FKBP-ligand interface to generate chemical dimerizers with novel specificity. Proc Natl Acad Sci USA. 1998; 95:10437-10442). Immature DCs expressed endogenous CD40, which was induced by LPS and CD40L. Transduction of Ad-iCD40 led to expression of the distinctly sized iCD40, which did not interfere with endogenous CD40 expression. Interestingly, the expression of iCD40 was also significantly enhanced by LPS stimulation, likely due to inducibility of ubiquitous transcription factors binding the "constitutive" CMV promoter.

One of the issues for the design of DC-based vaccines is to obtain fully matured and activated DCs, as maturation status is linked to the transition from a tolerogenic to an activating, immunogenic state (Steinman R M, et al., Annu Rev Immunol. 2003; 21:685-711; Hanks B A, et al., Nat Med. 2005; 11:130-137; Banchereau J, Steinman R M. Dendritic cells and the control of immunity. Nature. 1998; 392:245-252). It has been shown that expression of mouse variant Ad-iCD40 can induce murine bone marrow-derived DC maturation (Hanks B A, et al., Nat Med. 2005; 11:130-137). To determine whether humanized iCD40 affects the expression of maturation markers in DCs, DCs were transduced with Ad-iCD40 and the expression of maturation markers CD40, CD80, CD83, and CD86 were evaluated. TLR-4 signaling mediated by LPS or its derivative MPL is a potent inducer of DC maturation (Ismaili J, et al., J Immunol. 2002; 168:926-932; Cisco R M, et al., J Immunol. 2004; 172:7162-7168; De Becker G, Moulin V, Pajak B, et al. The adjuvant monophosphoryl lipid A increases the function of antigen-presenting cells. Int Immunol. 2000; 12:807-815; Granucci F, Ferrero E, Foti M, Aggujaro D, Vettoretto K, Ricciardi-Castagnoli P. Early events in dendritic cell maturation induced by LPS. Microbes Infect. 1999; 1:1079-1084). It was also previously reported that endogenous CD40 signaling specifically up-regulates CD83 expression in human DCs (Megiovanni A M, Sanchez F, Gluckman J C, Rosenzwajg M. Double-stranded RNA stimulation or CD40 ligation of monocyte-derived dendritic cells as models to study their activation and maturation process. Eur Cytokine Netw. 2004; 15:126-134). Consistent with these previous reports, the expression levels of CD83 were upregulated upon Ad-iCD40 transduction, and CD83 expression was further upregulated following LPS or MPL addition.

Example 3

Assay for Synergy of iCD40 Signaling and Inducible PRR Adapter Protein Ligation

Those of ordinary skill in the art are able to modify the assays presented in this example to observe synergy between iCD40 signaling and inducible PRR adapter protein ligation.

Interleukin-12 (IL-12) activates T and NK cell responses, and induces IFN-gamma production. It also favors the differentiation of TH1 cells and is a vital link between innate and adaptive immunity (Banchereau J, et al., Ann N Y Acad. Sci. 2003; 987:180-187; Puccetti P, Belladonna M L, Grohmann U. Effects of IL-12 and IL-23 on antigen-presenting cells at the interface between innate and adaptive immunity. Crit Rev Immunol. 2002; 22:373-390). Therefore, induction of biologically active IL-12p70 heterodimer is likely critical for optimum DC-based vaccines. Nonetheless, current DC vaccination protocols that include PGE2 produce only limited IL-12 (Lee A W, Truong T, Bickham K, et al. A clinical grade cocktail of cytokines and PGE2 results in uniform maturation of human monocyte-derived dendritic cells: implications for immunotherapy. Vaccine. 2002; 20 Suppl 4:A8-A22). IL-12 is a heterodimeric cytokine consisting of p40 and p35 chains. Previously, it was reported that inducible CD40 signaling promotes the expression of the p35 subunit of IL-12p70 in mouse bone marrow-derived DCs (Hanks B A, et al., Nat Med. 2005; 11:130-137). It was also reported that TLR-4 ligation can promote p40 expression (Liu J, Cao S, Herman L M, Ma X. Differential regulation of interleukin (IL)-12 p35 and p40 gene expression and interferon (IFN)-gamma-primed IL-12 production by IFN regulatory factor 1. J Exp Med. 2003; 198:1265-1276). Therefore, iCD40-DCs were cultured in the presence of LPS or MPL and assayed supernatants by ELISA for production of IL-12p70.

Predictably, similar to DCs treated with standard MC, iCD40-DCs did not produce detectable IL-12p70 heterodimer. If PGE2 was withheld from the MC, DCs produced detectable but low levels of IL-12p70, consistent with a potentially deleterious role for PGE2. Furthermore, DCs cultured for 12 h in the presence of LPS or MPL alone also failed to produce IL-12 (<30 pg/ml). However, when Ad-iCD40-transduced DCs were cultured in the presence of either MPL or LPS they produced very high levels of IL-12p70 (16.4±7.8 ng/ml for MPL). This level of IL-12 was about 25-fold higher than levels induced by standard MC lacking PGE2. Interestingly, this synergism of iCD40 and TLR4 was partially independent of AP20187 addition, implying that basal iCD40 signaling can also synergize with TLR4 ligation. IL-12p70 production in iCD40-DCs was also dose-dependent as IL-12 levels correlated with viral particles dose.

Since CD40 signaling is normally tightly restricted to a relatively short time period (Contin C, Pitard V, Itai T, Nagata S, Moreau J F, Dechanet-Merville J. Membrane-anchored CD40 is processed by the tumor necrosis factor-alpha-converting enzyme. Implications for CD40 signaling. J Biol Chem. 2003; 278:32801-32809; Tone M, Tone Y, Fairchild P J, Wykes M, Waldmann H. Regulation of CD40 function by its isoforms generated through alternative splicing. Proc Natl Acad Sci USA. 2001; 98:1751-1756), potentially limiting adaptive immunity, it was determined whether iCD40 could induce not only enhanced, but also prolonged, expression of IL-12p70 in TLR-4-stimulated DCs. To evaluate the kinetics of IL-12 expression, LPS-treated iCD40-DCs with LPS and CD40L-stimulated DCs were compared. It was observed that iCD40-DCs were able to produce IL-12p70 for over 72 hours post stimulation compared to CD40L or control vector-transduced DCs in which IL-12p70 expression ceased when LPS stimulation was removed. These results indicate that inducible CD40 signaling allows DCs to produce increased levels of IL-12p70 continuously in response to TLR-4 stimulation.

Finally, the induction of the suppressor of cytokine signaling (SOCS1) was evaluated. SOCS1 is negative feedback inhibitor of DC activation, that can attenuate (Wesemann D R, Dong Y, O'Keefe G M, Nguyen V T, Benveniste E N. Suppressor of cytokine signaling 1 inhibits cytokine induction of CD40 expression in macrophages. J Immunol. 2002; 169:2354-2360) responsiveness to LPS and cytokine stimulation (Evel-Kabler K, Song X T, Aldrich M, Huang X F, Chen S Y. SOCS1 restricts dendritic cells' ability to break self tolerance and induce antitumor immunity by regulating IL-12 production and signaling. J Clin Invest. 2006; 116:90-100). LPS stimulation up-regulated SOCS1 expression in DCs, as previously reported (Wesemann D R, et al., J Immunol. 2002; 169:2354-2360). Strikingly, however, in the presence of LPS, iCD40-DCs expressed 3-fold lower levels of SOCS1 than CD40L-stimulated DCs. Moreover, iCD40 did not induce SOCS1 by itself, unlike CD40L. These data indicate that iCD40 can partially bypass SOCS1 induction in human DCs and may partly explain the observed sustained elevation of IL-12 levels and DC maturation markers.

In addition to IL-12, IL-6 plays an important role in cell survival and resistance to T regulatory cells (Rescigno M, et al., J Exp Med. 1998; 188:2175-2180; Pasare C, Medzhitov R. Toll pathway-dependent blockade of CD4+CD25+ T cell-mediated suppression by dendritic cells. Science. 2003; 299: 1033-1036). It was observed that upon transfection with Ad-iCD40, IL-6 expression was significantly enhanced and further upregulated when iCD40-DCs were stimulated with dimerizer drug and TLR-4 ligands. Thus, iCD40 signaling is sufficient for production of some pro-inflammatory cytokines, but requires additional TLR signaling for production of the key TH1 cytokine, IL-12.

Example 4

Antigen-Specific TH1 Polarization

Antigen-specific TH1 polarization assays are presented herein. Those of ordinary skill in the art are able to modify the examples presented in order to assay polarization in the context of inducible PRR and PRR adapter proteins.

To further investigate whether iCD40-DCs matured with TLR-4 ligands can effectively prime CD4+ T helper (TH) cells, it was determined whether they can augment CD4+ epitope-specific T-cell responses in vitro. Naïve CD4+ CD45RA+ T cells were stimulated for 7 days in the presence of autologous Ad-iCD40 DCs pulsed with the model antigen, tetanus toxoid. At day 7, T cells were stimulated with the MHC class II-restricted tetanus toxoid epitope, TTp30. The production of IFN-gamma was significantly increased in the CD4+ T cells co-cultured with iCD40-DCs and iCD40-DCs stimulated with either MPL or MC. IFN-gamma production was iCD40-specific, as it was not induced by control virus Ad-GFP-transduced DCs or by MPL or MC stimulation alone. In addition, T cell polarization was analyzed by assessing TH1/TH2 cytokine levels in the supernatants of T cells using a cytometric bead array. The levels of IFN-gamma, TNF-alpha, IL-4, and IL-5 secreted cytokines were increased in helper T cells stimulated by iCD40-DCs, indicating the expansion of both TH1 and TH2-polarized T cells. However, the levels of TH1 cytokines were significantly higher than TH2-associated cytokines, indicating a predominant expansion of TH1 cells. In contrast, induction of TT-specific CD4+ T-helper cells from naive CD4+CD45RA+ cells, using MC-matured DCs, led to only a modest bias in TT epitope-specific TH1 differentiation. These results suggest that iCD40 signaling in DCs enables them to effectively induce antigen-specific TH1 differentiation, possibly due to higher IL-12 production.

Example 5

Tumor Antigen-Specific CTL Response Assay

Antigen-specific TH1 polarization assays are presented herein. Those of ordinary skill in the art are able to modify the examples presented in order to assay polarization in the context of inducible PRR and PRR adapter proteins.

It was determined whether iCD40 and MPL could enhance cytotoxic T lymphocyte (CTL) responses to poorly immunogenic melanoma self-antigen MAGE-3. iCD40-DCs from HLA-A2-positive donors were pulsed with class-I HLA-A2.1-restricted MAGE3-derived immunodominant peptide, FLWGPRALV (SEQ ID NO: 19), and co-cultured with autologous T cells. After a series of stimulations, the frequency of antigen-specific T cells was assessed by IFN-gamma-specific ELISPOT assay. iCD40-DCs stimulated with MPL led to a 50% increase in MAGE-3-specific T cells relative to iCD40-DCs stimulated with MC and about a five-fold increase in antigen-specific T cells compared to control non-transduced (WT) DCs.

It also was determined whether iCD40-DCs were capable of enhancing CTL-mediated killing of tumor cells in an antigen-specific fashion. Immature DCs from HLA-A2-positive volunteers were transfected with Ad-iCD40, pulsed with MAGE-3 protein, and used as stimulators to generate CTLs in vitro. SK-MEL-37 cells (HLA-A2+, MAGE-3+) and T2 cells pulsed with MAGE-3 A2.1 peptide (HLA-A2+, MAGE-3+) were utilized as targets. NA-6-MEL cells (HLA A2-, MAGE-3+) and T2 cells (HLA-A2+) pulsed with an irrelevant A2.1-restricted influenza matrix peptide served as negative controls. CTLs induced by iCD40-DCs were capable of efficiently recognizing and lysing their cognate targets (SK-MEL-37), and also T2 cells pulsed with MAGE-3 A2.1 peptide, indicating the presence of MAGE-3-specific CTLs. In contrast, control targets were lysed at significantly lower levels. Improved lytic activity was consistently observed when iCD40-DCs treated with MPL or MC were used as stimulators compared with non-transduced DCs treated with MPL or MC alone. In addition, a significant expansion of MAGE-3/HLA-A2-specific tetramer positive CD8+CTLs by iCD40-DCs that were treated with MPL was observed.

Similarly, to test whether LPS and iCD40-stimulated DCs could enhance CTL lytic activity, their ability to break tolerance to prostate-specific membrane antigen (PSMA) was examined. DCs generated from healthy HLA-A2+ volunteers were pulsed with PSMA protein (Davis M I, Bennett M J, Thomas L M, Bjorkman P J. Crystal structure of prostate-specific membrane antigen, a tumor marker and peptidase. Proc Natl Acad Sci USA. 2005; 102:5981-5986) or MAGE-3, transduced with AD-iCD40 or Ad-Luc, and were co-cultured with autologous T cells. After three rounds of stimulation, antigen-specific CTL activity was measured by chromium-release assay using LNCaP cells (HLA-A2+PSMA+) as targets and SK-Mel-37 (HLA-A2+PSMA−) as control cells for PSMA-pulsed DCs. SK-Mel-37 cells (MAGE-3+) were used as targets when DCs of the same donor were pulsed with MAGE-3, and LNCaP cells (MAGE-3−) were used as negative controls. Collectively, these data indicate that iCD40-transduced DCs are capable of inducing significantly more potent antigen-specific CTL responses in vitro than MC-treated DCs. Those of ordinary skill in the art may modify this assay to examine tumor antigen specific CTL responses using chimeric iCD40-inducible PRR adapter proteins.

Example 6

Inducible CD40 Enhances CCR7 Expression and Migratory Abilities of DCs without PGE2

Antigen-specific TH1 polarization assays are presented herein. Those of ordinary skill in the art are able to modify the examples presented in order to assay polarization in the context of inducible PRR and PRR adapter proteins.

In addition to other maturation markers, CCR7 is up-regulated on DCs upon maturation and is responsible for directing their migration to draining lymph nodes (Cyster J G. Chemokines and cell migration in secondary lymphoid organs. Science. 1999; 286:2098-2102). Recently, several reports have indicated that, apart from chemotaxis, CCR7 also affects DC "cytoarchitecture", the rate of endocytosis, survival, migratory speed, and maturation (Sanchez-Sanchez N, Riol-Blanco L, Rodriguez-Fernandez J L. The Multiple Personalities of the Chemokine Receptor CCR7 in Dendritic Cells. J Immunol. 2006; 176:5153-5159). Along with costimulatory molecules and TH1 cytokines, iCD40 specifically up-regulates CCR7 expression in human DCs. Moreover, CCR7 expression correlated with Ad-iCD40 viral dose-escalation.

Because CCR7 expression levels correlate with enhanced migration toward MIP-3 beta CCL19), it was determined whether human iCD40-DCs could migrate in vitro toward MIP-3 beta in transwell assays. iCD40-DCs treated with AP20187 dimerizer have migration levels comparable to those induced by MC. Moreover, iCD40-DC migration was further increased by MPL or MC stimulation, even when PGE2 was not present. These data were highly reproducible and indicate that iCD40 is sufficient to induce CCR7 expression and DC migration in vitro in contrast to the widely held belief that PGE2 is essential for lymph node homing of human DC.

Chemokines and chemokine receptors share a high degree of sequence identity within a species and between species (De Vries I J, Krooshoop D J, Scharenborg N M, et al. Effective migration of antigen-pulsed dendritic cells to lymph nodes in melanoma patients is determined by their maturation state. Cancer Res. 2003; 63:12-17). On the basis of this knowledge, a novel xenograft model was developed for monitoring the migration of human DCs in vivo. Human DCs were transduced with iCD40 and matured with LPS or MC, and mouse DCs were matured with LPS. Since DCs were co-transduced with Ad5-CBR, bioluminescence was immediately visible. As expected, immature DCs did not migrate to the draining popliteal lymph nodes. However, iCD40-DCs matured with LPS or MC were detectable in the xenogeneic popliteal lymph nodes within 2 days post-inoculation. The migration of iCD40-DCs stimulated with LPS was significantly ($p=0.036$) higher than non-stimulated DCs and was comparable to mouse DC migration. Moreover, at day 2 the iCD40-DCs were detected in inguinal LNs while MC-stimulated DCs were undetectable, suggesting higher migratory abilities of iCD40-DCs than stimulated with MC. Collectively, these results indicate that iCD40 signaling in DCs plays a critical role in controlling CCR7 expression and is sufficient for DC migration to lymph nodes. The migration of iCD40-DCs is further enhanced when the cells are stimulated with LPS, correlating with enhanced CCR7 expression. Those of ordinary skill in the art may modify this assay for assaying chimeric iCD40-inducible PRR adapter proteins.

Example 7

Summary of Observations from Assays Presented in Example 2 to Example 6 with iCD40 and PRRs Dendritic cell efficacy depends on many variables, especially maturation status and efficient migration to lymph nodes. Several clinical trials in cancer patients showed the potency of DCs to induce adaptive immunity to tumor-specific antigens (Nestle F O, Banchereau J, Hart D. Dendritic cells: On the move from bench to bedside. Nat Med. 2001; 7:761-765; Schuler G, Schuler-Thurner B, Steinman R M. The use of dendritic cells in cancer immunotherapy. Curr Opin Immunol. 2003; 15:138-147; Cranmer L D, Trevor K T, Hersh E M. Clinical applications of dendritic cell vaccination in the treatment of cancer. Cancer Immunol Immunother. 2004; 53:275-306). However, clinical responses were transient, and warrant further improvement in DC vaccine design (Ridgway D. The first 1000 dendritic cell vaccines. Cancer Invest. 2003; 21:873-886; Dellal R M, Lotze M T. The dendritic cell and human cancer vaccines. Curr Opin Immunol. 2000; 12:583-588). Limitation of current DC-based vaccines are the transient activation state within lymphoid tissues, low induction of CD4+ T cell immunity, and impaired ability to migrate to the draining lymph nodes (Adema G J, de Vries I J, Punt C J, Figdor C G. Migration of dendritic cell based cancer vaccines: in vivo veritas? Curr Opin Immunol. 2005; 17:170-174). Less than 24 hours following exposure to LPS, DCs terminate synthesis of the TH1-polarizing cytokine, IL-12, and become refractory to further stimuli (Langenkamp A, Messi M, Lanzavecchia A, Sallusto F. Kinetics of dendritic cell activation: impact on priming of TH1, TH2 and nonpolarized T cells. Nat Immunol. 2000; 1:311-316), limiting their ability to activate T helper cells and CTLs. Other studies indicate that less than 5% of intradermally administered mature DCs reach the lymph nodes, showing inefficient homing[39]. These findings underscore the need for either prolonging the activation state and migratory capacities of the DCs and/or temporally coordinating the DC activation "window" with engagement of cognate T cells within lymph nodes.

A method for promoting mouse DC function in vivo was developed by manipulation of a chimeric inducible CD40 receptor (Hanks B A, et al., Nat Med. 2005; 11:130-137). It has been observed that the inducible CD40 approach is also effective in enhancing the immunostimulatory function of human DCs. Consistent with previous reports of the synergistic activity of combining TLR and CD40 signaling for IL-12p70 secretion, iCD40 plus TLR4 signaling induced high level IL-12 secretion, DC maturation, T cell stimulatory functions, and extensive migratory capacities (Lapointe R, et al., Eur J Immunol. 2000; 30:3291-3298; Napolitani G, Rinaldi A, Bertoni F, Sallusto F, Lanzavecchia A. Selected Toll-like receptor agonist combinations synergistically trigger a T helper type 1-polarizing program in dendritic cells. Nat Immunol. 2005; 6:769-776).

It was also demonstrated that increased and prolonged secretion of IL-12p70 in DCs could break self tolerance, which likely is attributable in part to over-riding the production of SOCS1, which inhibits IL-12 signaling (Evel-Kabler K, et al., J Clin Invest. 2006; 116:90-100). It has been determined that although endogenous CD40 signaling stimulated by soluble CD40L leads to SOCS1 upregulation, iCD40 activates DCs without significant SOCS1 induction. Additionally, iCD40 signaling unleashes high and prolonged expression of IL-12p70 in DCs, which exhibit enhanced potency in stimulating CD4+ T cells and CTLs.

IL-6 is implicated in the survival of many different cell types by activation of anti-apoptotic pathways, such as p38 MAPK, ERK1, 2 47 and PI3-kinase (Bisping G, Kropff M, Wenning D, et al. Targeting receptor kinases by a novel indolinone derivative in multiple myeloma: abrogation of stroma-derived interleukin-6 secretion and induction of apoptosis in cytogenetically defined subgroups. Blood. 2006; 107:2079-2089). The induction of IL-6 expression by iCD40 and TLR-4 signaling in DCs also was identified. This finding could partly explain the prolonged survival of DCs described previously (Hanks B A, et al., Nat Med. 2005; 11:130-137). Furthermore, IL-6 expression is critical in the ability of DCs to inhibit the generation of CD4+CD25+ T regulatory cells (Pasare C, and Medzhitov R., Science. 2003; 299:1033-1036). In this context, an iCD40-DCs-based vaccine could potentially suppress negative regulators in vivo, inhibiting peripheral tolerance to targeting antigens.

One major focus of cancer immunotherapy has been the design of vaccines to promote strong tumor antigen-specific CTL responses in cancer patients (Rosenberg S A., Immunity. 1999; 10:281-287). However, accumulating evidence suggests that CD4+ T cells also play a critical role in antitumor immunity, as they contribute to the induction, persistence and expansion of CD8+ T cells (Kalams S A, Walker B D. The critical need for CD4 help in maintaining effective cytotoxic T lymphocyte responses. J Exp Med. 1998; 188:2199-2204). Our study showed that iCD40-DCs could effectively prime naïve T cells and effectively expand antigen-specific cells representing both arms of the immune response (i.e. MAGE-3 and PSMA specific CTLs and TT-specific CD4+ T cells). It was demonstrated that TH1 (IFN-gamma and TNF-alpha) cytokines were produced predominantly in the milieu of iCD40-DC-stimulated CD4+ T cells, indicating expansion of TH1 cells. As expected, these cytokines were not detected when T cells were stimulated with MC-treated DCs, because PGE2 (a key MC component) is a powerful suppressor of TH1 responses (Kalinski P, Hilkens C M, Snijders A, Snijdewint F G, Kapsenberg M L. Dendritic cells, obtained from peripheral blood precursors in the presence of PGE2, promote Th2 responses. Adv Exp Med Biol. 1997; 417:363-367; McIlroy A, Caron G, Blanchard S, et al. Histamine and prostaglandin E up-regulate the production of Th2-attracting chemokines (CCL17 and CCL22) and down-regulate IFN-gamma-induced CXCL10 production by immature human dendritic cells. Immunology. 2006; 117:507-516; Meyer F, Ramanujam K S, Gobert A P, James S P, Wilson K T. Cutting edge: cyclooxygenase-2 activation suppresses Th1 polarization in response to *Helicobacter pylori*. J. Immunol. 2003; 171:3913-3917).

Recent mouse studies have shown that DC migration directly correlates with T cell proliferation (Martln-Fontecha A, Sebastiani S, Hopken U E, et al. Regulation of dendritic cell migration to the draining lymph node: impact on T lymphocyte traffic and priming. J Exp Med. 2003; 198:615-621). Therefore, the increase in migration should enhance the efficacy of DC-based vaccines[45]. Current DC vaccine protocols include pre-conditioning the vaccine injection site with inflammatory cytokines or ex vivo stimulation of DCs with TLR ligands and pro-inflammatory cytokines, consisting primarily of MC constituents (Martln-Fontecha A, et al., J Exp Med. 2003; 198:615-621; Prins R M, Craft N, Bruhn K W, et al. The TLR-7 agonist, imiquimod, enhances dendritic cell survival and promotes tumor antigen-specific T cell priming: relation to central nervous system antitumor immunity. J Immunol. 2006; 176:157-164). Despite its numerous immunosuppressive functions[8-12], PGE2 has been used for the past few years as an indispensible component of the DC maturation cocktail because it stimulates the migratory capacity of DCs by up-regulating both CCR7 and sensitization to its ligands. Alternative approaches enhancing DCs migration without PGE2, should be beneficial for DC-based vaccine improvement.

The results of these studies show that iCD40 signaling not only up-regulates CCR7 expression on DCs but also stimulates their chemotaxis to CCL19 in vitro. Additionally, immature DCs transduced with iCD40 were able to migrate as efficiently as MC-stimulated DCs both in vitro and in vivo. Moreover, migration of iCD40-DCs was further induced when cells were stimulated with TLR-4 ligands. It was recently shown that stimulation of CCR7 increases the migratory rate of DCs, indicating that this receptor can regulate DC locomotion and motility (Riol-Blanco L, Sanchez-Sanchez N, Torres A, et al. The chemokine receptor CCR7 activates in dendritic cells two signaling modules that independently regulate chemotaxis and migratory speed. J Immunol. 2005; 174:4070-4080; Palecek S P, Loftus J C, Ginsberg M H, Lauffenburger D A, Horwitz A F. Integrin-ligand-binding properties govern cell migration speed through cell-substratum adhesiveness. Nature. 1997; 385:537-540; Yanagawa Y, Onoe K. CCL19 induces rapid dendritic extension of murine dendritic cells. Blood. 2002; 100:1948-1956). It has been shown that stimulation of CCR7 enhances the mature phenotype of DCs58. Thus, by transduction of DCs with iCD40, CCR7 expression, DC migration and maturation status have been enhanced, obviating the need for PGE2.

Finally, iCD40 stimulation of DCs was capable of inducing a potent cytotoxic T cell response to the prostate-specific antigen, PSMA, which was capable of significantly increased killing of target LNCaP cells. (Dudley M E, Wunderlich J R, Yang J C, et al. Adoptive cell transfer therapy following non-myeloablative but lymphodepleting chemotherapy for the treatment of patients with refractory metastatic melanoma. J Clin Oncol. 2005; 23:2346-2357; Morgan R A, Dudley M E, Wunderlich J R, et al. Cancer Regression in Patients After Transfer of Genetically Engineered Lymphocytes. Science. 2006). Other documents cited herein are referenced in U.S. patent application Ser. No. 10/781,384, filed Feb. 18, 2004, entitled "Induced Activation In Dendritic Cells," and naming Spencer et al. as inventors, now issued as U.S. Pat. No. 7,404,950.

Example 8

Inducible CD40

The innate immune system uses several families of pattern recognition receptors PRRs to sense pathological infection or injury. One family of PRRs is the Toll-like receptors (TLRs) that now include about 11 members in mammals. These typically bind to multi-valent ligands through a leucine-rich motif (LRM). The ligands can come from bacteria, viruses, fungi, or host cells and can bind to TLRs either on the cell surface or within endocytic vesicles (especially TLR 3, 7, 8 and 9). Within their cytoplasmic signaling domains, they share a conserved TIR (Toll/IL-1R) domain that binds to downstream TIR-containing adapter molecules, such as MyD88 and TRIF/TICAM-1, and adapters TIRAM/TICAM-2 and MAL/TIRAP. Additional PRRs include the NOD-like receptors (e.g. NOD1 and NOD2) and the RIG-like helicases, RIG-I and Mda-5. Many PRRs bind to ligands through flexible LRMs and couple to downstream signaling molecules through protein-protein binding motifs, such as TIR or CARD (caspase recruitment domain) domains.

Stimulation through TLR-4 in conjunction with signaling through the costimulatory molecule CD40 can promote high-level maturation and migratory properties in human monocyte-derived dendritic cells (MoDCs). Based on both published and unpublished data[2-7], this prolonged and enhanced activation state of human MoDCs in vitro and/or in vivo may both promote the activation and expansion of autologous tumor-specific T cells for adoptive immunotherapy and overcome the problems of self-limiting ex vivo-matured DCs for vaccination.

Various approaches are available for assessing the use of different PRRs in combination with inducible CD40. These approaches, and the experimental methods used to conduct these assessments, may also be used to study inducible CD40 in combination with inducible PRR adapter proteins such as, for example, MyD88 and TRIF.

To replace complex, poorly understood MoDC maturation cocktails or combinations of adjuvants and CD40 signaling, CID-inducible versions of toll-like receptor 4 (called iTLR4) and other iTLRs (i.e. TLR3, 7, 8, and 9) are developed and iTLRs are assayed for synergy with iCD40 either in trans or in cis within the same polypeptide chain. Efficacy is based on induction of transcription factors NF-kappaB and IRF3/7s, and phosphorylation of p38 and JNK in the DC line, D2SC/1. The most potent inducible receptor is subcloned into an adenovector for efficient transduction of MoDCs.

Dendritic cells (DCs) play a critical role in initiating and regulating adaptive immunity[7,8]. Upon detection of "danger signals", DCs physiologically adapt to their microenvironment by undergoing a genetic maturation program[6]. Using a broad repertoire of antigen presentation and costimulatory molecules, DCs are capable of potently activating naïve antigen-specific T lymphocytes and regulating their subsequent phenotype and function[9]. In most cases, the development of robust cytotoxic T lymphocyte (CTL) immunity by DCs requires a "helper" signal from CD4+ T cells[10]. This signal is comprised of both soluble cytokines, such as IL-2, as well as CD40L-mediated stimulation of the surface CD40 receptor on the DC[11-13]. A member of the tumor necrosis factor receptor (TNFR) superfamily, CD40 triggers various pathways within the DC resulting in the upregulation of several antigen presentation, costimulatory, cytokine, and pro-survival genes, which collectively enable the DC to induce CTL activation[14,15].

Given the pre-eminent role of DCs as antigen-presenting cells (APCs), they may be exploited as natural adjuvants in vaccination protocols for the treatment of various malignancies[16,17]. Typical applications include harvesting peripheral blood monocytes via leukapheresis, differentiation in culture in GM-CSF and IL-4, and loading immature monocyte (or CD34$^+$ precursor cell)-derived DCs (MoDC) with tumor antigens by one of several methods, such as pulsing immature DCs with unfractionated tumor lysates, MHC-eluted peptides, tumor-derived heat shock proteins (HSPs), tumor associated antigens (TAAs (peptides or proteins)), or transfecting DCs with bulk tumor mRNA, or mRNA coding for TAAs (reviewed in 18,19). Antigen-loaded DCs are then typically matured ex vivo with inflammatory cytokines (e.g. TNFalpha, IL1beta, IL6, and $PGE_2$) or other adjuvants (e.g. LPS, CpG oligonucleotides) and injected into patients. In each case, the immuno-stimulatory properties of the DCs depend on many variables, especially the ability to migrate to lymph nodes and full maturation status. However, the limited success in recent clinical trials with DC immunotherapy has suggested that current protocols need to be refined if DC-based immunotherapy is to be included in the treatment arsenal alongside more conventional modalities of anti-cancer therapy[20,21].

Two key limitations of DC-based vaccines are the short lifespan of matured DCs and their transient activation state within lymphoid tissues. Less than 24 hours following exposure to lipopolysaccharide (LPS), DCs terminate synthesis of the $T_H1$-polarizing cytokine, IL-12, and become refractory to further stimuli[22], limiting their ability to activate cytotoxic T lymphocytes (CTLs). Other studies indicate that the survival of antigen-pulsed DCs within the draining lymph node (LN) is limited to only 48 hours following their delivery, due primarily to elimination by antigen-specific CTLs[23]. These findings underscore the need for improved methods of either prolonging the activation state and life span of the DCs and/or temporally coordinating the DC activation "window" with engagement of cognate T cells within LNs. Thus, enhancing the activation and survival of DCs may be critical to promoting immunity against tumors.

DC survival is regulated, at least partly, by pathogen-derived molecules acting through one or more conserved Toll-like receptors (TLRs) and T cell-expressed costimulatory molecules (e.g. CD40L and TRANCE), which are partly dependent on Bcl-2 and Bcl-$x_L$ for anti-apoptotic activity[3,24-27]. Although the importance of TLR-, CD40-, or Bcl-2-mediated DC longevity has been well documented, homeostatic feedback mechanisms are also likely to limit the utility of TLR-ligands or Bcl-2 family members to extend DC longevity in tumor vaccine protocols. These include receptor desensitization or downregulation[4,28,29], expression of negative regulators for TLR/IL-1Rs, like IRAK-M[30] and SOCS-1[5], and induction of pro-apoptotic molecules, like Bim[31], resulting in the neutralization of anti-apoptotic molecules by TLR signals.

An attractive target for manipulation is the TNF family receptor, CD40. Unlike pro-inflammatory cytokines or pathogen-associated molecules that DCs encounter throughout the periphery, the DC-expressed CD40 receptor is engaged by CD4+ T helper cells within the LN paracortex via its cognate ligand, CD40L[12,13,37]. Recent studies have further shown that CD40 stimulation enables DCs to "cross-present" antigen[38] and overcome peripheral T cell tolerance[39], prompting therapeutic studies based on CD40 stimulation. Strategies included systemic delivery of CD40-specific monoclonal antibodies (mAbs) or of trimerized CD40L[40], the utilization of CD40-stimulated, antigen-loaded DC-based vaccines[41], and administration of genetically modified CD40 ligand (CD40L)-expressing DCs[42]. Despite great potential, several properties of CD40 limit its therapeutic development, including ubiquitous expression of CD40 by a variety of other cell types, including B cells, macrophages, and endothelial cells[14], increasing the likelihood for side effects due to systemic administration of CD40 stimuli. Moreover, several mechanisms regulate the surface expression of CD40 by targeting its extracellular domain, including CD40L-induced cleavage by matrix metalloproteinase enzymes[29], negative feedback degradation by an alternatively spliced CD40 isoform[28], and CD40L-mediated endocytosis of CD40.

Figure 2:
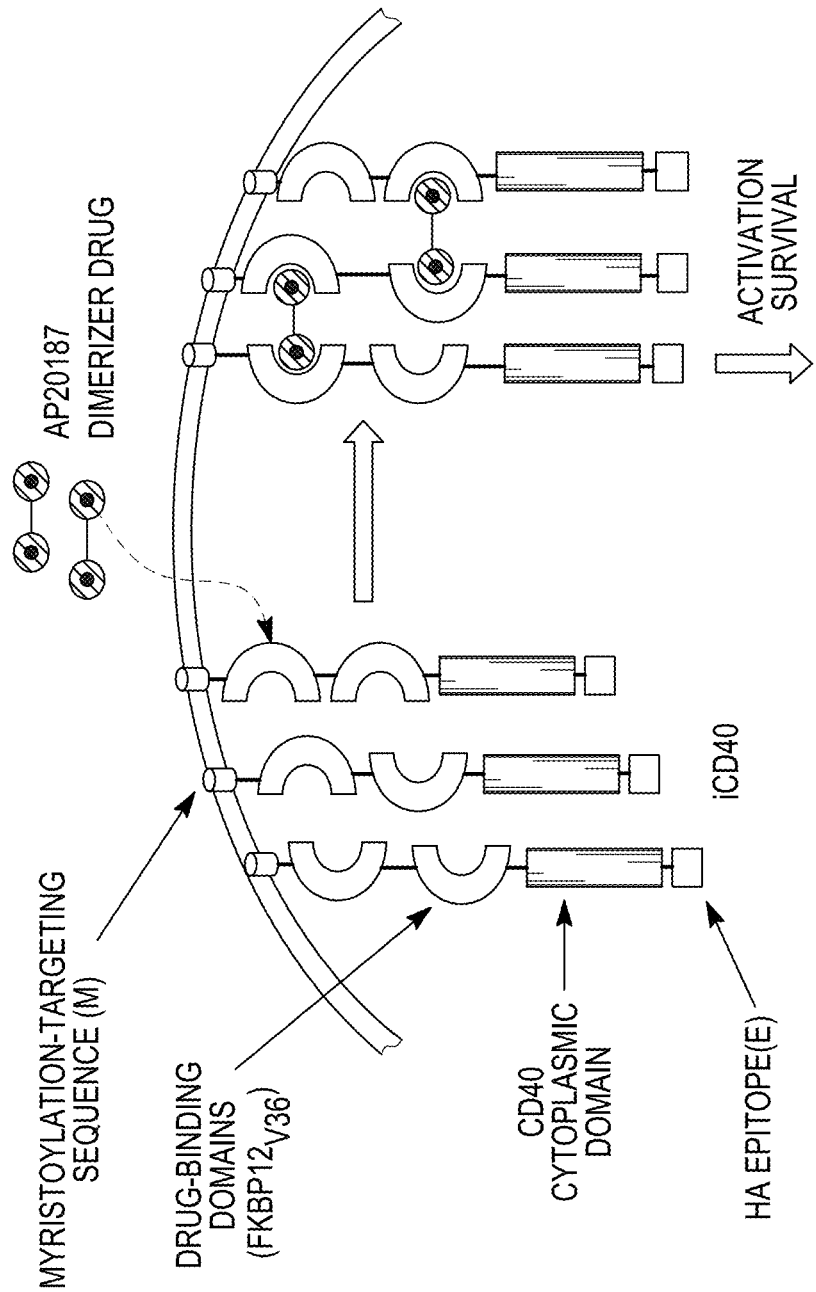
FIG. 2. Schematic of iCD40. Administration of the lipid-permeable dimerizing drug, AP20187/AP1903[1], leads to oligomerization of the cytoplasmic domain of CD40, modified to contain AP20187-binding domains and a myristoylation-targeting sequence.

Therefore, a DC activation system based on the CD40 signaling pathway to extend the pro-stimulatory state of DCs within lymphoid tissues by providing DC-targeted functionality, temporal control, and resistance to CD40 regulatory mechanisms has been developed. This engineered recombinant receptor was comprised of the cytoplasmic domain of CD40 fused to ligand-binding domains and a membrane-targeting sequence (FIG. 2). Administration of a lipid-permeable, dimerizing drug intraperitoneally led to the potent induction of CD40-dependent signaling cascades and greatly improved immunogenicity against both defined antigens and tumors in vivo relative to other activation modalities[4]. Hence the chimeric CD40 was named inducible CD40 (iCD40). The high utility of iCD40-activated DCs in mice, suggested that methods to stabilize endogenous CD40 signaling might also enhance the potency of DC vaccines.

TLRs bind to a variety of viral and bacterial-derived molecules, which trigger activation of target cells, such as T cells, macrophages and dendritic cells. Although the majority of the 10 or so mammalian TLRs utilize a signaling pathway initiated by the inducible PRR adapter protein, MyD88, leading to NF-kappaB activation, TLR3 relies instead on the inducible PRR adapter TRIF, leading to IRF3 and Type I interferon induction. Together, these signaling pathways can synergize to produce high levels of the Th1 cytokine, IL-12[43]. Interestingly, TLR-4 can utilize both pathways following binding of the potent mitogen, LPS, or derivatives. Stimulation through TLR-4 in conjunction with signaling through the costimulatory molecule CD40 can promote high-level maturation and migratory properties in human MoDCs.

Like many cell-surface receptors that make a single pass through the plasma membrane, TLRs are likely to all be activated by homo or heterodimerization or oligomerization. There have been reports of homodimerization-mediated activation of TLR-4 and heterodimerization-mediated activation of TLR2 with TLR1 and TLR6[44-48]. Moreover, in a recent article, Ian Wilson and colleagues crystallized TLR-3 and identified dimerization regions within the extracellular domain, suggesting that it signals as a homodimer followed dsRNA binding[49]. Therefore, it is likely that chemically induced dimerization of TLRs, especially TLR-4, will lead to their induction.

Considerations for the Development of Ex Vivo-Matured, Monocyte-Derived "Enhanced" Human DCs.

Published and unpublished studies have suggested two potent methods to enhance DC function in vivo, ectopic expression of an optimized, constitutive Akt (Myr$_F$-ΔAkt) and manipulation of a chimeric inducible CD40 in vivo. Complementing this work, Si-Yi Chen (Baylor College of Medicine, Houston, Tex.) has shown that lowering SOCS-1 levels in DCs can also enhance efficacy[5]. While significant supporting data in mice for iCD40, Myr$_F$-ΔAkt, and SOCS-1 approaches has been accumulated, human MoDCs are not identical to murine bone marrow-derived DCs. In particular, the most commonly used human DC vaccine protocol involves differentiation of MoDCs from monocytes, prior to treatment with the "gold standard" pro-inflammatory maturation cocktail, containing TNF-alpha, IL-1-beta, IL-6, and PGE$_2$. Although PGE$_2$ is considered necessary to upregulate CCR7 and gain chemotactic responsiveness to lymph node-derived chemokines, CCL19 and CCL21[50,51], PGE$_2$ can also impair DC signaling by suppressing bioactive IL12p70 production[52]. While it is unlikely that IL12 suppression is permanent in vivo, given the slowly building success rate of DC vaccines[7], it will be important to determine prior to clinical applications which of the methods outlined above can best overcome PGE$_2$-mediated IL12 suppression in human MoDCs without interfering with migratory capacity.

Although clinical success in DC-based vaccines has been modest[7,20], extremely low side effects and potentially exquisite specificity and sensitivity make this modality attractive. Because interaction with antigen-specific T cells is likely to be prolonged, these enhanced DCs are likely to improve the clinical outcome of DC vaccines. The development of enhanced antigen-expressing DCs not only has potential applicability to treating malignancy, but also should be applicable to the treatment of numerous pathogens, as well. Moreover, this high impact approach should complement prior efforts by numerous labs, which have identified tumor antigens.

Characterization of iCD40 Functionality in Primary DCs and Development of an iCD40-Expressing DC-Based Prostate Cancer Vaccine.

After demonstrating functionality of iCD40 in murine D2SC/1 cells ([4] and not shown), which possess many characteristics of freshly isolated DCs, iCD40 functionality in primary bone marrow-derived DCs (BMDCs) by utilizing an iCD40-expressing adenovirus was examined. A helper-dependent, ΔE1, ΔE3-type 5 adenoviral vector, named Ad-iCD40-GFP, was engineered to express both iCD40 and EGFP under the control of the CMV early/immediate promoter/enhancer. Ad-iCD40-GFP successfully transduced and expressed the iCD40 transgene, as well as the EGFP marker, in purified BMDCs. Titrating Ad-iCD40-GFP while measuring iCD40-induced upregulation of B7.2 (CD86) showed that maximum drug-mediated iCD40 activation occurred at around 100 moi and proceeded asymptotically to plateau at higher viral titers (data not shown). Although the effects were modest, AP20187 induced the surface expression of MHC class I $K^b$, B7.2, as well as endogenous CD40 on iCD40-expressing BMDCs at 100 moi but not on non-transduced DCs. The effects of Ad-iCD40-GFP on BMDCs using intracellular cytokine staining to evaluate DC expression of the $T_H1$-polarizing cytokine, IL-12 was then investigated. These findings confirmed numerous previous reports that an empty adenoviral vector can contribute to background fluorescence readings by stimulating the production of low levels of this cytokine[53]. These experiments also revealed that the iCD40 transgene could generate a significant level of basal signaling at these titers even in the absence of CID. However, AP20187 exposure of these iCD40-expressing DCs managed to reproducibly overcome these cumulative effects to further increase the percentage of IL-12+ DCs. Interestingly, the stimulation of IL-12p70/p40 synthesis with LPS and CD40L peaked at 8 hrs and decreased thereafter, while the percentage of IL-12+ DCs continued to increase until at least 24 hrs following Ad-iCD40-GFP transduction. Previous work by Langenkamp et al. has demonstrated that prolonged treatment of DCs with LPS exhausts their capacity for cytokine production[54]. These results imply that the Ad-iCD40-GFP vector, as opposed to the LPS danger signal, is capable of promoting and maintaining a more durable IL-12 response by BMDCs.

In addition to DC activation state, DC longevity is another critical variable that influences the generation of T cell-dependent immunity. In fact, CTL-mediated killing of DCs is considered to be a significant mechanism for modulating immune responses while protecting the host from autoimmune pathologies[55,56]. Other work has established that CD40 stimulation of DCs prolongs their survival by a variety of mechanisms, including upregulation of the anti-apoptotic protein bcl-$X_L$ and the granzyme B inhibitor, Spi-6[57,58]. The effects of iCD40 relative to CD40L on DC survival were compared in an in vitro serum-starvation culture assay. By analyzing the vital dye (propidium iodide (PI))-positive cell population by flow cytometry, iCD40 expressing-BMDCs were found to exhibit greater longevity under these conditions relative to non-transduced DCs treated with CD40L. This effect was iCD40-dependent since Ad-GFP-transduced DCs failed to reflect improved survival under these conditions. This work also showed that exposure of iCD40 BMDCs to the AP20187 dimerizer drug even further enhanced this survival effect relative to untreated BMDCs. Moreover, when Ad-iCD40 transduced DCs were CFSE-stained and injected into footpads, significantly increased numbers of DCs were found in popliteal lymph nodes following i.p. injections of AP20187 versus in vitro stimulated iCD40 DCs or LPS/CD40L-treated DCs.

Despite well-known Ad-dependent maturation signals and basal signaling effects of iCD40 in primary BMDCs, enhanced DC activation was detected in the presence of AP20187. Overall, this data suggests that an inducible CD40 receptor designed to respond to a pharmacological agent is capable of maintaining primary DCs in a sustained state of activation compared to the more transient effects of CD40L stimulation and the potentially more complex effects of anti-CD40 antibodies. This data is consistent with earlier findings describing only short-term DC modulation for stimuli that target endogenous CD40.

The iCD40 Activation Switch Functions as a Potent Adjuvant for Anti-Tumor DNA Vaccines.

Previous studies have demonstrated that DCs play a critical role in the processing and presentation of DNA vaccines to responding T cells[59]. The in vivo anti-tumor efficacy of iCD40 DC-based vaccines as well as the in situ role of iCD40-expressing DCs in tumor immuno-surveillance was then studied. To establish a therapeutic tumor model, C57BL/6 mice were inoculated subcutaneously. with the EG.7-OVA thymoma tumor line and allowed to progress until tumor volumes reached approximately 0.5 cm$^3$. These tumor-bearing mice were vaccinated with either SIINFEKL (SEQ ID NO: 26)-pulsed wt or iCD40 BMDCs. Vaccination with wt BMDCs, either untreated or stimulated in culture with LPS and CD40L or in vivo with anti-CD40 mAb, failed to slow the overall tumor growth rate. However, in vivo drug-mediated iCD40 activation of BMDC vaccines resulted in sustained decreases in tumor size. In addition, the response rate to in vivo activated iCD40-expressing BMDC vaccines was significantly higher than the response rates to wild type BMDCs under all other vaccination conditions (70% vs. 30%). To confirm the elicitation of tumor antigen-specific T cell responses in tumor-bearing mice, we performed H-2$K^b$ OVA$_{257-264}$ tetramer analysis was performed on peripheral blood CD8+ T cells. This analysis verified the presence of a expanded population of $K^b$OVA$_{257-264}$-specific CD8+ T cells exclusively in mice vaccinated with in vivo activated iCD40 BMDCs.

Although subcutaneous tumor models provide a convenient tool for approximating tumor size, their utility is typically limited to non-orthotopic tumors that are reasonably symmetrical. Also quantitation of metastasis necessitates euthanasia and is limited to a single measurement. As an improvement on this mainstay approach, tumor cells were developed that stably express a red-shifted luciferase from Caribbean click beetles (*Pyrophorus plagiophthalamus*). Imaging in mice following administration of substrate D-Luciferin, confirms easy detection by either a cooled CCD camera (IVIS™ Imaging System, Xenogen Corp.) or standard calipers. Furthermore, the red-shifted (~613 nM emission) luciferase reporter should permit more linear quantitation of surface distant metastasis.

Figure 3:
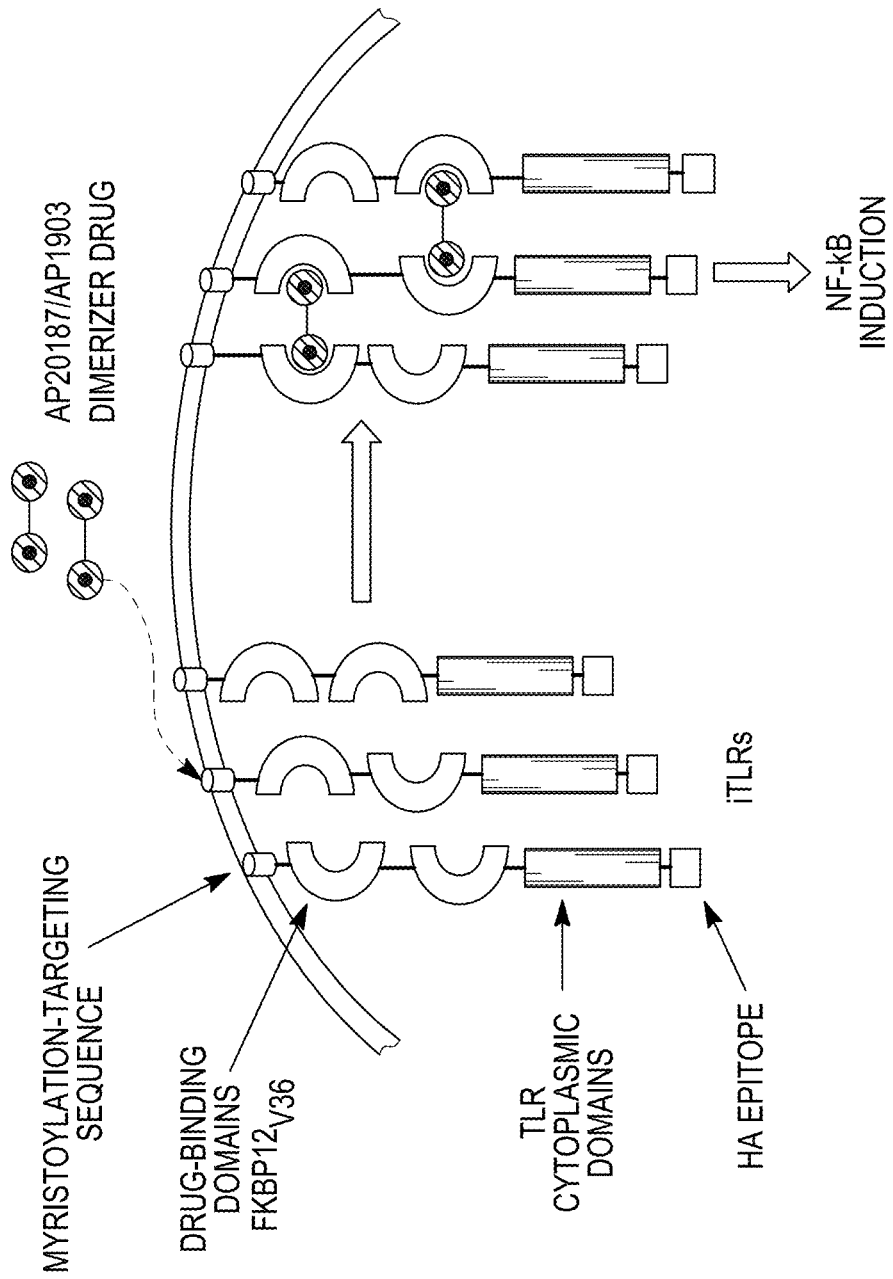
FIG. 3 is a schematic of CID-inducible TLRs.

Development of CID-Inducible TLRs (iTLRs):

There are several subgroups of TLRs based on sublocalization and signaling pathways utilized. Regardless of the normal subcellular localization of the ligand-binding extracellular domains, the signaling domains are cytoplasmic and should signal properly in all cases if homodimerization is the normal signaling mechanism. Analogous to iCD40, the TLR cytoplasmic signaling domains were PCR-amplified with flanking XhoI and SalI restriction sites for subcloning on the 5' or 3' side of two chemical inducers of dimerization (CID) binding domains (CBD), FKBP12$_{v36}$[1]. The chimeric CBD-TLRs were localized to the plasma membrane using myristoylation-targeting motifs (FIG. 3).

Initial testing of TLRs involved co-transfection of expression vectors into Jurkat-TAg or 293 cells along with an NF-kappaB-responsive SEAP (secreted alkaline phosphatase) reporter plasmid[66]. Interestingly, the preliminary data suggested that only iTLR7 and iTLR8 functioned in Jurkat-TAg cells, but not iTLR3, 4, and 9, regardless of the relative position of the CBDs and TLRs. Additional transfections in a panel of cells will be required to determine whether this reflects physiological tissue-specific signaling differences or other idiosyncrasies of these chimeric constructs.

Those of ordinary skill in the art will recognize the modifications that may be made for the use of adapter proteins rather than TLRs in the following methods.

Developing Inducible TLRs:

Inducible chimeric TLRs may be developed to circumvent the requirement for pathogen-derived (or synthetic) adjuvant in DC activation. Initially, chimeric iTLR 3, 4, 7, 8, and 9, were developed by cloning the cytoplasmic signaling domains of TLRs 5' (upstream) or 3' (downstream) of CID-binding domains (FIG. 3). Initial screening in Jurkat-TAG cells revealed that iTLR8 (and to a lesser extent iTLR7) triggered the largest induction of NF-kappaB. However, the relative strength of various TLRs may be a tissue-specific parameter. To address this. these constructs may be tested in the DC cell line, D2SC/1 initially with regard to NF-kappaB activation using an NF-kappaB SEAP reporter system based on transient transfection of multiple expression plasmids into target cells. 2DSC/1 cells represent a rare subset of immortalized DC lines that retain both the immature DC phenotype and the ability to mature following activation signals[67]. Since NF-kappaB induction is not the only function of TLRs, IRF3/7 induction may also be screened using an interferon (IFN)-stimulated response element (ISRE)-SEAP reporter plasmid that binds IRFs and induces reporter activity. To develop ISRE-SEAP, the ISRE-containing promoter from ISRE-luc (Stratagene) may replace the SRalpha promoter in the constitutive reporter plasmid pSH1/kSEAP. As a secondary induction of TLR signaling, JNK and p38 phosphorylation are monitored by Western blotting using phosphorylation-specific antibodies.

Figure 4:
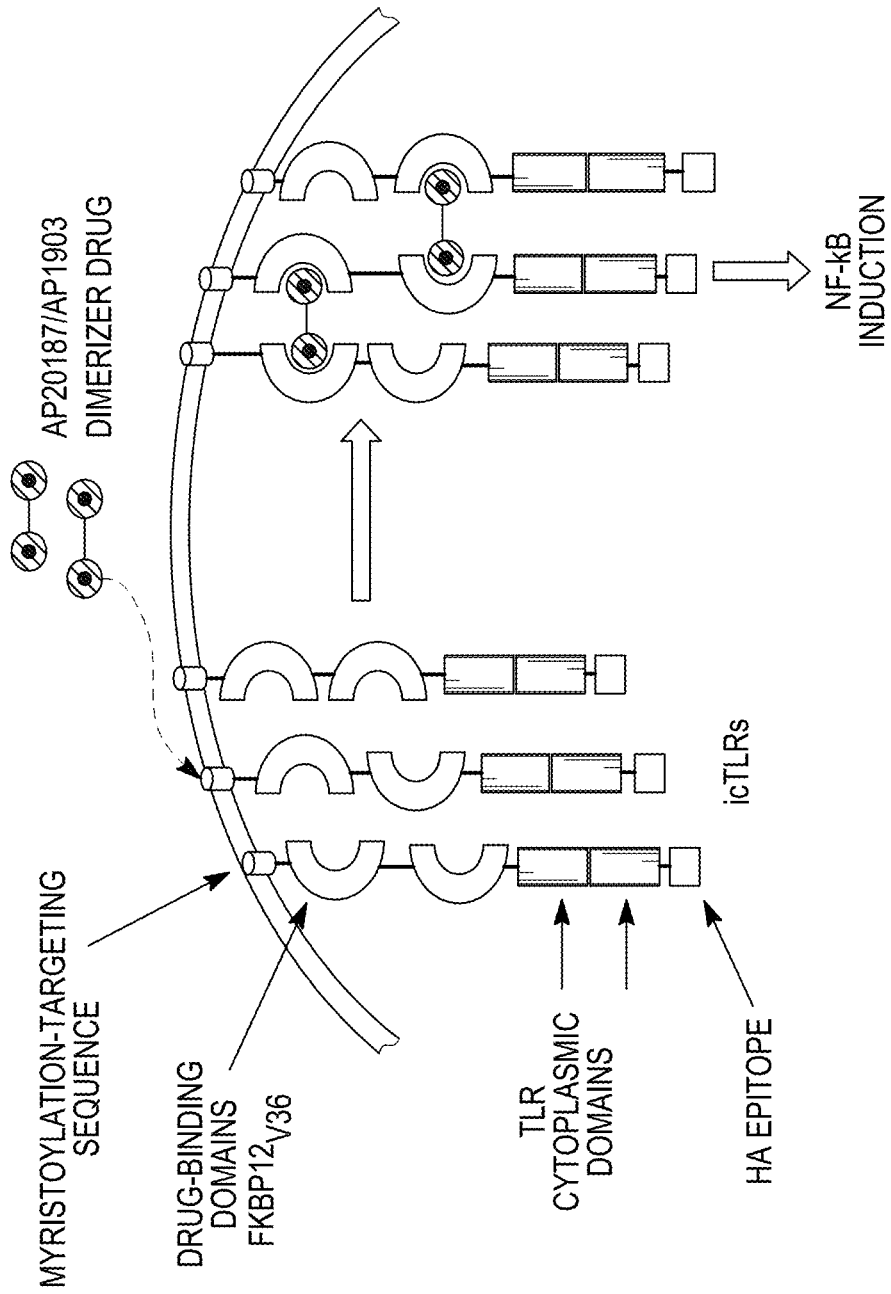
FIG. 4 is a schematic of CID-inducible composite Toll-like receptors (icTLRs).
Figure 5:
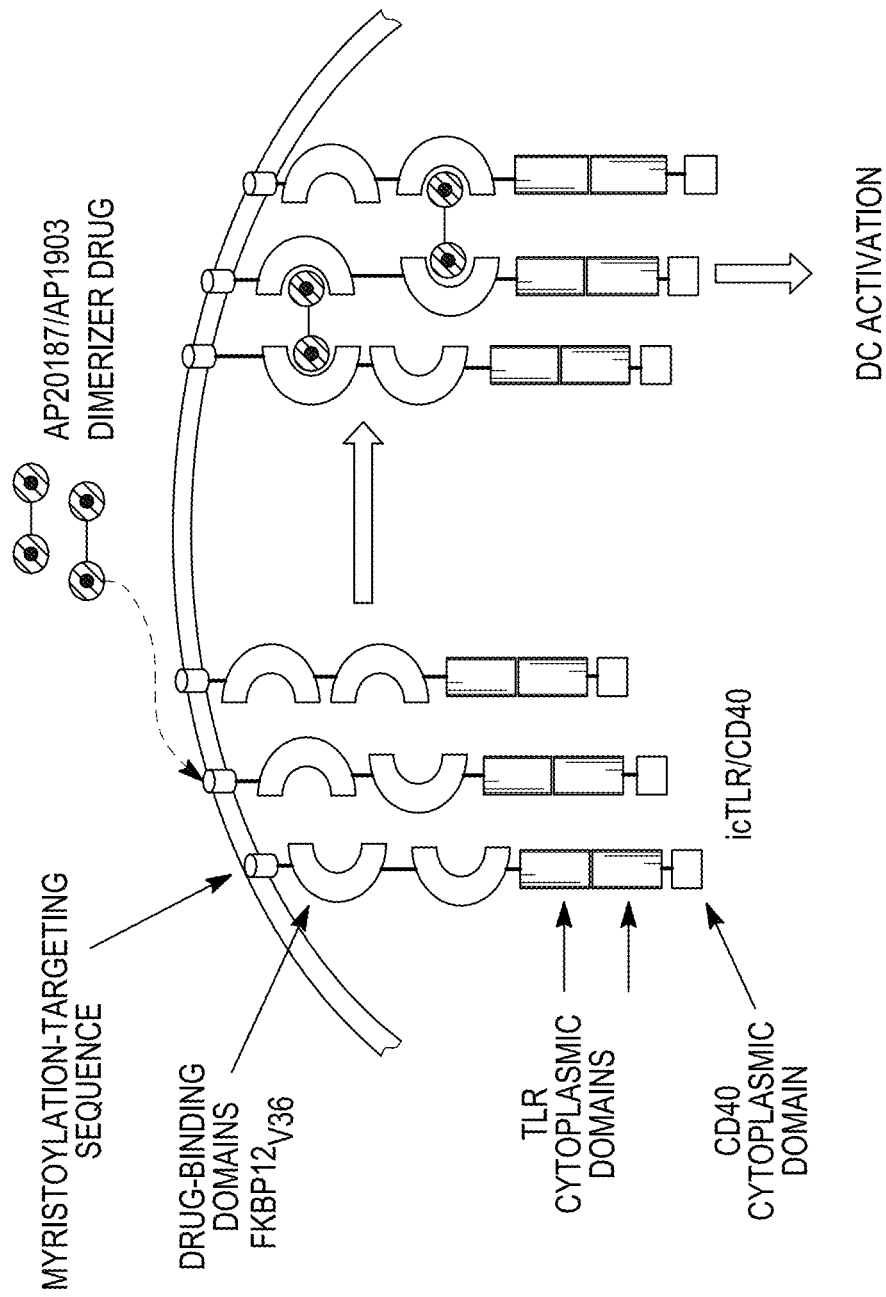
FIG. 5 is a schematic of CID-inducible composite TLR (icTLRs)/CD40.
Figure 6:
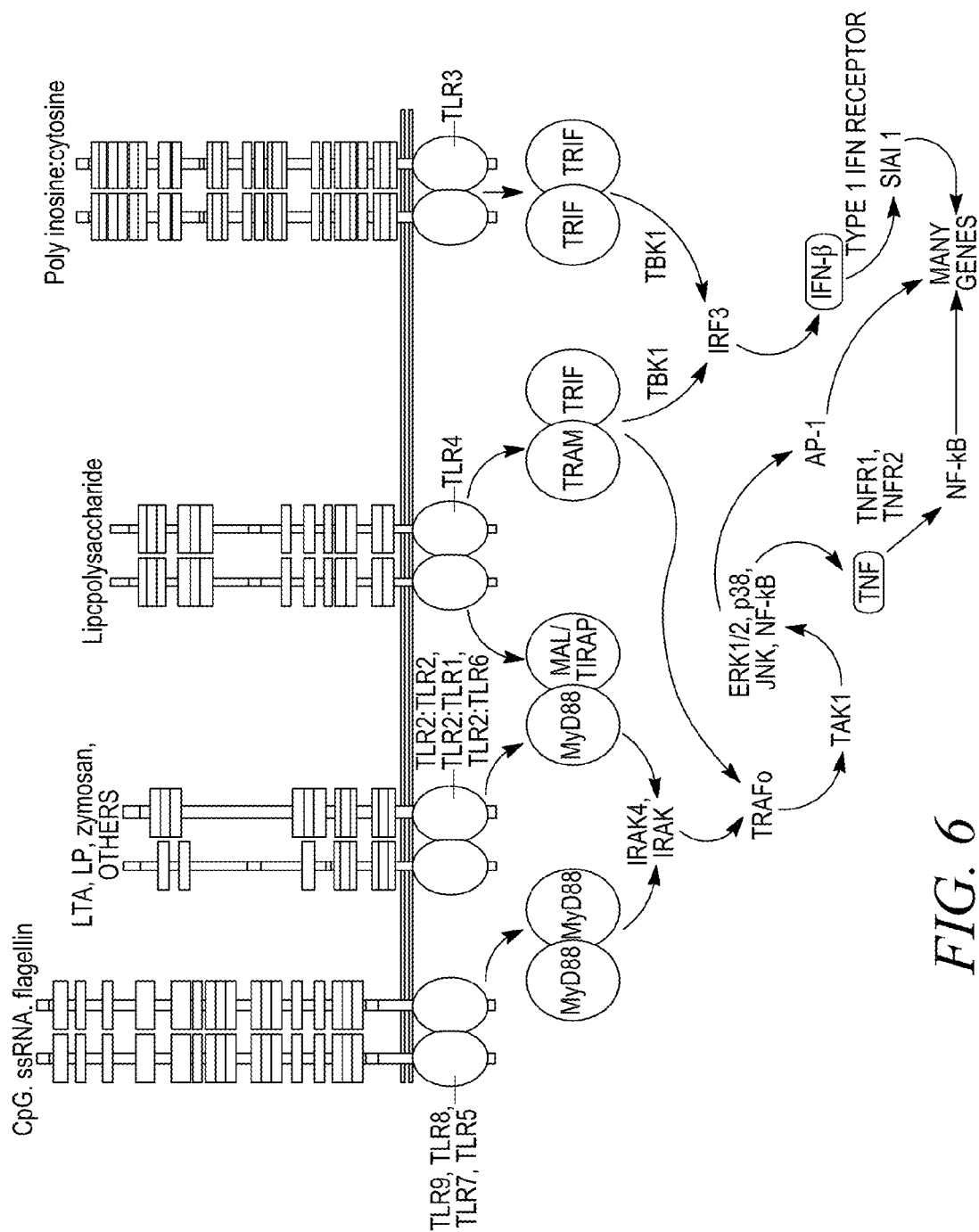
FIG. 6: The principal relationships between the Toll-like receptors (TLRs), their adapters, protein kinases that are linked to them, and downstream signaling effects. Nature 430, 257-263(8 Jul. 2004).

Since various distinct TLRs can differentially induce IRF and NF-kappaB and may synergize in DC activation and IL-12 production[43], initial testing of inducible TLRs, may be followed by combinatorial testing by cotransfection of iTLRs, two-at-a-time. Although both normal homodimerization and more unpredictable heterodimerization may occur, this approach should reveal synergism between different classes of TLRs. Activation of synergistic TLR pairs should confer enhanced immunostimulatory capacities to DCs. If synergism can be detected, a new series of constructs that are comprised of two tandem distinct (or identical) TLRs, called inducible composite TLRs (icTLRs) are tested (FIG. 4). In this case cytoplasmic XhoI-SalI-flanked TLR signaling domains from above are combined in various arrangements upstream and downstream of CBDs. Finally, the two most potent constructs are modified to contain the cytoplasmic domain of CD40, previously demonstrated to be activated by CID (FIG. 5).

Although transfection of DCs can be problematic, an improved method of electroporation was recently described by Vieweg and colleagues[68]. In their approach, survival following electroporation (300 V, 150 mF (Gene Pulser II: Bio-Rad)) is enhanced by resuspending DCs ($4\times10^7$/ml) in high potassium ion ViaSpan buffer (Barr Laboratories). Additionally, if the transfection efficiency is still too low, expression vector pRSV-TAg, containing SV40 large T antigen for amplifying our pSH1 series expression vectors, which all contain the SV40 origin of replication will be cotransfected.

Developing an Adenovector Expressing Unified Activation Gene icTLR/CD40:

Although D2SC/1 is a useful cell model for preclinical studies, the immunoregulatory genes will next be assayed in primary mouse and human DCs prior to clinical applications. To facilitate efficient gene transfer to primary cells, the most potent construct(s) is subcloned into adenovirus shuttle vector, pShuttle-X or pDNR-CMV and further transferred into Ad5 vector, pAdeno-X (BD) or AdXLP (BD), respectively. Preparation of high-titer virus is carried out. As has been achieved with previously developed Ad5/f35-iCD40, this vector is tested in both human and mouse DCs. Although Ad5/f35 pseudotyped adenovectors improve transduction efficiency a bit in human DCs, "pure" Ad5 enveloped adenovectors may be used to permit additional transduction of murine DCs.

For human studies, MoDCs are prepared by standard incubation of adherent peripheral blood DC precursors in GM-CSF and IL-4. Immature DCs are transduced with the developed icTLR/CD40 vector and control vectors (e.g. Ad5/f35-iCD40 and Ad5/f35-EGFP). Standard MoDC assays for maturation and activity are described herein and also include, for example, flow cytometry analysis of maturation markers (e.g. CD40, CD80, CD86, HLA class I and II, CCR7), IL-12 production, migration, and activation of antigen-specific T cells.

In the event that placing CD40 and TLR signaling domains in tandem may interfere with the signaling pathways activated by isolated domains, the constructs may be coexpressed in viral vectors using alternative strategies, such as use of bicistronic expression cassettes or cloning into the E3 region of deltaE1deltaE3 adenovectors. Also, chimeric receptors may not signal identical to the endogenous proteins. Although certain PRRs or PRR adapters may be thought to be the most potent TLR for activation of myeloid DCs, alternatives may function better when converted to a CID-activated receptor. Moreover, synergism between various inducible PRRs and PRR adapters and constitutive Akt, $M_F$-deltaAkt, or siRNA SOCS-1 may be found to be more potent. In these cases, various combinations of immune regulatory genes may be combined in multicistronic adenovectors.

Additional Methods of Assaying CID-Inducible Adapters

Those of ordinary skill in the art will recognize the modifications that may be made for the use of adapter proteins rather than TLRs in the following methods.

Due to the pivotal role that DCs play in regulating adaptive immunity, there are many homeostatic mechanisms that downregulate DC activity. Nevertheless, heightened activation may be required for overcoming tumor- or viral-derived tolerogenic mechanisms. Several methods to circumvent these homeostatic mechanisms are discussed herein. Inducible CD40 can be activated in vivo within the context of an immunological synapse and lacks its extracellular domain, bypassing several negative feedback mechanisms that target this domain. "Optimized", constitutively active Akt, $M_F$-deltaAkt, is based on lipid-raft targeting of a truncated Akt1 allele. Reducing the inhibitor SOCS-1 with siRNA technology increases toll-receptor signaling and Type I interferon production. Thus, all three methods have the capacity to enhance MoDCs.

Preparation of MoDCs:

For most experiments based on optimization of enhanced DCs (eDCs), monocyte-derived DCs are differentiated and enriched from peripheral blood mononuclear cells obtained from the Blood Bank or healthy volunteers. Briefly, DC precursors are isolated by buoyant density techniques (Histopaque: Sigma-Aldrich) and then adherent (and semi-adherent) cells are cultured for 5 days in serum free X-VIVO 15 DC medium (Cambrex Bio Science) in the presence of cytokines GM-CSF (800 U/ml) and IL-4 (500 U/ml) (R&D Systems, Minneapolis, Minn.). Following 5 days in culture, immature DCs are incubated for an additional 24 hours in the presence of adenovectors expressing iCD40 (i.e. Ad5/f35-iCD40), constitutive Akt (Ad5/f35-MF-deltaAkt), shRNA SOCS1 (Ad5-shSOCS1), or Ad5-iTLR/CD40 at 10,000 viral particles (vp) per cell. (Note: Ad5 vectors may be added at 20,000 vp to compensate partly for somewhat reduced transduction efficiency). In a subset of samples, additional TLR4 ligand monophosphoryl lipid A (MPL; 1 mg/ml) or dimerizer AP20817 (100 nM; iCD40-DCs only) will be added for complete maturation.

Determination of Maturation State of MoDCs:

A number of surface proteins ("markers") are induced during MoDC activation, including CD25, CD40, CD80, CD83, CD86, HLA class I and class II, CCR7 and others. Preliminary studies demonstrated that iCD40 signaling alone is sufficient to upregulate CD83 and CCR7 on MoDCs (not shown). Additional TLR4 signaling (via MPL) leads to additive (or synergistic) activation of all maturation markers. Therefore, at a fixed vp number, induction of maturation markers (determined by flow cytometry) by all four viral vectors either alone or in combination with MPL is evaluated. Maturation by the previous "gold standard" maturation cocktail (MC), comprised of IL-1a, IL-6, TNFalpha, and PGE$_2$, acts as positive control and non-treated (mock) immature DCs serve as negative controls in these and the following experiments. In addition to phenotypic analysis of cell surface markers, production of IL-12 and other T$_H$1-polarizing cytokines (e.g. IL-23, TNFalpha), are also important for optimal anti-tumor immunity. While iCD40 is not sufficient for IL-12 production, combinations of MPL and iCD40 lead to potent synergistic production of IL-12. Therefore, DC culture supernatants, stimulated as above, are harvested 24 and 48 hours after transduction and maturation. IL-12 p70 levels, IL-12/IL-23 p40 dimers and TNFalpha concentrations are determined by colorimetric sandwich ELISA assays (BD Biosciences). Alternatively, multiplex beads developed by BD to simultaneously assay multiple additional cytokines (e.g. IL-1, IL-6, IFNalpha, etc.) may be used.

Determination of Migration Capacity:

Unlike murine bone marrow-derived DCs (BMDCs) that are competent for LN migration, immature MoDCs are deficient in this crucial function. While PGE$_2$ is typically used to upregulate CCR7 and migratory capacity, the utility of PGE$_2$ is tempered by potential deleterious effects, which include down regulation of CD40 signaling and IL-12 production and upregulation of IL-10[50,52,69]. Moreover, even in the presence of PGE$_2$, migration to LNs is modest and around 1-2% of injected cells[70]. Although CCR7 expression is likely a prerequisite for migration to lymph nodes, chemotactic responsiveness to the LN-derived CCR7 chemokines, CCL19 and CCL21, is a more direct measure of likely migration to lymph nodes. Therefore, migration to CCL19/MIP3b may be compared in a modified 2-chamber assay.

Preliminary experiments demonstrate the surprising result that iCD40 signaling is sufficient for migratory capacity even in the absence of PGE$_2$. In this assay MoDCs were transduced with Ad5/f35-ihCD40 and labeled with fluorescent dye, Green-CMFDA (Molecular Probes). Cells were placed in the top chamber of a 2-chamber 8-mm assay plate and total fluorescence in the bottom chamber was quantitated and compared with PGE$_2$-mediated stimulation. Similarly, the migratory capacity in vitro of iCD40-TLR-, iCD40-, and Akt-MoDCs, and SOCS1-deficient MoDCs individually and in combination with and without TLR4 ligands may be compared.

As a second more direct assay for migration capacity, migration in vivo may be compared by injecting eDCs into the lower leg of non-myeloablatively irradiated immunodeficient SCID mice. Minimal radiation (~250 Rad) is needed to suppress natural killer (NK) cell activity against xenogeneic cells. Despite species differences, human MoDCs can respond to murine chemokines and migrate to draining LNs[71]. To visualize successfully migrated MoDCs, cells are labeled with the fluorescent dye, Green-CMFDA cell tracker, which is quantitated by flow cytometry. Second, in addition to adenovector-mediated "enhancement", MoDCs are transduced with adenovector, Ad5/f35-CBR, expressing red-shifted (510 nm excitation peak) click beetle (*Pyrophorus plagiophthalamus*) luciferase (Promega). Use of the CBR luciferase allele should more easily allow detection of bioluminescent DCs (using our IVIS® Imaging System (Xenogen Corp, Alameda, Calif.)) both within the draining popliteal LN and at more distant and membrane-distal sites.

Activation and Polarization of Autologous T Cells:

In addition to maturation and migration, ability to activate a T$_H$1-biased antigen-specific immune response in vivo is the sine qua non of DC vaccination against solid tumors. Therefore, the ability of eDCs to stimulate both T helper and cytotoxic function may be evaluated. Initially, stimulation of proliferation of allogeneic CD4$^+$ T cells may be assayed. Enhanced DCs are matured and activated using the conditions described above, irradiated (3000 rad) and cultured 1:10 with allogeneic magnetic bead-purified (Miltenyi Biotec, Auburn, Calif.) CD4$^+$ T cells. Proliferation is assessed 4 days later after 16-hour incubation with [$^3$H]-thymidine. To complement these studies, the T$_H$1 polarization (determined by ELISpot assays to IL-4 and IFNgamma) ability by various standard or eDCs may be determined To more specifically assay DC maturation state, ability to stimulate naïve CTL function is determined using HLA-A2-restricted tetramer analysis and CTL assays. (Note: several HLA-A2 carriers have recently been genotyped). Activation of autologous T cells in healthy donors by various eDCs presenting 2 distinct cocktails of HLA-A2-restricted antigens, one strong and one weak, is compared. CTL assays will be based on antigen-specific lytic activity of T cells stimulated with standard or eDCs as above. These 4 T cell assays should provide a balanced preclinical analysis of enhanced DCs along with a functional analysis of the various approaches.

CITATIONS REFERRED TO IN THIS EXAMPLE AND/OR PROVIDING FURTHER TECHNICAL SUPPORT

1. Clackson, T. et al. Redesigning an FKBP-ligand interface to generate chemical dimerizers with novel specificity. *Proc Natl Acad Sci USA* 95, 10437-10442 (1998).
2. Labeur, M. S. et al. Generation of tumor immunity by bone marrow-derived dendritic cells correlates with dendritic cell maturation stage. *J Immunol* 162, 168-75 (1999).
3. Nopora, A. & Brocker, T. Bcl-2 controls dendritic cell longevity in vivo. *J Immunol* 169, 3006-14 (2002).
4. Hanks, B. A. et al. Re-engineered CD40 receptor enables potent pharmacological activation of dendritic-cell cancer vaccines in vivo. *Nat Med* 11, 130-7 (2005).
5. Shen, L., Evel-Kabler, K., Strube, R. & Chen, S. Y. Silencing of SOCS1 enhances antigen presentation by dendritic cells and antigen-specific anti-tumor immunity. *Nat Biotechnol* 22, 1546-53 (2004).
6. Reis e Sousa, C. Dendritic cells as sensors of infection. *Immunity* 14, 495-8 (2001).
7. Banchereau, J. & Palucka, A. K. Dendritic cells as therapeutic vaccines against cancer. *Nat Rev Immunol* 5, 296-306 (2005).
8. Banchereau, J. et al. Immunobiology of dendritic cells. *Annu Rev Immunol* 18, 767-811 (2000).
9. Lanzavecchia, A. & Sallusto, F. Regulation of T cell immunity by dendritic cells. *Cell* 106, 263-6 (2001).
10. Smith, C. M. et al. Cognate CD4(+) T cell licensing of dendritic cells in CD8(+) T cell immunity. *Nat Immunol* 5, 1143-8 (2004).

11. Schoenberger, S. P., Toes, R. E., El, v.d.V., Offring a, R. & Melief, C. J. T-cell help for cytotoxic T lymphocytes is mediated by CD40-CD40L interactions [see comments]. *Nature* 393, 480-3 (1998).
12. Bennett, S. R. et al. Help for cytotoxic-T-cell responses is mediated by CD40 signaling. *Nature* 393, 478-80 (1998).
13. Ridge, J. P., Di Rosa, F. & Matzinger, P. A conditioned dendritic cell can be a temporal bridge between a CD4+ T-helper and a T-killer cell. *Nature* 393, 474-8 (1998).
14. Grewal, I. S. & Flavell, R. A. CD40 and CD154 in cell-mediated immunity. *Annu Rev Immunol* 16, 111-35 (1998).
15. O'Sullivan, B. & Thomas, R. CD40 and dendritic cell function. *Crit Rev Immunol* 23, 83-107 (2003).
16. Nestle, F. O., Banchereau, J. & Hart, D. Dendritic cells: On the move from bench to bedside. *Nat Med* 7, 761-5 (2001).
17. Schuler, G., Schuler-Thurner, B. & Steinman, R. M. The use of dendritic cells in cancer immunotherapy. *Curr Opin Immunol* 15, 138-47 (2003).
18. Gilboa, E. & Vieweg, J. Cancer immunotherapy with mRNA-transfected dendritic cells. *Immunol Rev* 199, 251-63 (2004).
19. Gilboa, E. The promise of cancer vaccines. *Nat Rev Cancer* 4, 401-11 (2004).
20. Ridgway, D. The first 1000 dendritic cell vaccinees. *Cancer Invest* 21, 873-86 (2003).
21. Dallal, R. M. & Lotze, M. T. The dendritic cell and human cancer vaccines. *Curr Opin Immunol* 12, 583-8 (2000).
22. Langenkamp, A., Messi, M., Lanzavecchia, A. & Sallusto, F. Kinetics of dendritic cell activation: impact on priming of TH1, TH2 and nonpolarized T cells. *Nat Immunol* 1, 311-6 (2000).
23. Hermans, I. F., Ritchie, D. S., Yang, J., Roberts, J. M. & Ronchese, F. CD8+ T cell-dependent elimination of dendritic cells in vivo limits the induction of antitumor immunity. *J Immunol* 164, 3095-101 (2000).
24. Park, Y., Lee, S. W. & Sung, Y. C. Cutting Edge: CpG DNA inhibits dendritic cell apoptosis by up-regulating cellular inhibitor of apoptosis proteins through the phosphatidylinositide-3'-OH kinase pathway. *J Immunol* 168, 5-8 (2002).
25. Josien, R. et al. TRANCE, a tumor necrosis factor family member, enhances the longevity and adjuvant properties of dendritic cells in vivo. *J Exp Med* 191, 495-502 (2000).
26. Miga, A. J. et al. Dendritic cell longevity and T cell persistence is controlled by CD154-CD40 interactions. *Eur J Immunol* 31, 959-65 (2001).
27. Cremer, I. et al. Long-lived immature dendritic cells mediated by TRANCE-RANK interaction. *Blood* 100, 3646-55 (2002).
28. Tone, M., Tone, Y., Fairchild, P. J., Wykes, M. & Waldmann, H. Regulation of CD40 function by its isoforms generated through alternative splicing. *Proc Natl Acad Sci USA* 98, 1751-1756. (2001).
29. Contin, C. et al. Membrane-anchored CD40 is processed by the tumor necrosis factor-alpha-converting enzyme. Implications for CD40 signaling. *J Biol Chem* 278, 32801-9 (2003).
30. Kobayashi, K. et al. IRAK-M is a negative regulator of Toll-like receptor signaling. *Cell* 110, 191-202 (2002).
31. Hou, W. S. & Van Parijs, L. A Bcl-2-dependent molecular timer regulates the lifespan and immunogenicity of dendritic cells. *Nat Immunol* 5, 583-9 (2004).
32. Kandel, E. S. & Hay, N. The regulation and activities of the multifunctional serine/threonine kinase Akt/PKB. *Exp Cell Res* 253, 210-29 (1999).
33. Vassiliou, E., Sharma, V., Jing, H., Sheibanie, F. & Ganea, D. Prostaglandin E2 promotes the survival of bone marrow-derived dendritic cells. *J Immunol* 173, 6955-64 (2004).
34. Ardeshna, K. M., Pizzey, A. R., Devereux, S. & Khwaja, A. The PI3 kinase, p38 SAP kinase, and NF-kappaB signal transduction pathways are involved in the survival and maturation of lipopolysaccharide-stimulated human monocyte-derived dendritic cells. *Blood* 96, 1039-46 (2000).
35. Kanto, T., Kalinski, P., Hunter, O. C., Lotze, M. T. & Amoscato, A. A. Ceramide mediates tumor-induced dendritic cell apoptosis. *J Immunol* 167, 3773-84 (2001).
36. Mochizuki, T. et al. Akt protein kinase inhibits non-apoptotic programmed cell death induced by ceramide. *J Biol Chem* 277, 2790-7 (2002).
37. Bennett, M. R., Evan, G. I. & Schwartz, S. M. Apoptosis of rat vascular smooth muscle cells is regulated by p53-dependent and -independent pathways. *Circ. Res.* 77, 266-273 (1995).
38. Albert, M. L., Jegathesan, M. & Darnell, R. B. Dendritic cell maturation is required for the cross-tolerization of CD8+ T cells. *Nat Immunol* 2, 1010-7 (2001).
39. Diehl, L. et al. CD40 activation in vivo overcomes peptide-induced peripheral cytotoxic T-lymphocyte tolerance and augments anti-tumor vaccine efficacy. *Nat Med* 5, 774-9 (1999).
40. Vonderheide, R. H. et al. CD40 activation of carcinoma cells increases expression of adhesion and major histocompatibility molecules but fails to induce either CD80/CD86 expression or T cell alloreactivity. *Int J Oncol* 19, 791-8 (2001).
41. Mazouz, N. et al. CD40 triggering increases the efficiency of dendritic cells for antitumoral immunization. *Cancer Immun* 2, 2 (2002).
42. Kikuchi, T., Worgall, S., Singh, R., Moore, M. A. & Crystal, R. G. Dendritic cells genetically modified to express CD40 ligand and pulsed with antigen can initiate antigen-specific humoral immunity independent of CD4+ T cells. *Nat Med* 6, 1154-9 (2000).
43. Napolitani, G., Rinaldi, A., Bertoni, F., Sallusto, F. & Lanzavecchia, A. Selected Toll-like receptor agonist combinations synergistically trigger a T helper type 1-polarizing program in dendritic cells. *Nat Immunol* 6, 769-76 (2005).
44. Medzhitov, R., Preston-Hurlburt, P. & Janeway, C. A., Jr. A human homologue of the *Drosophila* Toll protein signals activation of adaptive immunity. *Nature* 388, 394-7 (1997).
45. Hoshino, K. et al. Cutting edge: Toll-like receptor 4 (TLR4)-deficient mice are hyporesponsive to lipopolysaccharide: evidence for TLR4 as the Lps gene product. *J Immunol* 162, 3749-52 (1999).
46. Ozinsky, A. et al. The repertoire for pattern recognition of pathogens by the innate immune system is defined by cooperation between toll-like receptors. *Proc Natl Acad Sci USA* 97, 13766-71 (2000).
47. Zhang, H., Tay, P. N., Cao, W., Li, W. & Lu, J. Integrin-nucleated Toll-like receptor (TLR) dimerization reveals subcellular targeting of TLRs and distinct mechanisms of TLR4 activation and signaling. *FEBS Lett* 532, 171-6 (2002).
48. Lee, H. K., Dunzendorfer, S. & Tobias, P. S. Cytoplasmic domain-mediated dimerizations of toll-like receptor 4 observed by beta-lactamase enzyme fragment complementation. *J Biol Chem* 279, 10564-74 (2004).

49. Choe, J., Kelker, M. S. & Wilson, I. A. Crystal structure of human toll-like receptor 3 (TLR3) ectodomain. *Science* 309, 581-5 (2005).
50. Luft, T. et al. Functionally distinct dendritic cell (DC) populations induced by physiologic stimuli: prostaglandin E(2) regulates the migratory capacity of specific DC subsets. *Blood* 100, 1362-72 (2002).
51. Scandella, E. et al. CCL19/CCL21-triggered signal transduction and migration of dendritic cells requires prostaglandin E2. *Blood* 103, 1595-601 (2004).
52. Kalinski, P., Vieira, P. L., Schuitemaker, J. H., de Jong, E. C. & Kapsenberg, M. L. Prostaglandin E(2) is a selective inducer of interleukin-12 p40 (IL-12p40) production and an inhibitor of bioactive IL-12p70 heterodimer. *Blood* 97, 3466-9 (2001).
53. Korst, R., Mahtabifard, A., Yamada, R., and Crystal, R. Effect of Adenovirus Gene Transfer Vectors on the Immunologic Functions of Mouse Dendritic Cells. *Molecular Therapy* 5, 307-315 (2002).
54. Langenkamp, A., Messi, M., Lanzavecchia, A., and Sallusto, F. Kinetics of dendritic cell activation: impact on priming of Th1, Th2, and nonpolarized T cells. *Nature Immunology* 1, 311-316 (2000).
55. Hermans, I., Ritchie, D., Yang, J., Roberts, J., and Ronchese, F. CD8 T cell-dependent elimination of dendritic cells in vivo limits the induction of antitumor immunity. *Journal of Immunology* 164, 3095-3101 (2000).
56. Wong, P. a. P., E. Feedback Regulation of Pathogen-Specific T Cell Priming. *Immunity* 188, 499-511 (2003).
57. Miga, A., Masters, S., Durell, B., Gonzalez, M., Jenkins, M., Maliszewski, C., Kikutani, H., Wade, W., and Noelle, R. Dendritic cell longevity and T cell persistence is controlled by CD154-CD40 interactions. *European Journal of Immunology* 31, 959-965 (2001).
58. Medema, J., Schuurhuis, D., Rea, D., van Tongeren, J., de Jong, J., Bres, S., Laban, S., Toes, R., Toebes, M., Schumacher, T., Bladergroen, B., Ossendorp, F., Kummer, J., Melief, C., and Offringa, R. Expression of the serpin serine protease inhibitor 6 protects dendritic cells from cytotoxic T lymphocyte-induced apoptosis: differential modulation by T helper type 1 and type 2 cells. *Journal of Experimental Medicine* 194, 657-667 (2001).
59. Steinman, R. a. P., M. Exploiting dendritic cells to improve vaccine efficacy. *Journal of Clinical Investigation* 109, 1519-1526 (2002).
60. Woltman, A. M. et al. Rapamycin specifically interferes with GM-CSF signaling in human dendritic cells, leading to apoptosis via increased p27KIP1 expression. *Blood* 101, 1439-45 (2003).
61. Granucci, F. et al. Inducible IL-2 production by dendritic cells revealed by global gene expression analysis. *Nat Immunol* 2, 882-8 (2001).
62. Fujio, Y. & Walsh, K. Akt mediates cytoprotection of endothelial cells by vascular endothelial growth factor in an anchorage-dependent manner. *J Biol Chem* 274, 16349-54 (1999).
63. Mukherjee, A., Arnaud, L. & Cooper, J. A. Lipid-dependent recruitment of neuronal Src to lipid rafts in the brain. *J Biol Chem* 278, 40806-14 (2003).
64. Li, B., Desai, S. A., MacCorkle-Chosnek, R. A., Fan, L. & Spencer, D. M. A novel conditional Akt 'survival switch' reversibly protects cells from apoptosis. *Gene Ther* 9, 233-44. (2002).
65. Sporri, R. & Reis e Sousa, C. Inflammatory mediators are insufficient for full dendritic cell activation and promote expansion of CD4+ T cell populations lacking helper function. *Nat Immunol* 6, 163-70 (2005).
66. Spencer, D. M., Wandless, T. J., Schreiber, S. L. & Crabtree, G. R. Controlling signal transduction with synthetic ligands. *Science* 262, 1019-1024 (1993).
67. Granucci, F. et al. Modulation of cytokine expression in mouse dendritic cell clones. *Eur J Immunol* 24, 2522-6 (1994).
68. Su, Z. et al. Telomerase mRNA-transfected dendritic cells stimulate antigen-specific CD8+ and CD4+ T cell responses in patients with metastatic prostate cancer. *J Immunol* 174, 3798-807 (2005).
69. Scandella, E., Men, Y., Gillessen, S., Forster, R. & Groettrup, M. Prostaglandin E2 is a key factor for CCR7 surface expression and migration of monocyte-derived dendritic cells. *Blood* 100, 1354-61 (2002).
70. Morse, M. A. et al. Migration of human dendritic cells after injection in patients with metastatic malignancies. *Cancer Res* 59, 56-8 (1999).
71. Hammad, H. et al. Monocyte-derived dendritic cells induce a house dust mite-specific Th2 allergic inflammation in the lung of humanized SCID mice: involvement of CCR7. *J Immunol* 169, 1524-34 (2002).

Example 9

Expression Constructs and Testing

TLRs 3, 4, 7, 8 and 9 were initially selected to construct inducible chimeric proteins as they represent TLRs from the different subfamilies that are know to trigger the Th1 cytokine, IL-12, in monocyte-derived DCs. Further, TLR4 has been shown to trigger signaling following cross linking of chimeric TLR4 alleles via heterologous extracellular domains. The cytoplasmic domains of each (including TIRs) were PCR-amplified and placed adjacent (5' and 3') to two (2) FKBP12 (V36) ($F_v$ and $F_v$ (wobbled)) genes, which were attached to the plasma membrane using a myristoylation-targeting sequence from c-Src. Chimeric proteins having a third FKBP gene have been developed to improve oligomerization.

Additionally, chimeric versions of inducible PRR adapters MyD88 and TRIF have been generated by fusing these cytoplasmic proteins to two (2) FKBPs. Finally, the tandem CARD domains from cytoplasmic PRRs, NOD2 and RIG-I, have been fused to tandem FKBPs. These constructs and reporter assays are described below.

Constructs:

(i) Inducible iTLRs:

TLR3, 4, 7, 8 and 9 were PCR-amplified from cDNA derived from MoDCs. PCR primers were flanked by XhoI and SalI restriction sites to permit cloning 5' and 3' of tandem FKBPs in the XhoI and SalI sites, respectively, of pSH1/M-$F_v$-$F_{vls}$-$E^{1,2}$. The primers used were (a) 5TLR3cX (5'-cgatcactcgagggctggaggatatclitttattgg-3' (SEQ ID NO: 27)) and 3TLR3cS (5'-tgatcggtcgacatgtacagagtlittggatccaagtg-3' (SEQ ID NO: 28)) to give pSH1/M-TLR3-$F_v$-$F_{vls}$-E and pSH1/M-$F_v$-$F_{vls}$-TLR3-E; (b) 5TLR4cX (5'-cgatcactcgagtataaglictatlitcacctgatgcttc-3' (SEQ ID NO: 29)) and 3TLR4cS (5'-tgatcggtcgacgatagatgttgclicctgccaattg-3' (SEQ ID NO: 30)) to give pSH1/M-TLR4-$F_v$-$F_{vls}$-E and pSH1/M-$F_v$-$F_{vls}$-TLR4-E; (c) 5TLR7cS (5'-cgatcagtcgacgatgtgtgg-tatatttaccatlictg-3' (SEQ ID NO: 31)) and 3TLR7cS (5'-tgatcggtcgacgaccgtttccttgaacacctgac-3' (SEQ ID NO: 32)) to give pSH1/M-TLR7-$F_v$-$F_{vls}$-E and pSH1/M-$F_v$-$F_{vls}$-TLR7-E; (d) 5TLR8cX (5'-cgatcactcgaggatgtligglitatatataatgtgtg-3' (SEQ ID NO: 33)) and 3TLR8cS (5'-tcggtcgacgtattgcttaatg-gaatcgacatac-3' (SEQ ID NO: 34)) to give pSH1/M-TLR8-$F_v$-$F_{vls}$-E and pSH1/M-$F_v$-$F_{vls}$-TLR8-E; (e) 5TLR9cX (5'-cgatcactcgaggacctctggtactgcttccacc-3' (SEQ ID NO: 35))

and 3TLR9cS (5'-tgatctgtcgacttcggccgtgggtccctggc-3' (SEQ ID NO: 36)) to give pSH1/M-TLR9-$F_{v'}$-$F_{vls}$-E and pSH1/M-$F_{v'}$-$F_{vls}$-TLR9-E. All inserts were confirmed by sequencing and for appropriate size by Westernblot to the 3' hemagluttinin (HA) epitope (E). M, myristoylation-targeting sequence from c-Src (residues 1-14). pSH1, expression vector. Additionally, a third XhoI/SalI-linkered $F_{v'}$ domain was added to the XhoI sites of pSH1/M-$F_{v'}$-$F_{vls}$-TLR4-E and pSH1/M-$F_{v'}$-$F_{vls}$-TLR8-E to get pSH1/M-$F_{v'}$2-$F_{vls}$-TLR4-E and pSH1/M-$F_{v'}$2-$F_{vls}$-TLR8-E, respectively, to improve oligomerization.

To faithfully reflect physiological TLR4 signaling, full-length 2.5-kb TLR4 was PCR-amplified from TLR4 cDNA (from the Medzhitov lab) using SacII and XhoI-linkered primers 5hTLR4 (5'-aatctaccgcggccaccatgatgtctgcctcgcgcctg-3' (SEQ ID NO: 37)) and 3hTLR4 (5'-tcagttctcgaggatagatgligclicctgccaattg-3' (SEQ ID NO: 38)), respectively. The 2546-bp PCR product was subcloned into pCR-Blunt-TOPO and sequenced. The sequence-verified insert was SacII/XhoI-digested and subcloned into SacII/XhoI digested (and "CIPped") pSH1/M-$F_{v'}$-$F_{vls}$-E to give pSH1/hTLR4-$F_{v'}$-$F_{vls}$-E. An additional $F_{v'}$ was added to XhoI site to give pSH1/hTLR4-$F_{v'}$2-$F_{vls}$-E.

(ii) Inducible Composite iTLR4-CD40:

The 191-bp XhoI-SalI-linkered human CD40 cytoplasmic domain was PCR-amplified with primers hCD405X (5'-atatactcgagaaaaaggtggccaagaagccaacc-3' (SEQ ID NO: 23)) and hCD403Sns (5'-acatagtcgacctgtctctcctgcactgagatg-3' (SEQ ID NO: 39)) and subcloned into the SalI site of pSH1/hTLR4-$F_{v'}$-$F_{vls}$-E and pSH1/hTLR4-$F_{v'}$2-$F_{vls}$-E to get pSH1/hTLR4-$F_{v'}$-$F_{vls}$-CD40-E and pSH1/hTLR4-$F_{v'}$2-$F_{vls}$-CD40-E.

(iii) Inducible iNOD2:

The ~800-bp amino terminus of the PRR NOD2 (containing tandem CARD domains) was PCR-amplified with XhoI/SalI-linkered primers 5NOD2X (5'-atagcactcgagatgggggaagagggtggttcag-3' (SEQ ID NO: 40)) and 3NOD2Sb (5'-cttcatgtcgacgacctccaggacattctctgtg-3' (SEQ ID NO: 41)) and subcloned into the XhoI and SalI sites of pSH1/M-$F_{v'}$-$F_{vls}$-E to give pSH1/M-NOD2-$F_{v'}$-$F_{vls}$-E and pSH1/M-$F_{v'}$-$F_{vls}$-NOD2-E=Fv' NOD2.

(iv) Inducible TRIG-I:

The ~650 bp amino terminus of the RNA helicase RIG-I (containing tandem CARD domains) was PCR-amplified with XhoI/SalI-linkered primers 5RIGX (5'-atagcactcgagaccaccgagcagcgacgcag-3' (SEQ ID NO: 42)) and 3RIGS (5'-cttcatgtcgacaatctgtatgtcagaagtttccatc-3' (SEQ ID NO: 43)) and subcloned into the XhoI and SalI sites of pSH1/M-$F_{v'}$-$F_{vls}$-E to give pSH1/M-RIGI-$F_{v'}$-$F_{vls}$-E and pSH1/M-$F_{v'}$-$F_{vls}$-RIGI-E=Fv'RIG-I.

(v) Inducible iMyD88:

Human TIR-containing inducible PRR adapter MyD88 (~900-bp) was PCR-amplified from 293 cDNA using XhoI/SalI-linkered primers 5MyD88S (5'-acatcaactcgagatggctgcaggaggtcccgg-3' (SEQ ID NO: 44)) and 3MyD88S (5'-actcatagtcgaccagggacaaggccttggcaag-3' (SEQ ID NO: 45)) and subcloned into the XhoI and SalI sites of pSH1/M-$F_{v'}$-$F_{vls}$-E to give pSH1/M-MyD88-$F_{v'}$-$F_{vls}$-E and pSH1/M-$F_{v'}$-$F_{vls}$-MyD88-E, respectively.

(vi) Inducible iTRIF:

Human TIR-containing inducible PRR adapter TRIF2 (~2150-bp) was PCR-amplified from 293 cDNA using XhoI/SalI-linkered primers 5TRIFX (5'-acatcaactcgagatggcctgcacaggcccatcac-3' (SEQ ID NO: 46)) and 3TRIFS (5'-actcatagtcgacttctgcctcctgcgtcttgtcc-3' (SEQ ID NO: 47)) and subcloned into SalI-digested pSH1/M-$F_{v'}$-$F_{vls}$-E to give pSH1/M-$F_{v'}$-$F_{vls}$-TRIF-E.

(vii) IFNb-SEAP:

The minimal IFNbi promoter was PCR-amplified from human genomic DNA using primers 5IFNbMI (5'-aactagacgcgtactactaaaatgtaaatgacataggaaaac-3' (SEQ ID NO: 48)) and 3IFNbH (5'-gacttgaagcttaacacgaacagtgtcgcctactac-3' (SEQ ID NO: 49)). The MluI-HindIII-digested fragment was subcloned into a promoter-less SEAP reporter plasmid.

Certain constructs were specifically targeted to plasma membrane lipid rafts using myristoylation sequences from Fyn as well as the PIP2 membrane targeting domain of TIRAP.(5)

Secreted Alkaline Phosphatase (SEAP) Assays:

Reporters assays were conducted in human Jurkat-TAg (T cells) or 293 (kidney embryonic epithelial) cells or murine RAW264.7 (macrophage) cells. Jurkat-TAg cells ($10^7$) in log-phase growth were electroporated (950 mF, 250V) with 2 mg expression plasmid and 2 mg of reporter plasmid NF-kB-SEAP[3] or IFNb-TA-SEAP (see above). 293 or RAW264.7 cells (~$2 \times 10^5$ cells per 35-mm dish) in log phase were transfected with 6 ml of FuGENE-6 in growth media. After 24 hr, transformed cells were stimulated with CID. After an additional 20 h, supernatants were assayed for SEAP activity as described previously[3].

Tissue Culture:

Jurkat-TAg and RAW264.7 cells were grown in RPMI 1640 medium, 10% fetal bovine serum (FBS), 10 mM HEPES (pH 7.14), penicillin (100 U/ml) and streptomycin (100 mg/ml). 293 cells were grown in Dulbecco's modified Eagle's medium, 10% FBS, and pen-strep.

Western Blot Analysis:

Protein expression was determined by Westernblot using antibodies to the common hemagluttinin (HA) epitope (E) tag.

Results

Figure 7:
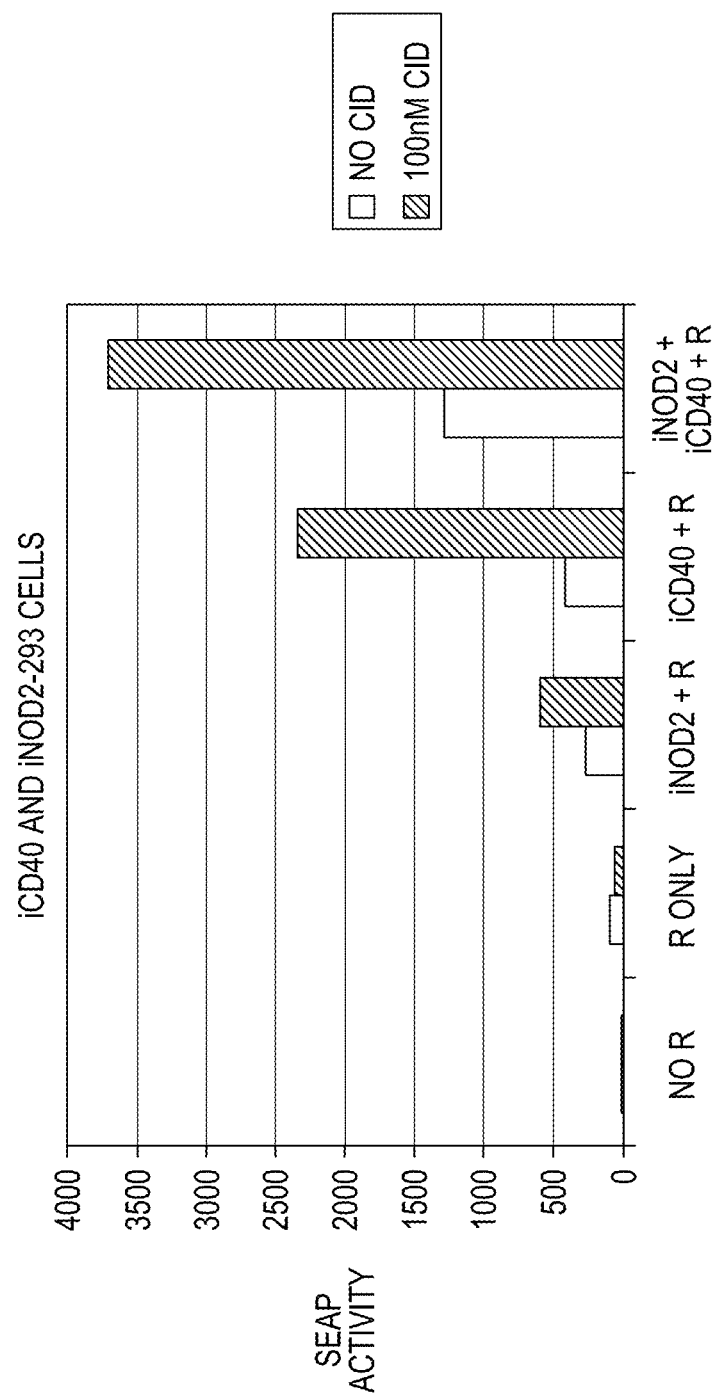
FIG. 7. iNod2 and iCD40 in 293 cells. 293 cells were cotransfected transiently at the rate of 1 million cells/well (of a 6-well plate) with 3 microgram expression plasmids for chimeric iNod-2 and 1 microgram NF-kappaB-dependent SEAP reporter plasmid (indicated as R in Figure). iCD40 was used as the positive control.
Figure 8:
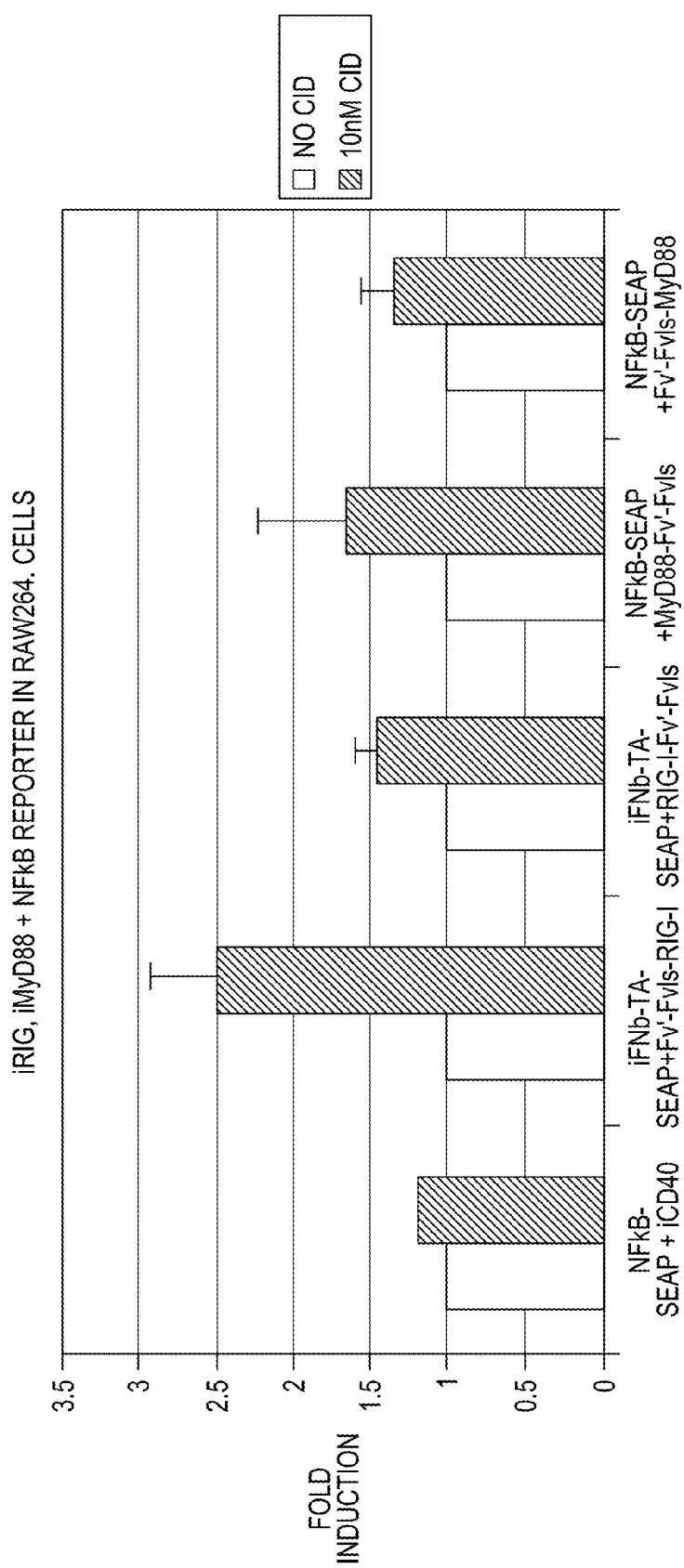
FIG. 8. iRIG-1 and iMyD88 in RAW264.7 cells. RAW 264.7 cells were cotransfected transiently with 3 micrograms expression plasmids for iRIG-1 and 1 microgram IFN-gamma-dependent SEAP reporter plasmid; and 3 micrograms iMyD88 with 1 microgram NF-kappaB-dependent SEAP reporter plasmid.
Figure 9:
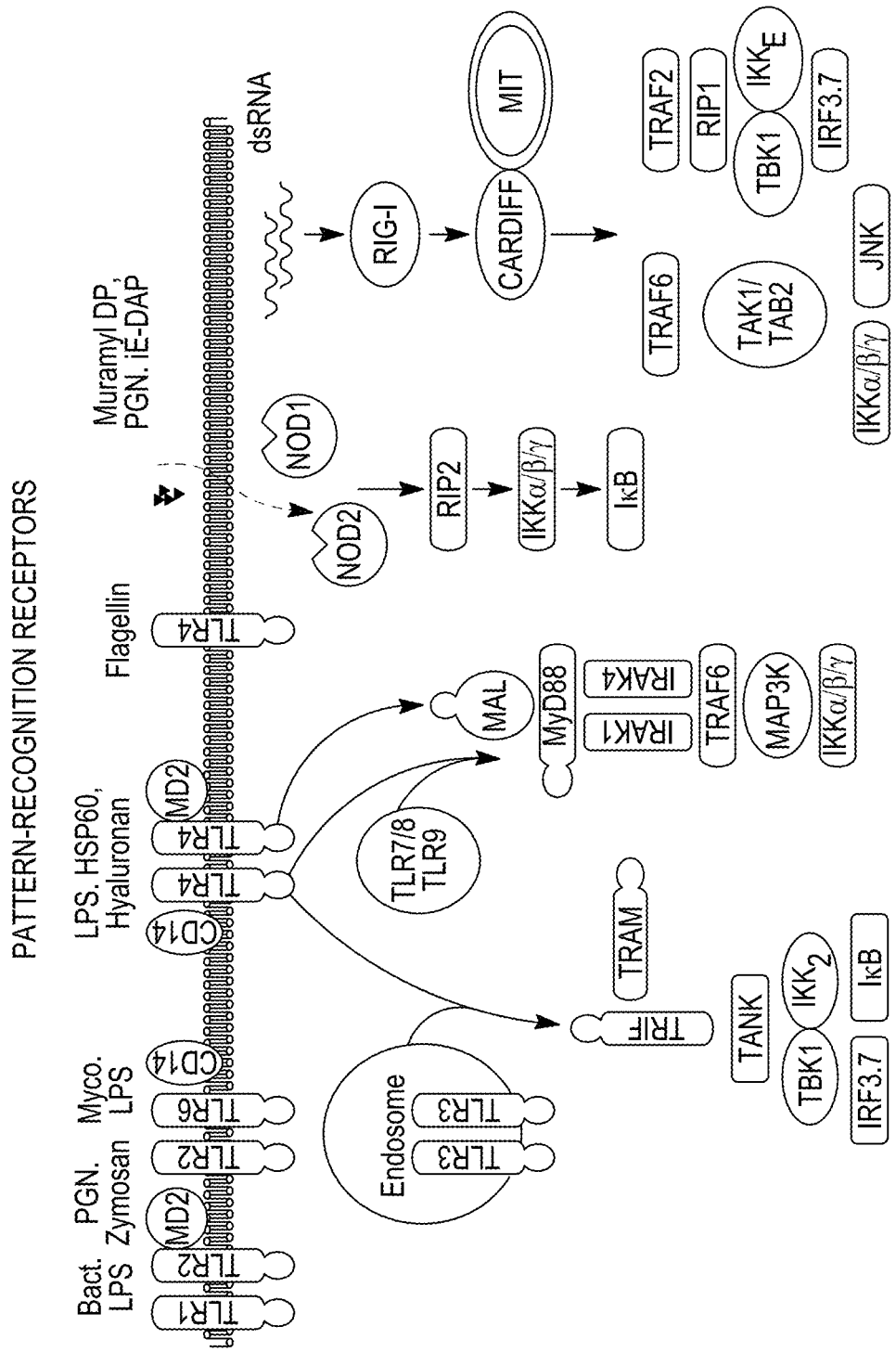
FIG. 9. Schematic of Pattern recognition receptors
FIG. 10A. Schematic of an example iPRR plasmid.
Figure 10A:
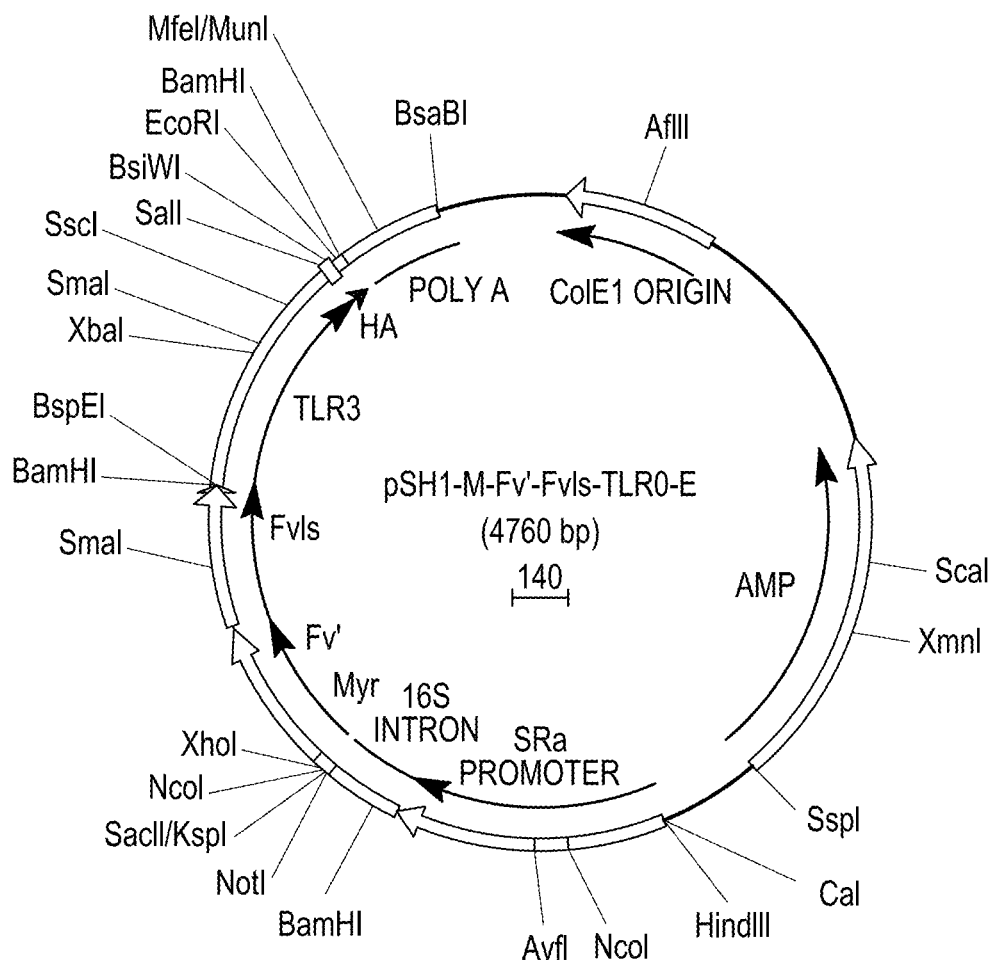
FIG. 10B. Schematic of an example iPRR plasmid.
FIG. 10C. Schematic of an example iPRR plasmid.
Figure 10A:
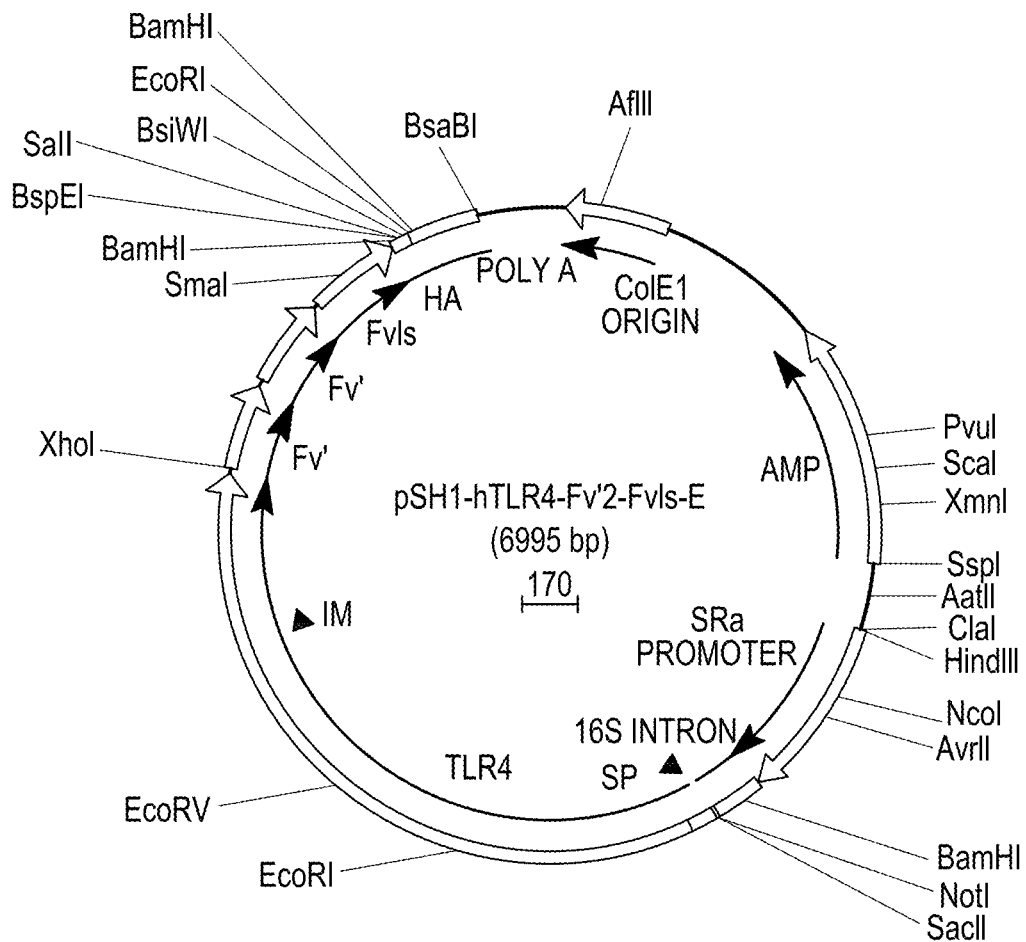
Figure 10B:
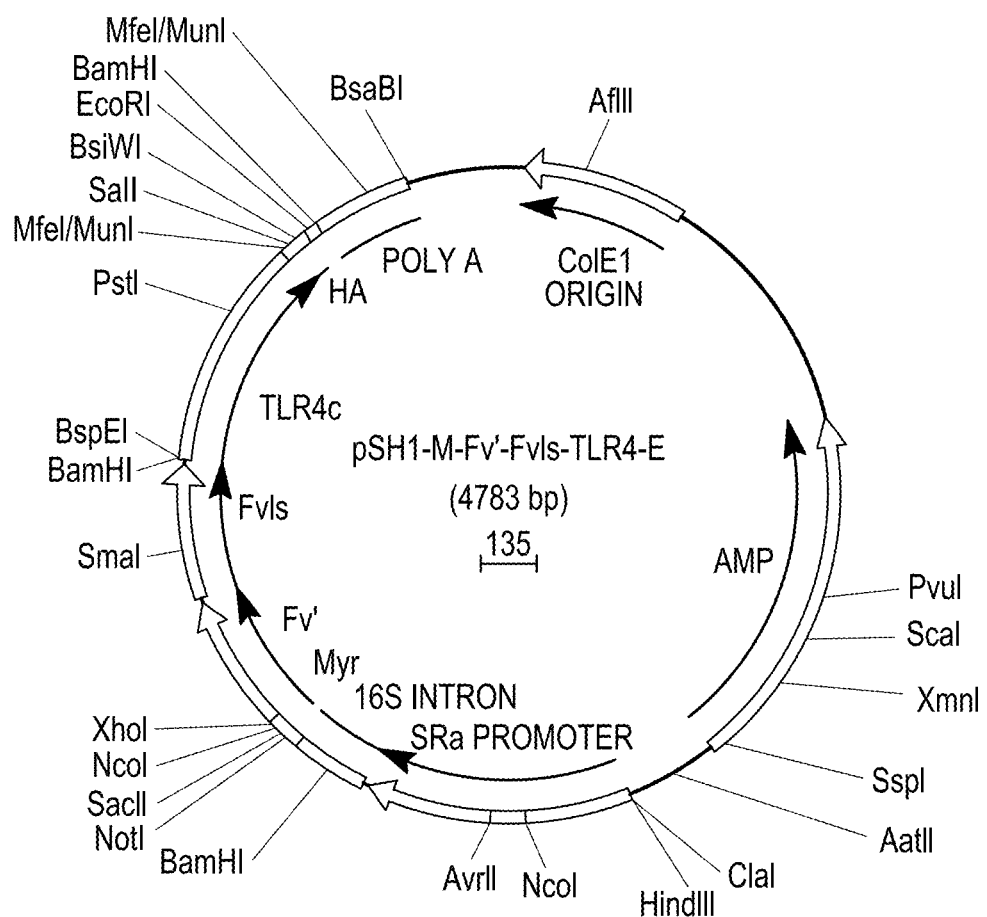
Figure 10B:
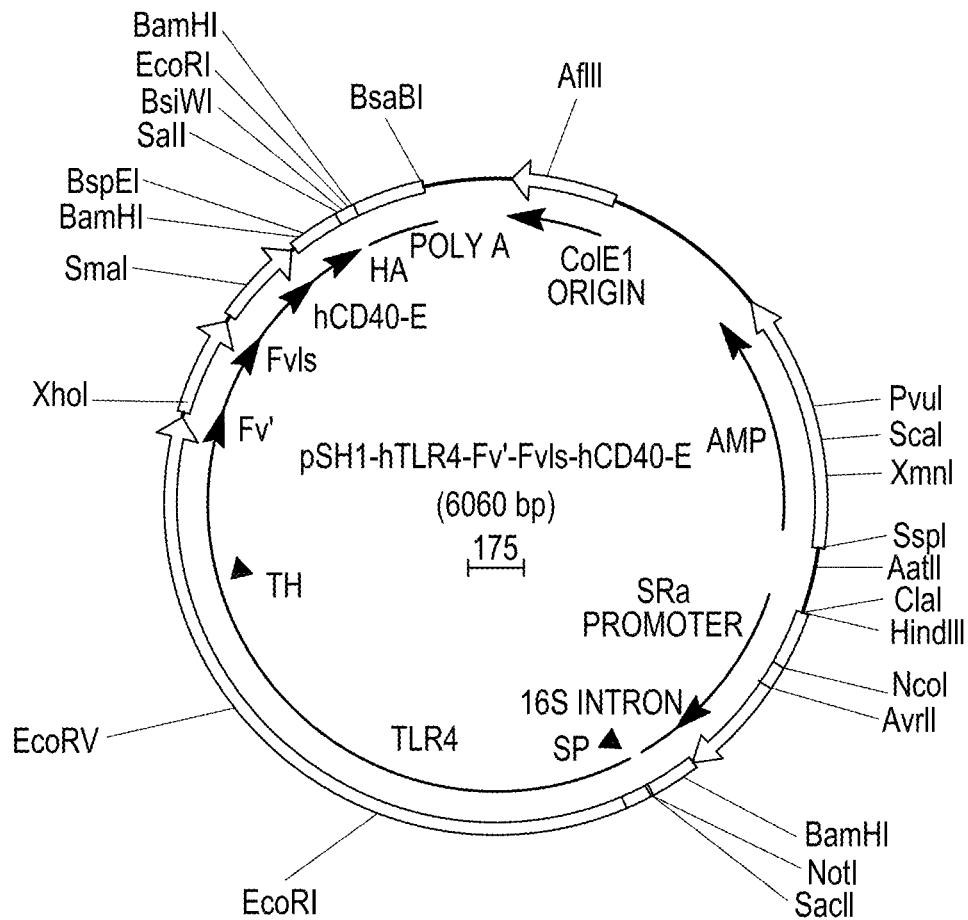
Figure 10C:
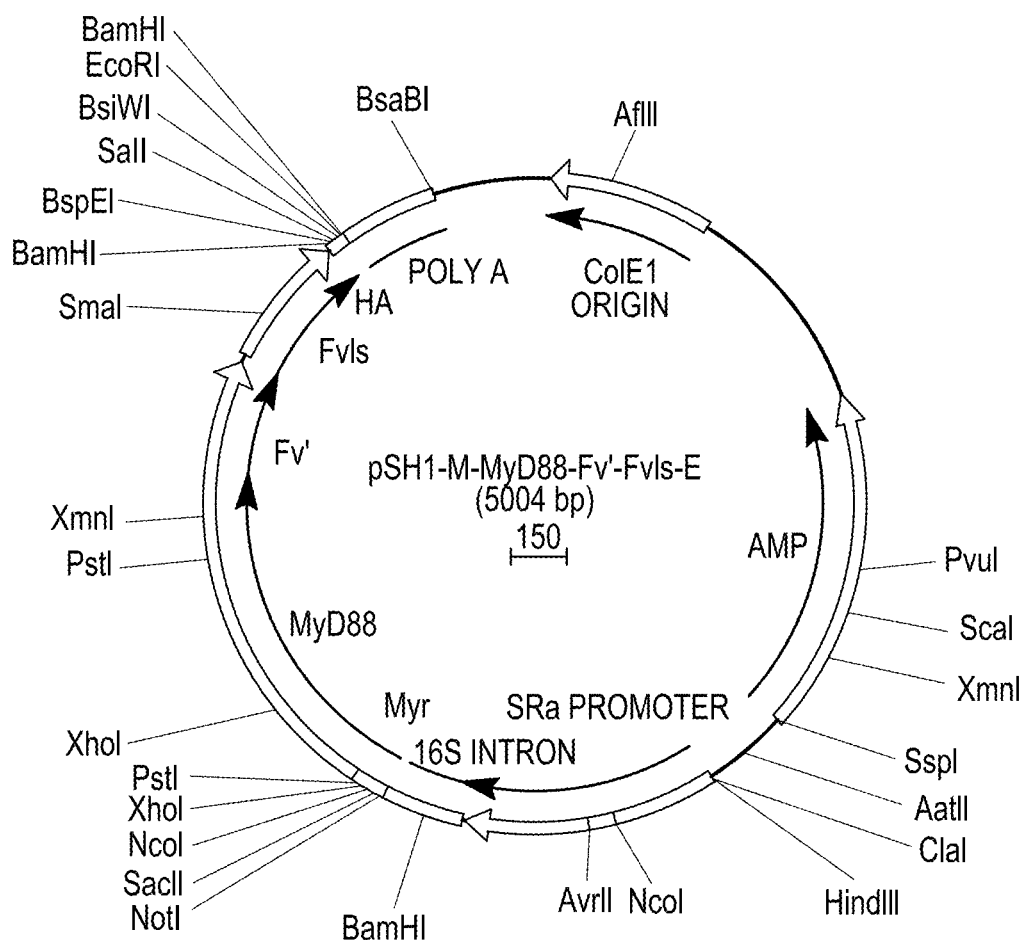
Figure 11:
FIG. 11 is a graph of induction of NF-kappa B SEAP reporter in iRIG, iNOD2, and iCD40-transfected 293 cells.
Figure 12:
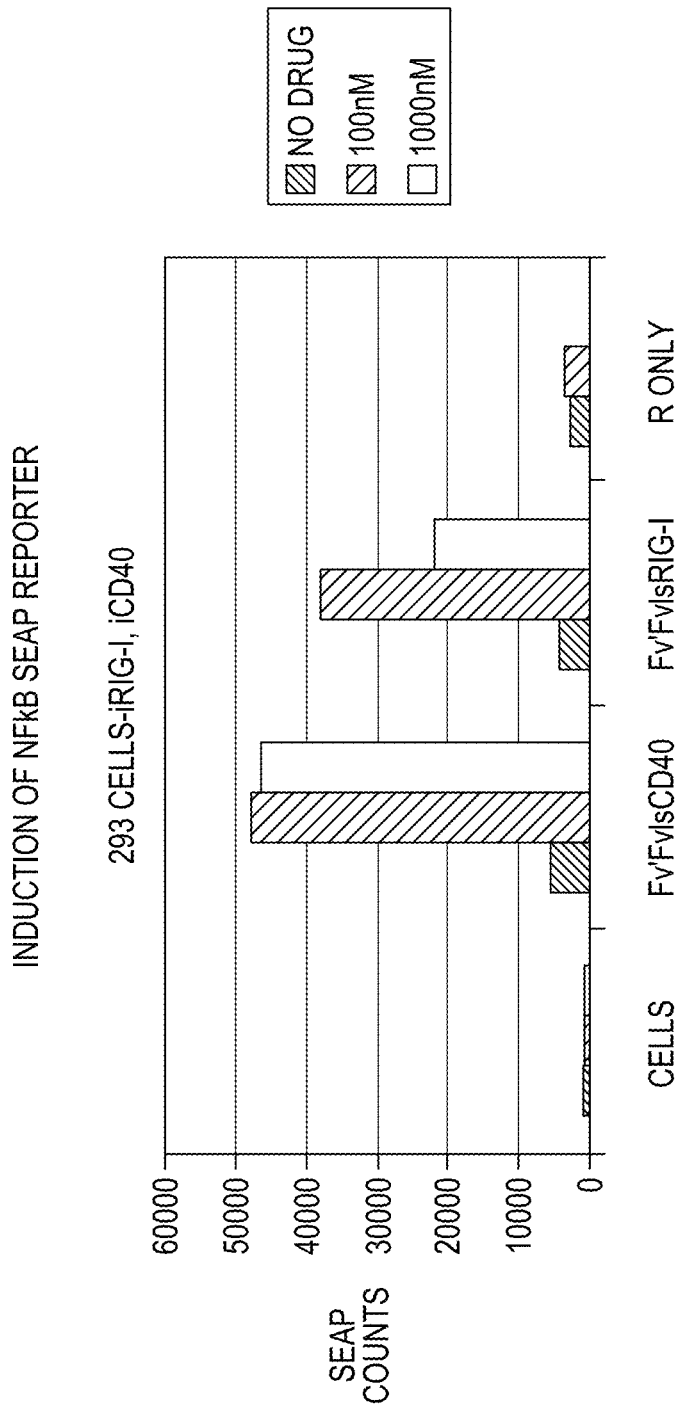
FIG. 12 is a graph of induction of NF-kappa B SEAP reporter in iRIG-I and iCD40 transfected 293 cells.
Figure 13:
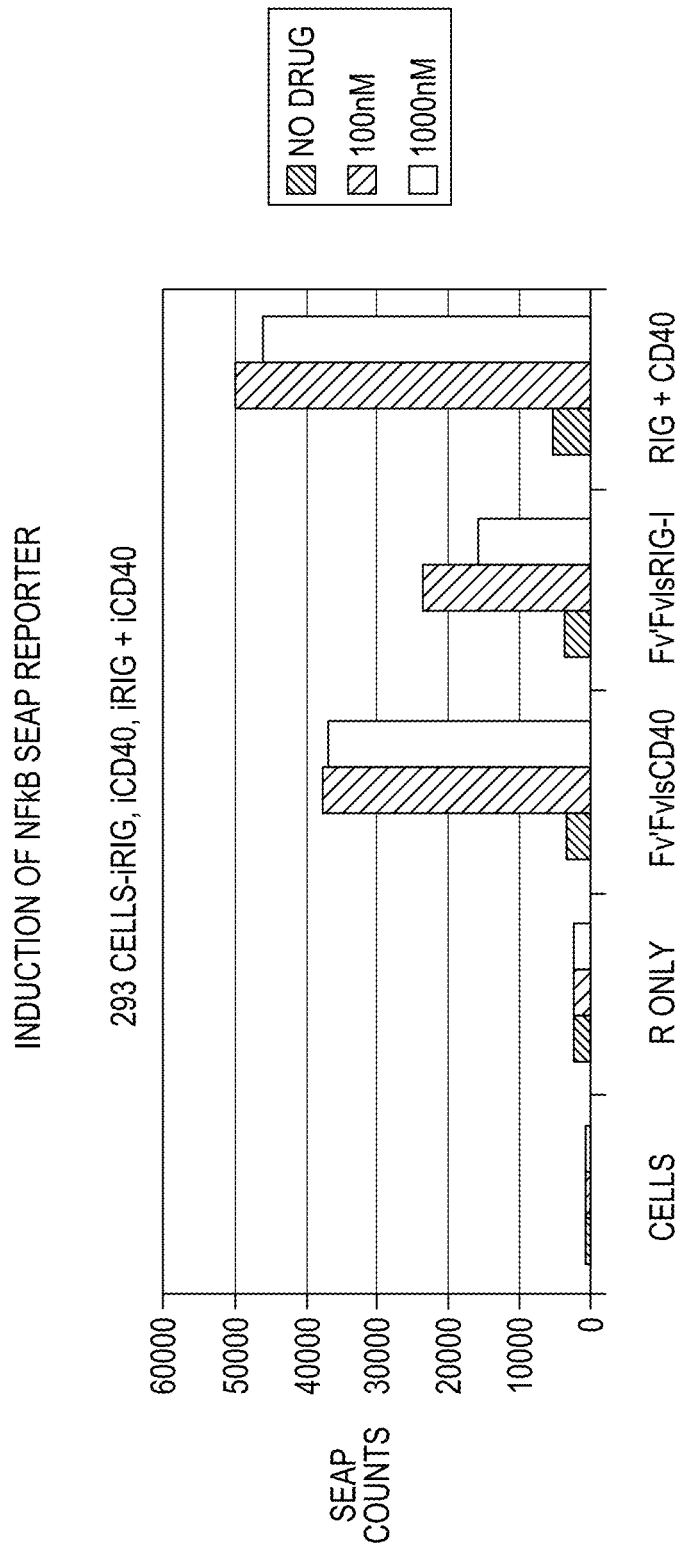
FIG. 13 is a graph of induction of NF-kappa B SEAP reporter in iRIG, iCD40), and iRIG+CD40 transfected 293 cells.
Figure 14:
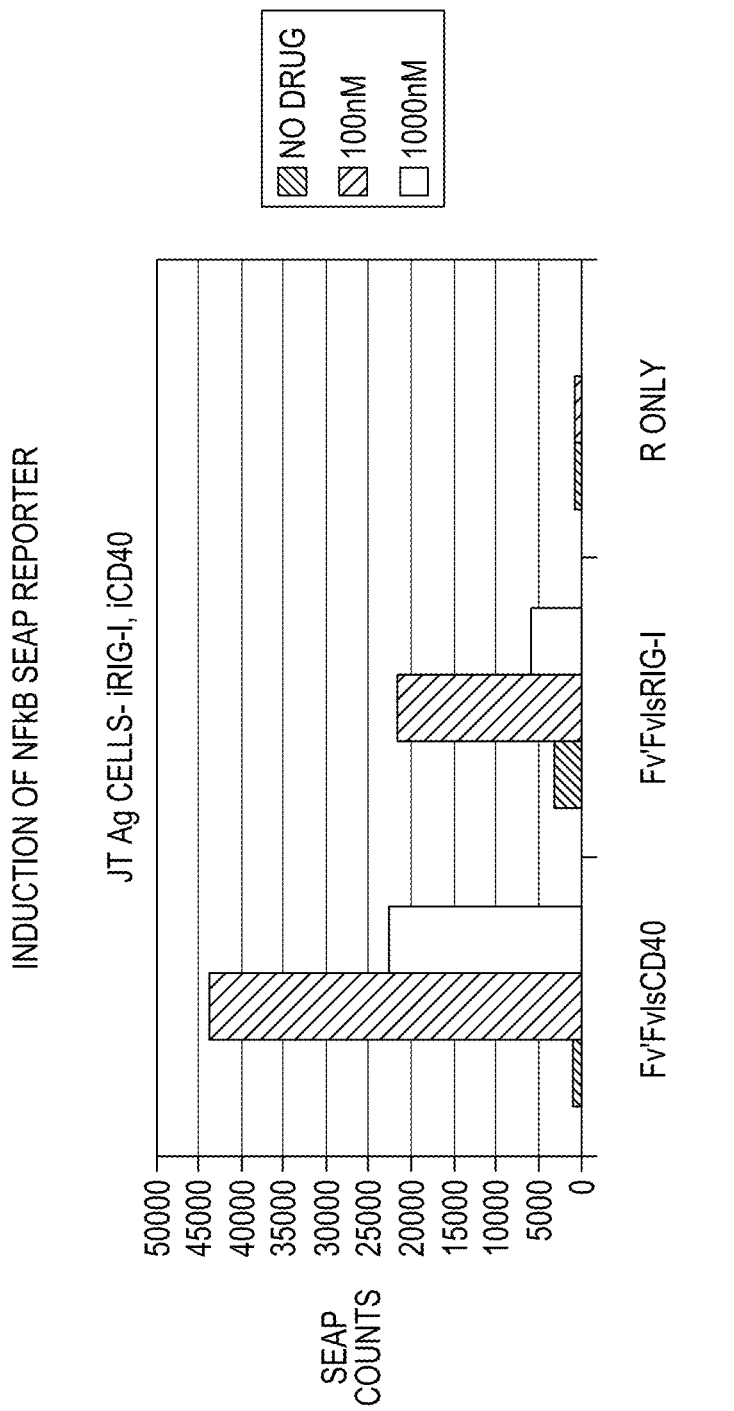
FIG. 14 is a graph of induction of NF-kappa B SEAP reporter in iRIG-I and iCD40 transfected Jurkat Tag cells.
Figure 15A:
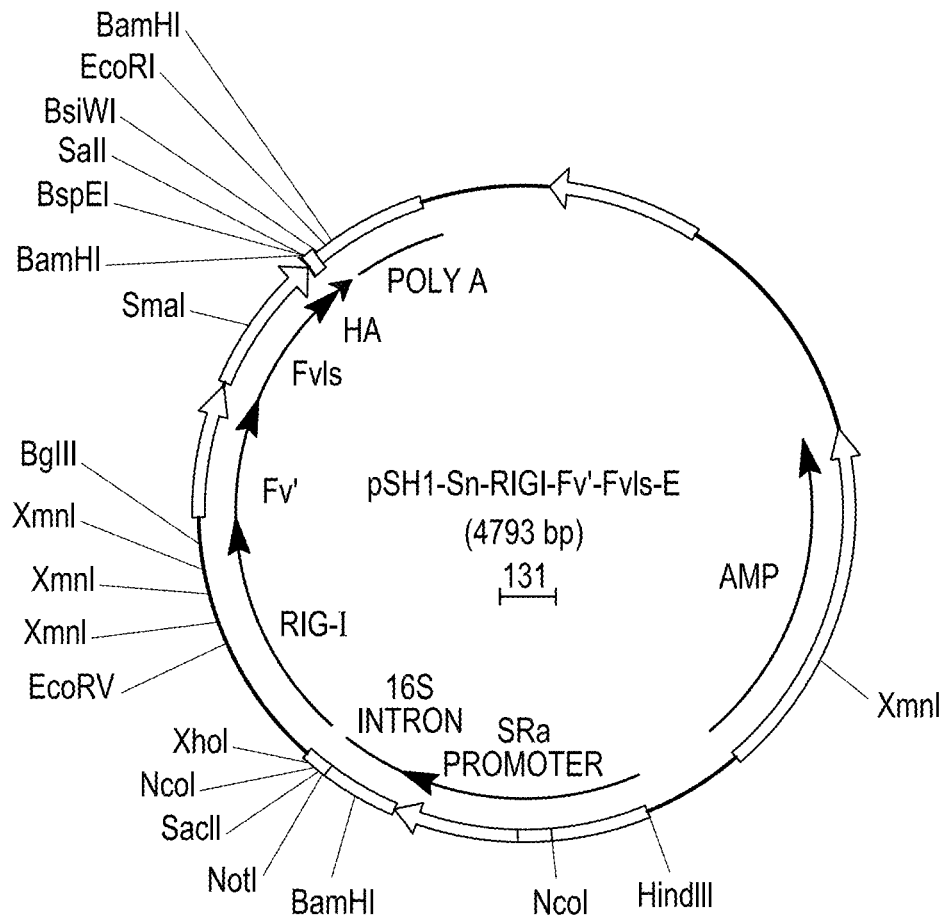
FIGS. 15A and 15B provide plasmid maps for pSH1-Sn-RIGI-Fv'-Fvls-E and pSH1-Sn-Fv'-Fvls-RIGI-E, respectively. The term "Sn" represents "S" with a NcoI site, added for cloning purposes. The term "S" represents the term non-targeted.
Figure 15B:
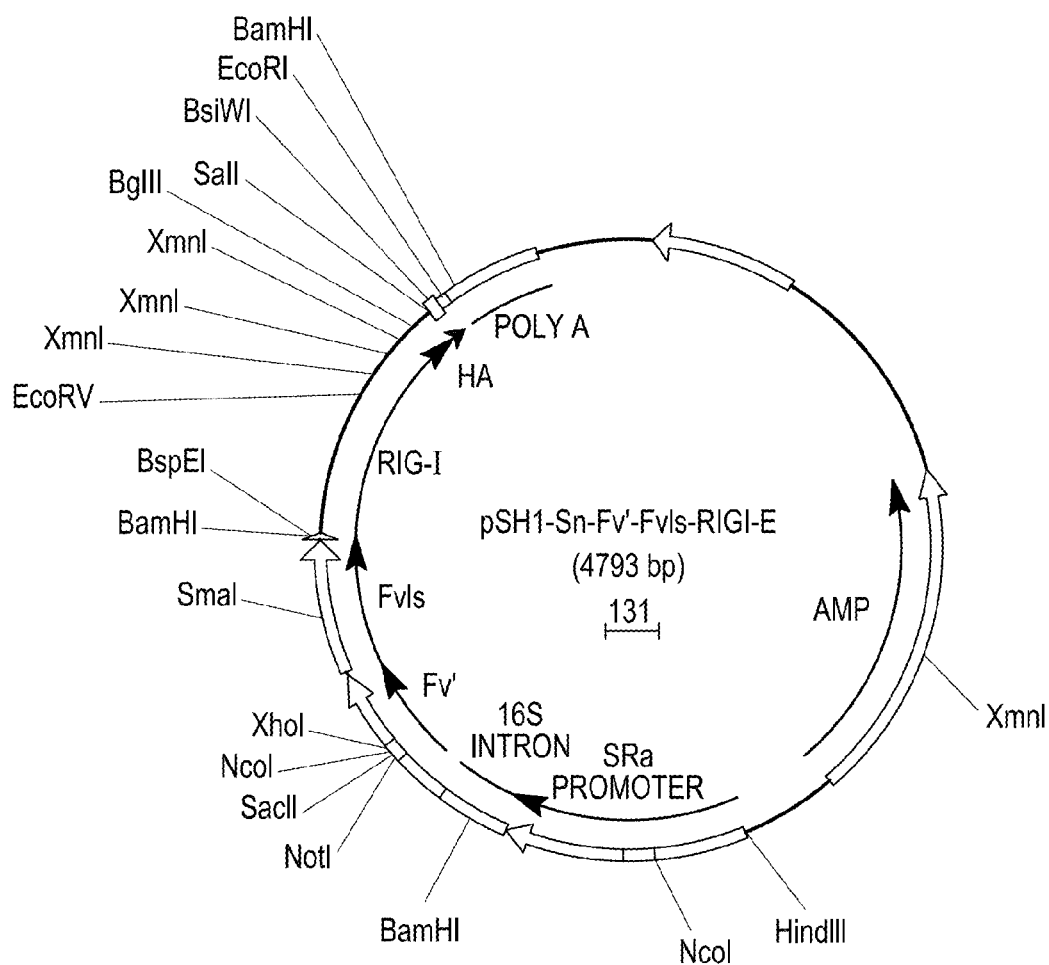

Chimeric iTLR4 with the PIP2 membrane targeting motif is activated 2 fold. The construct encoded two ligand-binding domains. However, the rest of the iTLRs are not induced at robust levels by CID in 293, RAW or D2SC1 cells, as observed in reporter assays. This might be attributed to the varied membrane targeting requirements of the iTLRs. Therefore, we developed inducible Nod2 and RIG-1, which are cytoplasmic PRRs that do not need targeting to the plasma membrane. While iNod2 was activated 2 fold by the dimerizer drug in 293 cells, no such effect is observed in RAW 264.7 cells. With the addition of increasing concentrations of CID, iNod2 activity decreases in RAW cells. Also the effect of iNod2 and iCD40 together, on NF-kappaB activation, is additive in 293 cells (FIG. 7). iRIG-1 is activated by 2.5 fold (FIG. 8). Inducible versions of the full length inducible PRR adapter molecules MyD88 and TRIF that are the primary mediators of signaling downstream of TLRs are in the screening process.

CITATIONS REFERRED TO IN THIS EXAMPLE AND PROVIDING ADDITIONAL TECHNICAL SUPPORT

1. Xie, X. et al. Adenovirus-mediated tissue-targeted expression of a caspase-9-based artificial death switch for the treatment of prostate cancer. Cancer Res 61, 6795-804. (2001).
2. Fan, L., Freeman, K. W., Khan, T., Pham, E. & Spencer, D. M. in Human Gene Therapy 2273-2285 (1999).
3. Spencer, D. M., Wandless, T. J., Schreiber, S. L. & Crabtree, G. R. Controlling signal transduction with synthetic ligands. Science 262, 1019-1024 (1993).

4. Thompson, B. S., P. M. Chilton, J. R. Ward, J. T. Evans, And T. C. Mitchell. 2005. The Low-Toxicity Versions Of Lps, Mpl Adjuvant And Rc529, Are Efficient Adjuvants For Cd4+ T Cells. J Leukoc Biol 78:1273-1280.
5. Salkowski, C. A., G. R. Detore, And S, N. Vogel. 1997. Lipopolysaccharide And Monophosphoryl Lipid A Differentially Regulate Interleukin-12, Gamma Interferon, And Interleukin-10 Mrna Production In Murine Macrophages. Infect Immun 65:3239-3247.
6. Beutler, B. 2004. Inferences, Questions And Possibilities In Toll-Like Receptor Signalling. Nature 430:257-263.
7. Werts, C., S. E. Girardin, And D. J. Philpott. 2006. Tir, Card And Pyrin: Three Domains For An Antimicrobial Triad. Cell Death Differ 13:798-815.
8. Kagan, J. C., And R. Medzhitov. 2006. Phosphoinositide-Mediated Adapter Recruitment Controls Toll-Like Receptor Signaling. Cell 125:943-955.

Example 10

Drug-Dependent Induction of NF-Kappa B Activity in Cells Transfected with iRIG-I, iCD40, and iNOD2

293 cells were transfected with 1 microgram NF-KappaB-SEAP reporter construct +1 microgram inducible PRR construct using Fugene 6 transfection reagent. The transfections were performed in a 6-well plate at $1*10^6$ cells/well or transfection.

Jurkat TAg cells were transfected with 2 micrograms NF-kappa B-SEAP reporter construct and 3 micrograms inducible PRR construct using electroporation at 950 microF and 0.25 kV. The cells were transfected at $10*10^6$ cells/transfection.

24 hours later, the cells were plated in a 96-well plate with 2 different concentrations of AP20187 (100 nM and 1000 nM). After a further 24 hour incubation at 37° C., 5% $CO_2$, supernatants were collected and analyzed for SEAP activity by incubation with SEAP substrate, 4-methylumbilliferyl phosphate (MUP). Fluorescence was determined at excitation 355 nm and emission 460 nm using a FLUOstar Optima plate reader (BMG Labtech).

For iNOD2 and combination experiments, transfections were normalized for total DNA using an "empty" expression vector, pSH1/S-Fv'-Fvls-E.

FIGS. 11-14 are graphs that show drug-dependent induction of NF-kappaB activity and SEAP reporter counts. Each graph is representative of a separate individual experiment.

For purposes of clarity in the graphs, some of the vectors were renamed for the figures.
Fv'RIG-I=pSH1-Fv'Fvls-RIG-1=pSH1/M-Fv'-Fvls-RIG-1
Fv'NOD2=pSH1-Fv'Fvls-NOD2=pSH1/M-Fv'-Fvls-NOD2-E
Fv'2NOD2=pSH1-Fv'2Fvls-NOD2
Fv'NOD2+=pSH1-Fv'Fvls-NOD2 (same as Nunez NOD2 sequence)
Fv'CD40=pSH1-Fv'Fvls-CD40

Example 11

Inducible MyD88 and Composite MyD88-CD40 Activate NF-kappaB in 293 Cells

Figure 16:
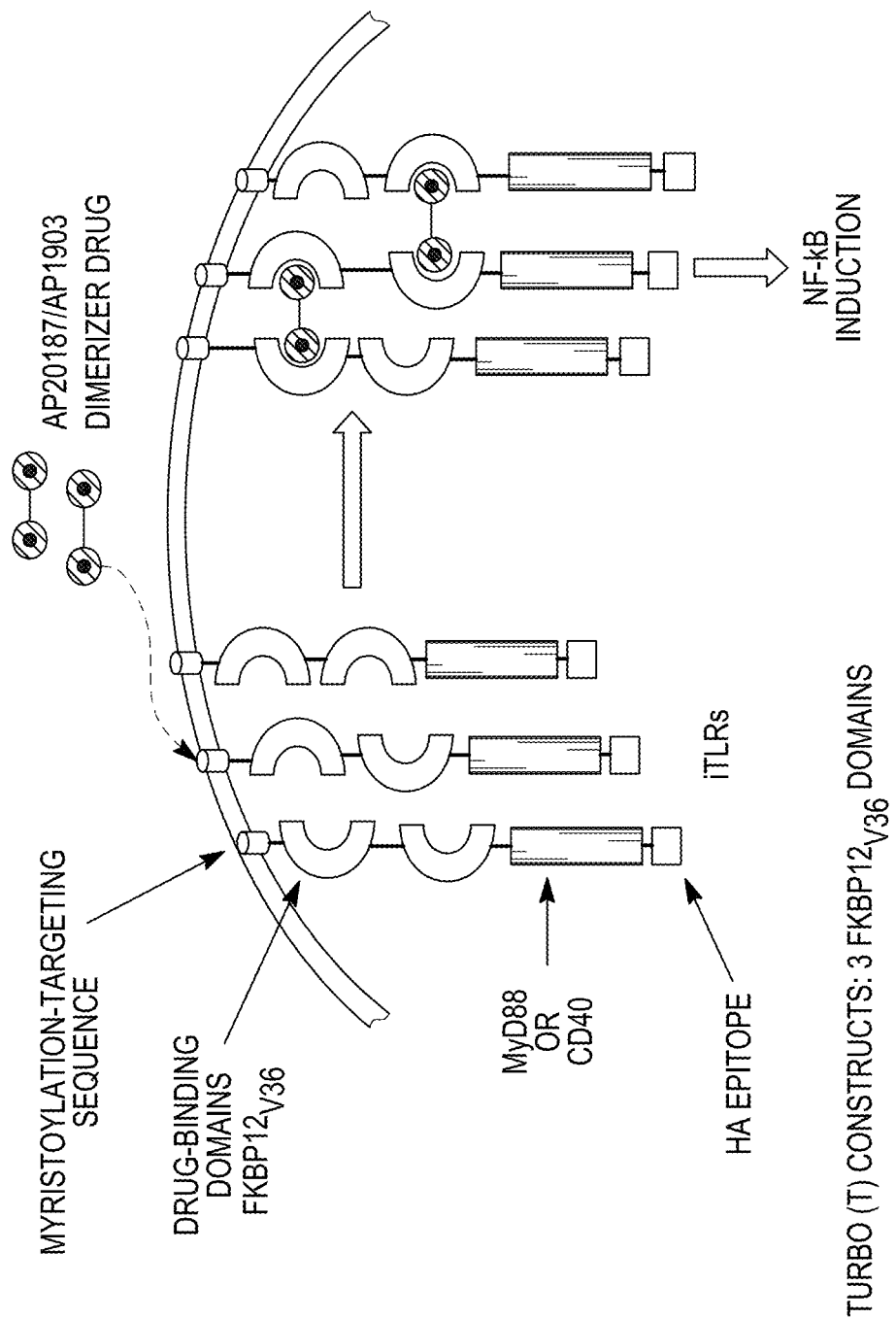
FIG. 16 is a schematic of inducible CD40 and MyD88 receptors and induction of NF-kappa B activity.
Figure 17:
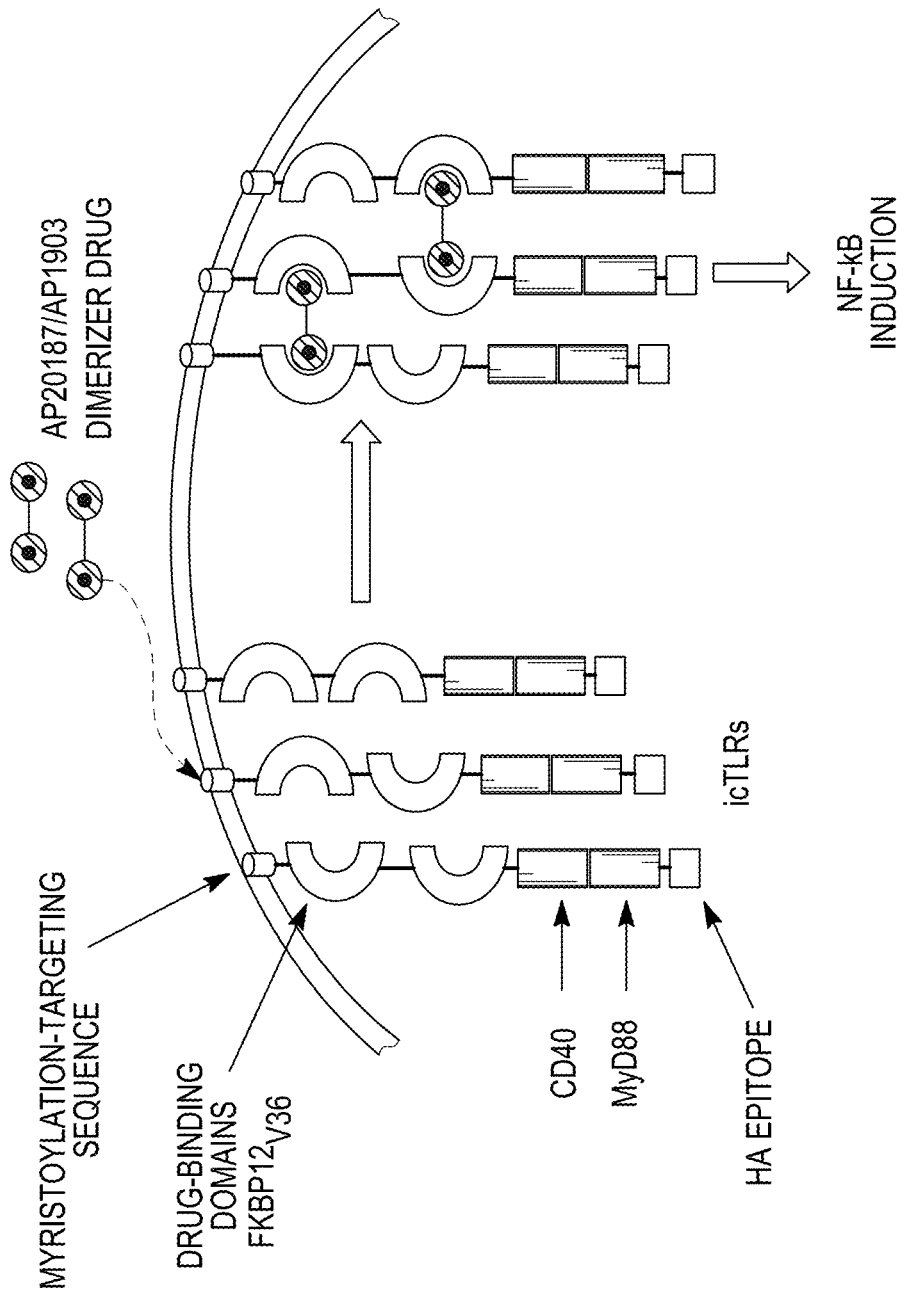
FIG. 17 is a schematic of inducible chimeric CD40/MyD88 receptors and induction of NF-kappaB activity.
Figure 18:
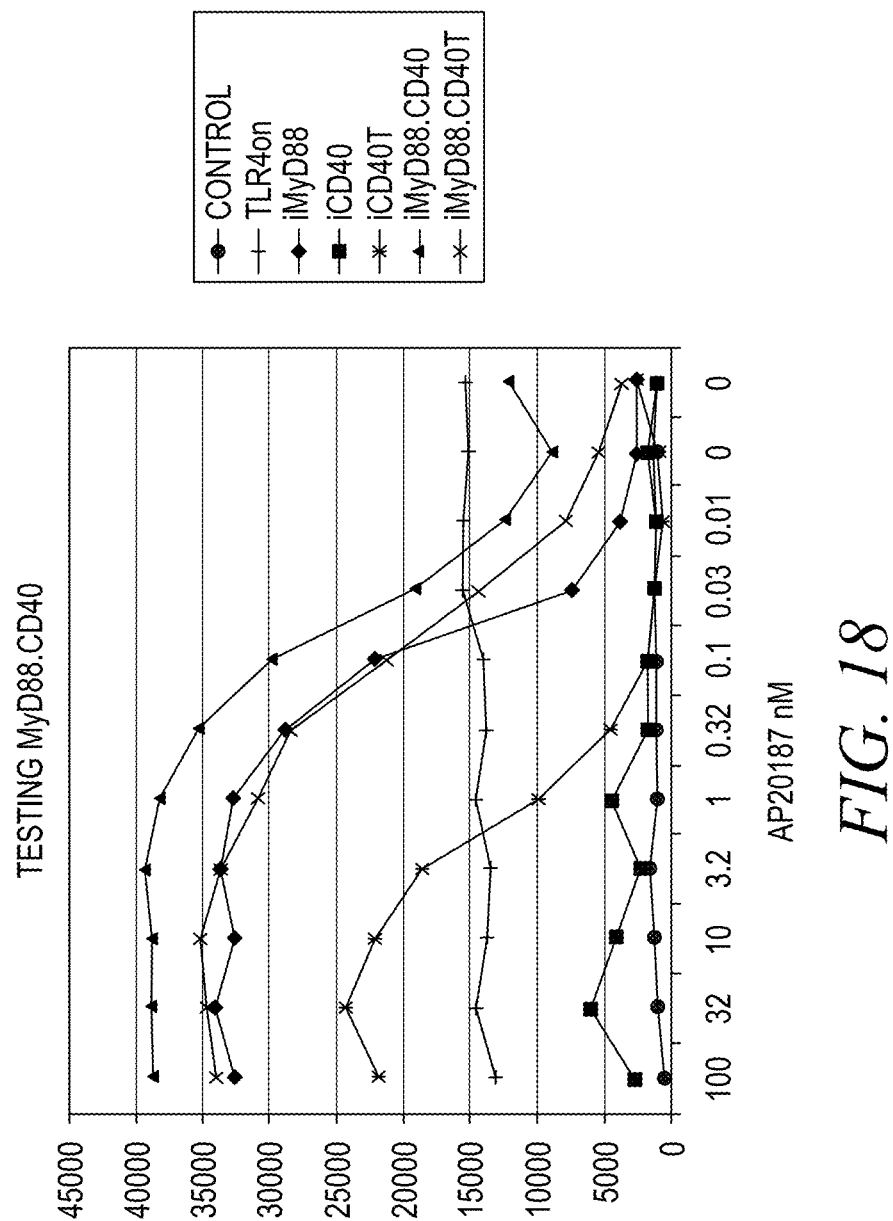
FIG. 18 is a graph of NF-kappa B activation in 293 cells by inducible MyD88 and chimeric MyD88-CD40 receptors. CD40T indicates "turbo" CD40, wherein the receptor includes 3 copies of the FKBP12$_{v36}$ domain (Fv').

A set of constructs was designed to express inducible receptors, including a truncated version of MyD88, lacking the TIR domain. 293 cells were cotransfected with a NF-kappaB reporter and the SEAP reporter assay was performed essentially as described in Spencer, D. M., Wandless, T. J., Schreiber, S. L. & Crabtree, G. R. Controlling signal transduction with synthetic ligands. Science 262, 1019-1024 (1993). The vector originally designed was pBJ5-M-MyD88L-Fv'Fvls-E. pShuttleX-M-MyD88L-Fv'Fvls was used to make the adenovirus. Both of these vectors were tested in SEAP assays. After 24 hours, AP20187 was added, and after 20 additional hours, the cell supernatant was tested for SEAP activity. Graphics relating to these chimeric constructs and activation are provided in FIGS. 16 and 17. The results are shown in FIG. 18.

Constructs:
Control: Transfected with NF-kappaB reporter only.
TLR4 on: pShuttleX-CD4/TLR4-L3-E: CD4/TLR4L3-E is a constitutive version of TLR4 that contains the extracellular domain of mouse CD4 in tandem with the transmembrane and cytoplasmic domains of human TLR4 (as described in Medzhitov R, Preston-Hurlburt P, Janeway C A Jr, A human homologue of the *Drosophila* Toll protein signals activation of adaptive immunity. *Nature*. 1997 Jul. 24; 388(6640):394-7.) followed by three 6-amino acid linkers and an HA epitope.
iMyD88: contains M-MyD88L-Fv'Fvls-E
iCD40: contains M-Fv'-Fvls-CD40-E
iCD40T: contains M-Fv'-Fv'-Fvls-CD40-E-iCD40T contains an extra Fv' (FKBP with wobble at the valine)
iMyD88:CD40: contains M-MyD88L-CD40-Fv'Fvls-E
iMyD88:CD40T: contains M-MyD88LCD40-Fv'Fv'Fvls-E—contains an extra Fv' compared to iMyD88:CD40.

Example 12

Inducible CD40-MyD88, CD40-RIG-1, and CD40:NOD2

Figure 19:
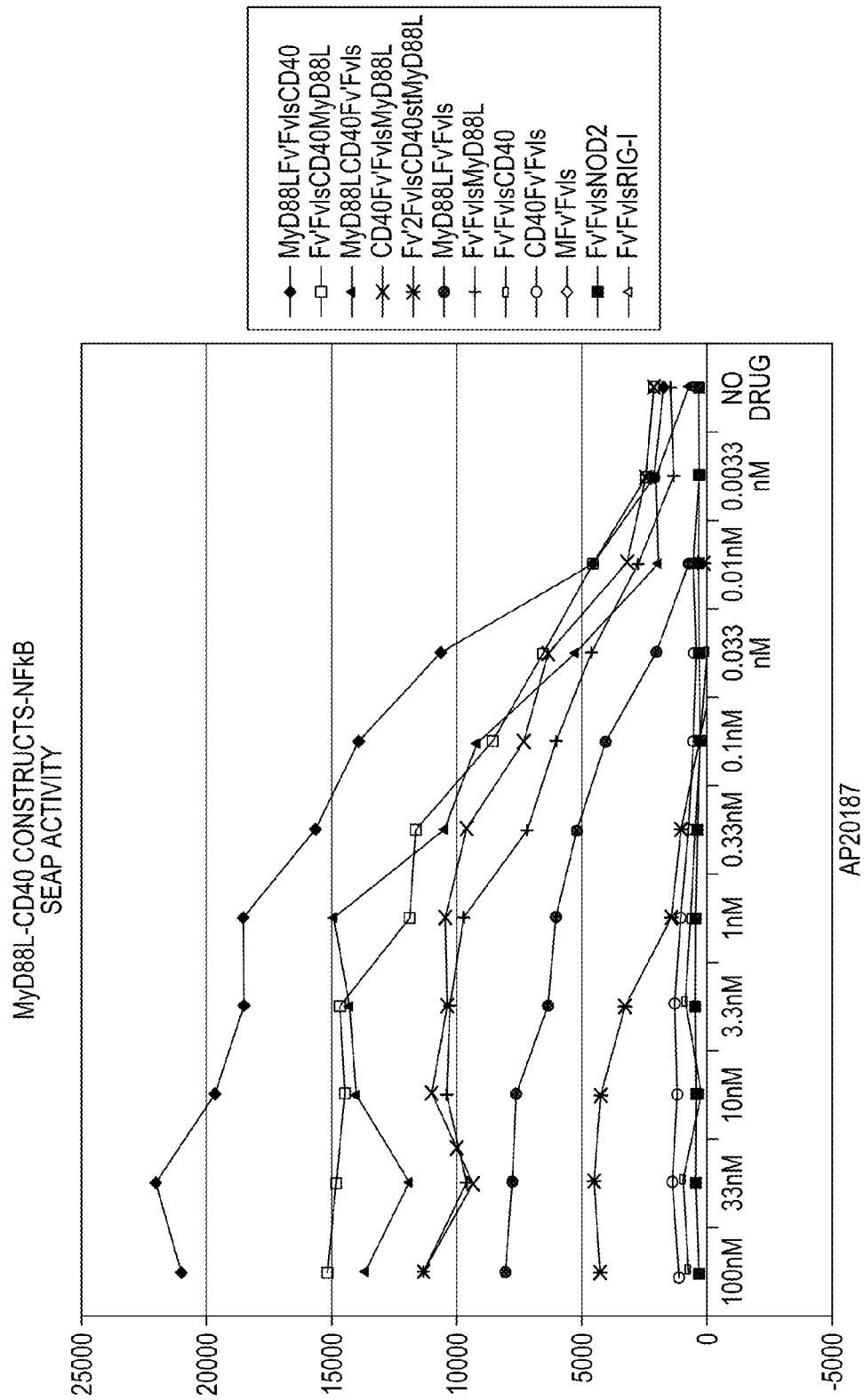
FIG. 19 is a graph of NF-kappa B activity by inducible truncated MyD88 (MyD88L) and chimeric inducible truncated MyD88/CD40 after 3 hours of incubation with substrate.
Figure 20:
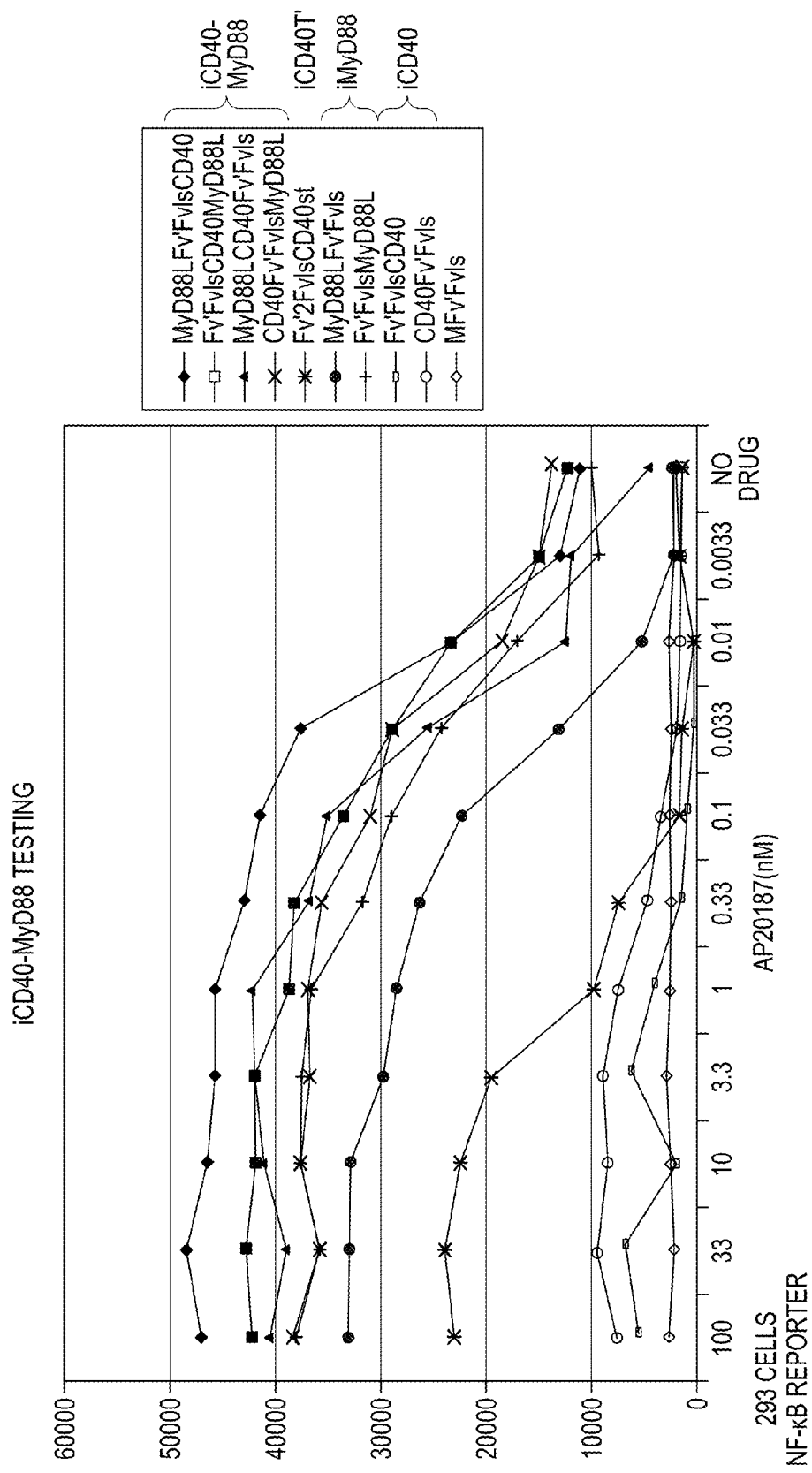
FIG. 20 is a graph of NF-kappa B activity by inducible truncated MyD88 (MyD88L) and chimeric inducible truncated MyD88/CD40 after 22 hours of incubation with substrate. Some assay saturation is present in this assay.

The following constructs were designed and assayed in the NF-kappaB reporter system. 293 cells were cotransfected with a NFkappaB reporter and one of the constructs. After 24 hours, AP20187 was added, and after an additional 3 hours (FIG. 19) or 22 hours (FIG. 20), the cell supernatant was tested for SEAP activity. About 20-24 hours after transfection, the cells were treated with dimer drug AP20187. About 20-24 hours following treatment with dimer drug, cells were treated with SEAP substrate 4-methylumbelliferyl phosphate (MUP). Following an overnight incubation (anywhere from 16-22 hrs), the SEAP counts were recorded on a FLUOStar OPTIMA machine.
MyD88LFv'FvlsCD40: was made in pBJ5 backbone with the myristoylation sequence upstream from MyD88L
Fv'FvlsCD40MyD88L: was made in pBJ5 backbone with the myristoylation sequence upstream from Fv'.
MyD88LCD40Fv'Fvls: was made in 2 vector backbone (pBJ5) with the myristoylation sequence upstream from the MyD88L.
CD40Fv'FvlsMyD88L: was made in pBJ5 backbone with the myristoylation sequence upstream from CD40.
Fv'2FvlsCD40stMyD88L: is a construct wherein a stop sequence after CD40 prevented MyD88L from being translated. Also named iCD40T'.
Fv'2Fvls includes 2 copies of Fv', separated by a gtcgag sequence.
MyD88LFv'Fvls
Fv'FvlsMyD88L: was made in pBJ5 backbone with the myristoylation sequence upstream from the Fv'.
Fv'FvlsCD40: is available in pBJ5 and pShuttleX
CD40Fv'Fvls: is available in pBJ5 backbone with the myristoylation sequence upstream from the CD40.
MFv'Fvls: is available in pBJ5 backbone with the myristoylation sequence indicated by the M. Fv"FvlsNOD2: pBJ5-Sn- Fv'Fvls-NOD2-E in pBJ5 backbone with no myristoylation sequence, contains 2 FKBPs followed by 2 CARD domains of NOD2 and the HA epitope.

Fv'FvlsRIG-1: pBJ5-Sn-Fv'Fvls-RIG-1-E in pBJ5 backbone with no myristoylation sequence, contains 2 FKBPs followed by 2 CARD domains of RIG-I and the HA epitope.

Figure 30:
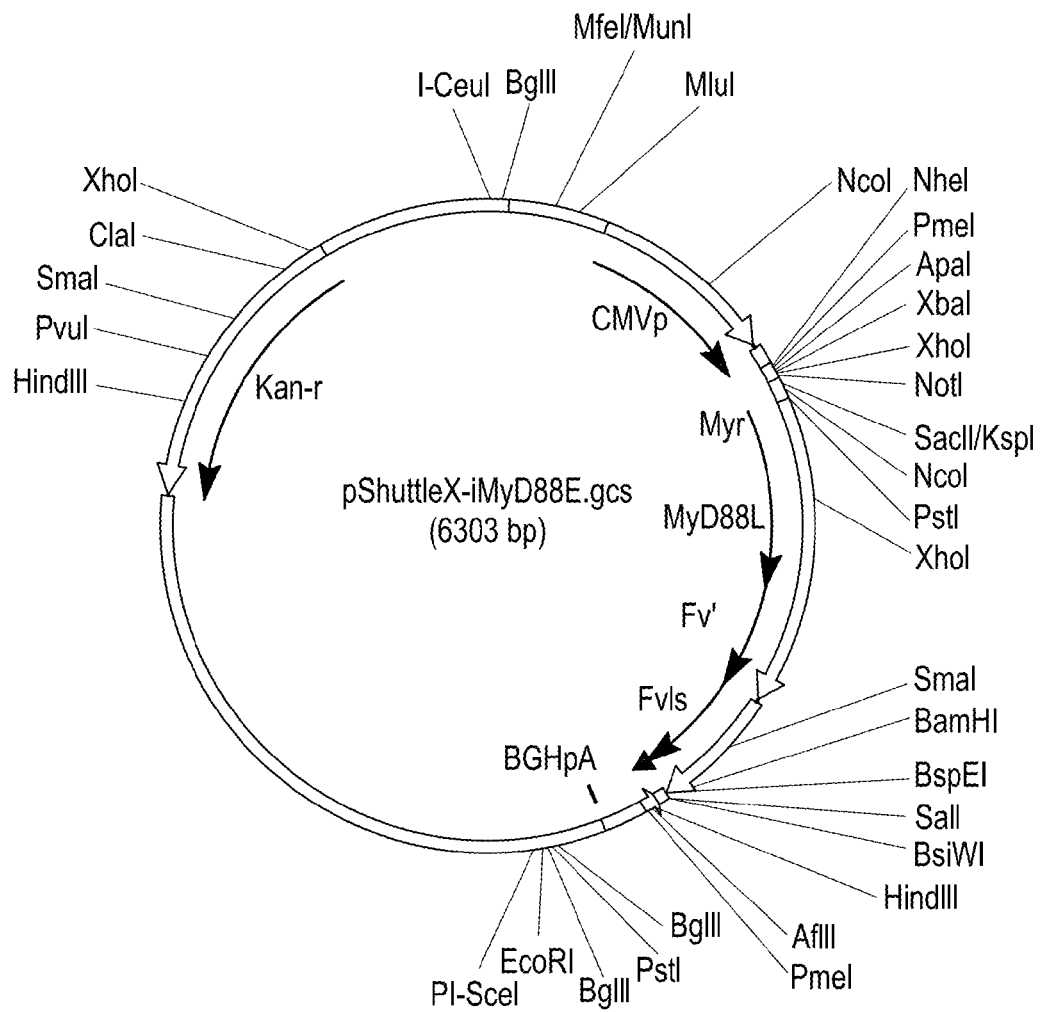
FIG. 30 is a construct map of pShuttleX-iMyD88.
Figure 31:
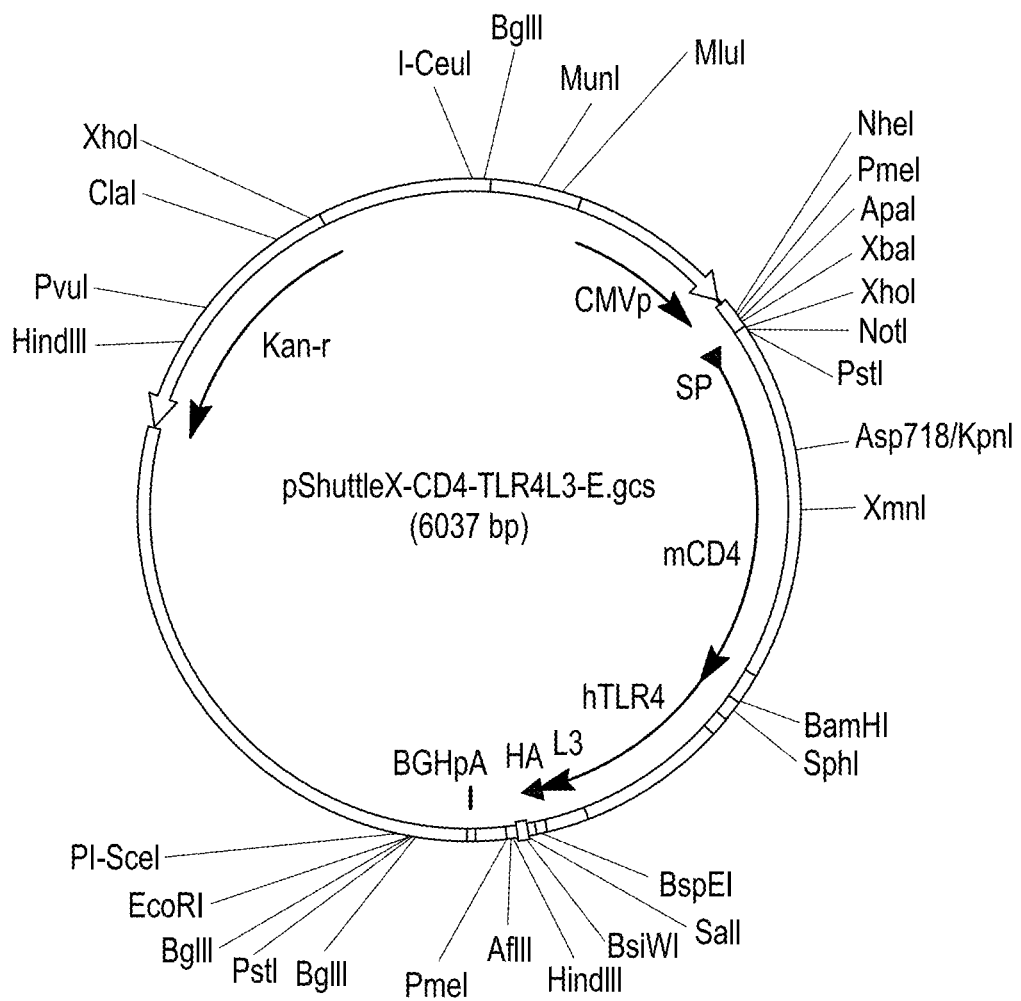
FIG. 31 is a construct map of pShuttleX-CD4-TLR4L3-E.
Figure 32:
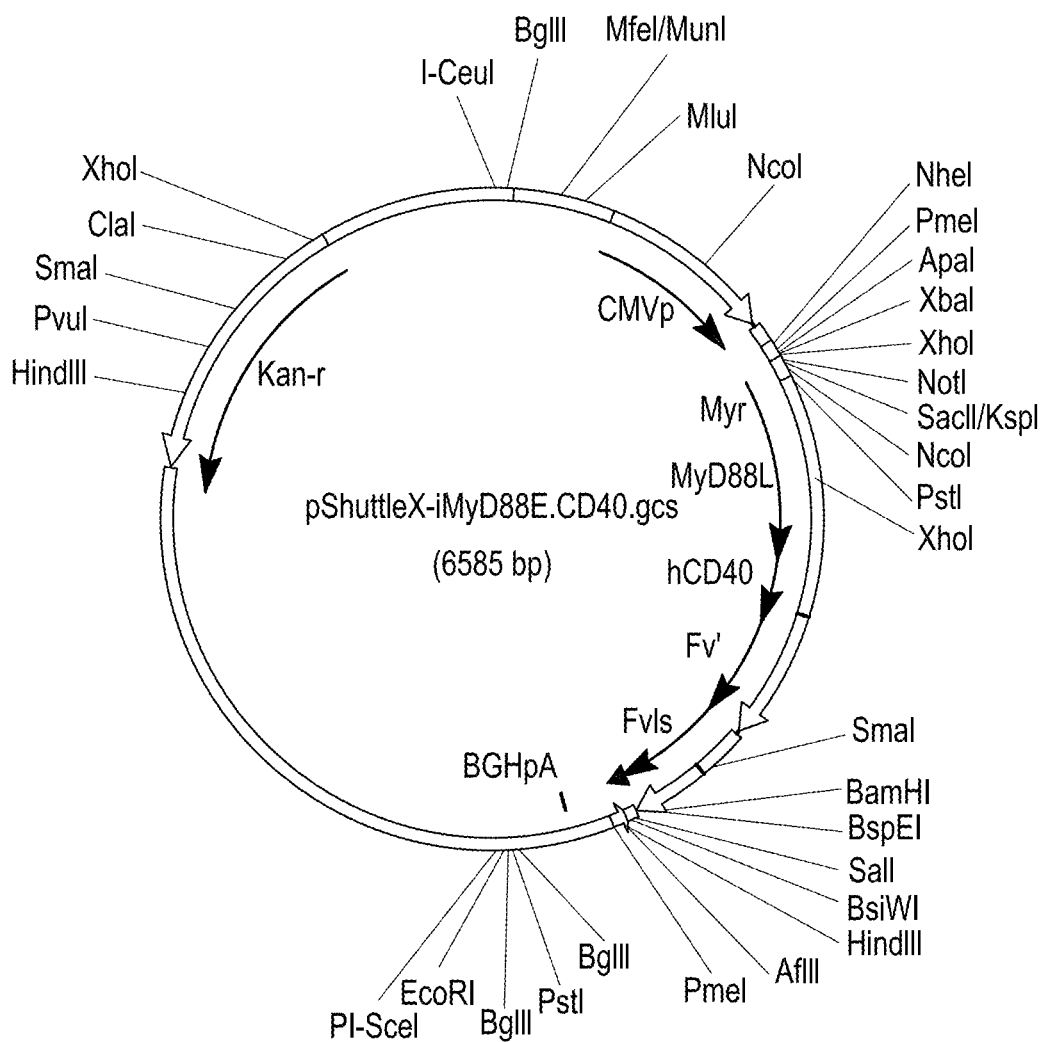
FIG. 32 is a construct map of pShuttleX-iMyD88E-CD40.

Examples of construct maps for pShuttleX versions used for Adenovirus production are presented in FIGS. 30, 31, and 32. Those of ordinary skill in the art are aware of methods of modifying these constructs to produce other constructs used in the methods and compositions described herein.

Example 13

MyD88L Adenoviral Transfection of 293T Cells Results in Protein Expression

The following pShuttleX constructs were constructed for adenovirus production:

pShuttleX-MyD88L-Fv'Fvls-E pShuttleX-MyD88LCD40-Fv'Fvls-E pShuttleX-CD4/TLR4-L3-E L3 indicates three 6 amino acid linkers, having the DNA sequence:

```
                                         (SEQ ID NO: 50)
GGAGGCGGAGGCAGCGGAGGTGGCGGTTCCGGAGGCGGAGGTTCT

Protein sequence:
                                         (SEQ ID NO: 51)
GlyGlyGlyGlySerGlyGlyGlyGlySerGlyGlyGlyGlySer
```

E is an HA epitope.

Recombinant adenovirus was obtained using methods known to those of ordinary skill in the art, and essentially as described in He, T. C., S. Zhou, et al. (1998) Proc. Natl. Acad. Sci. USA 95(5):2509-14.

For each of the adenovirus assays, crude lysates from several virus plaques were assayed for protein expression by Western blotting. Viral particles were released from cell pellets supplied by the Vector Core at Baylor College of Medicine (world wide web address of vector.bcm.tmc.edu) by freeze thawing pellets three times. 293T cells were plated at $1 \times 10^6$ cells per well of a 6 well plate. 24 hours following culture, cells were washed twice with serum-free DMEM media with antibiotic, followed by the addition of 25 microliters or 100 microliters virus lysate to the cell monolayer in 500 microliters serum-free media. 2 hours later, 2.5 ml of serum-supplemented DMEM was added to each well of the 6-well plate.

Figure 21:
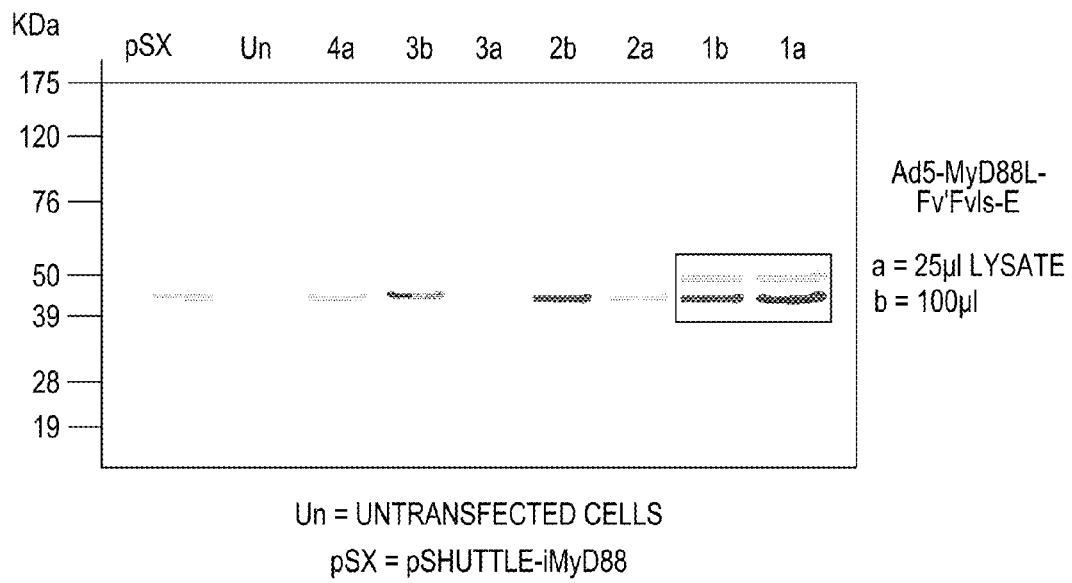
FIG. 21 is a Western blot of HA protein, following adenovirus-MyD88L transduction of 293T cells.
Figure 22:
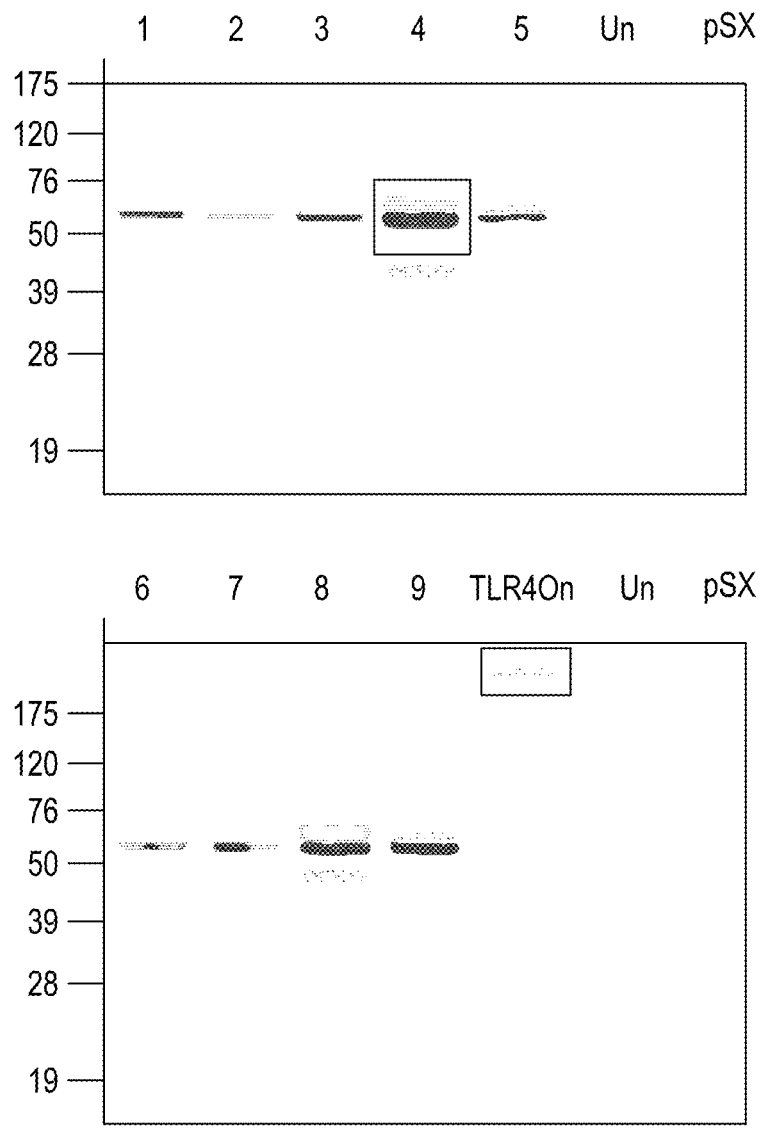
FIG. 22 is a Western blot of HA protein, following adenovirus-MyD88L-CD40 transduction of 293T cells.

24-48 hours later, cells were harvested, washed twice with 1×PBS and resuspended in RIPA lysis buffer (containing 100 micromolar PMSF) (available from, for example, Millipore, or Thermo Scientific). Cells were incubated on ice for 30 minutes with mixing every 10 minutes, followed by a spin at 10,000 g for 15 minutes at 4° C. The supernatants were mixed with SDS Laemmli buffer plus beta-mercaptoethanol at a ratio of 1:2, incubated at 100° C. for 10 minutes, loaded on a SDS gel, and probed on a nitrocellulose membrane using an antibody to the HA epitope. Results are shown in FIGS. 21 and 22. Remaining cell lysates were stored at −80° C. for future use. The cells were transduced separately with each of the viruses, viz., Ad5-iMyD88 and Ad5-TLRon separately.

Example 14

IL-12p70 Expression in MyD88L-Adenoviral Transduced Cells

Figure 23:
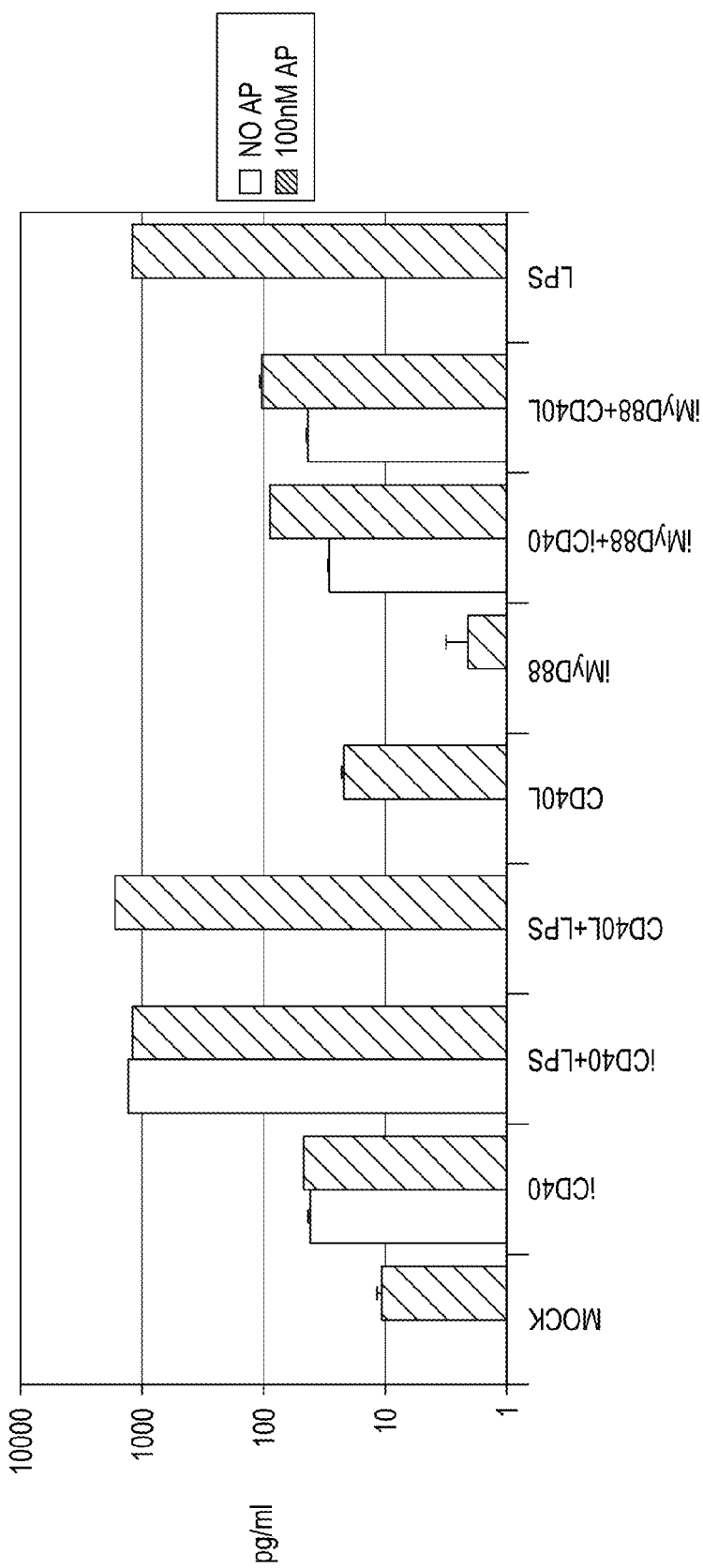
FIG. 23 is a graph of an ELISA assay after adenovirus infection of bone marrow derived DCs with the indicated inducible CD40 and MyD88 constructs.
Figure 24:
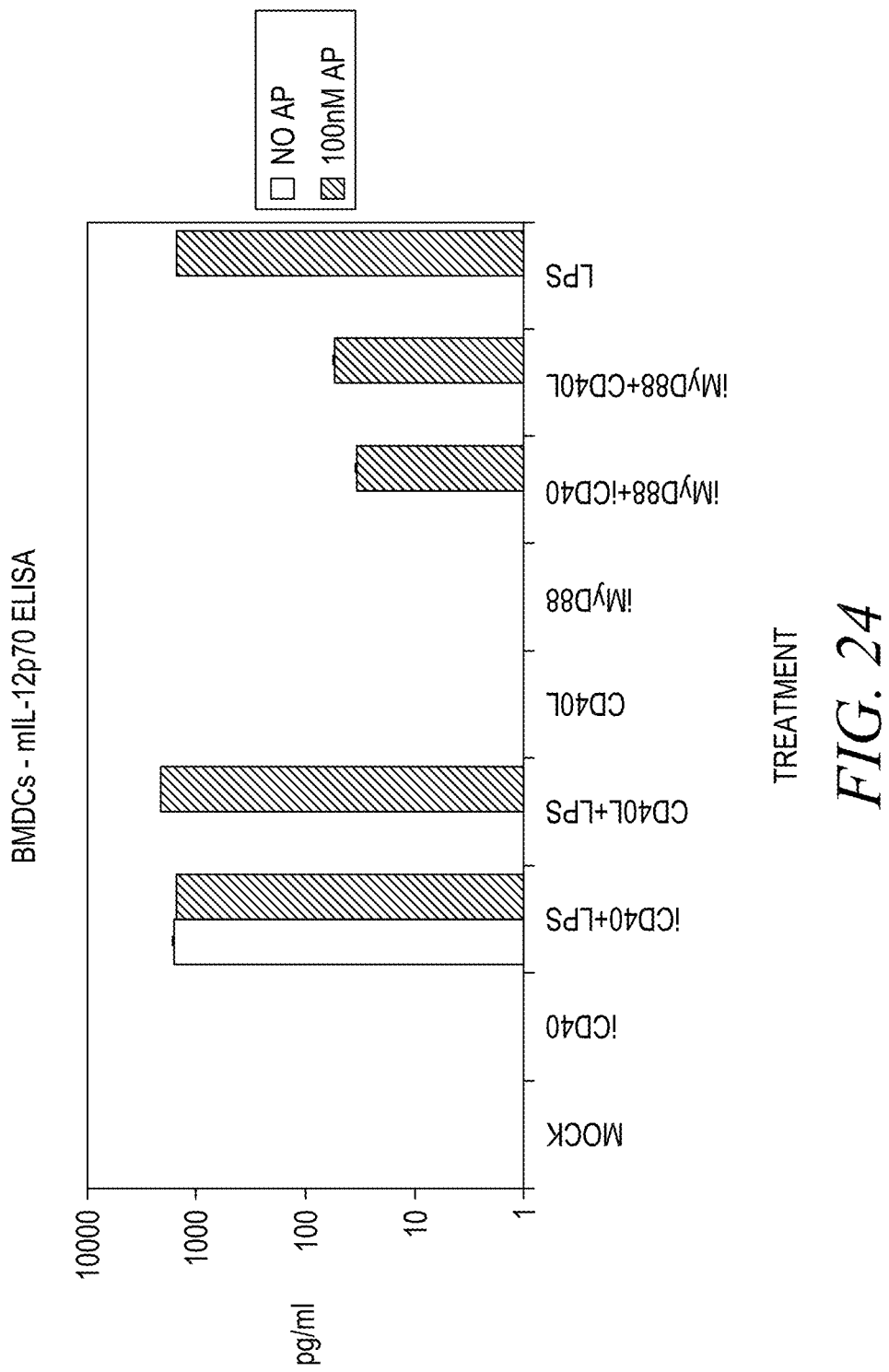
FIG. 24 is a graph of the results of an ELISA assay similar to that in FIG. 23.
Figure 25:
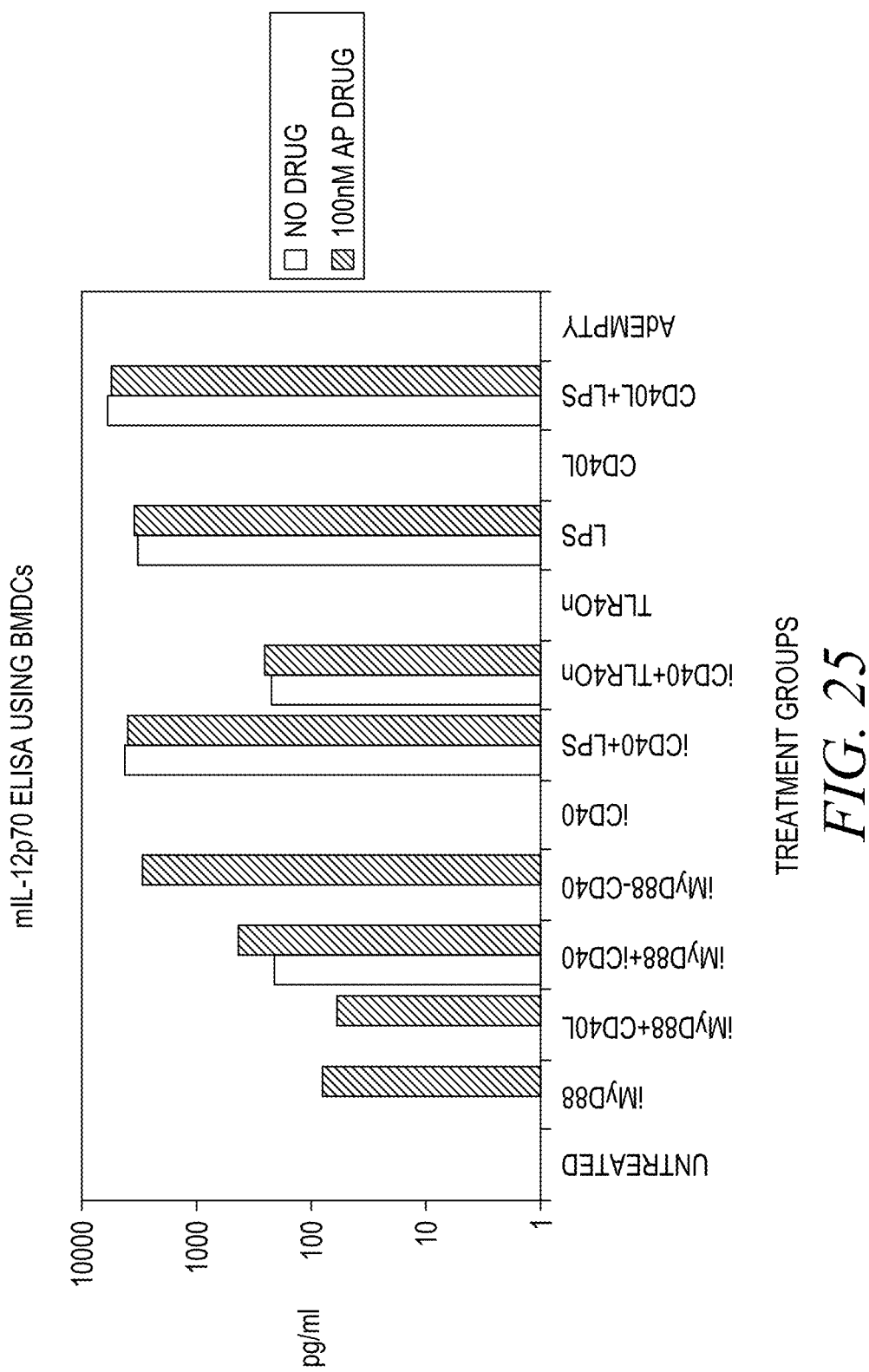
FIG. 25 is a graph of the results of an ELISA assay similar to that in FIGS. 23 and 24, after infection with a higher amount of adenovirus.

Bone marrow-derived dendritic cells (BMDCs) were plated at $0.25 \times 10^6$ cells per well of a 48-well plate after washing twice with serum-free RPMI media with antibiotic. Cells were transduced with 6 microliters crude virus lysate in 125 microliters serum-free media. 2 hours later, 375 microliters of serum-supplemented RPMI was added to each well of the 48-well plate. 48 hours later, supernatants were harvested and analyzed using a mouse IL-12p70 ELISA kit (BD OptEIA (BD BioSciences, New Jersey). Duplicate assays were conducted for each sample, either with or without the addition of 100 nM AP21087. CD40-L is CD40 ligand, a TNF family member that binds to the CD40 receptor. LPS is lipopolysaccharide. The results are shown in FIG. 23. Results of a repeat of the assay are shown in FIG. 24, crude adenoviral lysate was added at 6.2 microliters per 0.25 million cells. FIG. 25 shows the results of an additional assay, where more viral lysate, 12.5 microliters per 0.25 million cells was used to infect the BMDCs.

Example 15

Inducible iRIG-1, iNOD2 and iTRIF Activities

Figure 26:
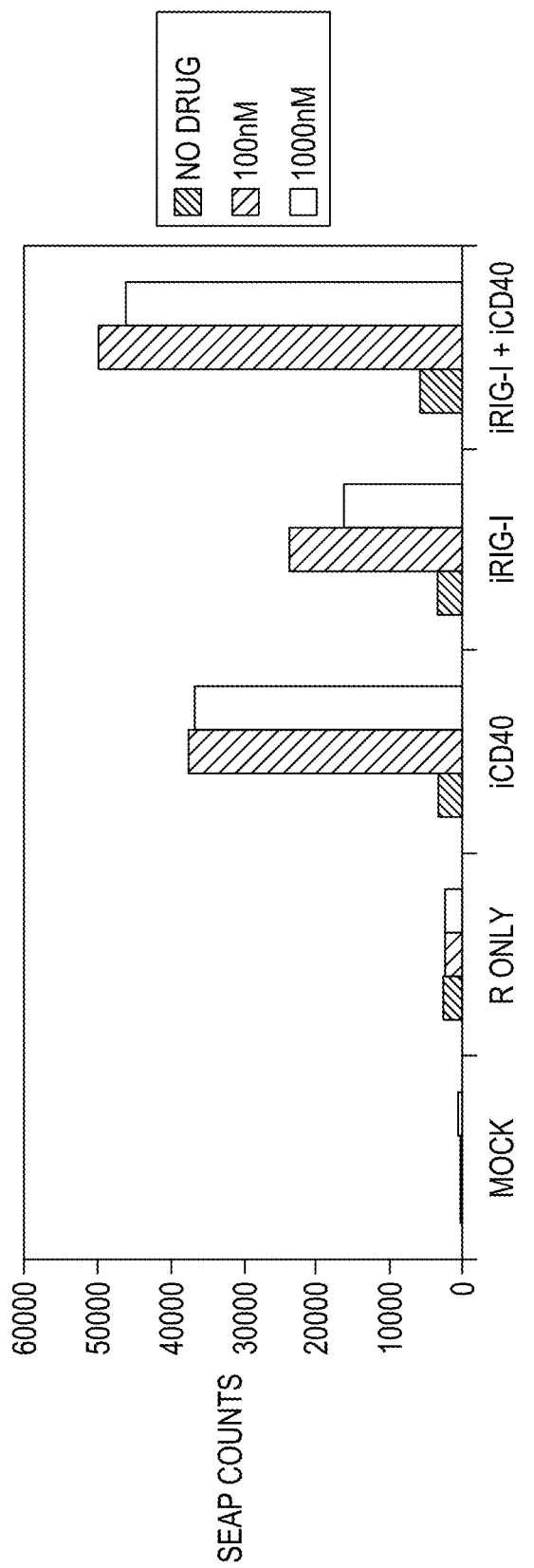
FIG. 26 is a graph of results of a NF-kappaB SEAP reporter assay in iRIG-1 and iCD40 transfected cells.

One microgram each of pBJ5-Fv'Fvls-RIG-1 and pBJ5-Fv'Fvls-CD40 were transfected into 293 cells with one microgram of NF-kappaB-SEAP reporter and cells were analyzed for reporter activity on treatment with an increasing dose of dimer drug AP20187. A pBJ5-RIG-1-Fv'Fvls construct was also tested. The results are shown in FIG. 26. The results show that iRIG-I could potentially work well with iCD40 as demonstrated by the additive effects seen in the NF-kappaB reporter assay when both the iRIG-I and iCD40 constructs were transfected into 293 cells.

Figure 28:
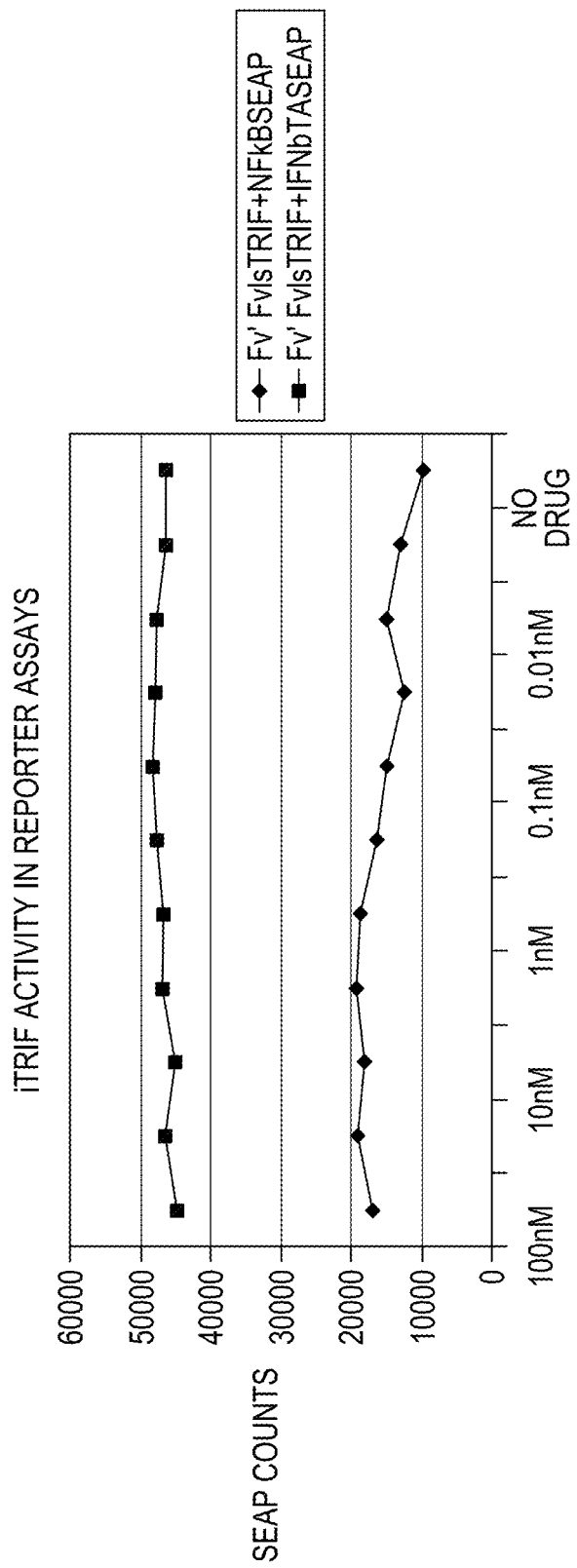
FIG. 28 is a graph comparing iTRIF activation of NF-kappa B and IFN-beta reporters in transfected cells.

One microgram of pBJ5-Fv'Fvls-RIG-1 was transfected into 293 cells with 1 micrograms of IFNbeta-SEAP reporter and cells were analyzed for reporter activity on treatment with half-log dilutions of dimer drug AP20187. Simultaneously the iTRIF (pBJ5-Fv'Fvls-TRIF) construct was also tested by transfecting increasing amounts into 293 cells. pBJ5-M-Fv'Fvls-TRIF-E—was made in pBJ5 backbone with a myristoylation sequence, 2 FKBPs, full length TRIF and a HA epitope. The results are shown in FIGS. 27 and 28. The results demonstrate that iTRIF constitutively activates NF-kappaB, and, to a higher extent, IFNbeta reporters in 293 cells.

Figure 29:
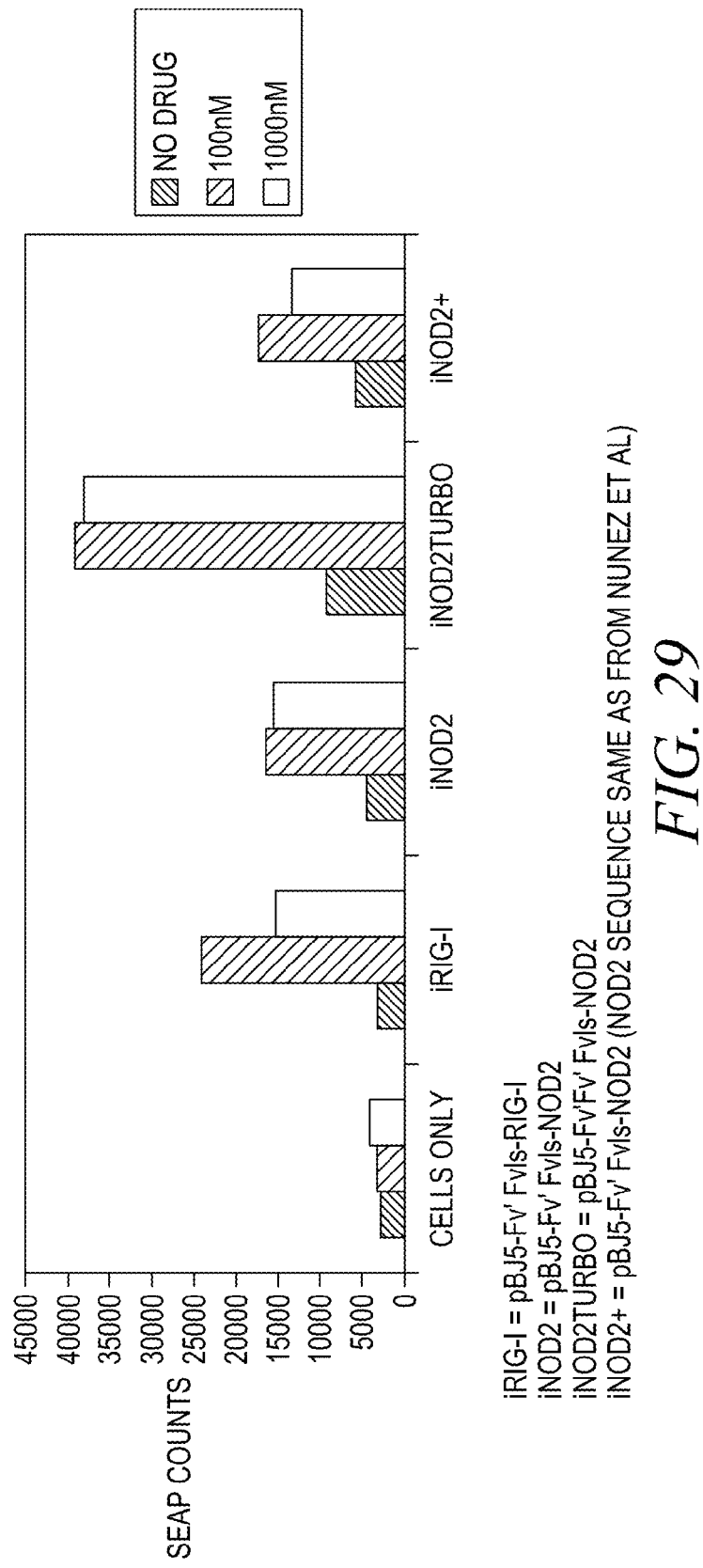
FIG. 29 is a graph of iNOD2 activation of a NF-kappaB reporter in transfected cells.

A similar assay was conducted using iNOD2, as shown in FIG. 29. The results show that iNOD2 activates NF-kappaB in a drug dependent manner. This activation of NF-kappa B increases on the addition of a third FKBP domain to iNOD2 (iNOD2Turbo). pBJ5-Sn-Fv'Fv'Fvls-NOD2-E—was made in pBJ5 backbone, and contains a myristoylation sequence, 3 FKBPs, 2 CARD domains of NOD2 and a HA epitope.

Example 16

Figure 33:
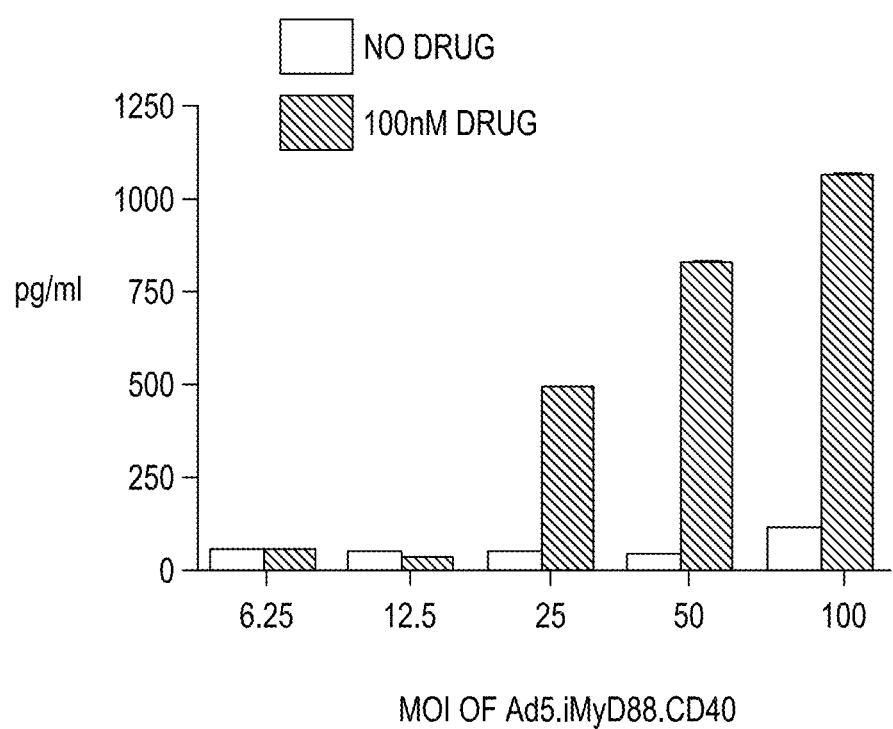
FIG. 33 is a bar graph depicting the results of a dose-dependent induction of IL-12p70 expression in human monocyte-derived dendritic cells (moDCs) transduced with different multiplicity of infections of adenovirus expressing an inducible MyD88.CD40 composite construct.

IL-12p70 Expression in MyD88L-Adenoviral Transduced Human Monocyte-Derived Dendritic Cells Immature human monocyte-derived dendritic cells (moDCs) were plated at $0.25 \times 10^6$ cells per well of a 48-well plate after washing twice with serum-free RPMI media with antibiotic. Cells were transduced with different multiplicity of infections (MOI) of adenovirus AD5-iMyD88.CD40 and stimulated with 100 nM dimer drug AP20187. The virus used was an optimized version of the viral lysate used in Examples 13 and 14. 48 hours later, supernatants were harvested and assayed in an IL12p70 ELISA assay. FIG. 33 depicts the results of this titration.

Immature human moDCs were plated at $0.25 \times 10^6$ cells per well of a 48-well plate after washing twice with serum-free RPMI media with antibiotic. Cells were then transduced with either Ad5f35-iCD40 (10,000 VP/cell); Ad5-iMyD88.CD40 (100 MOD; Ad5.1MyD88 (100 MOD or Ad5-TLR4 on (100 MOD and stimulated with 1 microgram/milliliter LPS where indicated and 100 nM dimer drug AP20187 where indicated in FIG. 34. 48 hours later, supernatants were harvested and assayed in an IL12p70 ELISA assay.

Figure 34:
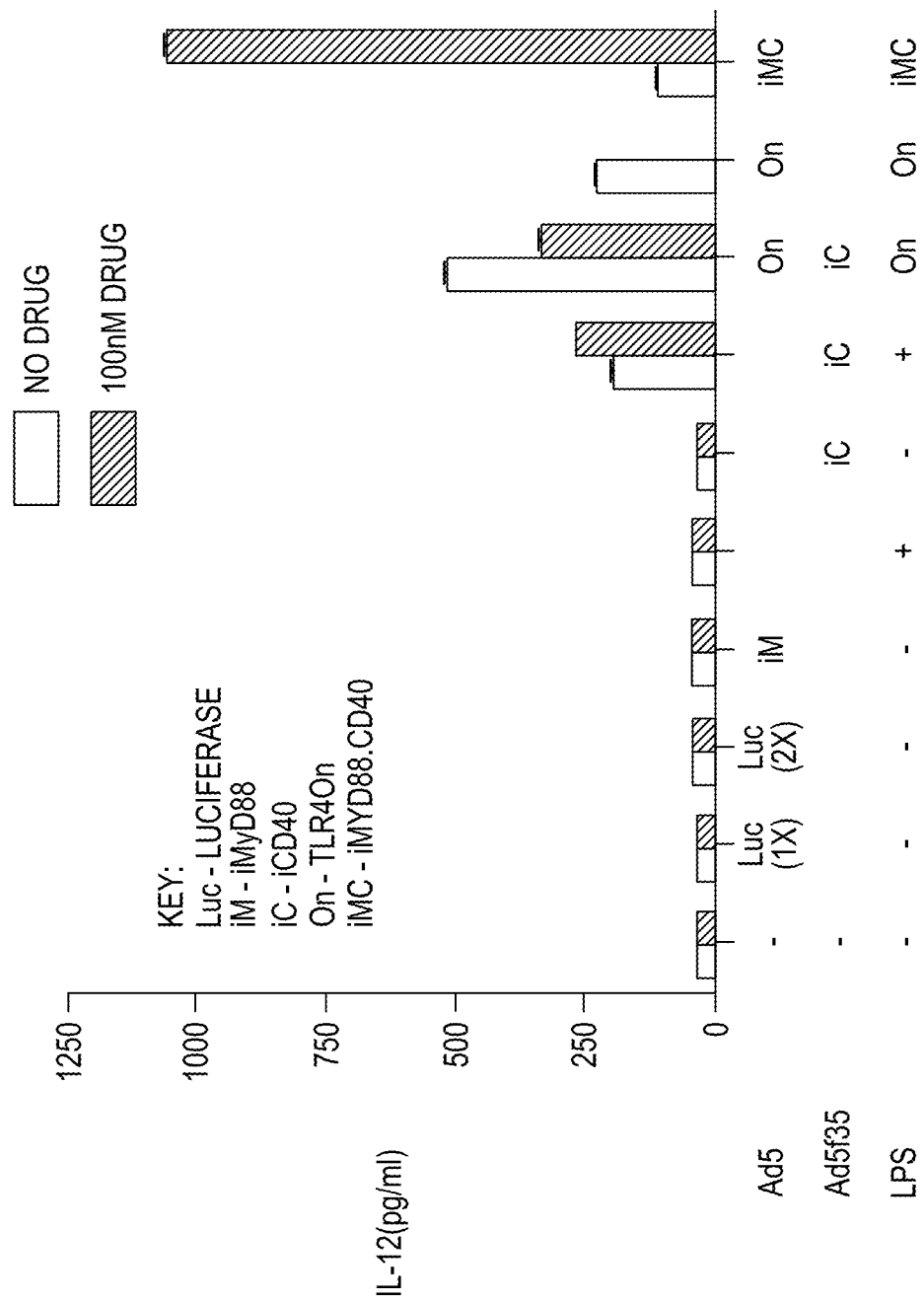
FIG. 34 is a bar graph depicting of the results of a drug-dependent induction of IL-12p70 expression in human monocyte-derived dendritic cells (moDCs) transduced with adenoviruses expressing different inducible constructs.

Ad5f35-iCD40 was produced using pShuttleX-ihCD40 (also known as M-Fv'-Fvls-hCD40; pShuttleX-M-Fv'-Fvls-hCD40). MyD88, as indicated in FIGS. 33 and 34, is the same truncated version of MyD88 as the version indicated as MyD88L herein. The adenovirus indicated as Ad5.1MyD88 was produced using pShuttleX-MyD88L-Fv'Fvls-E. The adenovirus indicated as Ad5-iMyD88.Cd40 was produced using pShuttleX-MyD88LCD40-Fv'Fvls-E. The adenovirus indicated as Ad5-TLR4On was produced using pShuttleX-CD4/TLR4-L3-E.

Example 17

Non-Viral Transformation of Dendritic Cells

A plasmid vector is constructed comprising the iMyD88-CD40 sequence operably linked to the Fv'Fvls sequence, such as, for example, the pShuttleX-MyD88LCD40-Fv'Fvls-E Insert. The plasmid construct also includes the following regulatory elements operably linked to the MyD88ICD40-Fv'Fvls-E sequence: promoter, initiation codon, stop codon, polyadenylation signal. The vector may also comprise an enhancer sequence. The MyD88L, CD40, and FvFvls sequences may also be modified using synthetic techniques known in the art to include optimized codons.

Immature human monocyte-derived dendritic cells (MoDCs) are plated at $0.25 \times 10^6$ cells per well of a 48-well plate after washing twice with serum-free RPMI media with antibiotic. Cells are transduced with the plasmid vector using any appropriate method known to those of ordinary skill in the art such as, for example, nucleofection using AMAXA kits, electroporation, calcium phosphate, DEAE-dextran, sonication loading, liposome-mediated transfection, receptor mediated transfection, or microprojectile bombardment.

DNA vaccines are discussed in, for example, U.S. Patent Publication 20080274140, published Nov. 6, 2008. The iMyD88-CD40 sequence operably linked to the Fv'Fvls sequence is inserted into a DNA vaccine vector, which also comprises, for example, regulatory elements necessary for expression of the iMyD88-Cd40 Fv'Fvls chimeric protein in the host tissue. These regulatory elements include, but are not limited to, promoter, initiation codon, stop codon, polyadenylation signal, and enhancer, and the codons coding for the chimeric protein may be optimized.

Example 18

Evaluation of MyD88CD40 Transformed Dendritic Cells In Vivo Using a Mouse Tumor Model Bone marrow dendritic cells were transduced using adenoviral vectors as presented in the examples herein. These transduced BMDCs were tested for their ability to inhibit tumor growth in a EG.7-OVA model. EG.7-OVA cells ($5 \times 10^5$ cells/100 ml) were inoculated into the right flank of C57BL/6 female mice. BMDCs of all groups were pulsed with 50 microgram/ml of ovalbumin protein and activated as described above. Approximately 7 days after tumor cell inoculation, BMDCs were thawed and injected subcutaneously into the hind foot-pads of mice.

Tumor growth was monitored twice weekly in mice of all groups. Peripheral blood from random mice of all groups was analyzed by tetramer staining and by in vivo CTL assays. Table 1 presents the experimental design, which includes non-transduced dendritic cells (groups 1 and 2), dendritic cells transduced with a control adenovirus vector (group 3), dendritic cells transduced with a CD40 cytoplasmic region encoding vector (group 4), dendritic cells transduced with a truncated MyD88 vector (groups 5 and 6), and dendritic cells transduced with the chimeric CD40-truncated MyD88 vector (groups 7 and 8). The cells were stimulated with AP-1903, LPS, or CD40 ligand as indicated.

TABLE 1

| Group | Treatment | Dose Level | ADV vp/cell | [LPS] | [AP1903] (in vitro) | Other reagents (in vitro) | Route of Administration (Vaccine) | Route of Administration (AP1903) | N |
|---|---|---|---|---|---|---|---|---|---|
| 1 | PBS | NA | | | N/A | | SC | N/A | 6 |
| 2 | DCs + CD40L + LPS | 1.5e6 cells | | 200 ng/ml | N/A | CD40L 2 μg/ml | SC | N/A | 6 |
| 3 | DCs + Ad-Luc + LPS + AP1903 | 1.5e6 cells 5 mg/kg (AP1903) | 20K wGJ | 200 ng/ml | 100 nM | | SC | IP | 6 |
| 4 | DCs +Ad-iCD40 + LPS + AP1903 | 1.5e6 cells 5 mg/kg (AP1903) | 20K wGJ | 200 ng/ml | 100 nM | | SC | IP | 6 |
| 5 | DCs + Ad-iMyD88 + AP1903 | 1.5e6 cells 5 mg/kg (AP1903) | 20K wGJ | | 100 nM | | SC | IP | 6 |
| 6 | DCs + Ad-iMyD88 | 1.5e6 cells | 20K wGJ | | N/A | | SC | N/A | 6 |

TABLE 1-continued

| Group | Treatment | Dose Level | ADV vp/cell | [LPS] | [AP1903] (in vitro) | Other reagents (in vitro) | Route of Administration (Vaccine) | Route of Administration (AP1903) | N |
|---|---|---|---|---|---|---|---|---|---|
| 7 | DCs + Ad-iMyD88.CD40 + AP1903 | 1.5e6 cells 5 mg/kg (AP1903) | 20K wGJ | | 100 nM | | SC | IP | 6 |
| 8 | DCs + Ad-iMyD88.CD40 | 1.5e6 cells | 20K wGJ | | N/A | | SC | N/A | 6 |

Figure 35:
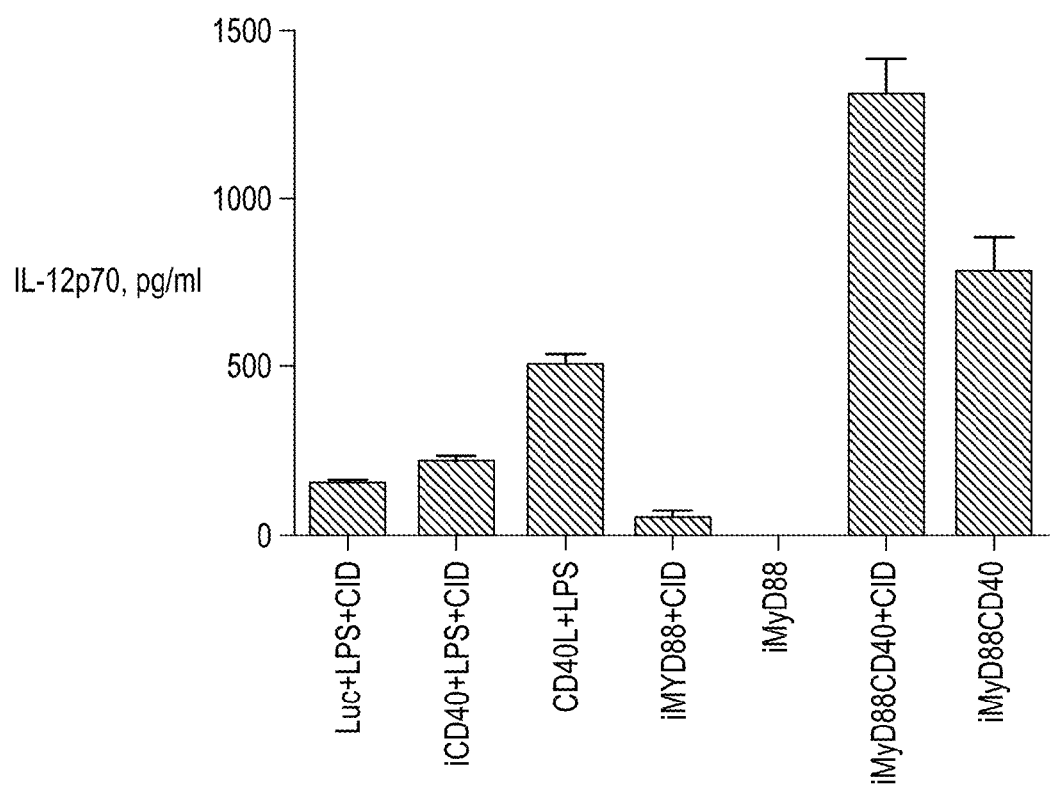
FIG. 35 is a bar graph depicting the IL-12p70 levels in transduced dendritic cells prior to vaccination.
Figure 36A:
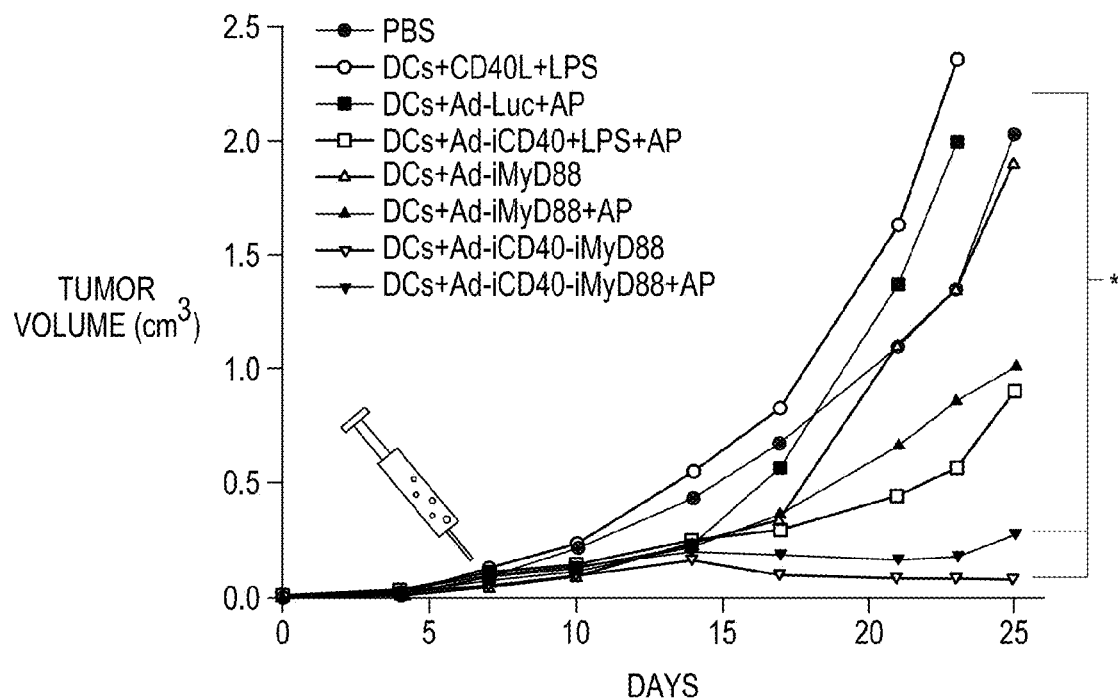
FIG. 36A is a graph of EG.7-OVA tumor growth inhibition in mice vaccinated with transduced dendritic cells.
Figure 36B:
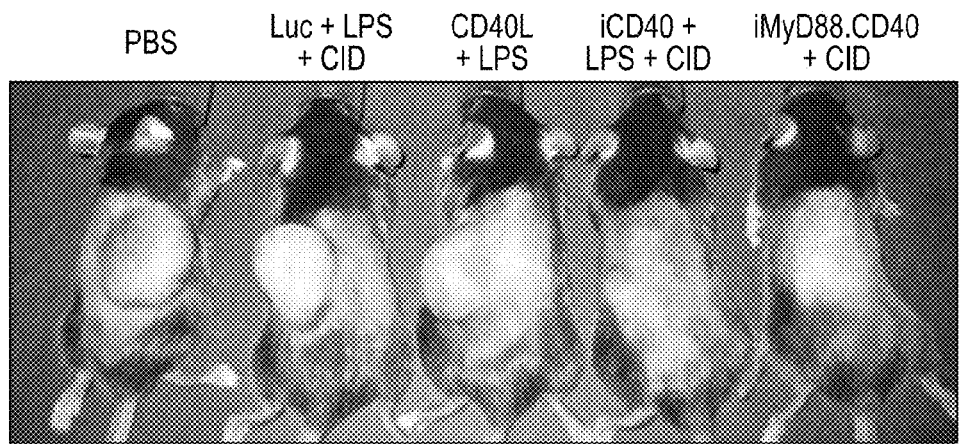
FIG. 36B presents photos of representative vaccinated mice.
Figure 36C:
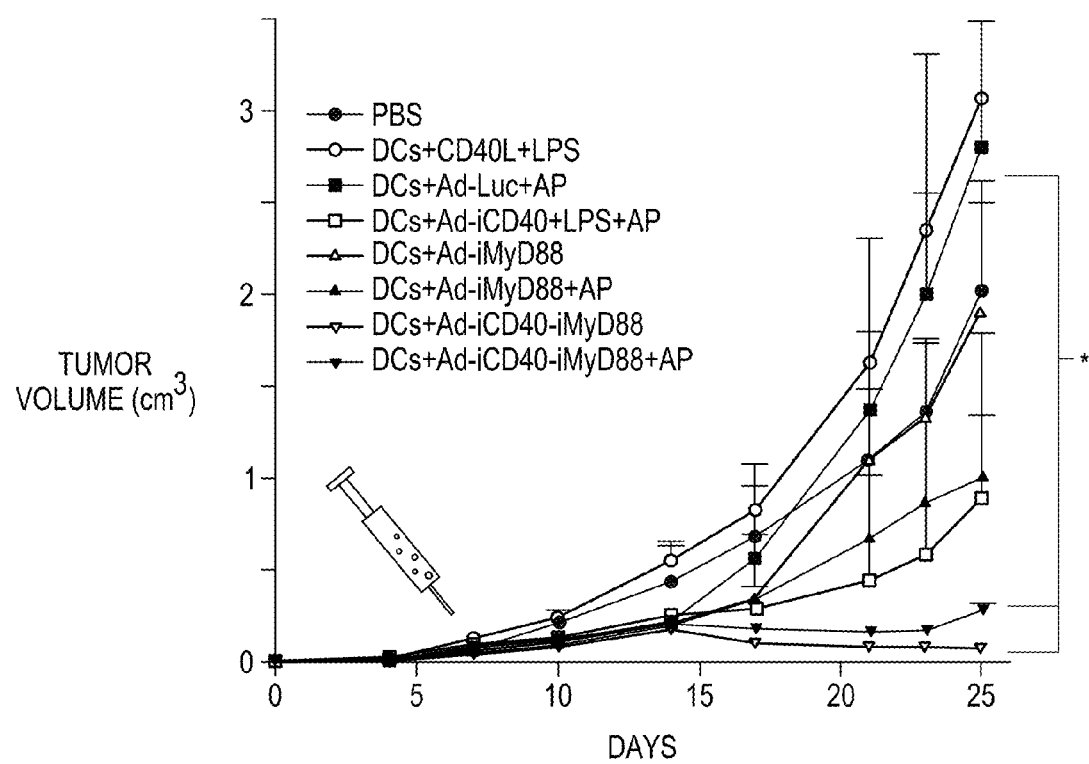
FIG. 36C is the graph of 36A, including error bars.

Prior to vaccination of the tumor-inoculated mice, the IL-12p70 levels of the transduced dendritic cells were measured in vitro. The IL-12p70 levels are presented in FIG. 35. FIG. 36 shows a chart of tumor growth inhibition observed in the transduced mice. Inoculation of the MyD88 transduced and AP1903 treated dendritic cells resulted in a cure rate of 1/6, while inoculation of the MyD88-CD40 transduced dendritic cells without AP1903 resulted in a cure rate of 4/6, indicating a potential dimerizer-independent effect. The asterix indicates a comparison of Luc+LPS+AP and iCD40MyD88+LPS+/−AP1903. FIG. 36 also provides photographs of representative vaccinated mice.

Figure 37B:
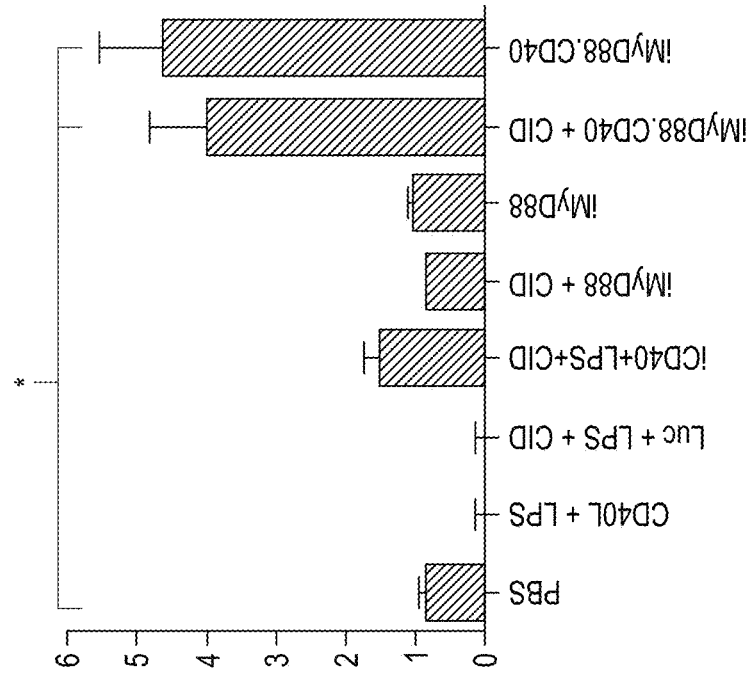
FIG. 37B is a bar graph, showing the enhanced frequency of Ag-specific CD8+ T cells induced by transduced dendritic cells. Figure discloses 'SIINFEKL' as SEQ ID NO: 26.
Figure 37A:
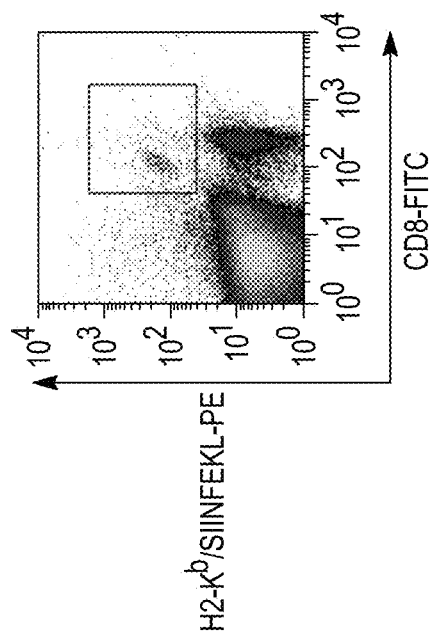
FIG. 37A is a scatter plot.

FIG. 37 presents an analysis of the enhanced frequency of Ag-Specific CD8+ T cell induction in mice treated with iMyD88-CD40 transduced dendritic cells. Peripheral bone marrow cells from treated mice were harvested ten days after vaccination on day 7. The PBMCs were stained with anti-mCD8-FITC and H2-$K^b$-SIINFEKL (SEQ ID NO: 26)-tetramer-PE and analyzed by flow cytometry.

Figure 38:
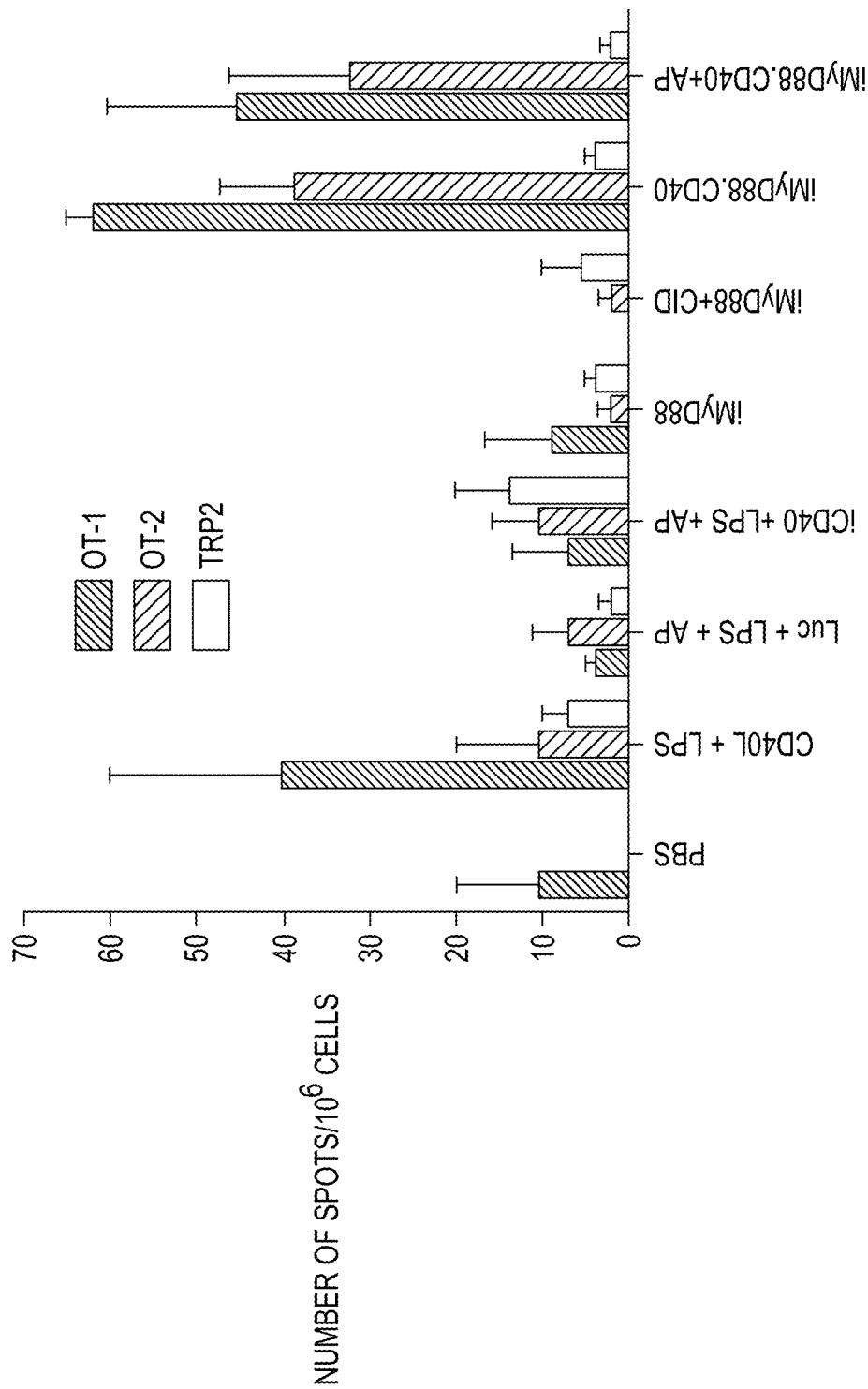
FIG. 38 is a bar graph showing the enhanced frequency of Ag-Specific IFN gamma+ CD8+ T cells and CD4+ $T_H1$ cells induced by transduced dendritic cells.

FIG. 38 presents the enhanced frequency of Ag-specific CD8+ T cell and CD4+ $T_H1$ cells induced in mice after treatment iMyD88-CD40-transduced dendritic cells. Three mice of all experimental groups were sacrificed 18 days after the vaccination. Splenocytes of three mice per group were "pooled" together and analyzed by IFN-gamma ELISPOT assay. Millipore MultiScreen-HA plates were coated with 10 micrograms/ml anti-mouse IFN-gamma AN18 antibody (Mabtech AB, Inc., Nacka, Sweden). Splenocytes were added and cultured for 20 hours at 37 degrees C. in 5% $CO_2$ in complete ELISpot medium (RPMI, 10% FBS, penicillin, streptomycin). Splenocytes were incubated with 2 micrograms/ml OT-1 (SIINFEKL (SEQ ID NO: 26)), OT-2 (ISQAVHAAHAEINEAGR (SEQ ID NO: 52)) or TRP-2 peptide (control non-targeted peptide). After washes, a second biotinylated monoclonal antibody to mouse IFN-gamma (R4-6A2, Mabtech AB) was applied to the wells at a concentration of 1 microgram/ml, followed by incubation with streptavidin-alkaline phosphatase complexes (Vector Laboratories, Ltd., Burlingame, Calif.). Plates were then developed with the alkaline phosphatase substrate, 3-amino-9 ethylcarbazole (Sigma-Aldrich, Inc., St. Louis, Mo.). The numbers of spots in the wells were scored by ZellNet Consulting, Inc. with an automated ELISPOT reader system (Carl Zeiss, Inc, Thornwood N.Y.).

Figure 39:
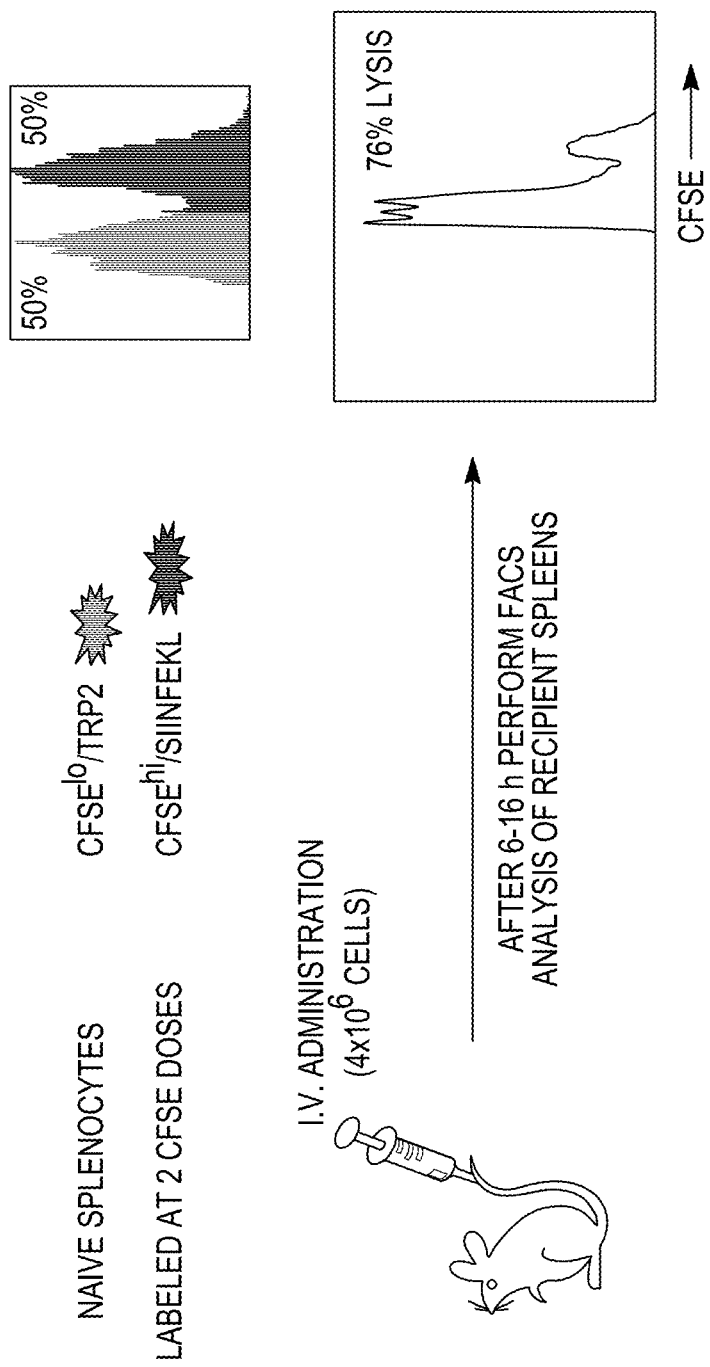
FIG. 39 presents a schematic and the results of an in vivo cytotoxic lymphocyte assay. Figure discloses 'SIINFEKL' as SEQ ID NO: 26.
Figure 40:
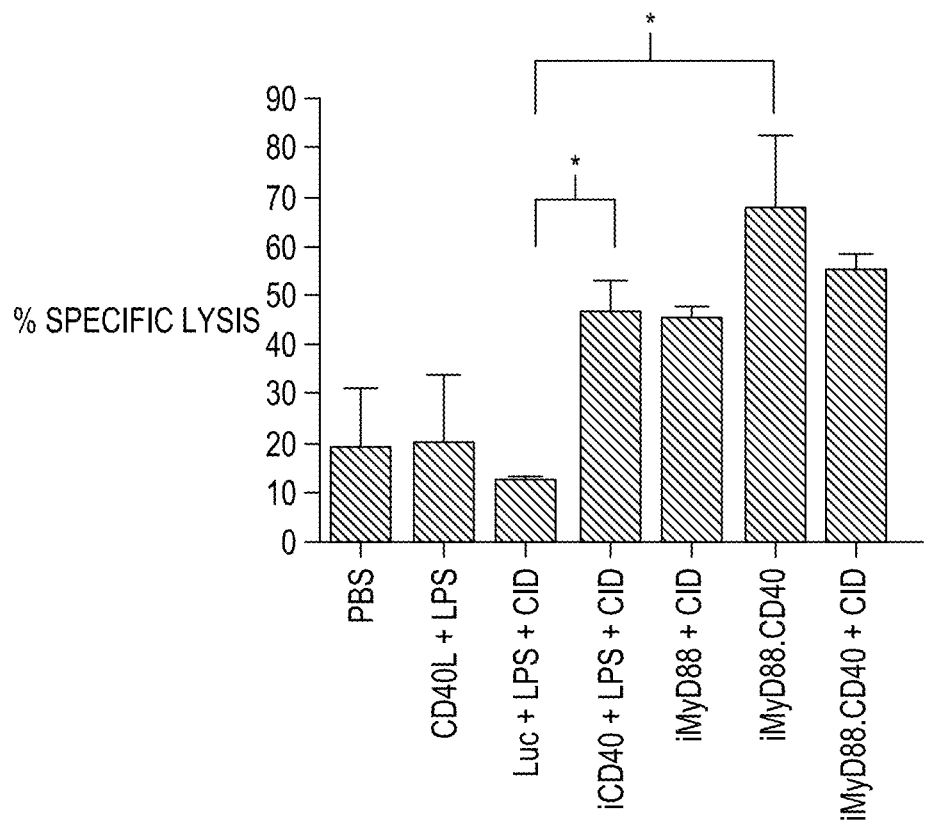
FIG. 40 is a bar graph summarizing the data from an enhanced in vivo CTL activity induced by dendritic cells.

FIG. 39 presents a schematic and the results of an in vivo cytotoxic lymphocyte assay. Eighteen days after DC vaccinations an in vivo CTL assay was performed. Syngeneic naive splenocytes were used as in vivo target cells. They were labeled by incubation for 10 minutes at 37 degrees C. with either 6 micromolar CFSE ($CFSE^{hi}$ cells) or 0.6 micromolar CFSE in CTL medium ($CFSE^{lo}$ cells). $CFSE^{lo}$ cells were pulsed with OT-1 SIINFEKL peptide (SEQ ID NO: 26), and $CFSE^{lo}$ cells were incubated with control TRP2 peptide. A mixture of $4 \times 10^6$ $CFSE^{hi}$ plus $4 \times 10^6$ $CFSE^{lo}$ cells was injected intravenously through the tail vein. After 16 hours of in vivo incubation, splenocytes were collected and single-cell suspensions are analyzed for detection and quantification of CFSE-labeled cells. FIG. 40 is a chart presenting the enhanced CTL activity induced by iMyD88-CD40-transduced dendritic cells in the inoculated mice. FIG. 41 shows the raw CTL histograms for select samples, indicating the enhanced in vivo CTL activity induced by the iMyD88-CD40 transduced dendritic cells.

Figure 42:
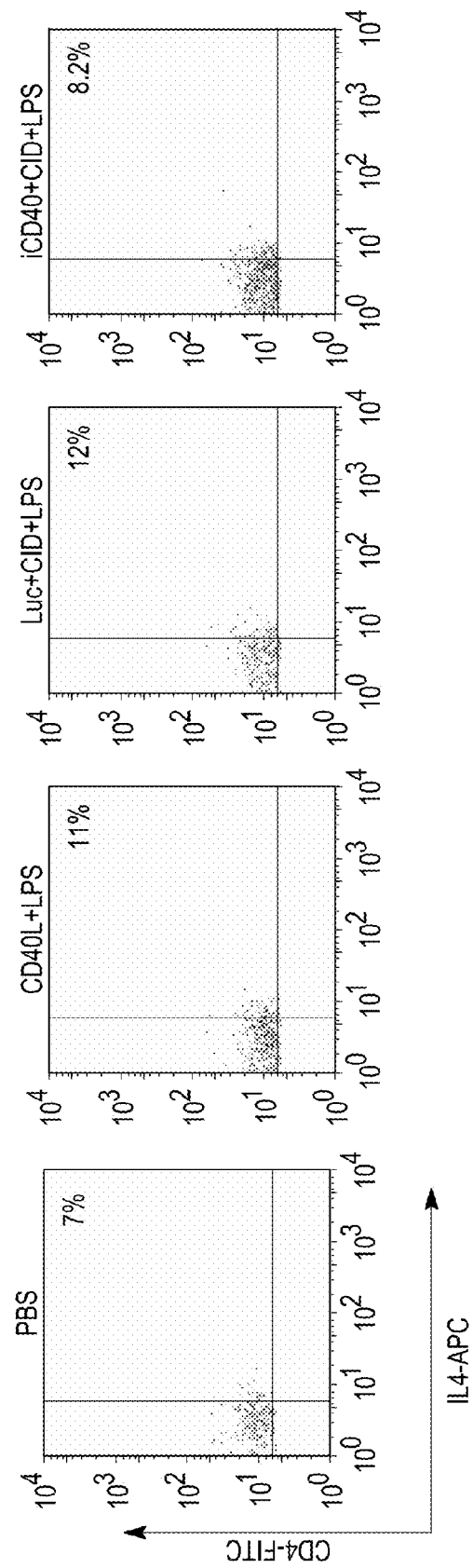
FIG. 42 presents the results of intracellular staining for IL-4 producing $T_H2$ cells in mice inoculated by transduced dendritic cells.
Figure 42:
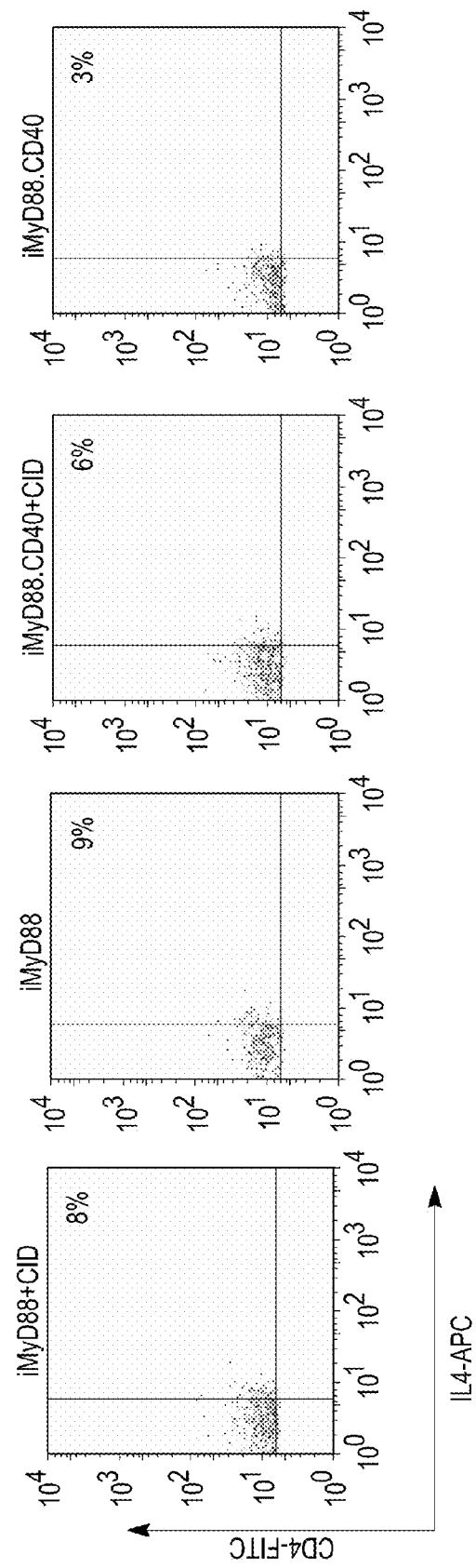

FIG. 42 presents the results of intracellular staining for IL-4 producing $T_H2$ cells in the mice vaccinated with the transduced cells. Splenocytes of mice (pooled cells from three mice) were reconstituted with 2 micrograms/ml of OT-2 peptide. Cells were incubated for 6 hours with 10 micrograms/ml of brefeldin A to suppress secretion. Then cells were fixed and permealized and analyzed by intracellular staining with anti-mIL-4-APC and anti-mCD4-FITC.

Figure 43A:
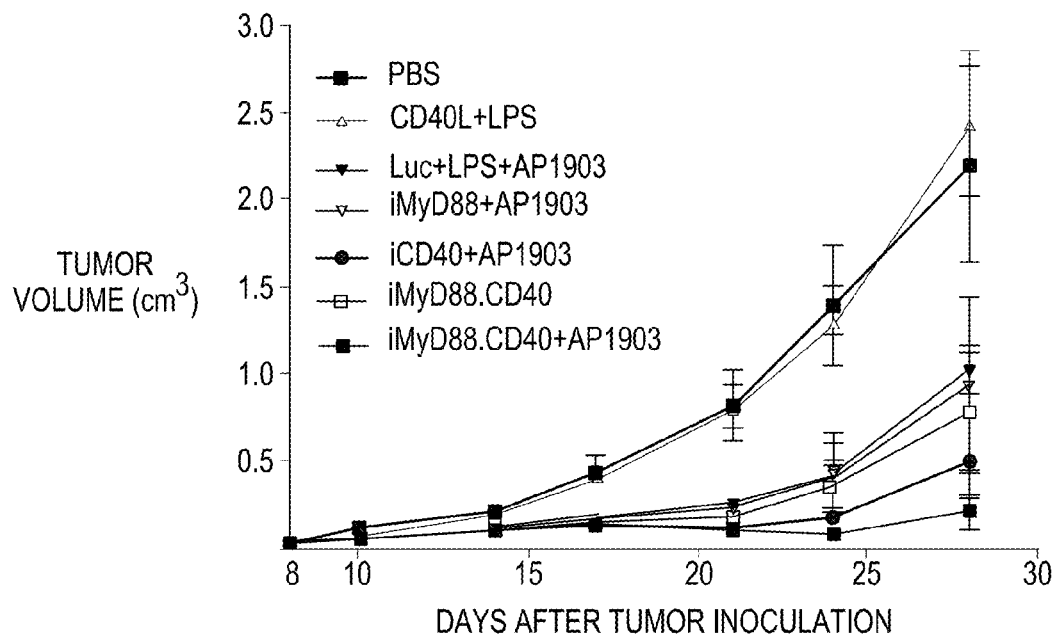
FIG. 43A is a line graph of tumor volume.
Figure 43B:
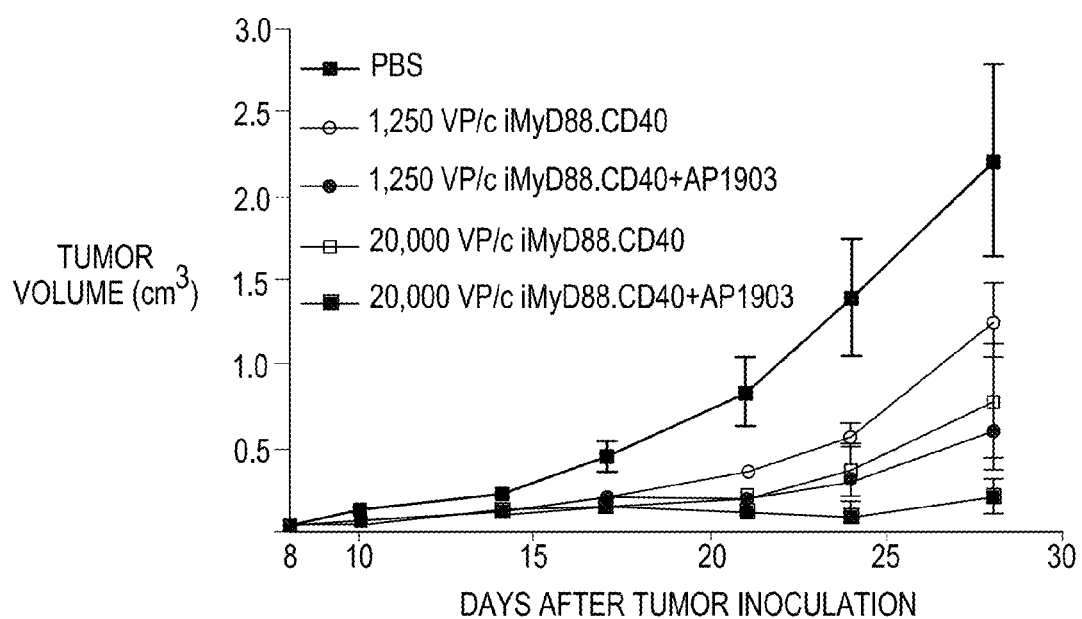
FIG. 43B is a line graph of tumor volume.
Figure 43C:
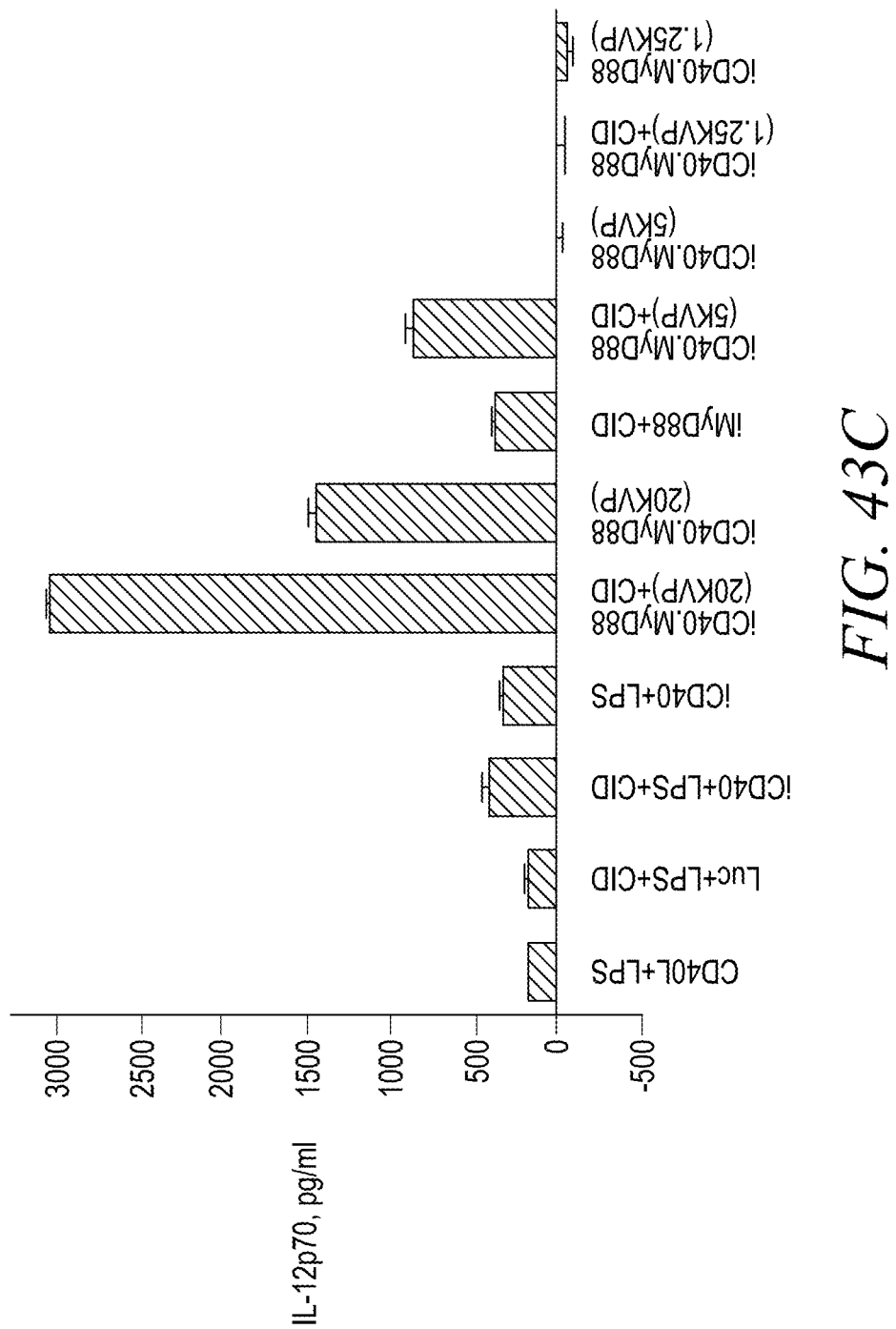
FIG. 43C is a bar graph of IL-12p70 concentration.

The adenoviral vector comprising the iCD40-MyD88 sequence was again evaluated for its ability to inhibit tumor growth in a mouse model. In the first experiment, drug-dependent tumor growth inhibition was measured after inoculation with dendritic cells modified with the inducible CD40-truncated MyD88 vector (Ad-iCD40.MyD88). Bone marrow-derived dendritic cells from C57BL/6 mice were pulsed with 10 micrograms/ml of ovalbumin and transduced with 20,000 viral particles/cell (VP/c) of the adenovirus constructs Ad5-iCD40.MyD88, Ad5-iMyD88 or Ad5-Luc (control). Cells were activated with either 2 micrograms/ml CD40L, 200 ng/ml LPS, or 50 nM AP1903 dimerizer drug. $5 \times 10^5$ E.G7-OVA thymoma cells were inoculated into the backs of C57BL/6 mice (N=6/group). When tumors reached ~5 mm in diameter (day 8 after inoculation), mice were treated with subcutaneous injections of $2 \times 10^6$ BMDCs. The next day, after cellular vaccinations, mice were treated with intraperitoneal injections of 5 mg/kg AP1903. Tumor growth was monitored twice weekly. The results are shown in FIG. 43A. In another set of experiments, E.G7-OVA tumors were established as described above. Mice (N=6/group) were treated with $2 \times 10^6$ BMDCs (ovalbumin pulsed) and transduced with either 20,000 or 1,250 VP/c of Ad5-iCD40.MyD88. BMDCs of AP1903 groups were treated in vitro with 50 nM AP1903. The next day, after cellular vaccinations, mice of AP1903 groups were treated by intraperitoneal injection with 5 mg/kg AP1903. The results are shown in FIG. 43B. FIG. 43C depicts relative IL-12p70 levels produced following overnight culture of the various vaccine cells prior to cryopreservation. IL-12p70 was assayed by ELISA assay.

Figure 44A:
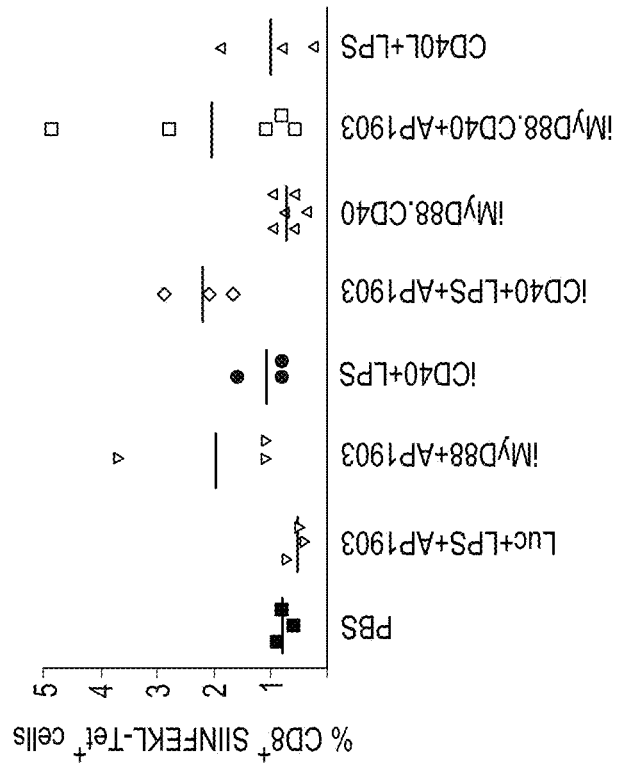
FIGS. 44AA and 44AB are scatter plots, FIGS. 44BA and 44BB provide graphs of CFSE FITC-A, FIG. 44BC is a bar chart of percent specific lysis.
Figure 44A:
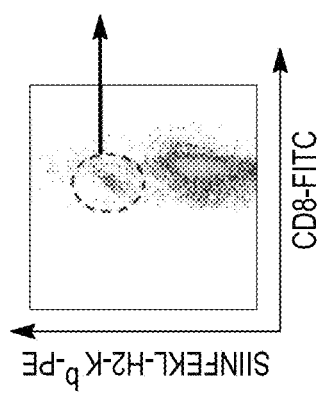
Figure 44B:
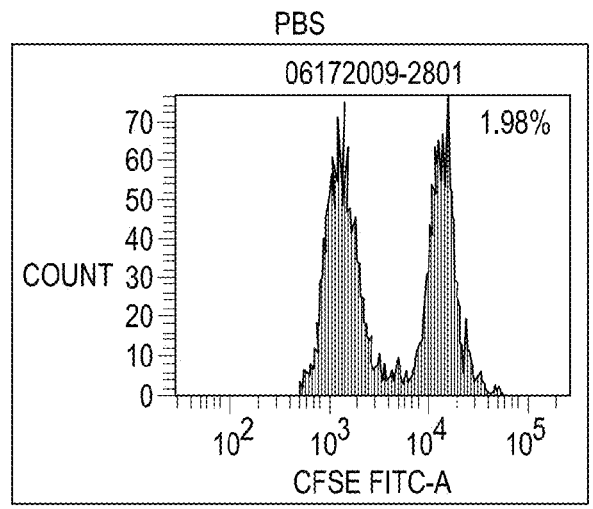
FIG. 44 presents a tumor specific T cell assay in mice treated with Ad5-iCD40.MyD88 transduced cells.
FIGS. 44C and 44D are bar charts.
Figure 44B:
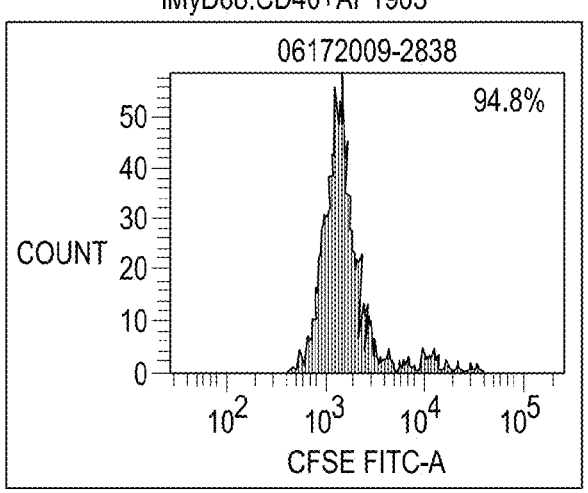
Figure 44B:
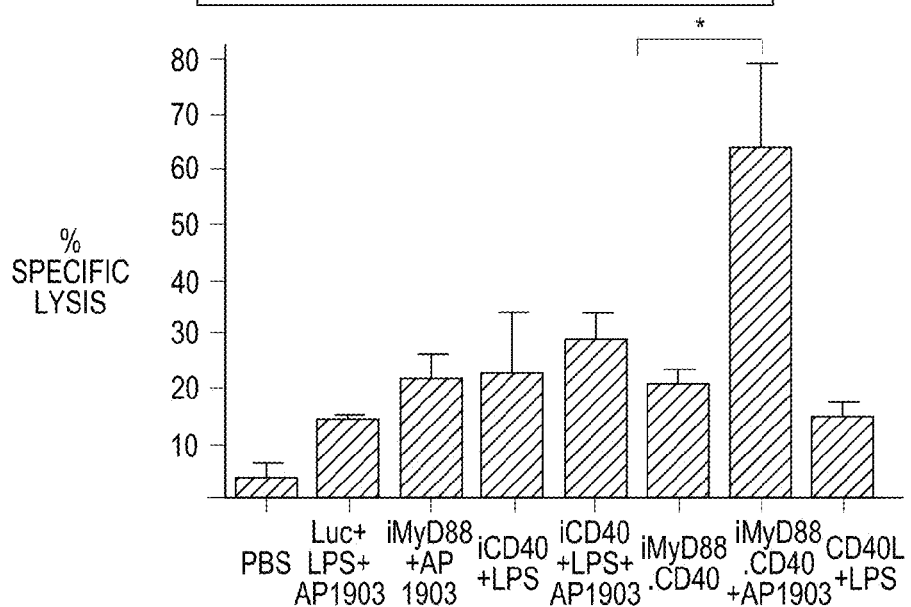
Figure 44C:
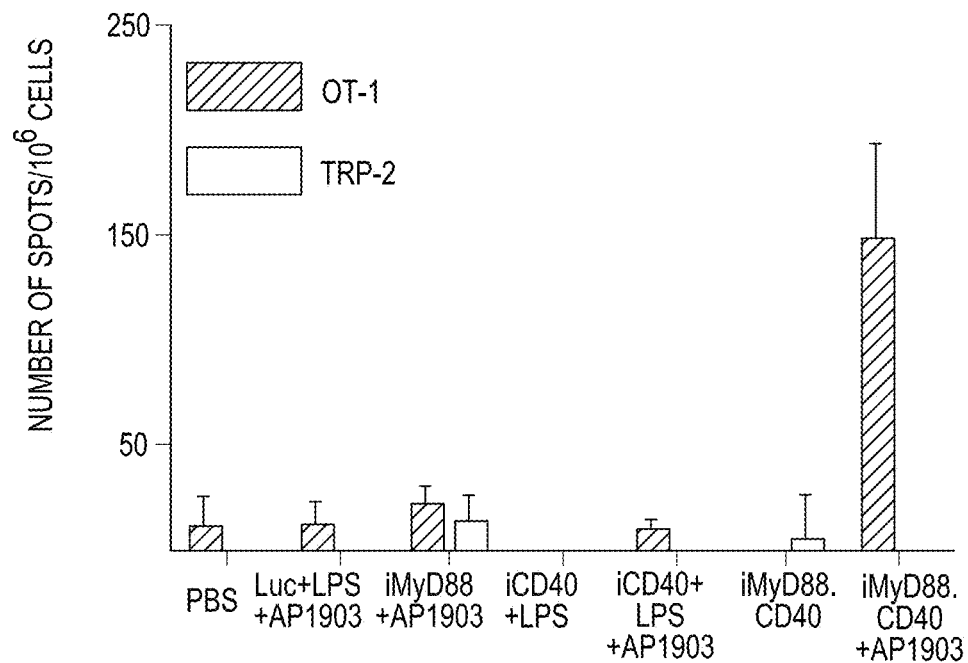
Figure 44D:
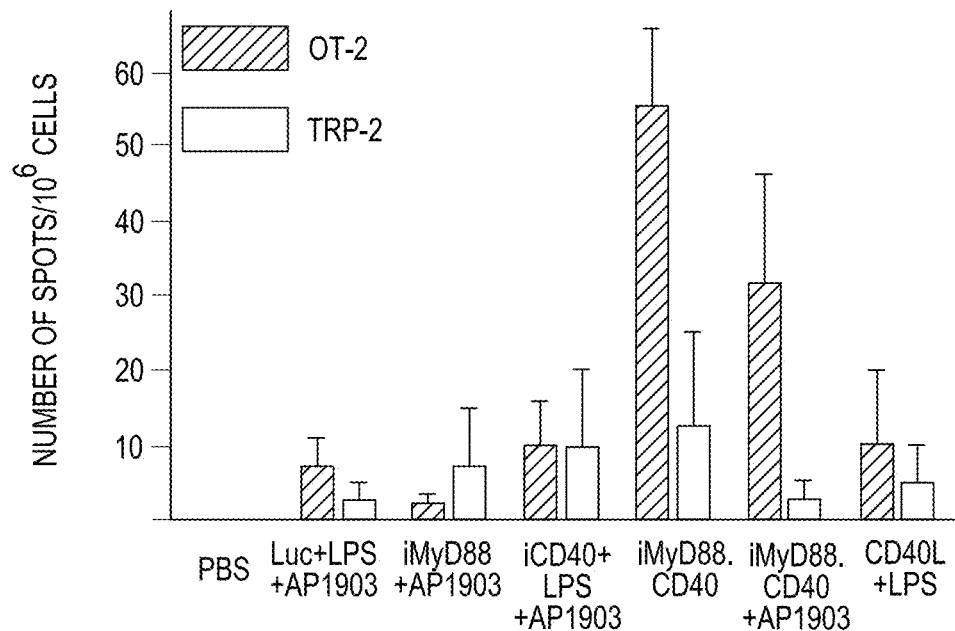

Blood from mice immunized with the modified bone marrow dendritic cells was analyzed for the frequency and function of tumor specific T cells using tetramer staining. FIG. 44A shows the results of an experiment in which mice (N=3-5) were immunized subcutaneously with BMDCs pulsed with ovalbumin and activated as described in FIG. 43. One week after the vaccination, peripheral blood mononuclear cells (PBMCs) were stained with anti-mCD8-FITC and SIIN-FEKL (SEQ ID NO: 26)-H2-K$^b$-PE and analyzed by flow cytometry. FIG. 44B shows the results of an in vivo CTL assay that was performed in mice vaccinated with BMDCs as described above. Two weeks after the BMDC immunization, splenocytes from syngeneic C57BL/6 mice were pulsed with either TRP-2 control peptide, SVYDFFVWL (SEQ ID NO: 53), or target peptide, SIINFEKL target (SEQ ID NO: 26), and were used as in vivo targets. Half of the splenocytes were labeled with 6 micromolar CFSE (CFSE$^{hi}$ cells) or 0.6 micromolar CFSE (CFSE$^{lo}$ cells). CFSE$^{hi}$ cells were pulsed with OT-1 (SIINFEKL (SEQ ID NO: 26)) peptide and CFSE$^{lo}$ cells were incubated with control TRP-2 (SVYDFFVWL (SEQ ID NO: 53)) peptide. A mixture of 4×10$^6$ CFSE$^{hi}$ plus 4×10$^6$ CFSE$^{lo}$ cells was injected intravenously through the tail vein. The next day, splenocytes were collected and single-cell suspensions were analyzed for detection and quantification of CFSE-labeled cells. FIGS. 44C and 44D show the results of an IFN-gamma assay. Peripheral blood mononuclear cells (PBMCs) from E.G7-OVA-bearing mice treated as described in FIG. 43, were analyzed in IFN-gamma ELISpot assays with 1 microgram/ml of SIINFEKL peptide (SEQ ID NO: 26) (OT-1), ISQAVHAAHAEINEAGR (SEQ ID NO: 52) (OT-2) and TRP-2 (irrelevant H2-K$^b$-restricted) peptides. The number of IFN-gamma-producing lymphocytes was evaluated in triplicate wells. Cells from three mice per group were pooled and analyzed by IFN-gamma ELISpot in triplicate wells. The assays were performed twice.

Figure 45:
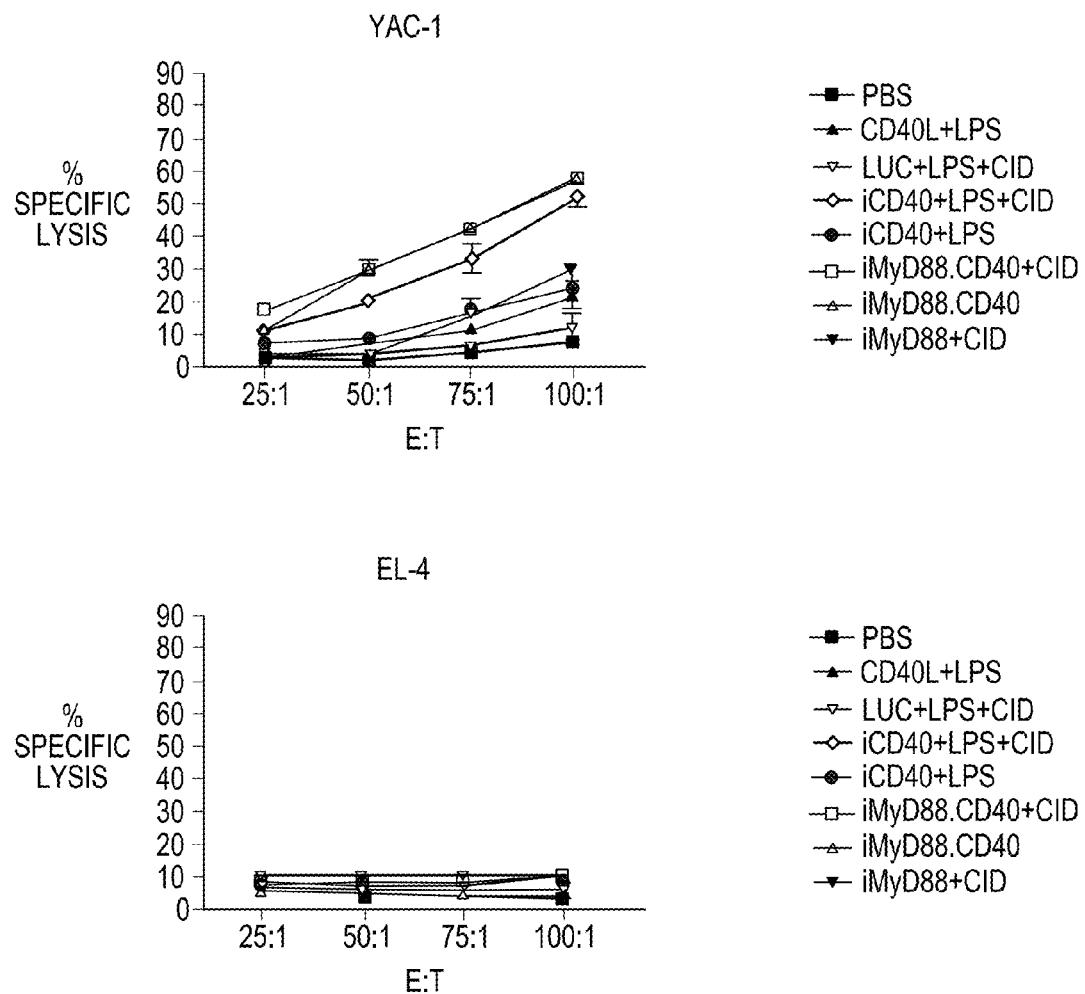
FIG. 45 presents the results of a natural killer cell assay using splenocytes from the treated mice as effectors.

FIG. 45 presents the results of a natural killer cell assay performed using the splenocytes from mice treated as indicated in this example. Splenocytes obtained from mice (3 per group) were used as effectors (E). Yac-1 cells were labeled with $^{51}$Cr and used as targets (T). The EL-4 cell line was used as an irrelevant control.

FIG. 46 presents the results of an assay for detection of antigen-specific cytotoxic lymphocytes. Splenocytes obtained from mice (3 per group) were used as effectors. EG.7-Ova cells were labeled with $^{51}$Cr and used as targets (T). The EL-4 cell line was used as an irrelevant control.

Figure 47:
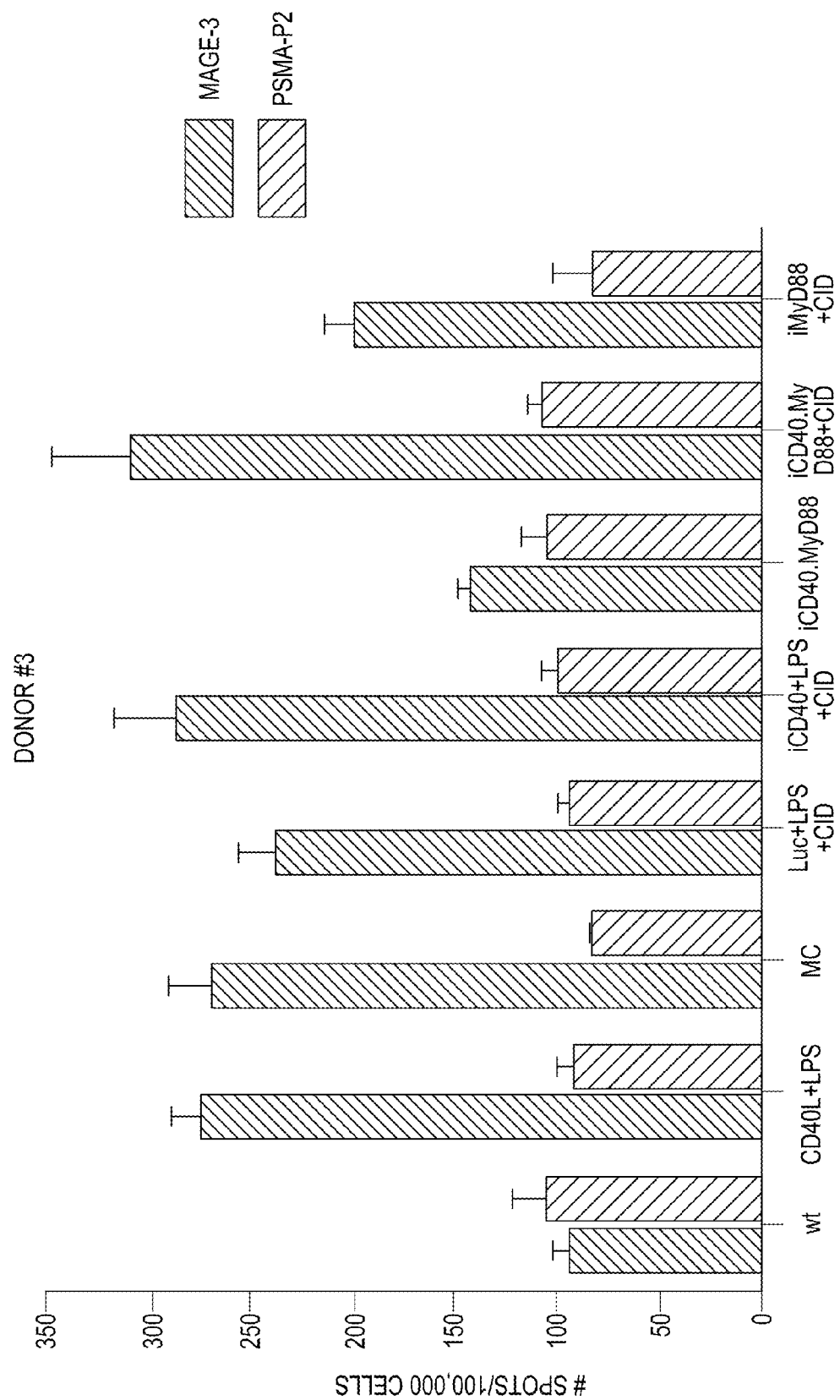
FIG. 47 presents the results of an IFN-gamma ELISPot assay using T cells co-cultured with dendritic cells transduced with the indicated vector.

FIG. 47 presents the results of the activation of human cells transduced with the inducible CD40-truncated MyD88 (iCD40.MyDD) adenovirus vector. Dendritic cells (day 5 of culture) from three different HLA-A2+ donors were purified by the plastic-adhesion method and transduced with 10,000 VP/cell of Ad5-iCD40.MyD88, Ad5-iMyD88 or Ad5-Luc. Cells were activated with 100 nM AP1903 or 0.5 micrograms/ml of CD40L and 250 ng/ml of LPS or standard maturation cocktail (MC), containing TNF-alpha, IL-1 beta, IL-6, and prostaglandin E2 (PGE$_2$). Autologous CD8+ T cells were purified by negative selection using microbeads and co-cultured with DCs pulsed with 10 micrograms/ml of HLA-A2-restricted FLWGPRALV (SEQ ID NO: 19) MAGE-3 peptide at 1:5 (DC:T) ratio for 7 days. Five days after the second of round of stimulation with DCs (on day 7) T cells were assayed in standard IFN-gamma ELISpot assay. Cells were pulsed with 1 micrograms/ml of MAGE-3 or irrelevant HLA-A2-restricted PSMA peptide (PSMA-P2). Experiments were performed in triplicate.

Figure 48:
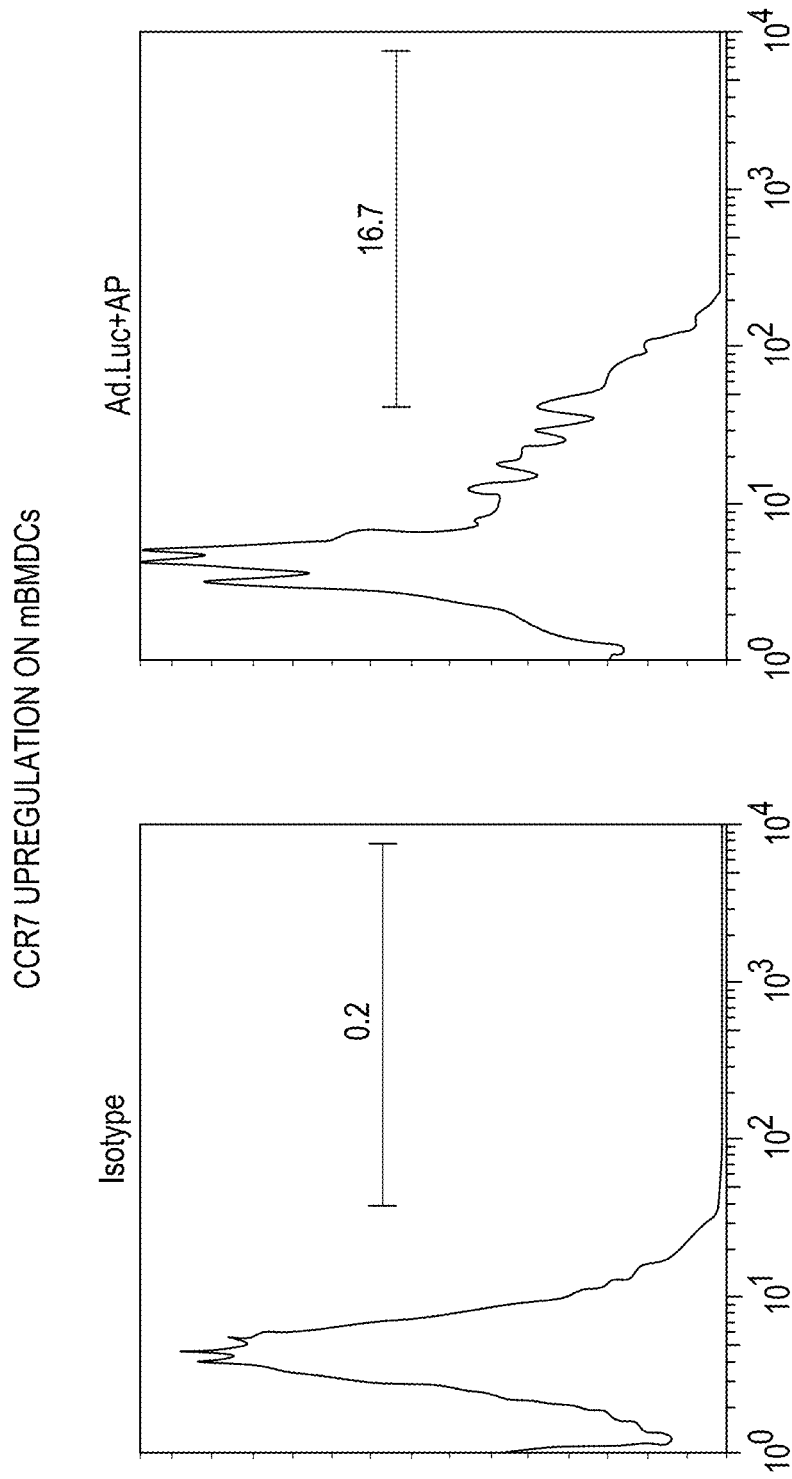
FIG. 48 presents the results of a CCR7 upregulation assay using dendritic cells transformed with the indicated vector, with or without LPS as an adjuvant.
Figure 48:
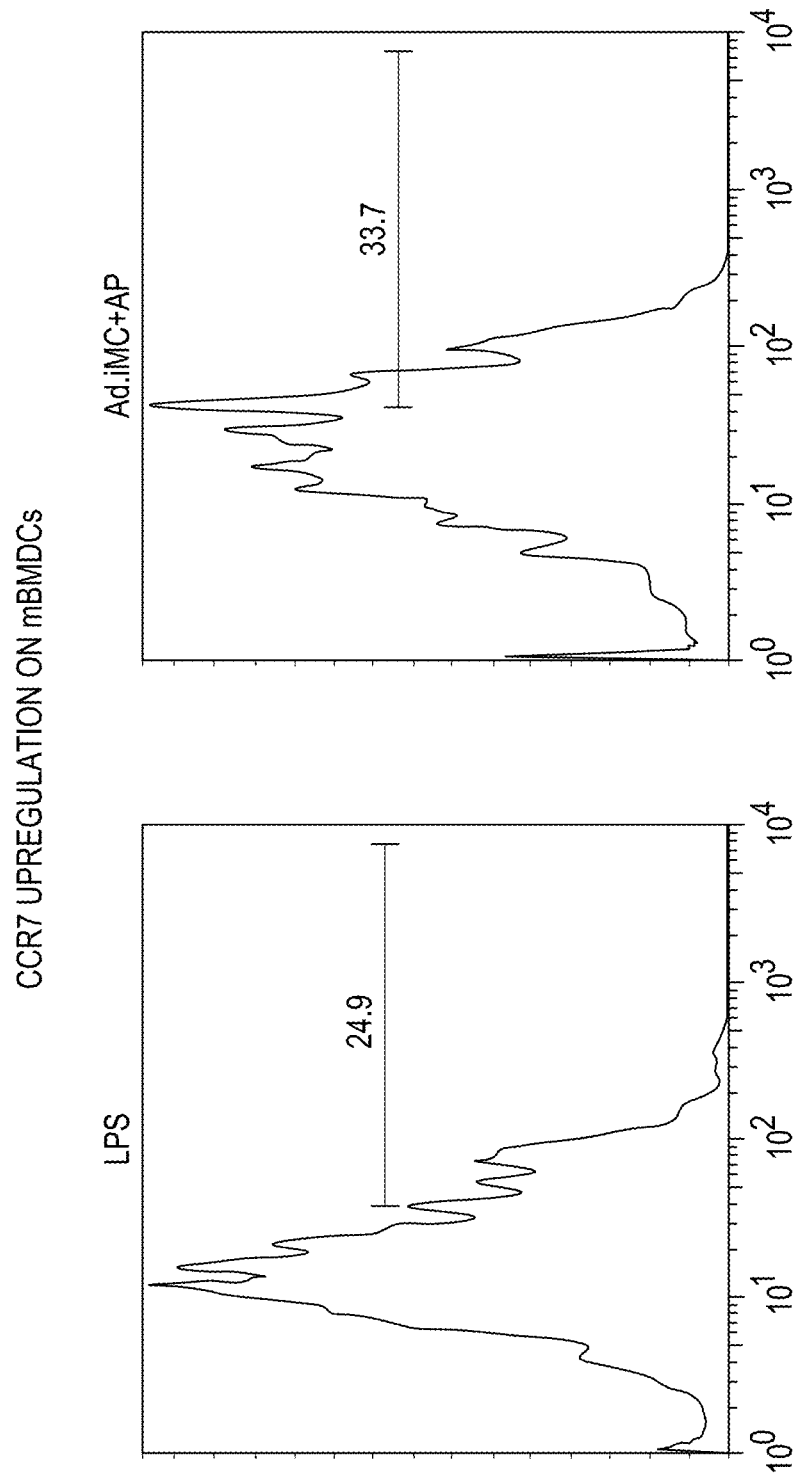
Figure 49:
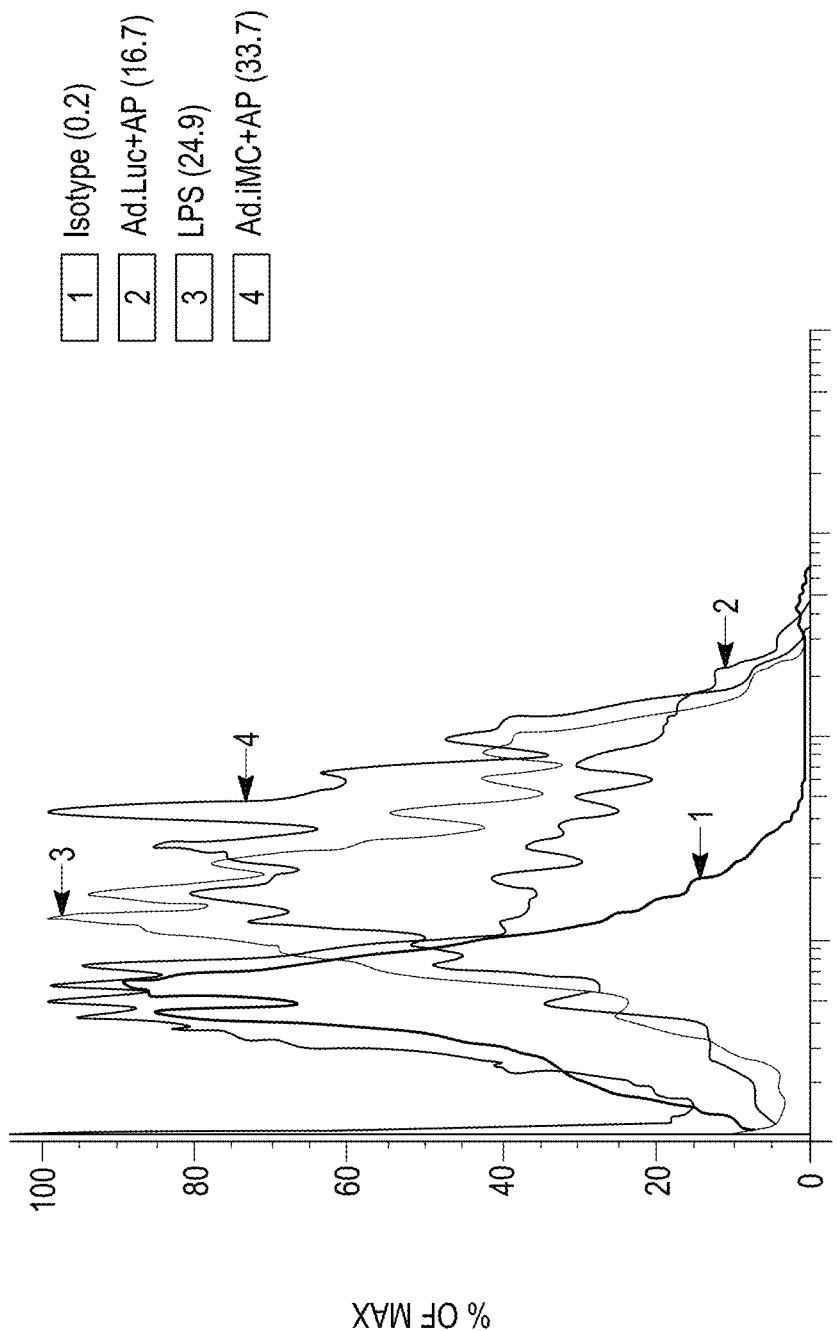
FIG. 49 presents the results of the CCR7 upregulation assay presented in FIG. 48, with the data from multiple animals included in one graph.

FIGS. 48 and 49 present the results of a cell migration assay. mBMDCs were transduced with 10,000 VP/cell of Ad5.Luciferase or Ad5.1MyD88.CD40 in the presence of Gene Jammer (Stratagene, San Diego, Calif.) and stimulated with 100 nM AP1903 (AP) or LPS (1 microgram/ml) for 48 hours. CCR7 expression was analyzed on the surface of CD11c+ dendritic cells by intracellular staining using a Per-CP.Cy5.5 conjugated antibody. FIG. 48 shows the results of the experiment, with each assay presented separately; FIG. 49 provides the results in the same graph.

Example 19

Examples of Particular Nucleic Acid and Amino Acid Sequences

```
(nucleic acid sequence encoding human CD40; Genbank accession no.
NM_001250; cytoplasmic region indicated in bold)
                                                                    SEQ ID NO: 1
  1  gccaaggctg gggcagggga gtcagcagag gcctcgctcg ggcgcccagt ggtcctgccg 61  cctggtctca cctcgctatg gttcgtctgc ctctgcagtg cgtcctctgg ggctgcttgc 121  tgaccgctgt ccatccagaa ccacccactg catgcagaga aaacagtac  ctaataaaca 181  gtcagtgctg ttctttgtgc cagccaggac agaaactggt gagtgactgc acagagttca 241  ctgaaacgga atgccttcct tgcggtgaaa gcgaattcct agacacctgg aacagagaga 301  cacactgcca ccagcacaaa tactgcgacc caacctagg gcttcgggtc cagcagaagg 361  gcacctcaga aacagacacc atctgcacct gtgaagaagg ctggcactgt acgagtgagg 421  cctgtgagag ctgtgtcctg caccgctcat gctcgcccgg ctttgggtc aagcagattg 481  ctacagggt ttctgatacc atctgcgagc cctgcccagt cggcttcttc tccaatgtgt 541  catctgcttt cgaaaaatgt cacccttgga caagctgtga gaccaaagac ctggttgtgc 601  aacaggcagg cacaaacaag actgatgttg tctgtggtcc ccaggatcgg ctgagagccc 661  tggtggtgat ccccatcatc ttcgggatcc tgtttgccat cctcttggtg ctggtcttta 721  tcaaaaaggt ggccaagaag ccaaccaata aggcccccca ccccaagcag gaacccccagg

781  agatcaattt tcccgacgat cttcctggct ccaacactgc tgctccagtg caggagactt

841  tacatggatg ccaaccggtc acccaggagg atggcaaaga gagtcgcatc tcagtgcagg
```

```
  901 agagacagtg aggctgcacc cacccaggag tgtggccacg tgggcaaaca ggcagttggc 961 cagagagcct ggtgctgctg ctgctgtggc gtgagggtga ggggctggca ctgactgggc 1021 atagctcccc gcttctgcct gcaccccTgc agtttgagac aggagacctg gcactggatg 1081 cagaaacagt tcaccttgaa gaacctctca cttcaccctg gagcccatcc agtctcccaa 1141 cttgtattaa agacagaggc agaagtttgg tggtggtggt gttggggtat ggtttagtaa 1201 tatccaccag accttccgat ccagcagttt ggtgcccaga gaggcatcat ggtggcttcc 1261 ctgcgcccag gaagccatat acacagatgc ccattgcagc attgtttgtg atagtgaaca 1321 actggaagct gcttaactgt ccatcagcag gagactggct aaataaaatt agaatatatt 1381 tatacaacag aatctcaaaa acactgttga gtaaggaaaa aaaggcatgc tgctgaatga 1441 tgggtatgga acttttttaaa aaagtacatg cttttatgta tgtatattgc ctatggatat 1501 atgtataaat acaatatgca tcatatattg atataacaag ggttctggaa gggtacacag 1561 aaaacccaca gctcgaagag tggtgacgtc tggggtgggg aagaagggtc tggggg
```

(amino acid sequence encoding human CD40; cytoplasmic region indicated in bold)

SEQ ID NO: 2

MVRLPLQCVLWGCLLTAVHPEPPTACREKQYLINSQCCSLCQPGQKLVSDCTEFTETECLPC
GESEFLDTWNRETHCHQHKYCDPNLGLRVQQKGTSETDTICTCEEGWHCTSEACESCVLHR
SCSPGFGVKQIATGVSDTICEPCPVGFFSNVSSAFEKCHPWTSCETKDLVVQQAGTNKTDVV
CGPQDRLRALVVIPIIFGILFAILLLVLVFI**KKVAKKPTNKAPHPKQEPQEINFPDDLPGSNTAAPV
QETLHGCQPVTQEDGKESRISVQERQ**

(nucleotide sequence encoding PSMA)

SEQ ID NO: 3

```
gcggatccgcatcatcatcatcatcacagctccggaatcgagggacgtggtaaatcctccaatgaagctactaacattactccaaag
cataatatgaaagcatttttggatgaattgaaagctgagaacatcaagaagttcttatataattttacacagataccacatttagcagga
acagaacaaaactttcagcaagcaaagcaaattcaatcccagtggaaagaatttggcctggattctgttgagctagcacattatgatgt
cctgttgtcctacccaaataagactcatcccaactacatctcaataattaatgaagatgaaaatgagatttttcaacacatcattatttgaa
ccacctcctccaggatatgaaaatgtttcggatattgtaccacctttcagtgcttctctcctcaaggaatgccagagggcgatctagtgta
tgttaactatgcacgaactgaagacttcttTaaattggaacgggacatgaaaatcaattgctctgggaaaattgtaattgccagatatgg
gaaagttttcagaggaaataaggttaaaaatgcccagctggcaggggccaaaggagtcattctctactccgaccctgctgactacttt
gctcctggggtgaagtcctatccagatggttggaatctTcctggaggtgttcagcgtgaaatatccTaaatctgaatggtgcagg
agaccctctcacaccaggttacccagcaaatgaatatgcTtataggcgTggaattgcagaggctgttggtcttccaagtattcctgttcat
ccaattggatactatgatgcacagaagctcctagaaaaaatgggtggctcagcaccaccagatagcagctggagaggaagtctca
aagtgccctacaatgttggacctggctttactggaaacttttctacacaaaaagtcaagatgcacatccactctaccaatgaagtgaca
agaattacaatgtgataggtactctcagaggagcagtgaacagacagatatgtcattctgggaggtcaccgggactcatgggtgt
ttggtggtattgaccctcagagtggagcagctgttgttcatgaaattgtgaggagcttggaacactgaaaaaggaaaggtggagacc
tagaagaacaattttgtttgcaagctgggatcagaagaattTggtcttcttggttctactgagtgggcagaggagaattcaagactcctt
caagagcgtggcgtggcttatattaatgctgactcatctatagaaggaaactacactctgagagttgattgtacaccgctgatgtacag
cttggtacacaaccTaaacaaaagagctgaaaagccctgatgaaggcctttgaaggcaaatctcttTatgaaagtTggactaaaaaaag
tccttcccccagagttcagtggcatgcccaggataagcaaattgggactctggaaatgatttTgaggtgttcttccaacgactTggaattgctt
caggcagagcacggTatactaaaaattgggaaacaaacaaattcagcggctatccactgtatcacagtgtctatgaaacatatgagt
tggtggaaagttttatgatccaatgttTaaatatcacctcactgTggcccaggttcgaggagggatggtgtttgagctagccaattccat
agtgctccctttTgattgtcgagatTatgctgtagttttTaagaaagTatgctgacaaatctacagtattTctatgaaacatccacaggaaat
gaagacatacagtgtatcatttgattcacttttTctgcagtaaagaattTtacagaaattgcttccaagttcagtgagagactccaggactt
tgacaaaagcaagcatgtcatctatgctccaagcagccacaacaagtatgcagggagtcattcccaggaattTatgatgctctgtTtg
atattgaaagcaaagtggacccttccaaggcctggggagaagtgaagagacagatttatgttgcagccttcacagtgcaggcagct
gcagagactttgagtgaagtagcctaagcggccgcatagca
```

(PSMA amino acid sequence encoded by SEQ ID NO: 3)

SEQ ID NO: 4

MWNLLHETDSAVATARRPRWLCAGALVLAGGFFLLGFLFGWFIKSSNEATNITPKHNMKAFLD
ELKAENIKKFLYNFTQIPHLAGTEQNFQLAKQIQSQWKEFGLDSVELAHYDVLLSYPNKTHPNYI
SIINEDGNEIFNTSLFEPPPPGYENVSDIVPPFSAFSPQGMPEGDLVYVNYARTEDFFKLERDM
KINCSGKIVIARYGKVFRGNKVKNAQLAGAKGVILYSDPADYFAPGVKSYPDGWNLPGGGVQR
GNILNLNGAGDPLTPGYPANEYAYRRGIAEAVGLPSIPVHPIGYYDAQKLLEKMGGSAPPDSS
WRGSLKVPYNVGPGFTGNFSTQKVKMHIHSTNEVTRIYNVIGTLRGAVEPDRYVILGGHRDSW
VFGGIDPQSGAAVVHEIVRSFGTLKKEGWRPRRTILFASWDAEEFGLLGSTEWAEENSRLLQE
RGVAYINADSSIEGNYTLRVDCTPLMYSLVHNLTKELKSPDEGFEGKSLYESWTKKSPSPEFS
GMPRISKLGSGNDFEVFFQRLGIASGRARYTKNWETNKFSGYPLYHSVYETYELVEKFYDPMF
KYHLTVAQVRGGMVFELANSIVLPFDCRDYAVVLRKYADKIYSISMKHPQEMKTYSVSFDSLFS
AVKNFTEIASKFSERLQDFDKSKHVIYAPSSHNKYAGESFPGIYDALFDIESKVDPSKAWGEVK
RQIYVAAFTVQAAAETLSEVA (nucleotide sequence of MyD88L with SalI linkers)

SEQ ID NO: 5

```
gtcgacatggctgcaggaggtcccggcgcggggtctgcggccccggtctcctccacatcctcccttcccctggctgctctcaacatg
cgagtgcggcgccgcctgtctctgttcttgaacgtgcggacacaggtggcggccgactggaccgcgctggcggaggagatggact
ttgagtacttggagatccggcaactggagacacaagcggaccccactggcaggctgctgacgcctgcagggacgccctggc
gcctctgtaggccgactgctcgagctgcttaccaagctgggccgcgacgacgtgctgctggagctgggaccagcattgaggagg
``` attgccaaaagtatatcttgaagcagcagcaggaggaggctgagaagcctttacaggtggccgctgtagacagcagtgtcccacg
gacagcagagctggcgggcatcaccacacttgatgaccccctggggcatatgcctgagcgtttcgatgccttcatctgctattgcccc
agcgacatcgtcgac

(amino acid sequence of MYD88L)

SEQ ID NO: 6

MAAGGPGAGSAAPVSSTSSLPLAALNMRVRRRLSLFLNVRTQVAADWTALAEEEMDFEYLEIR
QLETQADPTGRLLDAWQGRPGASVGRLLELLTKLGRDDVLLELGPSIEEDCQKYILK
QQQEEAEKPLQVAAVDSSVPRTAELAGITTLDDPLGHMPERFDAFICYCPSDI (sequence of Fv'Fvls with XhoI/SalI linkers, (wobbled codons lowercase in Fv'))

SEQ ID NO: 7 ctcgagGGcGTcCAaGTcGAaACcATtagtCCcGGcGAtGGcaGaACaTTtCCtAAaaGgGGaCAaAC
aTGtGTcGTcCAtTAtACaGGcATGtTgGAgGAcGGcAAaAAgGTgGAcagtagtaGaGAtcGcAA
tAAaCCtTTcAAaTTcATGtTgGGaAAaCAaGAaGTcATtaGgGGaTGGGAgGAgGGcGTgGCt
CAaATGtccGTcGGcCAacGcGCtAAgCTcACcATcagcCCcGAcTAcGCaTAcGGcGCtACcG
GaCAtCCcGGaATtATtCCcCCtCAcGCtACctTgGTgTTtGAcGTcGAaCTgtTgAAgCTcGAa**gt
cgag**ggagtgcaggtggaaaccatctccccaggagacgggcgcacctttccccaagcgcggccagacctgcgtggtgcac
tacaccgggatgcttgaagatggaaagaaagttgattcctcccgggacagaaacaagcccttTaagtttatgctaggcaagc
aggaggtgatccgaggctgggaagaagggggttgcccagatgagtgtgggtcagagagccaaactgactatatctccagatt
atgcctatggtgccactgggcacccaggcatcatcccaccacatgccactctcgtcttcgatgtggagcttctaaaactggaatc
tggcggtggatccggagtcgag

(FV'FVLS peptide sequence)

SEQ ID NO: 8

GlyValGlnValGluThrIleSerProGlyAspGlyArgThrPheProLysArgGlyGlnThrCysValValHisTyrThrGly
MetLeuGluAspGlyLysLysValAspSerSerArgAspArgAsnLysProPheLysPheMetLeuGlyLysGlnGlu
ValIleArgGlyTrpGluGluGlyValAlaGlnMetSerValGlyGlnArgAlaLysLeuThrIleSerProAspTyrAlaTyr
GlyAlaThrGlyHisProGlyIleIleProProHisAlaThrLeuValPheAspValGluLeuLeuLysLeuGlu (ValGlu)

GlyValGlnValGluThrIleSerProGlyAspGlyArgThrPheProLysArgGlyGlnThrCysValValHisTyrThrGly
MetLeuGluAspGlyLysLysValAspSerSerArgAspArgAsnLysProPheLysPheMetLeuGlyLysGlnGlu
ValIleArgGlyTrpGluGluGlyValAlaGlnMetSerValGlyGlnArgAlaLysLeuThrIleSerProAspTyrAlaTyr
GlyAlaThrGlyHisProGlyIleIleProProHisAlaThrLeuValPheAspValGluLeuLeuLysLeuGluSerGlyGly
GlySerGly (TRIF nucleotide sequence with XhoI/SalI linkers)

SEQ ID NO: 9 ctcgagatggcctgcacaggcccatcacttcctagcgccttcgacattctaggtgcagcaggccaggacaagctcttgtatctgaag
cacaaactgaagacccccacgcccaggctgccaggggcaggacctcctgcatgccatggttctcctgaagctgggccaggaaactg
aggccaggatctctctagaggcattgaaggccgatgcggtggcccggctggtggcccgccagtgggctggcgtggacagcaccga
ggacccagaggagccccagatgtgtcctgggctgtggcccgcttgtaccacctgctggctgaggagaagctgtgccccgcctcgct
gcgggacgtggcctaccaggaagccgtccgcaccctcagctccagggacgacaccggctggggggaacttcaggatgaggccc
gaaaccggtgtgggtgggacattgctgggatccagggagcatccggacgctccagtccaatctgggctgcctcccaccatcctcg
gctttgccctctgggaccaggagcctccacgccccattgacggtgtttcggactggagcaagggtgctccctgcgatccactggca
gccctgcctcctggccagcaacttggaaatcagccagtcccctaccatgcccttcctcagcctgcaccgcagcccacatgggccca
gcaagctctgtgacgaccccaggccagcnggtgcccgagcctgccggtggctgccaggagctgggagatgagctggcc
gccatcgggggagattgccagcccaccagagctgccaagcagcccacctcctgggctTccccgaagtggcccccagatgcaacctcc
actggcctccctgatacccccgcagctccagaaaccagcaccaactaccccagtggagtgcaccgaggggctgcaggccccccagt
ctctccccngcctattctggagccggtcaaaaaccctgctctgtcaaagaccgacgccactccaactttctgtagaagataccacc
tctccaaataccaagccgtgcccacctactcccaccaccccagaaacatcctcctcctcctcctcatctactcctccttgttc
agctcacctgacccccttcctcctgttccttcctcctggaatcatcatcggaacagaaattctataactttgtgatcctcacgccagg
gcagacgaacacatcgcctgcgggttcgggagaagctggaggcccttggcgtgcccgacggggccacctctgcgaggatttcc
aggtgccggggcgcggggagctgagctgcctgcaggacgccatagaccactcagctttcatcatcctacttctcacctccaacttcga
ctgtcgcctgagcctgcaccaggtgaaccaagccatgatgagcaacctcacgcgacaggggtcgccagactgtgtcatcccttcct
gcccctggagagctcccgccagctcagctccgacacggccagcctgctctccggggctggtgcggctggacgaacactccag
atcttcgccaggaaggtggccaacaccttcaagcccacaggcttcaggcccgaaaggccatgtggaggaaggaacaggacac
ccgagccctgcgggaacagagccaacacctggacggtgagcggatgcaggcggcggcactgaacgcagcctactcagcctacc
tccagagctacttgtcctaccaggcacagatggagcagctccaggtggcttttgggagccacatgtcatttgggactggggcgccctat
ggggctcgaatgcccttTggggccaggtgcccctgggagcccgcaccrttcccacttggccggggtgcccgcagcgccacc
cctgcacgcatggcaggctggcacccccaccgcctcccacagccagcagcctttcacagtcactgccttccccgcagtccc
cagccttccctacggcctcacccgcacccctcagagcccagggctgcaaccccctcattatccaccacgcacagatggtacagctg
gggctgaacaaccacatgtggaaccagagagggtcccaggcgcccgaggacaagacgcaggaggcagaagtcgac

(TRIF peptide sequence)

SEQ ID NO: 10

MetAlaCysThrGlyProSerLeuProSerAlaPheAspIleLeuGlyAlaAlaGlyGlnAspLysLeuLeuTyr
LeuLysHisLysLeuLysThrProArgProGlyCysGlnGlyGlnAspLeuLeuHisAlaMetValLeuLeuLys
LeuGlyGlnGluThrGluAlaArgIleSerLeuGluAlaLeuLysAlaAspAlaValAlaArgLeuValAlaArg
GlnTrpAlaGlyValAspSerThrGluAspProGluGluProProAspValSerTrpAlaValAlaArgLeuTyr
HisLeuLeuAlaGluGluLysLeuCysProAlaSerLeuArgAspValAlaTyrGlnGluAlaValArgThrLeu
SerSerArgAspAspHisArgLeuGlyGluLeuGlnAspGluAlaArgAsnArgCysGlyTrpAspIleAla
GlyAspProGlySerIleArgThrLeuGlnSerAsnLeuGlyCys (RIG-I nucleotide sequence (CARD domains underlined) with XhoI-SalI linkers:

SEQ ID NO: 11

Ctcgagaccaccgagcagc<u>gacgcagcctgcaagccttccaggattatatccggaagaccctggaccctacctacatcctgagct
acatggcccctggtttagggaggaagaggtgcagtatattcaggctgagaaaacaacaaggcccaatggaggctgccacact
ttttctcaagttcctgttggagctccaggaggaaggctggttccgtggctttttggatgccctagaccatgcaggttattctggactttatgaa
gccattgaaagtgggatttcaaaaaaattgaaaagtggaggagtata</u><u>agattactttttaaaacgtttacaaccagaatttaaaaccag
aattatcccaaccgatatcatttctgatctgtctgaatgtttaattaatcaggaatgtgaagaaattctacagatttgctctactaagggat</u>

-continued gatggcaggtgcagagaaattggtggaatgccttctcagatcagacaaggaaaactggcccaaaactttgaaacttgctttggagaa
agaaaggaacaagttcagtgaactgtggattgtagagaaaggtataaaagatgttgaaacagaagatcttgaggataagatggaa
acttctgacatacagattgtcgac

(RIG-1 peptide sequence (CARD domains underlined))

SEQ ID NO: 12

TTEQRRSLQAFQDYIRKTLDPTYILSYMAPWFREEEVQYIQAEKNNKGPMEAATLFLKFLLELQ
EEGWFRGFLDALDHAGYSGLYEAIESWDFKKIEKLEEYRLLLKRLQPEFKTRIIPTDIISDLSECLI
NQECEEILQICSTKGMMAGAEKLVECLLRSDKENWPKTLKLALEKERNKFSELWIVEKGIKDVE
TEDLEDKMETSDIQI (NOD2 nucleotide sequence (CARD domains underlined) with XhoI-SalI linkers

SEQ ID NO: 13

Ctcgagatgggggaagagggtggttcagcctctcacgatgaggaggaaagagcaagtgtcctcctcggacattctccgggttgtga
aatgtgctcgcaggaggcttttcaggcacagaggagccagctggtcgagctgctggtctcagggtccctggaaggcttcgagagtgt
cctggactggctgctgtcctgggaggtcctctcctgggaggactacgaggggcttccacctcctgggccagcctctctcccacttggcca
ggcgccttctggacaccgtctggaataagggtacttgggcctgtcagaagctcatcgcggctgcccaagaagcccaggccgacag
ccagtccccaagctgcatggctgctgggaccccccactcgctccaccccagcccgagacctgcagagtcaccggccagccattgtc
aggaggctccacagccatgtggagaacatgctggacctggcatgggagcggggtttcgtcagccagtatgaatgtgatgaaatcag
gttgccgatcttcacaccgtcccagagggcaagaagctgcttgatcttgccacggtgaaagcgaatggattggctgccttccttctac
aacatgttcaggaattaccagtcccattggccctgcctttggaagctgccacatgcaagaagtatatggccaagctgaggaccacgg
tgtctgctcagtctcgcttcctcagtacctatgatggagcagagacgctctgcctggaggacatatacacagagaatgtcctggaggtc
gtcgac

(NOD2 peptide sequence (CARD domains underlined))

SEQ ID NO: 14

MetGlyGluGluGlyGlySerAlaSerHisAspGluGluGluArgAlaSerValLeuLeuGlyHisSerProGlyCysGlu
MetCysSerGlnGluAlaPheGlnAlaGlnArgSerGlnLeuValGluLeuLeuValSerGlySerLeuGluGlyPheGlu
SerValLeuAspTrpLeuLeuSerTrpGluValLeuSerTrpGluAspTyrGluGlyPheHisLeuLeuGlyGlnProLeu
SerHisLeuAlaArgArgLeuLeuAspThrValTrpAsnLysGlyThrTrpAlaCysGlnLysLeuIleAlaAlaAlaGln
GluAlaGlnAlaAspSerGlnSerProLysLeuHisGlyCysTrpAspProHisSerLeuHisProAlaArgAspLeuGln
SerHisArgProAlaIleValArgArgLeuHisSerHisValGluAsnMetLeuAspLeuAlaTrpGluArgGlyPheVal
SerGlnTyrGluCysAspGluIleArgLeuProIlePheThrProSerGlnArgAlaArgArgLeuLeuAspLeuAlaThr
ValLysAlaAsnGlyLeuAlaAlaPheLeuLeuGlnHisValGlnGluLeuProValProLeuAlaLeuProLeuGluAla
AlaThrCysLysLysTyrMetAlaLysLeuArgThrThrValSerAlaGlnSerArgPheLeuSerThrTyrAspGlyAla
GluThrLeuCysLeuGluAspIleTyrThrGluAsnValLeuGluVal (MyD88 nucleotide sequence)

SEQ ID NO: 15 atggctgcaggaggtcccggcgcggggtctgcggccccggtctcctccacatcctcccttccccctggctgctctcaacatgcgagtgc
ggcgccgcctgtctctgttcttgaacgtgcggacacaggtggcggccgactggaccgcgctggcggaggagatggactttgagtact
tggagatccggcaactggagacacaagcggacccactggcaggctgctggacgcctggcagggacgccctggcgcctctgtag
gccgactgctcgagctgcttaccaagctgggccgcgacgacgtgctgctggagctgggacccagcattgaggaggattgccaaaa
gtatatcttgaagcagcagcaggaggaggctgagaagcctttacaggtggccgctgtagacagcagtgtcccacggacagcagag
ctggcgggcatcaccacacttgatgacccctggggcatatgcctgagcgtttcgatgccttcatctgctattgcccagcgacatcca
gtttgtgcaggagatgatccggcaactggaacagacaaactatcgactgaagttgtgtgtgtctgaccgcgatgtcctgcctggcacct
gtgtctggtctattgctagtgagctcatcgaaaagaggtgccgccggatggtggtggttgtctctgatgattacctgcagagcaaggaat
gtgacttccagaccaaatttgcactcagcctctctccaggtgcccatcagaagcgactgatccccatcaagtacaaggcaatgaaga
aagagttcccccagcatcctgaggttcatcactgtctgcgactacaccaaccctgcaccaaatcttggttctggactcgccttgccaag
gccttgtccctgccc (MyD88 peptide sequence)

SEQ ID NO: 16

M A A G G P G A G S A A P V S S T S S L P L A A L N M R V R R R L S
L F L N V R T Q V A A D W T A L A E E M D F E Y L E I R Q L E T Q A
D P T G R L L D A W Q G R P G A S V G R L L E L L T K L G R D D V L
L E L G P S I E E D C Q K Y I L K Q Q Q E E A E K P L Q V A A V D S S
V P R T A E L A G I T T L D D P L G H M P E R F D A F I C Y C P S D I
Q F V Q E M I R Q L E Q T N Y R L K L C V S D R D V L P G T C V W S
I A S E L I E K R C R R M V V V V S D D Y L Q S K E C D F Q T K F A L
S L S P G A H Q K R L I P I K Y K A M K K E F P S I L R F I T V C D Y T
N P C T K S W F W T R L A K A L S L P

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claim(s) that follow(s).

What is claimed is:

1. A method for activating an antigen-presenting cell, which comprises:
transfecting or transducing an antigen-presenting cell with a nucleic acid comprising a promoter operably linked to a polynucleotide that encodes a chimeric protein, wherein the chimeric protein comprises (i) a membrane targeting region, (ii) a multimeric ligand-binding region, (iii) a cytoplasmic CD40 polypeptide region lacking the extracellular domain, and (iv) a truncated MyD88 polypeptide lacking the TIR domain comprising the amino acid sequence SEQ ID NO: 6, wherein the chimeric protein is expressed in the antigen-presenting cell; and
contacting the antigen-presenting cell with a non-protein multimeric ligand that binds to the ligand-binding region;
whereby the antigen-presenting cell is activated.

2. A method for activating an antigen-presenting cell, which comprises:
transfecting or transducing an antigen-presenting cell with a nucleic acid comprising a promoter operably linked to a polynucleotide that encodes a chimeric protein, wherein the chimeric protein comprises (i) a membrane targeting region, (ii) a multimeric ligand-binding region, and (iii) a region comprising a truncated MyD88 polypeptide lacking the TIR domain comprising the amino acid sequence SEQ ID NO: 6, wherein the truncated MyD88 polypeptide activates the NF-kappa B pathway, and wherein the chimeric protein is expressed in the antigen-presenting cell; and
contacting the antigen-presenting cell with a non-protein multimeric ligand that binds to the ligand-binding region;
whereby the antigen-presenting cell is activated.

3. The method of claim 1, wherein the truncated MyD88 polypeptide is encoded by the nucleotide sequence of SEQ ID NO: 5.

4. The method of claim 1, wherein the membrane targeting region is selected from the group consisting of myristoylation-targeting region, palmitoylation targeting region, prenylation region, and receptor transmembrane region.

5. The method of claim 1, wherein the CD40 cytoplasmic polypeptide region has an amino acid sequence of the cytoplasmic region of SEQ ID NO: 2.

6. The method of claim 1, wherein the ligand-binding region comprises a Fv'Fvls sequence.

7. The method of claim 1, wherein the ligand is a small molecule.

8. The method of claim 1, wherein the ligand is dimeric.

9. The method of claim 8, wherein the ligand is dimeric FK506 or a dimeric FK506 analog.

10. The method of claim 1, wherein the nucleic acid is contained within a viral vector.

11. The method of claim 10, wherein the viral vector is an adenoviral vector.

12. The method of claim 10, wherein the antigen-presenting cell is contacted with the vector ex vivo.

13. The method of claim 1, wherein the antigen-presenting cell is contacted with an antigen.

14. The method of claim 1, wherein the antigen-presenting cell is a dendritic cell.

15. The method of claim 1, wherein the antigen-presenting cell is activated without the addition of an adjuvant.

16. The method of claim 1, wherein the truncated MyD88 polypeptide is encoded by a nucleotide sequence comprising the nucleotide sequence of SEQ ID NO: 5, wherein the nucleotide sequence of SEQ ID NO: 5 does not include SalI linkers.

17. The method of claim 13, wherein the antigen is a prostate specific membrane antigen.

18. The method of claim 1, wherein the ligand is AP1903 or AP20187.

* * * * *